United States Patent [19]
Lin et al.

[11] Patent Number: 6,127,386
[45] Date of Patent: *Oct. 3, 2000

[54] 3-PYRIDYLOXYMETHYL HETEROCYCLIC ETHER COMPOUNDS USEFUL IN CONTROLLING CHEMICAL SYNAPTIC TRANSMISSION

[75] Inventors: Nan-Horng Lin, Mundelein; Yun He, Zion; Mark W. Holladay, Libertyville; Keith B. Ryther, Round Lake Park; Yihong Li; Hao Bai, both of Grayslake, all of Ill.

[73] Assignee: Abbott Laboratories, Abbott Park, Ill.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/844,540

[22] Filed: Apr. 18, 1997

Related U.S. Application Data

[63] Continuation-in-part of application No. 08/660,004, Jun. 6, 1996, Pat. No. 5,629,325.

[51] Int. Cl.[7] .................. A61K 31/44; C07D 471/02; C07D 213/30
[52] U.S. Cl. .................. 514/318; 514/340; 514/343; 546/193; 546/194; 546/268.1; 546/276.4
[58] Field of Search .................. 214/318, 340, 214/343; 546/193, 194, 268.1, 276.4

[56] References Cited

U.S. PATENT DOCUMENTS 5,629,325   5/1997   Lin .......................................... 514/318

FOREIGN PATENT DOCUMENTS

| 0296560 | 12/1988 | European Pat. Off. |
| 94/08992 | 4/1994 | WIPO |
| 96/40682 | 12/1996 | WIPO |

OTHER PUBLICATIONS

A.D. Korczyn et al., *Psychopharacology: The Fourth Generation of Progress*, Chapter 126 "Parkinson's Disease", F.E. Bloom and David J. Kupfer, eds., Raven Press, Ltd., New York, (1995), pp. 1479–1495.

R.H. Roth et al., *Psychopharmacology: The Fourth Generation of Progress*, Chapter 21 "Biochemical Pharmacology of Midbrain Dopamine Neurons", Raven Press, Ltd., New York, (1995), pp. 227–243.

N.L. Benowitz et al., *Nicotine Psychopharmacology*, Chapter 4 "Pharmacokinetics, Metabolism, and Pharmacodynamics of Nicotine", S. Wonnacott, M.A.H. Russell, & I.P. Stolerman, eds., Oxford University Press, Oxford, (1990), pp. 112–157.

K. Tomioka et al., "Stereoselective Reactions. XIX. Asymetric Dihydroxylation of Olefins by Employing Osmium Tetroxide–Chiral Complexes", *Chemical and Pharmaceutical Bulletin*, vol. 38, No. 8, (1990), pp. 2133–2135.

M. Davidson et al., *Current Research Alzheimer Therapy*, "Cholinergic Agonists in Alzheimer's Disease Patients", E. Giacobini ans R. Becker, eds., Taylor & Francis, New York, (1988), pp. 333–336.

*Primary Examiner*—D. Margaret Seaman
*Attorney, Agent, or Firm*—Lawrence S. Pope

[57] ABSTRACT

Novel 3-pyridyloxymethyl heterocyclic ether compounds of the formula:

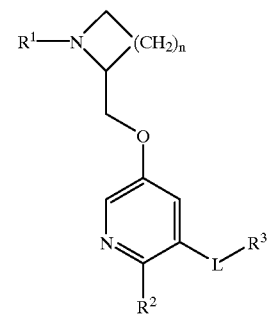

or the pharmaceutically-acceptable salts or prodrugs thereof are selective and potent ligands at neuronal nicotinic cholinergic channel receptors, and are effective in controlling synaptic transmission. Key intermediates and processes using this key intermediates to produce compounds of formula I with the variables defined in the specification are also described.

13 Claims, No Drawings

3-PYRIDYLOXYMETHYL HETEROCYCLIC ETHER COMPOUNDS USEFUL IN CONTROLLING CHEMICAL SYNAPTIC TRANSMISSION

RELATED APPLICATIONS

This application is a continuation-in-part of application Ser. No. 08/660,004 filed Jun. 6, 1996 now U.S. Pat. No. 5,629,325.

TECHNICAL FIELD

This invention relates to 3-pyridyloxymethyl heterocyclic ether compounds which control chemical synaptic transmission; to therapeutically-effective pharmaceutical compositions of these compounds; and to the use of said compositions to selectively control synaptic transmission.

BACKGROUND OF THE INVENTION

Compounds that selectively control chemical synaptic transmission offer therapeutic utility in treating disorders that are associated with dysfunctions in synaptic transmission. This utility may arise from controlling either pre-synaptic or post-synaptic chemical transmission. The control of synaptic chemical transmission is, in turn, a direct result of a modulation of the excitability of the synaptic membrane. Presynaptic control of membrane excitability results from the direct effect an active compound has upon the organelles and enzymes present in the nerve terminal for synthesizing, storing, and releasing the neurotransmitter, as well as the process for active re-uptake. Postsynaptic control of membrane excitability results from the influence an active compound has upon the cytoplasmic organelles that respond to neurotransmitter action.

An explanation of the processes involved in chemical synaptic transmission will help to illustrate more fully the potential applications of the invention. (For a fuller explanation of chemical synaptic transmission refer to Hoffman et al., "Neurotransmission: The autonomic and somatic motor nervous systems." In: *Goodman and Gilman's, The Pharmacological Basis of Therapeutics,* 9th ed., J. G. Hardman, L. E. Limbird, P. B. Molinoff, R. W. Ruddon, and A. Goodman Gilman, eds., Pergamon Press, New York, 1996, pp. 105–139).

Typically, chemical synaptic transmission begins with a stimulus that depolarizes the transmembrane potential of the synaptic junction above the threshold that elicits an all-or-none action potential in a nerve axon. The action potential propagates to the nerve terminal where ion fluxes activate a mobilization process leading to neurotransmitter secretion and "transmission" to the postsynaptic cell. Those cells which receive communication from the central and peripheral nervous systems in the form of neurotransmitters are referred to as "excitable cells." Excitable cells are cells such as nerves, smooth muscle cells, cardiac cells and glands. The effect of a neurotransmitter upon an excitable cell may be to cause either an excitatory or an inhibitory postsynaptic potential (EPSP or IPSP, respectively) depending upon the nature of the postsynaptic receptor for the particular neurotransmitter and the extent to which other neurotransmitters are present. Whether a particular neurotransmitter causes excitation or inhibition depends principally on the ionic channels that are opened in the postsynaptic membrane (i.e., in the excitable cell).

EPSPs typically result from a local depolarization of the membrane due to a generalized increased permeability to cations (notably $Na^+$ and $K^+$), whereas IPSPs are the result of stabilization or hyperpolarization of the membrane excitability due to a increase in permeability to primarily smaller ions (including $K^+$ and $Cl^-$). For example, the neurotransmitter acetylcholine excites at skeletal muscle junctions by opening permeability channels for $Na^+$ and $K^+$. At other synapses, such as cardiac cells, acetylcholine can be inhibitory, primarily resulting from an increase in $K^+$ conductance.

The biological effects of the compounds of the present invention result from modulation of a particular subtype of acetylcholine receptor. It is, therefore, important to understand the differences between two receptor subtypes. The two distinct subfamilies of acetylcholine receptors are defined as nicotinic acetylcholine receptors and muscarinic acetylcholine receptors. (See *Goodman and Gilman's, The Pharmacological Basis of Therapeutics,* op. cit.).

The responses of these receptor subtypes are mediated by two entirely different classes of second messenger systems. When the nicotinic acetylcholine receptor is activated, the response is an increased flux of specific extracellular ions (e.g. $Na^+$, $K^+$ and $Ca^{++}$) through the neuronal membrane. In contrast, muscarinic acetylcholine receptor activation leads to changes in intracellular systems that contain complex molecules such as G-proteins and inositol phosphates. Thus, the biological consequences of nicotinic acetylcholine receptor-activation are distinct from those of muscarinic receptor activation. In an analogous manner, inhibition of nicotinic acetylcholine receptors results in still other biological effects, which are distinct and different from those arising from muscarinic receptor inhibition.

As indicated above, the two principal sites to which drug compounds that affect chemical synaptic transmission may be directed are the presynaptic nerve terminal and the postsynaptic membrane. Actions of drugs directed to the presynaptic site may be mediated through presynaptic receptors that respond to the neurotransmitter which the same secreting structure has released (i.e., an autoreceptor), or through a presynaptic receptor that responds to another neurotransmitter (i.e., a heteroreceptor). Actions of drugs directed to the postsynaptic membrane mimic the action of the endogenous neurotransmitter or inhibit the interaction of the endogenous neurotransmitter with a postsynaptic receptor.

Classic examples of drugs that modulate postsynaptic membrane excitability are the neuromuscular blocking agents which interact with nicotinic acetylcholine-gated channel receptors on skeletal muscle, for example, competitive (stabilizing) agents, such as curare, or depolarizing agents, such as succinylcholine.

In the central nervous system, postsynaptic cells can have many neurotransmitters impinging upon them. This makes it difficult to know the precise net balance of chemical synaptic transmission required to control a given cell. Nonetheless, by designing compounds that selectively affect only one pre- or postsynaptic receptor, it is possible to modulate the net balance of all the other inputs. Obviously, the more that is understood about chemical synaptic transmission in CNS disorders, the easier it would be to design drugs to treat such disorders.

Knowing how specific neurotransmitters act in the CNS allows one to speculate about the disorders that may be treatable with certain CNS-active drugs. For example, dopamine is widely recognized as an important neurotransmitter in the central nervous systems in humans and animals. Many aspects of the pharmacology of dopamine have been reviewed by Roth and Elsworth, "Biochemical Pharmacology of Midbrain Dopamine Neurons", In: *Psychopharmacology: The Fourth Generation of Progress*, F. E. Bloom and D. J. Kupfer, Eds., Raven Press, NY, 1995, pp 227–243). Patients with Paridnson's disease have a primary loss of dopamine containing neurons of the nigrostriatal pathway, which results in profound loss of motor control. Therapeutic strategies to replace the dopamine deficiency with dopamine mimetics, as well as administering pharmacologic agents that modify dopamine release and other neurotransmitters have been found to have therapeutic benefit ("Parkinson's Disease", In: *Psychopharmacology: The Fourth Generation of Progress*, op. cit, pp 1479–1484).

New and selective neurotransmitter controlling agents are still being sought, in the hope that one or more will be useful in important, but as yet poorly controlled, disease states or behavior models. For example, dementia, such as is seen with Alzheimer's disease or Parkinsonism, remains largely untreatable. Symptoms of chronic alcoholism and nicotine withdrawal involve aspects of the central nervous system, as does the behavioral disorder Attention-Deficit Disorder (ADD). Specific agents for treatment of these and related disorders are few in number or non-existent.

A more complete discussion of the possible utility as CNS-active agents of compounds with activity as cholinergic ligands selective for neuronal nicotinic receptors, (i.e., for controlling chemical synaptic transmission) may be found in U.S. Pat. No. 5,472,958, to Gunn et al., issued Dec. 5, 1995, which is incorporated herein by reference.

Existing acetylcholine channel agonists are therapeutically sub-optimal in treating the conditions discussed above. For example, such compounds have unfavorable pharmacokinetics (e.g., arecoline and nicotine), poor potency and lack of selectivity (e.g., nicotine), poor CNS penetration (e.g., carbachol) or poor oral bioavailability and tolerability (e.g., nicotine). In addition, other agents have many unwanted central agonist actions, including hypothermia, hypolocomotion and tremor and peripheral side effects, including miosis, lachrymation, defecation and tachycardia (Benowitz et al, in: *Nicotine Psychopharmacology*, S. Wonnacott, M. A. H. Russell, & I. P. Stolerman, eds., Oxford University Press, Oxford, 1990, pp. 112–157; and M. Davidson, et al., in *Current Research in Alzheimer Therapy*, E. Giacobini and R. Becker, ed.; Taylor & Francis: New York, 1988; pp 333–336).

Various heterocyclic 2-pyrrolidinyloxy-substituted compounds with analgesic and hypotensive activities have been disclosed by Scheffler et al. (U.S. Pat. No. 4,643,995) and Tomioka et al. (Chem. Pharm. Bull, 38:2133–5, 1990).

Certain other 2-pyridyloxy-substituted compounds are disclosed inter alia by Engel et al. in U.S. Pat. No. 4,946,836 as having analgesic activity.

Various other compounds having a pyrrolidine or azetidine moiety substituted at the 3-position with a heterocycloxy group have also been disclosed (cf. U.S. Pat. Nos. 4,592,866 to A. D. Cale; 4,705,853 to A. D. Cale; 4,956,359 to Taylor et al.; and 5,037,841 to Schoehe et al. and European patent application EP296560A2, to Sugimoto et al.).

Certain nicotine-related compounds having utility in enhancing cognitive function have been reported by Lin in U.S. Pat. No. 5,278,176, issued Jan. 11, 1994. Also, 2-(nitro) phenoxy compounds with similar function have been reported by Gunn et al., U.S. Pat. No. 5,472,958, issued Dec. 5, 1995.

In the PCT Patent Application WO94 08992 of Abreo et al., published Apr. 28, 1994, are disclosed, inter alia, various 3-pyridyloxy-heterocyclic compounds that are either unsubstituted or mono-substituted on the pyridine ring with groups such as Br, Cl, F, hydroxyl, $C_1$–$C_3$-alkyl or $C_1$–$C_3$-alkoxy, such compounds also described having utility in enhancing cognitive function.

SUMMARY OF THE INVENTION

In accordance with the principal embodiment of the present invention, there is provided a class of 5-substituted 3-pyridyloxymethyl heterocyclic ether compounds which are selective and potent neuronal nicotinic cholinergic compounds useful in controlling synaptic transmission.

The compounds of the present invention are represented by formula (I):

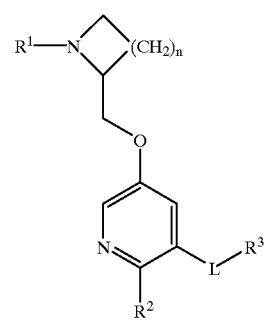

or a pharmaceutically acceptable salt thereof wherein n is selected from 1, 2 or 3.

The substituents $R^1$ is selected from the group consisting of hydrogen, allyl, and alkyl of one to six carbon atoms.

$R^2$ is selected from the group consisting of hydrogen, $C_1$–$C_3$ alkyl, fluorine, chlorine, ethenyl, and phenyl.

The linking group, L, is absent or is selected from the group consisting of alkylene of one to six carbon atoms, —C≡C—($C_0$–$C_6$-alkyl)-,

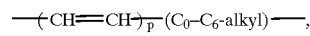

where p is one or two,

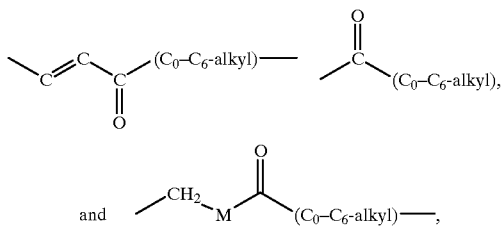

where M is selected from —$CH_2$—, and —NH—.

The substituent $R^3$ is selected from the group consisting of a) hydrogen, b) alkyl of one to eight carbon atoms, c) alkenyl of 2–6 carbon atoms d) haloalkyl of one to six carbon atoms, e) hydroxyalkyl of one to six carbon atoms, f) alkoxy of one to six carbon atoms, g) amino, h) alkylamino of one to six carbon atoms, h') azacycle attached to L through a nitrogen atom, i) dialkylamino in which the two alkyl groups are independently of one to six carbon atoms, j) phenyl, k) naphthyl, l) biphenyl, m) furyl, n) thienyl, o) pyridinyl, p) pyrazinyl, q) pyridazinyl, r) pyrimidinyl, s) pyrrolyl, t) pyrazolyl, u) imidazolyl, v) indolyl, w) thiazolyl, x) oxazolyl, y) isoxazolyl, z) thiadiazolyl, aa) oxadiazolyl, bb) quinolinyl, cc) isoquinolinyl, and cc) any of b) or j) through cc) above substituted with one or two substituents independently selected from the group consisting of alkyl of one to six carbon atoms, haloalkyl of one to six carbon atoms, alkoxy of one to six carbon atoms, alkoxyalkyl in which the alkoxy and alkyl portions are independently of one to six carbon atoms, alkoxyalkoxyl in which the alkoxy portions are independently of one to six carbon atoms, halogen, cyano, hydroxy, amino, alkylamino of one to six carbon atoms, carboxyl, and alkoxycarbonyl of two to six carbon atoms. Alternatively, L-$R_3$ is O— $CH_2$-$R_4$, wherein $R_4$ is selected from $CH_3OCH_2$—, or from substituents i) through bb) above, which may be substituted with one or two substituents independently selected from the group consisting of alkyl of one to six carbon atoms, haloalkyl of one to six carbon atoms, alkoxy of one to six carbon atoms, alkoxyalkyl in which the alkoxy and alkyl portions are independently of one to six carbon atoms, alkoxyalkoxyl in which the alkoxy portions are independently of one to six carbon atoms, halogen, cyano, hydroxy, amino, alkylamino of one to six carbon atoms, carboxyl, and alkoxycarbonyl of two to six carbon atoms.

The above definitions of the various linking and substituent groups in the compounds of the present invention are limited by the provisos that i) when L is absent, $R^3$ may not be hydrogen, alkyl of one to eight carbon atoms, alkoxy of 1–6 carbons, amino, alkylamino or dialkylamino; ii) when L is absent and $R^3$ is hydrogen, $R^2$ is selected from ethenyl, unsubstituted phenyl, and phenyl substituted as defined in bb) above; iii) when L is alkylene, $R^3$ may not be hydrogen or alkyl; iv) when L is

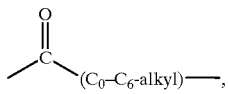

then $R^3$ is selected from alkyl of one to eight carbon atoms, a carbocyclic aryl or heterocyclic aryl ring selected from h') i), j), k), l), m), n), o), p), q), bb), and cc) as defined above, and any of i), j), k), l), m), n), o), p), q), bb) and cc) as substituted as defined in dd) above; v) when L is

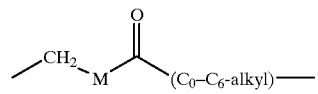

and M is —$CH_2$—, then $R^3$ may not be hydrogen; and vi) f) through y) above may be substituted as defined in z) above by no more than one alkylamino, carboxyl, or alkoxycarbonyl substituent.

DETAILED DESCRIPTION OF THE INVENTION

In one embodiment of the invention there are provided a class of substituted azetidine compounds of Formula (I) above wherein n is 1.

In another embodiment of the invention there are provided a class of substituted pyrrolidine compounds of Formula (I) above wherein n is 2.

In yet another embodiment of the present invention, there are provided a class of substituted piperidine compounds of Formula (I) above wherein n is 3.

Representative substituted azetidine compounds of the invention include, but are not limited to:

5-phenyl-3-(2-(S)-azetidinylmethoxy)pyridine;
5-phenyl-3-(1-methyl-2-(S)-azetidinylmethoxy)pyridine;
5-(1-hexynyl)-3-(2-(S)-azetidinylmethoxy)pyridine;
5-(2-(4-pyridinyl)ethenyl)-3-(2-(S)-azetidinylmethoxy)pyridine;
5-(2-(4-pyridinyl)ethyl)-3-(2-(S)-azetidinylmethoxy)pyridine;
5-(2-(4-pyridinyl)ethenyl)-3-(1-methyl-2-(S)-azetidinylmethoxy)pyridine;
5-(2-(4-pyridinyl)ethyl)-3-(1-methyl-2-(S)-azetidinylmethoxy)pyridine;
5-(1-octynyl)-3-(2-(S)-azetidinylmethoxy)pyridine;
5-(1-octynyl)-3-(1-methyl-2-(S)-azetidinylmethoxy)pyridine;
5-(3-aminophenyl)-3-(2-(S)-azetidinylmethoxy)pyridine;
5-phenyl-6-chloro-3-(2-(S)-azetidinylmethoxy)pyridine;
5-phenyl-6-chloro-3-(1-methyl2-(S)-azetidinylmethoxy)pyridine;
5-(2-(4-pyridinyl)ethenyl)-6-chloro-3-(2-(S)-azetidinylmethoxy)pyridine;
5-(3-thienyl)-3-(1-methyl-2-(R)-azetidinylmethoxy)pyridine;
5-((N-benzoylamino)methyl)-6-chloro-3-(2-(S)-azetidinylmethoxy)pyridine;
5-(N-benzoylamino)methyl)-6-chloro-3-(1-methyl-2-(S)-azetidinylmethoxy)pyridine;
5-(acetamidomethyl)-6-chloro-3-(2-(R)-azetidinylmethoxy)pyridine;
5-(6-chlorohexanamidomethyl)-6-chloro-3-(2-(S)-azetidinylmethoxy)pyridine;
5-(3-phenylpropionamidomethyl)-6-chloro-3-(1-methyl-2-(R)-azetidinyl-methoxy)pyridine;
5-(6-chlorobenzamidomethyl)-6-chloro-3-(1-methyl-2-(S)-azetidinyl-methoxy)pyridine;
5-benzoyl-6-chloro-3-(2-(S)-azetidinylmethoxy)pyridine;
5-hexanoyl-6-chloro-3-(2-(R)-azetidinylmethoxy)pyridine;
5-(3-quinolinoyl)-6-chloro-3-(2-(S)-azetidinylmethoxy)pyridine;
5-(3-nicotinoyl)-6-chloro-3-(1-methyl-2-(R)-azetidinylmethoxy)pyridine;
5-(5-pyrimidinecarbonyl)-6-chloro-3-(1-methyl-2-(S)-azetidinyl-methoxy)pyridine;
5-(5-carboxy-3-pyridinyl)-3-(2-(R)-azetidinylmethoxy)pyridine;
5-(5-formyl-3-pyridinyl)-3-(2-(S)-azetidinylmethoxy)pyridine;
5-(2-hydroxy-1-naphthyl)-3-(2-(R)-azetidinylmethoxy)pyridine; and
5-(4'-nitro-4-biphenyl)-3-(2-(S)-azetidinylmethoxy)pyridine.

Representative substituted pyrrolidine compounds of the present invention include, but are not limited to:
5-(3-nitrophenyl)-3-(1-methyl-2-(S)-pyrrolidinylmethoxy)pyridine;
5-(1-naphthalenyl)-3-(1-methyl-2-(S)-pyrrolidinylmethoxy)pyridine;
5-(4-methoxyphenyl)-3-(1-methyl-2-(S)-pyrrolidinylmethoxy)pyridine;
5-hexynyl-3-(1-methyl-2-(S)-pyrrolidinylmethoxy)pyridine;

5-(2-furanyl)-3-(1-methyl-2-(S)-pyrrolidinylmethoxy) pyridine;
5-(2-thienyl)-3-(1-methyl-2-(S)-pyrrolidinylmethoxy) pyridine;
5-(3-pyridyl)-3-(1-methyl-2-(S)-pyrrolidinylmethoxy) pyridine;
5-ethenyl-3-(1-methyl-2(S)pyrrolidinylmethoxy) pyridine;
5-(1-decynyl)-3-(1-methyl-2-(S)-pyrrolidinylmethoxy) pyridine;
5-acetyl-3-(1-methyl-2-(S)-pyrrolidinylmethoxy) pyridine;
5-(4-fluorophenyl)-3-(1-methyl-2-(S)-pyrrolidinylmethoxy)pyridine;
5-hexyl-3-(1-methyl-2-(S)-pyrrolidinylmethoxy) pyridine;
5-(2-(4-pyridinyl)ethenyl)-3-(1-methyl-2-(S)-pyrrolidinylmethoxy)pyridine;
5-(5-cyano-1-pentynyl)-3-(1-methyl-2-(S)-pyrrolidinylmethoxy)pyridine;
5-(2-(methoxycarbonyl)ethyl)-3-(1-methyl-2-(S)-pyrrolidinyl-methoxy)pyridine;
5-(2-(methoxycarbonyl)ethenyl)-3-(1-methyl-2-(S)-pyrrolidinyl-methoxy)pyridine;
5(5-phenyl-1-pentynyl)-3-(1-methyl-2-(S)-pyrrolidinylmethoxy)pyridine;
5-trans-(2-phenylethenyl)-3-(1-methyl-2-(S)-pyrrolidinylmethoxy)pyridine;
5-(1-pyrrolidinylcarbonyl)-3-(1-methyl-2-(S)-pyrrolidinylmethoxy)pyridine;
5-(4-chlorophenyl)-3-(2-(S)-pyrrolidinylmethoxy) pyridine;
5-(2-phenylethyl))-3-(1-methyl-2-(S)-pyrrolidinylmethoxy)pyridine;
5-(3-oxo-1-hexenyl)-3-(1-methyl-2-(S)-pyrrolidinylmethoxy)pyridinine;
5-(5-pyrimidinyl)-3-(1-methyl-2-(S)-pyrrolidinylmethoxy)pyridine;
5-phenyl-6-chloro-3-(1-methyl-2-(S)-pyrrolidinylmethoxy)pyridine;
5-methoxycarbonyl-3-(1-methyl-2-(S)-pyrrolidinylmethoxy)pyridine;
5-(6-hydroxy-1-hexynyl)-3-(1-methyl-2-(S)-pyrrolidinylmethoxy)pyridine;
5-(2-(4-pyridinyl)ethyl)-3-(1-methyl-2-(S)-pyrrolidinylmethoxy)pyridine;
5-(5,5-dimethyl-1,3-hexadienyl)-3-(1-methyl-2-(S)-pyrrolidinyl-methoxy)pyridine;
5-(2-naphthalenyl)-3-(1-methyl-2-(S)-pyrrolidinylmethoxy)pyridine;
5-acetyl-6-chloro-3-(2-(S)-pyrrolidinylmethoxy) pyridine;
5-(2-(4-pyridinyl)ethenyl)-6-chloro-3-(2-(S)-pyrrolidinylmethoxy)pyridine;
5-(3-pyridinyl)-6-chloro-3-(2-(S)-pyrrolidinylmethoxy) pyridine;
5-(3-quinolinyl)-3-(1-methyl-2-(S)-pyrrolidinylmethoxy) pyridine;
5-(1-methyl-2-indolyl)-3-(1-methyl-2-(S)-pyrrolidinylmethoxy)pyridine;
5-(3,5-bis(trifluoromethyl)phenyl)-3-(1-methyl-2-(S)-pyrrolidinyl-methoxy)pyridine;
5-(4-chlorophenyl)-3-(1-methyl-2-(S)-pyrrolidinylmethoxy)pyridine;
5-(2,4-dichlorophenyl)-3-(1-methyl-2-(S)-pyrrolidinylmethoxy)pyridine;
5-(2-phenylethynyl)-3-(1-methyl-2-(S)-pyrrolidinylmethoxy)pyridine;
5-(4-methylphenyl)-3-(1-methyl-2-(S)-pyrrolidinylmethoxy)pyridine;
5-(3-chloro-4-fluorophenyl)-3-(1-methyl-2-(S)-pyrrolidinylmethoxy)pyridine;
5-(3-aminophenyl)-3-(1-methyl-2-(S)-pyrrolidinylmethoxy) pyridine;
5-(2-formylphenyl)-3-(1-methyl-2-(S)-pyrrolidinylmethoxy)pyridine;
5-(2-methylphenyl)-3-(1-methyl-2-(S)-pyrrolidinylmethoxy)pyridine;
5-(4-(trifluoromethyl)phenyl)-3-(1-methyl-2-(S)-pyrrolidinyl-methoxy)pyridine;
5-(3,3-dimethylbutynyl)-3-(1-methyl-2-(S)-pyrrolidinylmethoxy)pyridine;
5-(2-(4-methylphenyl)ethynyl)-3-(1-methyl-2-(S)-pyrrolidinyl-methoxy)pyridine;
5-(1-octynyl)-3-(1-methyl-2-(S)-pyrrolidinylmethoxy) pyridine;
5-(2-(4pyridinyl)ethenyl)-6-chloro-3-(1-methyl-2-(S)-pyrrolidinyl-methoxy)pyridine;
5-phenyl-3-(2-(S)-pyrrolidinylmethoxy)pyridine;
5-phenyl-3-(2-(R)-pyrrolidinylmethoxy)pyridine;
5-phenyl-3-(1-methyl-2-(R)-pyrrolidinylmethoxy) pyridine;
5-(5,5-dimethyl-1,3-hexadienyl)-6-chloro-3-(2-(R)-pyrrolidinyl-methoxy)pyridine;
5-phenyl-6-chloro-3-(1-methyl-2-(R)-pyrrolidinylmethoxy)pyridine;
5-phenyl-6-chloro-3-(2-(R)-pyrrolidinylmethoxy) pyridine;
5,6-diphenyl-3-(2-(R)-pyrrolidinylmethoxy)pyridine;
5,6-diphenyl-3-(1-methyl-2-(R)-pyrrolidinylmethoxy) pyridine;
5-(3-aminophenyl)-6-chloro-3-(2-(R)-pyrrolidinylmethoxy)pyridine;
5-(4-chlorophenyl)-6-chloro-6-chloro-3-(1-methyl-2-(R)-pyrrolidinyl-methoxy)pyridine;
5-(5,5-dimethyl-1,3-hexadienyl)-6-chloro-3-(2-(R)-pyrrolidinyl-methoxy)pyridine;
5-(5,5-dimethyl-1,3-hexadienyl)-6-chloro-3-(1-methyl-2-(R)-pyrrolidinyl-methoxy)pyridine;
5-(1-octynyl)-6-chloro-3-(2-(R)-pyrrolidinylmethoxy) pyridine;
5-(1-octynyl)-6-chloro-3-(1-methyl-2-(R)-pyrrolidinylmethoxy)pyridine;
5-(2-(4-pyridinyl)ethenyl)-6-chloro-3-(2-(R)-pyrrolidinylmethoxy)pyridine;
5-(2-(4-pyridinyl)ethenyl)-6-chloro-3-(1-methyl-2-(R)-pyrrolidinyl-methoxy)pyridine;
5-(2-(4-pyridinyl)ethyl)-6-chloro-3-(1-methyl-2-(R)-pyrrolidinyl-methoxy)pyridine;
5-phenyl-6-chloro-3-(2-(S)-pyrrolidinylmethoxy) pyridine;
5-(2-thienyl)-6-chloro-3-(2-(R)-pyrrolidinylmethoxy) pyridine;

5-(2-(4-pyridinyl)ethenyl)-3-(2-(R)-pyrrolidinylmethoxy)pyridine;

5-(2-(4-pyridinyl)ethyl)-3-(2-(R)-pyrrolidinylmethoxy)pyridine;

5-(3-aminophenyl)-3-(2-(R)-pyrrolidinylmethoxy)pyridine;

5-phenyl-3-(1-methyl-2-(S)-pyrrolidinylmethoxy)pyridine;

5-(formamidomethyl)-6-chloro-3-(2-(R)-pyrrolidinylmethoxy)pyridine;

5-((N-methoxycarbonylamino)methyl)-6-chloro-3-(2-(S)-pyrrolidinyl-methoxy)pyridine;

5-(3-nitrobenzamidomethyl)-6-chloro-3-(1-methyl-2-(R)-pyrrolidinyl-methoxy)pyridine;

5-((N-2-pyrrolycarbonylamino)methyl)-6-chloro-3-(1-methyl-2-(S)-pyrrolidinylmethoxy)pyridine;

5-(2-naphthoyl)-6-chloro-3-(2-(R)-pyrrolidinylmethoxy)pyridine;

5-(4-methyl-1-naphthoyl)-6-chloro-3-(2-(S)-pyrrolidinylmethoxy)pyridine; methoxy)pyridine;

5-(3-pyridazinecarbonyl)-6-chloro-3-(1-methyl-2-(R)-pyrrolidinyl-methoxy)pyridine;

5-(2-thiophenecarbonyl)-6-chloro-3-(1-methyl-2-(S)-pyrrolidinyl-methoxy)pyridine;

5-(2-(5-carbomethoxypyridinyl)ethyl)-3-(2-(S)-pyrrolidinylmethoxy)pyridine;

5-(2-(5-bromopyridinyl)ethyl)-3-(2-(S)-pyrrolidinylmethoxy)pyridine;

5-(2-(6-amino-5-bromopyridinyl)ethyl)-3-(2-(S)-pyrrolidinyl-methoxy)pyridine;

5-(2-(5-bromo-6-methylaminopyridinyl)ethyl)-3-(2-(S)-pyrrolidinyl-methoxy)pyridine;

5-(5-hydroxymethyl-3-pyridinyl)-3-(2-(R)-pyrrolidinylmethoxy)pyridine;

5-(2,4-dimethoxy-5-pyrimidinyl)-3-(2-(S)-pyrrolidinylmethoxy)pyridine;

5-(4-methyl-3-thienyl)-3-(2-(R)-pyrrolidinylmethoxy)pyridine;

5-(4-hydroxymethyl-5-carbomethoxy-3-thienyl)-3-(2-(S)-pyrrolidinyl-methoxy)pyridine;

5-(4-methoxymethoxy-5-carbomethoxy-3-thienyl)-3-(2-(S)-pyrrolidinyl-methoxy)pyridine;

5-(2-(4-methyl-3-phenyl)ethyl)-3-(2-(S)-pyrrolidinylmethoxy)pyridine;

5-(2-(4-methoxy-3-phenyl)ethyl)-3-(2-(S)-pyrrolidinylmethoxy)pyridine;

5-(2-(4-trifluoromethyl-3-phenyl)ethyl)-3-(2-(S)-pyrrolidinyl-methoxy)pyridine;

5-(4'-fluoro-4-biphenyl)-3-(2-(R)-pyrrolidinylmethoxy)pyridine; and 5-(4'-methyl-4-biphenyl)-3-(2-(S)-pyrrolidinylmethoxy)pyridine; or a pharmaceutically acceptable salt thereof.

Representative substituted piperidine compounds of the present invention include, but are not limited to:

5-(furamidomethyl)-6-chloro-3-(2-(R)-piperidinylmethoxy)pyridine;

5-(nicotinamidomethyl)-6-chloro-3-(2-(S)-piperidinylmethoxy)pyridine;

5-(5-nitro-2-furamidomethyl)-6-chloro-3-(1-methyl-2-(R)-piperidinyl-methoxy)pyridine;

5-((N-2-pyrazincarbonylamino)methyl)-6-chloro-3-(1-methyl-2-(S)-piperidinylmethoxy)pyridine;

5-(2-phenylacetyl)-6-chloro-3-(1-methyl-2-(R)-piperidinylmethoxy)pyridine;

5-(3-(4methoxyphenyl)propionyl)-6-chloro-3-(1-methyl-2-(S)-piperidinyl-methoxy)pyridine;

5-(2-chloro-3-thienyl)-3-(2-(R)-piperidinylmethoxy)pyridine; and 5-(2-cyano-3-thienyl)-3-(2-(S)-piperidinylmethoxy)pyridine; or a pharmaceutically acceptable salt thereof.

The present invention also includes compounds selected from:

5-(5,5-dimethyl-1,3-hexadienyl)-3-(2-(R)-pyrrolidinylmethoxy)pyridine;

5-(4-chlorophenyl)-3-(2-(R)-pyrrolidinylmethoxy)pyridine;

6-Chloro-5-(1-octynyl)-3-(2-(R)-pyrrolidinylmethoxy)pyridine;

5-(4-chlorophenyl)-3-(1-methyl-2-(R)-pyrrolidinylmethoxy)pyridine;

5-(1-Octynyl)-3-(2-(R)-pyrrolidinylmethoxy)pyridine;

3-(1-Methyl-2-(R)-pyrrolidinylmethoxy)-5-(1-octynyl)pyridine;

6-Chloro-3-(1-methyl-2-(S)-pyrrolidinylmethoxy)-5-(1-octynyl)pyridine;

6-Chloro-3-(1-methyl-2-(S)-pyrrolidinylmethoxy)-5-(3-pyridyl)pyridine;

6-Chloro-5-(5,5-dimethyl-1,3-hexadienyl)-3-(2-(S)-pyrrolidinylmethoxy)pyridine;

6-Chloro-5-(5,5-dimethyl-1,3-hexadienyl)-3-(1-methyl-2-(S)-pyrrolidinylmethoxy)pyridine;

6-Chloro-5-(4-chlorophenyl)-3-(2-(S)-pyrrolidinylmethoxy)pyridine;

6-Chloro-5-(4-chlorophenyl)-3-(1-methyl-2-(S)-pyrrolidinylmethoxy)pyridine;

6-Chloro-3-(2-(S)-pyrrolidinylmethoxy)-5-(2-thienyl)pyridine;

6-Chloro-3-(1-methyl-2-(S)-pyrrolidinylmethoxy)-5-(2-thienyl)pyridine;

5-(2-(4-pyridinyl)ethenyl)-3-(2-(S)-pyrrolidinylmethoxyl)pyridine;

3-(2-(S)-Pyrrolidinylmethoxy)-5-(2-thienyl)pyridine;

5-Octynyl-3-(2-(S)-pyrrolidinylmethoxyl)pyridine;

5-(3-Aminophenyl)-3-(2-(S)-pyrrolidinylmethoxy)pyridine;

3-(2-(S)-Pyrrolidinylmethoxy)-5-(5,5-dimethyl-1,3-hexadienyl)pyridine;

5-Ethenyl-3-(1-methyl-2-(S)-pyrrolidinylmethoxy)pyridine;

5-Ethenyl-3-(2-(S)-pyrrolidinylmethoxy)pyridine;

6-Chloro-5-ethenyl-3-(2-(R)-pyrrolidinylmethoxy)pyridine;

6-Chloro-5-ethenyl-3-(1-methyl-2-(R)-pyrrolidinylmethoxy)pyridine;

6-Chloro-5-(5-pyrimidinyl)-3-(2-(S)-pyrrolidinylmethoxyl)pyridine;

6-Chloro-5-(5-pyrimidinyl)-3-(2-(R)-pyrrolidinylmethoxyl)pyridine;

5-(5-Pyrimidinyl)-3-(2-(S)-pyrrolidinylmethoxyl)pyridine;

6-Chloro-3-(1-methyl-2-(R)-pyrrolidinylmethoxyl)-5-pyrimidinylpyridine;

6-Chloro-3-(1-methyl-2-(S)-pyrrolidinylmethoxyl)-5-(5-pyrimidinyl)pyridine;

6-Ethenyl-5-methyl-3-(2-(S)-pyrrolidinylmethoxyl)pyridine;

6-Ethenyl-5-methyl-3-(1-methyl-2-(S)-pyrrolidinylmethoxyl)pyridine;

6-Chloro-5-ethenyl-3-(2-(S)-pyrrolidinylmethoxy)pyridine;

6-Chloro-5-ethenyl-3-(1-methyl-2-(S)-pyrrolidinylmethoxy)pyridine;

5,6-Diethenyl-3-(2-(S)-pyrrolidinylmethoxy)pyridine;

6-Chloro-5-(ethynyl-3-(2-(S)-pyrrolidinylmethoxy)pyridine;

6-Chloro-5-ethynyl-3-(1-methyl-2-(S)-pyrrolidinylmethoxy)pyridine;

5-Methoxyethoxy-3-(2-(S)-pyrrolidinylmethoxy)pyridine;

5-Methoxyethoxy-3-(1-methyl-(2S)-pyrrolidinylmethoxy)pyridine;

5-Allyl-6-chloro-3-(2-(S)-pyrrolidinylmethoxyl)pyridine;

5-Allyl-6-chloro-3-(2-(S)-pyrrolidinylmethoxyl)pyridine;

5-Allyl-6-chloro-3-(2-(R)-pyrrolidinylmethoxyl)pyridine;

5-Allyl-3-(2-(S)-pyrrolidinylmethoxyl)pyridine;

5-Allyl-3-(1-methyl-2-(S)-pyrrolidinylmethoxyl)pyridine;

and pharmaceutically acceptable salts or pro-drugs thereof.

The present invention also relates to:

an intermediate compound selected from the group consisting of:

3-(1-Boc-2-(S)-azetidinemethoxy)-5-bromo-6-chloropyridine;

3-(2-(S)-azetidinemethoxy)-5-bromo-6-chloropyridine;

5-bromo-6-chloro-3-(1-methyl-2-(S)-azetidinemethoxy)pyridine;

3-(1-Boc-2-(S)-azetidinemethoxy)-5-bromo-6-fluoropyridine;

3-(2-(S)-azetidinemethoxy)-5-bromo-6-fluoropyridine;

5-bromo-6-fluoro-3-(1-methyl-2-(S)-azetidinemethoxy)pyridine 3-(1-Boc-2-(S)-azetidinemethoxy)-5-bromo-6-methylpyridine;

3-(2-(S)-azetidinemethoxy)-5-bromo-6-methylpyridine;

5-bromo-6-methyl-3-(1-methyl-2-(S)-azetidinemethoxy)pyridine 5-bromo-6-chloro-3-(1-Boc-2-(S)-pyrrolidinemethoxy)pyridine;

5-bromo-6-chloro-3-(2-(S)-pyrrolidinemethoxy)pyridine;

5-bromo-6-chloro-3-(1-methyl-2-(S)-pyrrolidinemethoxy)pyridine;

3-(1-Boc-2-(S)-pyrrolidinemethoxy)-5-bromo-6-fluoropyridine;

5-bromo-6-fluoro-3-(2-(S)-pyrrolidinemethoxy)pyridine;

5-bromo-6-fluoro-3-(1-methyl-2-(S)-pyrrolidinemethoxy)pyridine 3-(1-Boc-2-(S)-pyrrolidinemethoxy)-5-bromo-6-methylpyridine;

5-bromo-6-methyl3-(2-(S)-pyrrolidinemethoxy)pyridine;

5-bromo-6-methyl-3-(1-methyl-2-(S)-pyrrolidinemethoxy)pyridine and to an intermediate compound selected from the group consisting of, 3-(1-Boc-2-(R)-azetidinemethoxy)-5-bromo-6-chloropyridine;

3-(2-(R)-azetidinemethoxy)-5-bromo-6-chloropyridine;

5-bromo-6-chloro-3-(1-methyl-2-(R)-azetidinemethoxy)pyridine;

3-(1-Boc-2-(R)-azetidinemethoxy)-5-bromo-6-fluoropyridine;

3-(2-(R)-azetidinemethoxy)-5-bromo-6-fluoropyridine;

5-bromo-6-fluoro-3-(1-methyl-2-(R)-azetidinemethoxy)pyridine 3-( -Boc-2-(R)-azetidinemethoxy)-5-bromo-6-methylpyridine;

3-($^2$-(R)-azetidinemethoxy)-5-bromo-6-methylpyridine;

5-bromo-6-methyl-3-(1-methyl-2-(R)-azetidinemethoxy)pyridine 5-bromo-6-chloro-3-(1-Boc-2-(R)-pyrrolidinemethoxy)pyridine;

5-bromo-6-chloro-3-(2-(R)-pyrrolidinemethoxy)pyridine;

5-bromo-6-chloro-3-(1-methyl-2-(R)-pyrrolidinemethoxy)pyridine;

3-(1-Boc-2-(R)-pyrrolidinemethoxy)-5-bromo-6-fluoropyridine;

5-bromo-6-fluoro-3-(2-(R)-pyrrolidinemethoxy)pyridine;

5-bromo-6-fluoro-3-(1-methyl-2-(R)-pyrrolidinemethoxy)pyridine 3-(1-Boc-2-(R)-pyrrolidinemethoxy)-5-bromo-6-methylpyridine;

5-bromo-6-methyl3-(2-(R):pyrrolidinemethoxy)pyridine;

5-bromo-6-methyl-3-(1-methyl-2-(R)-pyrrolidinemethoxy)pyridine.

The present invention also relates to a method of using a compound of formula (I) wherein $R^1$ is hydrogen, alkyl of one to six carbons, or a nitrogen protecting group, n is 1, 2, or 3, $R^2$ is hydrogen, fluoro, chloro, or $C_1$–$C_3$-allyl, L is absent and $R_3$ is bromo or iodo for preparation of a compound of formula (I) according to claim 1.

The present invention further relates to a process for producing a compound of formula (I) according to claim 1 comprising, (a) Preparing a compound of formula (I) wherein $R^1$ is hydrogen, alkyl of one to six carbons, or a nitrogen protecting group, n is 1, 2, or 3, $R^2$ is hydrogen, fluoro, chloro, or $C_1$–$C_3$-alkyl, L is absent and $R_3$ is bromo or iodo (b) Reacting the compound of formula (I) wherein $R^1$ is hydrogen, alkyl of one to six carbons, or a nitrogen protecting group, n is 1, 2, or 3, $R^2$ is hydrogen, fluoro, chloro, or $C_1$–$C_3$-alkyl, L is absent and $R_3$ is bromo or iodo with (i) An alkene, diene, alkyne, or carbon monoxide with C1–C3-alcohol;

(ii) An arylboronic acid;

(iii) An alkenyltin or alkyl Grignard reagent;

(iv) A metal cyanide;

to form in the case of step (i), a compound of formula (I) wherein $LR_3$ is an alkene, diene, alkyne, or alkoxycarbonyl; or in the case of step (ii), a compound of formula (I) wherein $LR_3$ is an aryl group; or in the case of step (iii), a compound of formula (I) wherein $LR_3$ is an alkenyl or alkyl group; or, in the case of step (iv), a compound of formula (I) wherein $LR_3$ is a cyano group, which is utilized as an intermediate to form a compound of formula (I) wherein L is carbonyl and $R_3$ is selected from alkyl of one to eight carbon atoms, h'), i), j), k), l), m), n), o), p), q), bb), and cc) as defined above, or any of i), j), k), l), m), n),o), p), q), bb) and cc) optionally substituted as defined in dd) above, or to form a compound of formula (I) wherein L is —CH$_2$NHC (=O)-(C$_0$–C$_6$-alkyl)- and R$^3$ is selected from (a) through (dd) in claim 1 above.

The invention also relates to a process according to claim 13 wherein the intermediate compound of formula (I) wherein R$^1$ is hydrogen, alkyl of one to six carbons, or a nitrogen protecting group, n is 1, 2, or 3, R$^2$ is hydrogen, fluoro, chloro, or C$_1$–C$_3$-alkyl, L is absent and R$_3$ is bromo or iodo is selected from those intermediate compounds identified above.

Definitions

The terms "C$_1$–C$_3$-alkyl" and "alkyl of one to three carbon atoms" as used herein refer to a univalent radical derived by removal of a single hydrogen atom from a saturated, straight- or branched-chain hydrocarbon containing between one and three carbon atoms. Examples of C$_1$–C$_3$-alkyl radicals include methyl, ethyl, propyl, and isopropyl, The terms "C$_1$–C$_6$-alkyl" and "alkyl of one to six carbon atoms" as used herein refers to a univalent radical derived by removal of a single hydrogen atom from a saturated, straight- or branched-chain hydrocarbon containing between one and six carbon atoms. Examples of C$_1$–C$_6$-alkyl radicals include, but are not limited to, methyl, ethyl, propyl, isopropyl, n-butyl, tert-butyl, neopentyl, n-hexyl.

The terms "C$_1$–C$_8$-alkyl" and "alkyl of one to eight carbon atoms" as used herein refers to a univalent radical derived by removal of a single hydrogen atom from a saturated, straight- or branched-chain hydrocarbon containing between one and six carbon atoms. Examples of C$_1$–C$_8$-alkyl radicals include, but are not limited to, methyl, ethyl, propyl, isopropyl, n-butyl, tert-butyl, neopentyl, n-hexyl, n-octyl, 2-octyl and the like.

The term "C$_2$–C$_6$-alkenyl" as used herein refers to a univalent radical derived by removal of a single hydrogen atom from a straight- or branched-chain hydrocarbon containing between one and six carbon atoms and one double bond. Examples of C$_2$–C$_6$-alkenyl radicals include ethenyl, 3-propenyl, 2-propenyl, 1-propenyl, hex-2-en-1-yl, and the like.

The term "haloalkyl" refers to an alkyl group, as defined above, substituted by one or more halogen atoms and includes, for example, trifluoromethyl, chloroethyl, bromobutyl, and the like.

The term "C$_1$–C$_6$-alkoxy" and "alkoxy of one to six carbon atoms" as used herein refer to an alkyl group, as previously defined, attached to the parent molecular moiety through an oxygen atom. Examples of C$_1$–C$_6$-alkoxy, but are not limited to, methoxy, ethoxy, propoxy, isopropoxy, n-butoxy, tert-butoxy, neopentoxy and n-hexoxy.

One or more asymmetric centers may exist in the compounds of the present invention. Except where otherwise noted, the present invention contemplates the various stereoisomers and mixtures thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, pahmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The term "prodrug" refers to compounds that are rapidly transformed in vivo to yield the parent compounds of Formula (I), as for example, by hydrolysis in blood. T. Higuchi and V. Stella provide a thorough discussion of the prodrug concept in *Prodrugs as Novel Delivery Systems,* Vol. 14 of the A.C.S. Symposium Series, American Chemical Society (1975). Examples of esters useful as prodrugs for compounds containing carboxyl groups may be found on pages 14–21 of *Bioreversible Carriers in Drug Design: Theory and Application,* edited by E. B. Roche, Pergamon Press (1987).

The term "prodrug ester group" refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyates, acrylates and ethylsuccinates.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, disorders in synaptic transmission are treated or prevented in a patient such as a human or lower mammal by administering to the patient a therapeutically effective amount of a compound of the invention, in such amounts and for such time as is necessary to achieve the desired result By a "therapeutically effective amount" of a compound of the invention is meant a sufficient amount of the compound to treat disorders in synaptic transmission, at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.001 to 50 mg/kg body weight or more usually from 0.01 to 25 mg/kg body weight. Single dose compositions may contain such amounts or submultiples thereof to make up the daily dose. In general, treatment regimens according to the present invention comprise administration to a patient in need of such treatment from about 1 mg to about 1000 mg of the compound(s) of this invention per day in single or multiple doses.

Abbreviations

Abbreviations which have been used in the descriptions of the scheme and the examples that follow are: BOC for t-butyloxycarbonyl; CBZ for benzyloxycarbonyl; DEAD for diethylazodicarboxylate; DMF for dimethyl formamide; DPPA for diphenylphosphoryl azide; EDC for 1-(3-dimethylaminopropyl)-3-ethylcarbodiimide HCl; $Et_2O$ for diethyl ether; EtOAc for ethyl acetate; MeOH for methanol; $NaN(TMS)_2$ for sodium bis(trimethylsilyl)amide; NMMO for N-methylmorpholine N-oxide; $(Ph)_3$ for triphenyl; TEA for triethylamine; THF for tetrahydrofuran; TFA for trifluoroacetic acid, TPP for triphenylphosphine; other abbreviations are found in J. Org. Chem. 1996, 62. 22A.

Synthetic Methods

The compounds and processes of the present invention will be better understood in connection with the following synthetic schemes which illustrate the methods by which the compounds of the invention may be prepared. The groups n, $R^1$, $R^2$, $R^3$ and $R^4$ are as defined above unless otherwise noted.

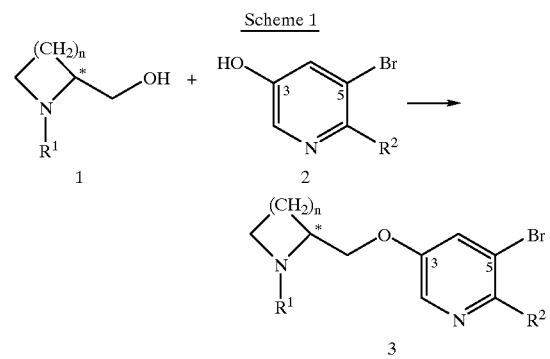

In accordance with Scheme 1 intermediate compounds are prepared by reaction of an alcohol compound (1), wherein n is 1 to 3 and $R^1$ is allyl or $C_1$–$C_6$-alkyl or a protecting group such as BOC or CBZ, for example, with a 3-hydroxypyridine compound (2), wherein $R^2$ is H, F or Cl, for compounds of Formula (I) above, in the presence of triphenylphosphine and DEAD under Mitsunobu reaction conditions (cf., Synthesis, 1981: 1) to form the 5-bromopyridyl ether compound (3).

Scheme 2

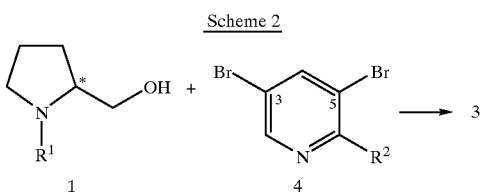

Alternately, in accordance with Scheme 2 selected intermediate pyrrolidine compounds (3), wherein $R^1$ is allyl or $C_1$–$C_6$-alkyl or a protecting group such as t-BOC or CBZ, for example, may be prepared by reaction of an pyrrolidinemethanol compound (1) with a 3,5-dibromopyridine compound (4), wherein $R^2$ is H or phenyl, in the presence of a strong base, such as an alkyl lithium compound, an alkali metal such as Na or Li, or an alkali metal hydride, such as NaH or KH, for example, in an aprotic solvent such as THF, DMSO or DMF under anhydrous conditions and inert atmospheres, at temperatures from room temperature to 120° C., for example.

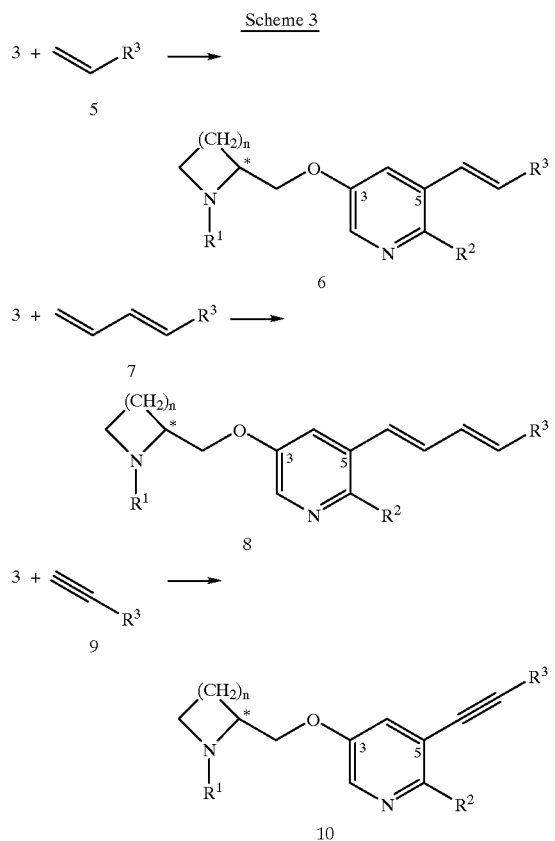

In accordance with Scheme 3 an intermediate compound (3), wherein $R^1$ is allyl or $C_1$–$C_6$-alkyl or a protecting group such as t-BOC or CBZ, for example, is reacted with an unsaturated compound (5), (7) or (9), to give compounds (6), (8) or (10), respectively, which are specific or protected compounds of Formula (I), by treatment with a palladium (II) catalyst under weakly basic conditions at reflux temperature in an organic or aqueous solvent. Compound (5) may be prepared by reacting a compound $R^3$—CHO, wherein $R^3$ is as described above, with (phenyl)$_3$P=CH$_2$ in refluxing toluene. Compound (7) may be prepared by reacting a compound $R^3$—CHO, wherein $R^3$ is as described above, with (Ph)$_3$P=CH—CHO in refluxing toluene to give $R^3$—CH=CH—CHO, then reacting $R^3$—CH=CH—CHO with (Ph)$_3$P=CH$_2$ in refluxing toluene. Compound (9) may be prepared by reacting $R^3$—CHO, wherein $R^3$ is as described above, with CBr$_4$ and P(Ph)$_3$ to give $R^3$—CH=CBr$_2$, then reacting $R^3$—CH=CBr$_2$ with 2 equivalents of n-butyllithium followed by treatment with H$^+$. Alternatively, a compound of formula (I) wherein L is carbonyl and $R_3$ is $C_1$–$C_3$-alkoxy is prepared by reaction of a compound of formula (3) with carbon monoxide and a $C_1$–$C_3$-alcohol in the presence of a palladium (II) catalyst in the presence of a weak base such as triethylamine. The resulting ester may then be treated with a cyclic secondary amine, for example, azetidine, pyrrolidine piperidine, or piperazine, to afford a compound of formula (I) wherein L is carbonyl and $R_3$ is an azacyclic group attached to the carbonyl through a nitrogen. In the cases wherein $R^1$ is a protecting group such as t-BOC or CBZ it must be removed under well-known standard conditions for removing those groups in order to give the desired compound of Formula (I). In some cases wherein $R^1$ is allyl or $C_1$–$C_6$-alkyl, it may be desirable to place this grouping in the compound after the protecting $R^1$ group has been removed. When $R^1$ is allyl, this may be accomplished by reacting the unprotected nitrogen atom with allyl chloride in the presence of a weak base such as triethylamine. When $R^1$ is $C_1$–$C_6$-alkyl, this may be accomplished by reacting the unprotected nitrogen atom with the appropriate aldehyde in the presence of NaCNBH$_3$, for example.

Scheme 4

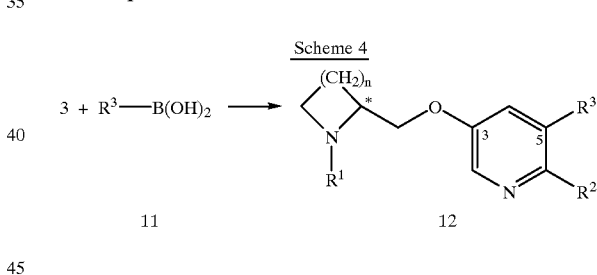

In accordance with Scheme 4 an intermediate compound (3), wherein $R^1$ is allyl or $C_1$–$C_6$-alkyl or a protecting group such as t-BOC or CBZ, for example, is reacted with a suitable boronic acid compound (11) wherein $R^3$ is as described in options (a)-(1) for Formula (I) above, in the presence of Pd(0) under the conditions of the Suzuki reaction, for example in the presence of a weak base such as NaHCO$_3$ and in an aprotic solvent, such as toluene, benzene or CH$_2$Cl$_2$ at reflux temperatures to give a compound (12), wherein $R^3$ is as described above, to produce specific compounds of Formula (I). In an alternate method, compound (11) may be replaced by $R^3$Sn(n-Bu)$_3$ or compound (11) and the palladium catalyst may be replaced by a $R^3$MgX compound and Ni(dppp)$_2$Cl$_2$ catalyst to give compound (12). In the cases wherein $R^1$ is a protecting group such as t-BOC or CBZ it must be removed under well-known standard conditions for removing those groups in order to give the desired compound of Formula (I). In some cases wherein $R^1$ is allyl or $C_1$–$C_6$-alkyl, it may be desirable to place this grouping in the compound after the protecting R¹ group has been removed. When R¹ is allyl, this may be accomplished by reacting the unprotected nitrogen atom with allyl chloride in the presence of a weak base such as triethylamine. When R¹ is $C_1$–$C_6$-alkyl, this may be accomplished by reacting the unprotected nitrogen atom with the appropriate aldehyde in the presence of $NaCNBH_3$, for example.

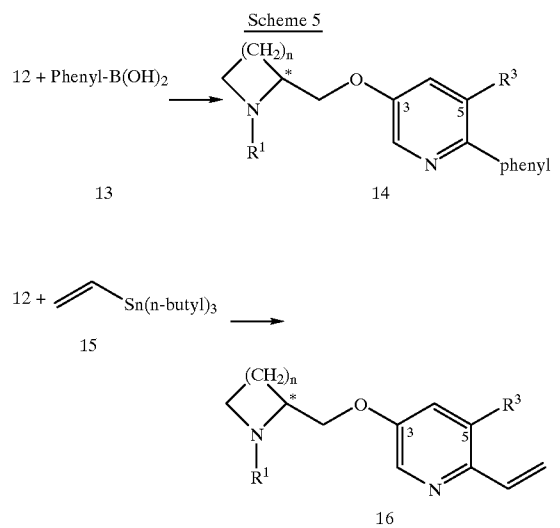

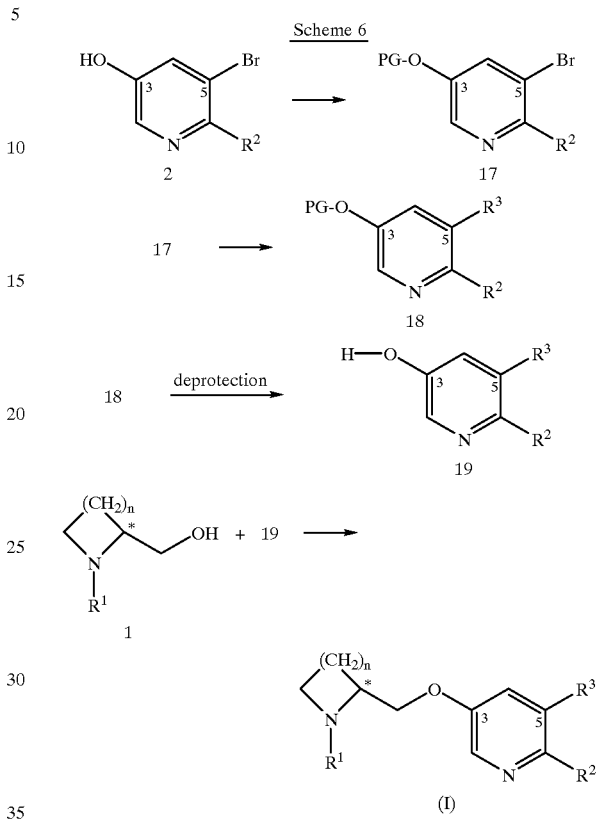

In accordance with Scheme 5 are prepared compounds of Formula (I) wherein $R^2$ is ethenyl, phenyl or substituted phenyl. Reaction of a starting material compound (12) wherein $R^2$ is chloro with phenylboronic acid (13) in the presence of Pd(0) under the conditions of the Suzuki reaction, for example in the presence of a weak base such as $NaHCO_3$ and in an aprotic solvent, such as toluene, benzene or $CH_2Cl_2$ at reflux temperatures to give the compound 14. Reaction of a starting material compound (12) wherein $R^2$ is chloro with vinyl-Sn(n-butyl)₃ (15) in the presence of Pd(0) under Stille reaction conditions to give the compound (16). In the cases wherein $R^1$ is a protecting group such as t-BOC or CBZ it must be removed under well-known standard conditions for removing those groups in order to give the desired compound of Formula (I). In some cases wherein $R^1$ is allyl or $C_1$–$C_6$-alkyl, it may be desirable to place this grouping in the compound after the protecting $R^1$ group has been removed. When $R^1$ is allyl, this may be accomplished by reacting the unprotected nitrogen atom with allyl chloride in the presence of a weak base such as triethylamine. When $R^1$ is $C_1$–$C_6$-alkyl, this may be accomplished by reacting the unprotected nitrogen atom with the appropriate aldehyde in the presence of $NaCNBH_3$, for example.

In Scheme 6 is shown an alternate process for preparing desired compounds of the invention. Whereas in Schemes 1 and 3, the heterocyclic and the pyridine moieties are first joined, and the $R^3$ grouping is added according to Schemes 4 and 5, Scheme 6 allows for the placement of the $R^3$ group before joining. Accordingly compound (2) is treated with the appropriate reagent, such as a trialkylsilyl or benzyl chloride, to protect the hydroxyl group with a protecting group PG, such as trialkylsilyl or benzyl, respectively, for example to give compound (17). Compound (17) may then be reacted with an appropriate reagent, as described in Schemes 4 and 5, to give the compound (18) having the desired substitution at $R^2$ and $R^3$. Subsequent deprotection of (18) by standard methods gives (19), which is then coupled with compound (1) according to the method of Scheme 1 to give the desired compound of Formula (I).

Scheme 7

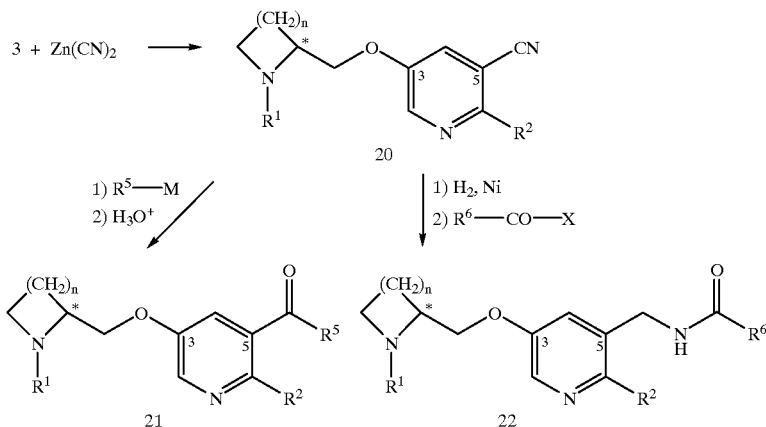

In accordance with Scheme 7 are prepared additional compounds of Formula (I). Compound (3) is first reacted with $Zn(CN)_2$ and tetrakis(triphenylphosphine)palladium(0) under anhydrous conditions in DMF or a similar solvent at room temperature to 120° C. for 12–24 hours, to give the cyano intermediate compound (20). Compound (20) may then be reacted with a reagent $R^5$-M, wherein $R^5$ is as described for Formula (I) above and M is lithium or a magnesium halide moiety, under the appropriate anhydrous conditions, with cooling if necessary, for 2–8 hours or until the reaction is complete to give, followed by treatment with aqueous acid to dissociate the metal complexes and give compound (21). Alternately, the cyano group of compound (20) may be reduced by treatment with 1 atm of $H_2$ in the presence of Raney nickel at room temperature for 1–8 hours to give an intermediate amino compound. The intermediate amino compound may then be treated with a suitable acylating reagent, for example ethyl formate, an acyl chloride $R^6$—Cl, wherein $R^6$ is, for example, $C_1$–$C_8$-alkyl, substituted-$C_1$–$C_8$-alkyl, phenyl, substituted-phenyl, heteroaryl, substituted-heteroaryl, aryl-$C_1$–$C_6$-alkyl-, substituted-aryl-$C_1$–$C_6$-alkyl-, heteroaryl-$C_1$–$C_6$-alkyl-, or substituted-heteroaryl-$C_1$–$C_6$-alkyl-, a di-$C_1$–$C_8$-alkyl dicarbonate, or an appropriate carbamylating reagent, Cl—CO—N—$R^7R^8$, for example, wherein $R^7$ may be H or $C_1$–$C_3$-alkyl-, and $R^8$ may be H, $C_1$–$C_3$-alkyl-, phenyl or substituted-phenyl.

Scheme 8

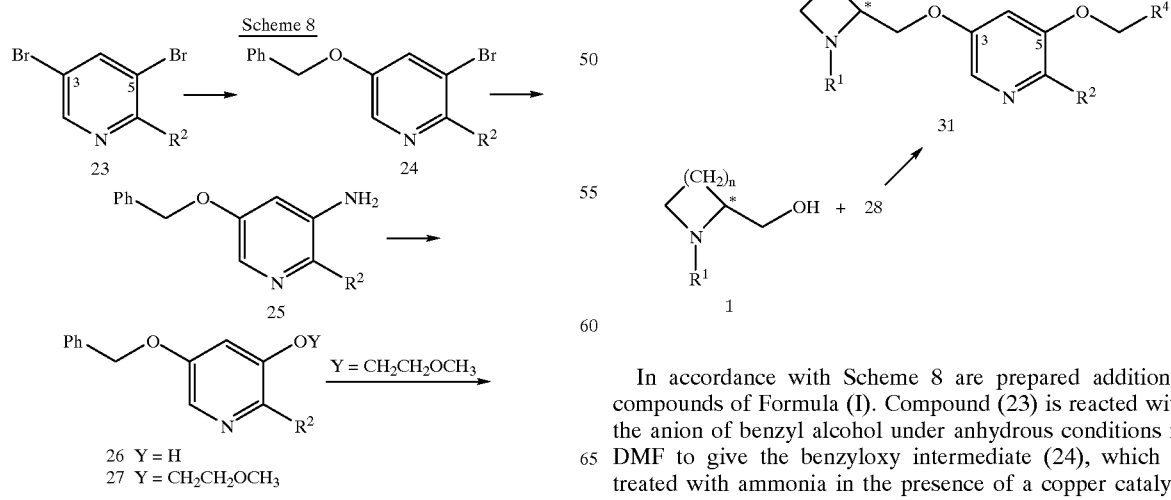

-continued

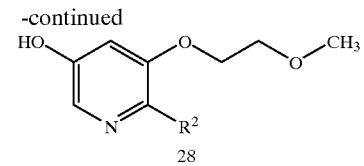

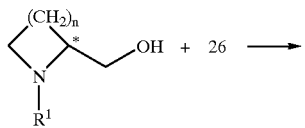

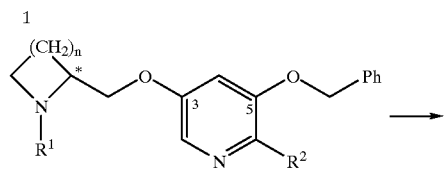

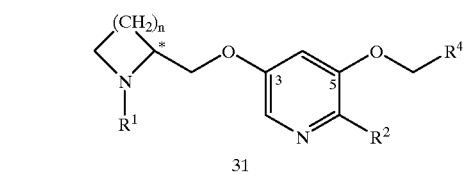

In accordance with Scheme 8 are prepared additional compounds of Formula (I). Compound (23) is reacted with the anion of benzyl alcohol under anhydrous conditions in DMF to give the benzyloxy intermediate (24), which is treated with ammonia in the presence of a copper catalyst and heat and pressure to afford amino compound (25).

Compound (25) is treated under diazotizing conditions followed by heating with aqueous acid (or alternatively by acetic anhydride and heat followed by saponification) to afford pyridinol (26). When the diazo intermediate is heated in the presence of 1,2-dimethoxyethane and a Lewis acid, intermediate (27) is obtained, which can be debenzylated by catalytic hydrogenolysis to afford pyridinol (28). The foregoing procedures are most applicable when $R^2$ is H, alkyl or phenyl. For $R^2$ is F or Cl, pyridinols (26) and (28) can be further substituted at the position para to the hydroxyl group by electrophilic aromatic substitution to provide directly $R^2$=F or Cl, or alternatively by a diazo coupling/hydrogenolysis sequence to install an amino substituent, which is readily converted to chloro or fluoro by well-known methods. If necessary or desired, selectively removable blocking groups, e.g. iodo, may be used at positions ortho to the hydroxyl group to achieve the desired regioselectivity for installation of $R^2$. Pyridinols are then coupled with alcohols (1) according to procedures described under Scheme 1 to afford intermediates (29), which can be elaborated (e.g. N-deprotection, optionally followed by N-alkylation) to compounds of Formula (I). Alternatively, (29) is debenzylated under acidic or hydrogenolytic or electrolytic conditions to (30), which is O-alkylated with alkylating agents $R^4CH_2$—X, where X is a leaving group, to provide (31), which can be elaborated to compounds of Formula (I). Coupling of (1) to (28) provides an intermediate compound which can be similarly elaborated to compounds of Formula (I).

In Vitro Determination of Neuronal Nicotinic Receptor Binding Potencies Selectivity and Functionality For the purpose of identifying compounds as cholinergic agents which are capable of interacting with cholinergic channel receptors in the brain, a ligand-receptor binding assay was carried out as the initial screen. Compounds of the present invention were effective at interacting with neuronal nicotinic cholinergic receptors as assayed in vitro for their ability to displace radioligand from neuronal nicotinic cholinergic channel receptors labeled with [$^3$H]-cytisine ([$^3$H]-CYT) (Protocol A below).

For the purpose of directly evaluating the ability of test compounds to functionally activate or inhibit certain subtypes of neuronal nicotinic cholinergic channels, an assay to determine $^{86}$Rb+ Efflux in IMR-32 cells was employed (Protocol B below).

A. Protocol For Determination of Nicotinic Cholinergic Channel Receptor Binding Potencies of Ligands Binding of [$^3$H]-cytisine ([$^3$H1]-CYT) to nicotinic receptors was accomplished using crude synaptic membrane preparations from whole rat brain (Pabreza et al., *Molecular Pharmacol.*, 1990, 39:9). Washed membranes were stored at −80° C. prior to use. Frozen aliquots were slowly thawed and resuspended in 20 volumes of buffer (containing: 120 mM NaCl, 5 mM KCl, 2 mM MgCl$_2$, 2 mM CaCl$_2$ and 50 mM Tris-Cl, pH 7.4 @4° C.). After centrifuging at 20,000× g for 15 minutes, the pellets were resuspended in 30 volumes of buffer. Homogenate (containing 125–150 μg protein) was added to triplicate tubes containing concentrations of test compound and [$^3$H]-CYT (1.25 nM) in a final volume of 500 μL. Samples were incubated for 60 minutes at 4° C., then rapidly filtered through Whatman GF/B filters presoaked in 0.5% polyethyleneimlne using 3×4 mL of ice-cold buffer. The filters are counted in 4 mL of Ecolume® (ICN). Nonspecific binding was determined in the presence of 10 μM (−)-nicotine and values were expressed as a percentage of total binding. IC$_{50}$ values were determined with the RS-1 (BBN) nonlinear least squares curve-fitting program and IC$_{50}$ values were converted to Ki values using the Cheng and Prusoff correction (Ki=IC$_{50}$/(1+[Rigand]/Kd of ligand). Alternately, data were expressed as a percentage of the total specific binding. The binding data (shown in Table 1) suggest that the compounds of the present invention have high affinity for the neuronal nicotinic cholinergic channel receptor.

B. Protocols for the Determination of Functional Effects of Cholinergic Channel Receptor Ligands on Synaptic Transmission Cells of the IMR-32 human neuroblastoma clonal cell line (ATCC, Rockville, Md.) were maintained in a log phase of growth according to established procedures (Lukas, 1993). Experimental cells were seeded at a density of 500,000 cells/ml into a 24-well tissue culture dish. Plated cells were allowed to proliferate for at least 48 hours before loading with 2 μCi/ml of $^{86}$Rb$^+$ (35 Ci/mmol) overnight at 37° C. The $^{86}$Rb$^+$ efflux assays were performed according to previously published protocols (Lukas, R. J., *J. Pharmacol. Exp. Ther.*, 265: 294–302, 1993) except serum-free Dulbecco's Modified Eagle's Medium was used during the $^{86}$Rb$^+$ loading, rinsing, and agonist-induced efflux steps.

EC$_{50}$ data and maximal responses (reported as percent relative to the response elicited by 100 μM (S)-nicotine) are shown for selected compounds of the invention. The inhibition data (given for a larger number of compounds) reflect inhibition of the efflux elicited by 100 μM (S)-nicotine for either a single dose (% inhibition at 1 μM or at 10 μM) or over a range of doses (IC$_{50}$ of inhibition). The results (also shown in Table 1) suggest that selected compounds of the present invention either activate or inhibit the initial ion flux aspects of synaptic transmission mediated by neuronal nicotinic acetylcholine receptors. This finding is in agreement with the results of others who have linked dopamine release, which is dependent upon the ion flux in synaptic transmission, to binding at nicotinic receptors (cf., for example, Lippiello and Caldwell, U.S. Pat. No. 5,242,935, issued Sep. 7, 1993; Caldwell and Lippiello, U.S.Patent 5,248,690, issued Sept. 28, 1993; and Wonnacott et al., Prog. Brain Res., 79: 157–163 (1989)).

TABLE 1

Binding to Neuronal Nicotinic Receptors
and
Activation or Inhibition of Neuronal Nicotinic Cholinergic Channels in Imr-32 Cells

| Ex. No. | Binding K$_i$ (nM) | IMR-32 EC$_{50}$ (μM) | IMR-32 maximal response | % Inhibition @ 1 μM | % Inhibition @ 10 μM | Inhibition IC$_{50}$ (μM) |
|---|---|---|---|---|---|---|
| 1 | 0.46 | | | 13 | | |
| 2 | 4.2 | | | 47 | | |
| 3 | 0.32 | | | 39 | | |
| 4 | 0.25 | | | 55 | | |
| 5 | 0.19 | | | 27 | | |
| 6 | 0.31 | | | 28 | | |
| 7 | 0.27 | | | | | 46 |
| 8 | 0.48 | | | | | 10 |
| 9 | 36 | | | | | 25 |
| 10 | 1.2 | | | 32 | | |
| 11 | 0.11 | | | 38 | | |

TABLE 1-continued

Binding to Neuronal Nicotinic Receptors and Activation or Inhibition of Neuronal Nicotinic Cholinergic Channels in Imr-32 Cells

| Ex. No. | Binding $K_i$ (nM) | IMR-32 $EC_{50}$ ($\mu$M) | IMR-32 maximal response |
|---|---|---|---|
| 12 | 0.32 | 25 | |
| 13 | 0.12 | 50 | |
| 14 | 0.16 | 50 | |
| 15 | 0.46 | 16 | 83 |
| 16 | 0.55 | 6 | |
| 17 | 0.65 | 32 | 100 |
| 18 | 0.24 | 43 | |
| 19 | 20 | 14 | |
| 20 | 0.12 | | |
| 21 | 0.22 | 22 | |
| 22 | 1.0 | 44 | |
| 23 | 0.065 | 27 | |
| 24 | 0.43 | 17 | |
| 25 | 0.46 | 4.5 | |
| 26 | 0.044 | 47 | |
| 27 | 1.5 | 26 | |
| 28 | 0.16 | 20 | |
| 29 | 0.064 | 32 | |
| 30 | 1.6 | 21 | 90 |
| 31 | 0.33 | 37 | |
| 32 | 0.15 | | |
| 33 | 0.039 | 2 | 47 |
| 34 | 0.021 | 0.6 | 88 |
| 35 | 0.39 | 34 | |
| 36 | 0.32 | 28 | |
| 37 | 2.4 | 41 | |
| 38 | 0.082 | 29 | 100 |
| 39 | 0.16 | 52 | |
| 40 | 0.16 | 30 | 100 |
| 41 | 0.13 | 41 | 100 |
| 42 | 0.055 | 38 | |
| 43 | 0.43 | 36 | |
| 44 | 0.56 | 30 | 97 |
| 45 | 1.1 | 41 | 100 |
| 46 | 0.15 | 37 | |
| 47 | 1.3 | 66 | |
| 48 | 0.34 | 40 | |
| 49 | 0.88 | 33 | |
| 50 | 0.0044 | | 2 |
| 51 | 0.42 | 42 | |
| 52 | 0.39 | 22 | 88 |
| 53 | 12 | 35 | 100 |
| 55 | 4.6 | >10,000 | 24.5 |
| 56 | 0.055 | 3 | 20 | 16 |
| 57 | 0.79 | 21 | |
| 58 | 0.056 | 0.8 | 47 |
| 59 | 0.16 | | |
| 60 | 0.22 | | |
| 61 | 0.46 | | |
| 62 | 0.13 | | |
| 63 | 1.6 | | |
| 64 | 5.6 | | |
| 65 | 0.34 | | |
| 67 | 0.024 | 0.13 | 90 |
| 68 | 0.11 | | |
| 69 | 5.01 | >10,000 | 6 |
| 70 | 0.023 | | |
| 71 | 1.9 | | |
| 72 | 90.3 | | |
| 75 | 0.16 | | |
| 76 | 3.2 | | |
| 77 | 4.5 | | |
| 78 | 92 | | |
| 79 | 4.1 | | |
| 80 | 23 | | |
| 81 | 0.027 | 1.9 | 32 |
| 82 | 0.81 | | |
| 83 | 0.15 | | |
| 84 | 0.0087 | 0.3 | 37 |
| 85 | 0.33 | | |
| 86 | 0.16 | 0.25 | 44 |
| 87 | 0.047 | 5 | 40 |
| 88 | 1.8 | | |
| 89 | 0.056 | 0.4 | 72 |
| 90 | 0.111 | | 9 |
| 91 | 1.84 | | |
| 92 | 0.62 | 4.9 | 25 |
| 138 | 1.6 | | |
| 139 | 0.2 | | |
| 140 | 0.13 | | |
| 141 | 20 | | |
| 142 | 0.014 | | |
| 143 | 0.014 | | |
| 144 | 0.64 | | |
| 145 | 16 | | |
| 146 | 8 | | |
| 147 | 0.11 | | |
| 148 | 0.46 | | |
| 149 | 0.75 | | |
| 150 | 0.057 | | |
| 151 | 0.026 | | |
| 152 | 2.24 | | |
| 153 | 0.12 | | |
| 154 | 0.19 | >1,000 | 1.5 |
| 155 | 0.11 | | |
| 156 | 0.44 | | |
| 157 | 0.7 | | |
| 158 | 0.29 | | |
| 159 | 0.13 | | |
| 160 | 1.24 | | |
| 161 | 2.29 | | |
| 162 | 0.97 | | |
| 163 | 0.42 | | |
| 164 | 2.6 | | |
| 165 | 1.93 | 2.7 | 127 |
| 166 | 4.1 | | |
| 167 | 0.34 | | |
| 168 | 5.5 | | |
| 169 | 0.10 | | |
| 170 | 0.26 | | |
| 171 | 0.26 | | |
| 172 | 0.04 | | |
| 173 | 0.10 | | |
| 174 | 1.3 | | |
| 175 | 0.039 | | |
| 176 | 0.21 | | |
| 177 | 0.22 | | |
| 178 | 0.18 | | |
| 179 | 0.17 | | |
| 180 | 4.8 | | |
| 181 | 0.06 | 1.5 | 82 |
| 182 | 0.27 | | |
| 183 | 0.4 | 0.74 | 110 |
| 184 | 0.092 | | |
| 185 | 0.049 | | |
| 186 | 0.037 | | |
| 187 | 0.27 | | |
| 188 | 0.61 | | |
| 189 | 0.65 | | |
| 190 | 0.01 | | |
| 191 | 0.035 | 0.86 | 106 |
| 192 | 0.12 | | |
| 193 | 2.7 | >1,000 | 9.5 |
| 194 | 0.037 | | |
| 195 | 0.14 | | |
| 196 | 0.46 | | |
| 197 | 0.49 | | |
| 198 | 0.41 | | |
| 199 | 0.03 | | |
| 200 | 0.14 | | |
| 201 | 1.13 | | |
| 202 | 26 | | |
| 203 | 0.16 | | |

TABLE 1-continued

Binding to Neuronal Nicotinic Receptors
and
Activation or Inhibition of Neuronal Nicotinic Cholinergic Channels in Imr-32 Cells

| | | | |
|---|---|---|---|
| 204 | 2.1 | | |
| 205 | 0.66 | | |
| 206 | 0.13 | >1,000 | 11 |
| 207 | 0.09 | | |
| 208 | 13.5 | | |
| 209 | 41 | | |
| 210 | 29.7 | | |
| 211 | 9.6 | | |
| 212 | 0.074 | | |
| 213 | 0.08 | | |

EXAMPLES

The present invention will be better understood in connection with the following examples, which are intended as an illustration of, and not a limitation upon, the scope of the invention.

Preparations of Starting materials

Several staring materials are used repeatedly throughout the examples that follow. 1-Methyl-2-(S)-pyrrolidinemethanol was obtained from Aldrich Chemical Co. 1-Methyl-2-(R)-pyrrolidinemethanol was obtained from Fluka.

In the PCT Patent Application WO94 08992 of Abreo et al., published Apr. 28, 1994, are disclosed, inter alia, the (R) and (S) 1-BOC-2-(S)-pyrrolidinemethanol compounds and the (R) and (S) 1-BOC-2-(S)-azetidinemethanol compounds The following procedures were also used to prepare starting materials.

1-BOC-2-S)-pyrrolidinemethanol

N-BOC-(S)-proline (Sigma Chemical Co., 12.97 g, 60.02 mmol) was dissolved in anhydrous THF and brought to 0° C. with stirring. Borane/ complex was added dropwise via syringe over a 10 minute period. The reaction mixture was stirred at room temperature for 1 hour, then the reaction was quenched slowly with saturated $NaHCO_3$ and stirred for an additional hour. The solvent was removed in vacuo, and the residue was diluted with $H_2O$. The desired compound was extracted from the aqueous phase with $Et_2O$ (3x). The organic layer was then washed with brine (2x) dried ($MgSO_4$) and evaporated.

1-BOC-2-(R)-pyrrolidinemethanol

N-BOC-(R)-proline was converted to the desired product by procedures similar to those for the preparation of the 1-BOC-2-(S)-pyrrolidinemethanol described above.

5-bromo-3-(2-(S)-pyrrolidinylmethoxy)pyridine dihydrochloride a. 5-bromo-3-methoxypyridine To a suspension of 12 g of 3,5-dibromopyridine and 40 g of 60% NaH in DMF was added 4.05 mL of MeOH, and the reaction mixture was stirred for 4 hours at room temperature and 1 hour at 60° C. The DMF was removed under reduced pressure, and the residue was taken directly to the next step. MS ($CI/NH_3$) m/z 188/190 $(M+H)^+$, 205/207 $(M+NH_4)^+$. $^1H$ NMR ($CDCl_3$, 300 MHz) δ: 8.32 (d, J=1.8 Hz, 1H), 8.27 (d, J=2.6 Hz, 1H), 7.42 (dd, J=1.8, 2.6 Hz, 1H), 3.88 (s, 3H).

b. 5-bromo-3-hydroxypyridine

The compound from the previous step was heated at reflux with 60 mL of HBr for 16 hours. The reaction was quenched with excess NaHCO3, and the basic mixture was extracted with EtOAc, and the extract was dried over Na2SO4. The solvent was removed, and the residue was chromatographed on silica gel, eluting with 10% MeOH in $CHCl_3$. MS ($CI/NH_3$) m/z 174/176 $(M+H)^+$, 191/193 $(M+NH_4)^+$. $^1H$ NMR ($CDCl_3$, 300 MHz) δ: 8.27 (d, J=1.8 Hz, 1H), 8.23 (d, J=2.6 Hz, 1H), 7.44 (dd, J=1.8, 2.6 Hz, 1H).

c. 5-bromo-3-(1-BOC-2-(S)-pyrrolidinylmethoxy)pyridine

A 332 mg (1.2 mmol) sample of 1-BOC-2-(S)-pyrrolidinemethanol, prepared as described above, and 240 mg (1.38 mmol) of 5-bromo-3-hydroxypyridine, prepared as in step b above, were reacted with triphenylphosphine and DEAD (1.2 mmol each) in 5 mL of THF at room temperature for 16 hours, to give 355 mg of the title compound. MS ($CI/NH_3$) m/z 357/359 $(M+H)^+$, 374/376 $(M+NH_4)^+$. $^1H$ NMR ($CDCl_3$, 300 MHz) δ: 8.28 (d, J=1.8 Hz, 1H), 8.24 (d, J=2.6 Hz, 1H), 7.44 (dd, J=1.8, 2.6 Hz, 1H), 8.24 (d, J=2.6 Hz, 1H), 7.44 (dd, J=1.8, 2.6 Hz, 1H), 4.21-4.05 (m, 2H), 4.03-3.92 (m, 1H), 3.48-3.82 (m, 2H), 2.10-1.80 (m, 4H), 1.47 (s, 9H).

d. 5-bromo-3-(2-(S)-pyrrolidinylmethoxy)pyridine dihydrochloride

The BOC group was removed from the compound of step c by treatment with TFA in $CH_2Cl_2$ to give, following extracting from alkaline solution, the free base of the title compound. The base was converted to the salt by treatment with hydrogen chloride saturated EtOH. The solvents were removed under vacuum to give the title compound. mp 168–170° C. MS ($CI/NH_3$) m/z 257/259 $(M+H)^+$, 274/276 $(M+NH_4)^+$. $^1H$ NMR ($D_2O$, 300 MHz) δ: 8.39 (d, J=1.8 Hz, 1H), 8.32 (d, J=2.6 Hz, 1H), 7.90 (dd, J=1.8,2.6 Hz, 1H), 4.50 (dd, J=11, 3.6 Hz, 1H), 4.28 (dd, J=11, 7.7 Hz, 1H), 4.16-4.08 (m, 1H), 3.41 (t, J=7.2 Hz, 2H). Anal. Calc. for $C_{10}H_{14}N_2OBrCl·0.9$ HCl: C, 36.80; H, 4.60; N, 8.58; Found C, 36.93; H, 4.52; N, 8.58. $[α]^{25}D=+8.65°$ (c 1.04, MeOH).

5-bromo-3-(1-BOC-2-(R)-pyrrolidinylmethoxy) pyridine dihydrochloride

Following the procedures described above for the 5-bromo-3-(2-(S)-pyrrolidinylmethoxy)pyridine, except substituting the 1-BOC-2-(R)-pyrrolidine-methanol for the 1-BOC-2-(R)-pyrrolidinemethanol of step c above, the title compound was prepared. mp MS ($CI/NH_3$) m/z 257/259 $(M+H)^+$, 274/276 $(M+NH_4)^+$. $^1H$ NMR ($D_2O$, 300 MHz) δ: 8.28 (d, J=1.8 Hz, 1H), 8.24 (d, J=2.6 Hz, 1H), 7.44 (dd, J=1.8, 2.6 Hz, 1H), 8.24 (d, J=2.6 Hz, 1H), 7.44 (dd, J=1.8, 2.6 Hz, 1H), 4.21-4.05 (m, 2H), 4.03-3.92 (m, 1H), 3.48-3.82 (m, 2H), 2.10-1.80 (m, 4H), 1.47 (s, 9H).
Anal. Calc. for $C_{10}H_{14}N_2OBrCl·0.9$ HCl: C, 36.80; H, 4.60; N, 8.58; Found C, 36.93; H, 4.52; N, 8.58.

5-bromo-3-((1-methyl-2-(S)-pyrrolidinyl)methoxy) pyridine (S)-1-Methyl-2-pyrrolidinemethanol (4.96 g, 40.0 mmol) was carefully added to a suspension of sodium hydride (1.32 g, 80% yield, 44.0 mmol) in anhydrous DMF (100 mL). After stirring at room temperature for 0.5 hour, 3,5-dibromopyridine (4.83 g, 20.0 mmol) was added, and the reacting mixture was stirred at 50° C. for 4 hours. Another 5.0 mL of water was added, and the solvents were removed under reduced pressure. Again, water (5.0 mL) was added, and the slurry was washed extensively with EtOAc (4×40 mL). The combined organic layers were dried (Na$_2$SO$_4$) and concentrated. The crude product was purified by flash chromatography on silica gel eluting with CHCl$_3$/MeOH (10:1) to provide 4.50 g (83% yield) of the title compound. TLC R$_f$ 0.33 (10:1 CHCl3/MeOH). MS (CI/NH$_3$) m/z 271/ 273 (M+H)$^+$; $^1$H NMR (CDCl$_3$, 300 MHz) δ: 8.37 (d, J=1.8 Hz, 1H), 8.26 (d, J=2.7 Hz, 1H,), 7.39 (dd, J=1.8, 2.7 Hz, 1H), 4.01 (dd, J=3.3, 11.1 Hz, 1H), 3.93 (dd, J=6.9, 11.1 Hz, 1H), 3.20-3.10 (m, 1H), 2.76-2.64 (m, 1H), 2.49 (s, 3H), 2.40-2.28 (m, 1H), 2.44-2.00 (m, 4H).

5-bromo-3-((1-methyl-2-(R)-pyrrolidinyl)methoxy) pyridine (R)-1-methyl-2-pyrrolidinemethanol (430 mg, 13.74 mmol) was dissolved in 14 mL of DMF and stirred under N$_2$, then 123.4 mg of NaH (80% dispersion in mineral oil) was added. The reaction mixture was stirred fifteen minutes, and 897.4 mg of 3,5-dibromomethylpyridine was added. The reaction mixture was stirred at 50° C. for 16 hours. The volatiles were removed under vacuum, and the residue was purified by chromatography on silica gel to give 484 mg of the title product. MS (CI/NH$_3$) m/z 271/273 (M+H)$^+$. $^1$H NMR (CDCl$_3$, 300 MHz) δ: 8.37 (d, J=1.8, Hz, 1H), 8.26 (d, J=2.7 Hz, 1H), 7.39 (dd, J=1.8, 2.7 Hz, 1H), 4.01 (dd, J=3.3, 11.0 Hz, 1H), 3.93 (dd, J=6.9, 11.1, Hz, 1H), 3.20-3.10 (m, 1H), 3.93 (dd, J=6.9, 11.1 Hz, 1H), 3.20-3.10 (m, 1H), 2.76-2.64 (m, 1H), 2.49 (s, 3H), 2.40-2.28 (m, 1H), 2.44-2.00 (m, 4H).

Example 1

5(3-Nitrophenyl)-3-(1-methyl-2-(S)-pyrrolidinylmethoxy)pyridine dihydrochloride 1a. 5-(3-Nitrophenyl)-3-(1-methyl-2-(S)-pyrrolidinylmethoxy)pyridine To a solution of 5-bromo-3-((1-methyl-2-(S)-pyrrolidinyl)methoxy)pyridine (272 mg, 1.00 mmol) in benzene (2.0 mL), were added sodium carbonate (2.0M, 1.0 mL), tetrakis(triphenylphosphine)palladium(0) (35 mg, 0.03 mmol) and 3-nitrophenylboronic acid (250 mg, 1.50 mmol). The reaction mixture was refluxed overnight then cooled to room temperature. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with NH$_4$OH/MeOH/EtOAc 0:1:9 and 1:10:90 to afford a light yellowish oil (187 mg, 60%). MS (CI/NH$_3$) m/z 314 (M+H)$^+$. $^1$H NMR (CDCl$_3$, 300 MHz) δ 1.72-1.97 (m, 3H), 2.03-2.14 (m, 1H), 2.30-2.47 (m, 1H), 2.53 (s, 3H), 2.67-2.80 (m, 1H), 3.12-3.22 (m, 1H), 4.00-4.15 (m, 2H), 7.43-7.46 (m, 1H), 7.63-7.70 (m, 1H), 7.88-7.94 (m, 1H), 8.25-8.31 (m, 1H), 8.38-8.51 (m, 3H).

1b. 5-(3-Nitrophenyl)-2-(1-methyl-2-S-pyrrolidinylmethoxy)pyridine dihydrochloride To a solution of 5-(3-nitrophenyl)-3-(1-methyl-2-(S)-pyrrolidinylmethoxy)-pyridine from step 1a (181 mg, 0.58 mmol) in THF (3.0 mL) was added hydrogen chloride (1.0M in Et$_2$O, 1.27 mL, 1.27 mmol). A precipitate formed which was filtered, washed (Et$_2$O) and vacuum-dried to afford the hydrochloride salt (202 mg, 95%). MS (CI/NH$_3$) m/z 314 (M+H)$^+$. $^1$H NMR (D$_2$O, 300 MHz) δ 2.07-2.51 (m, 4H), 3.08 (s, 3H), 3.22-3.38 (m, 1H), 3.73-3.86 (m, 1H), 3.91-4.04 (m, 1H), 4.40-4.47 (m, 1H), 4.55-4.64 (m, 1H), 7.72-7.81 (m, 2H), 8.06-8.11 (m, 1H), 8.39 (m, 2H), 8.49-8.57 (m, 2H). Anal. Calcd for C$_{17}$H19N$_3$O$_3$: C, 52.86; H, 5.48; N, 10.88. Found: C, 52.94; H, 5.53; N, 10.62. [α]$^{25}$D=3.4° (c 1.00, MeOH).

Example 2

5-(1-Naphthalenyl)-3(1-methyl-2-(S)-pyrrolidinylmethoxy)pyridine dihydrochloride 2a. 5-(1-Naphthalenyl)-3-(1-methyl-2-(S)-pyrrolidinylmethoxy)pyridine To a solution of 5-bromo-3-(1-methyl-2-(S)-pyrrolidinylmethoxy)-pyridine (272 mg, 1.00 mmol) in benzene (2.0 mL) were added aqueous sodium carbonate (2.0M, 1.0 mL), tetrakis(triphenylphosphine)palladium(0) (35 mg, 0.03 mmol) and 1-naphthaleneboronic acid (189 mg, 1.10 mmol). The reaction mixture was refluxed overnight, then cooled to room temperature. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with NH$_4$OH/MeOH/EtOAc 0:1:9 and 1:10:90 to afford a light yellowish oil (196 mg, 62%). MS (CI/NH$_3$) m/z 319 (M+H)$^+$. $^1$H NMR (CDCl$_3$, 300 MHz) δ 1.71-1.92 (m, 3H), 2.00-2.10 (m, 1H), 2.27-2.38 (m, 1H), 2.51 (s, 3H), 2.66-2.75 (m, 1H), 3.09-3.17 (m, 1H), 3.98-4.14 (m, 2H), 7.34-7.57 (m, 5H), 7.72-7.96 (m, 3H),8.36-8.43 (m, 1H).

2b. 5-(1-Naphthalenyl)-3-(1-methyl-2-(S)-pyrrolidinylmethoxy)pyridine dihydrochloride To a solution of 5-(1-naphthalenyl)-3-(1-methyl-2-(S)-pyrrolidinylmethoxy)-pyridine from step 2a (190 mg, 0.60 mmol) in THF (3.0 mL) was added hydrogen chloride (1.0M in Et$_2$O, 1.32 mL, 1.32 mmol). A precipitate formed which was filtered, washed (Et$_2$O) and vacuum-dried to afford the hydrochloride salt (183 mg, 78%). MS (CI/NH$_3$) m/z 319 (M+H)$^+$. $^1$H NMR (D$_2$O, 300 MHz) δ 2.04-2.46 (m, 4H), 3.06 (s, 3H), 3.21-3.36 (m, 1H), 3.72-3.84 (m, 1H), 3.88-4.00 (m, 1H), 4.36-4.44 (m, 1H), 4.51-4.57 (m, 1H), 7.51-7.71 (m, 5H), 7.83-7.87 (m, 1H), 8.05-8.11 (,2H), 8.33-8.43 (m, 2H). Anal. Calcd for C$_{21}$H$_{22}$N$_2$O·2.6 HCl: C, 61.04; H, 6.00; N, 6.78. Found: C, 60.94; H, 5.86; N, 7.03. [α]$^{25}$D= 3.2° (c 1.08, MeOH).

Example 3

5-(4-Methoxyphenyl)-3-(1-methyl-2-(S)-pyrrolidinylmethoxy)pyridine dihydrochloride 3a. 5-(4-Methoxyphenyl)-3-(1-methyl-2-(S)-pyrrolidinylmethoxy)pyridine To s solution of 5-bromo-3-(1-methyl-2-(S)-pyrrolidinylmethoxy)-pyridine (272 mg, 1.00 mmol) in benzene (2.0 mL) were added sodium carbonate (2.0M, 1.0 mL), tetrakis(triphenylphosphine)palladium(0) (35 mg, 0.03 mmol) and 4-methoxyphenylboronic acid (228 mg, 1.30 mmol). The reaction mixture was refluxed overnight, then cooled to room temperature. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with NH$_4$OH/MeOH/EtOAc 0:1:9 and 1:10:90 to afford a light yellowish oil (174 mg, 58%). MS (CI/NH$_3$) m/z 299 (M+H)$^+$. $^1$H NMR (CDCl$_3$, 300 MHz) δ 1.71-1.92 (m, 3H), 1.99-2.10 (m, 1H), 2.51 (s, 3H), 2.65-2.74 (m, 1H), 3.09-3.17 (m, 1H), 3.87 (s, 3H), 3.96-4.11 (m, 2H), 7.00 (d, J=8.8 Hz, 1H), 7.36 (t, J=3.0 Hz, J=2.1 Hz, 1H), 7.52 (d, J=8.8 Hz, 1H), 8.27 (d, J=3.0 Hz, 1H), 8.42 (d, J=2.1 Hz, 1H).

3b. 5-(4-Methoxyphenyl)-3-(1-methyl-2-(S)-pyrrolidinylmethoxy)pyridine dihydrochloride To s solution of 5-(4-methoxyphenyl)-3-(1-methyl-2-(S)-pyrrolidinylmethoxy)-pyridine from step 3a (165 mg, 0.55 mmol) in THF (3.0 mL) was added hydrogen chloride (1.0M in Et$_2$O, 1.22 mL, 1.22 mmol). A precipitate formed which was filtered, washed (Et$_2$O) and vacuum-dried to afford the hydrochloride salt (154 mg, 75%). MS (CI/NH$_3$) m/z 299 (M+H)$^+$. $^1$H NMR (D$_2$O, 300 MHz) δ 2.05-2.48 (m, 4H), 3.06 (s, 3H), 3.21-3.34 (m, 1H), 3.72-3.85 (m, 1H), 3.91 (s, 3H), 3.88-4.01 (m, 1H), 4.36-4.43 (m, 1H), 4.50-4.58 (m, 1H), 7.13 (d, J=8.8 Hz, 1H), 7.66 (d, J=8.8 Hz, 1H), 7.68 (s, 1H), 8.24 (s, 1H), 8.45 (s, 1H). Anal. Calcd for C$_{18}$H$_{22}$N$_2$O$_2$·2.2 HCl·0.8 H$_2$O: C, 55.01; H, 6.62; N, 7.13. Found: C, 54.91; H, 6.62; N, 7.05. [α]$^{25}$D=3.1° (c 1.09, MeOH).

Example 4

5-Hexynyl-3-(1-methyl-2-(S)-pyrrolidinylmethoxy) pyridine dihydrochloride 4a. 5-Hexynyl-3-(1-methyl-2-(S)-pyrrolidinylmethoxy) pyridine To a solution of 5-bromo-3-(1-methyl-2-(S)-pyrrolidinylmethoxy)-pyridine (272 mg, 1.00 mmol), bis(triphenylphosphine)palladium(II) chloride (18 mg, 0.025 mmol) and copper (I) iodide (2 mg, 0.025 mmol) in NEt$_3$ (6.0 mL) was added 1-hexyne (0.237 mL, 2.00 mmol). The mixture was refluxed overnight and cooled to room temperature. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with NH$_4$OH/MeOH/EtOAc 0:1:9 and 1:10:90 to afford an oil (174 mg, 64%). MS (CI/NH$_3$) m/z 273 (M+H(+. $^1$H NMR (CDCl$_3$, 300 MHz) δ 0.96 (t, J=7.0 Hz, 3H), 1.42-2.10 (m, 8H), 2.26-2.37 (m, 1H), 2.43 (t, J=7.0 Hz, 2H), 2.48 (s, 3H), 2.63-2.71 (m, 1H), 3.08-3.16 (m, 1H), 3.88-4.03 (m, 2H), 4.47-4.55 (m, 1H), 7.17-7.21 (m, 1H), 8.19-8.23 (m, 2H).

4b. 5-Hexynyl-3-(1-methyl-2-(S)-pyrrolidinylmethoxy) pyridine dihydrochloride

To a solution of 5-hexynyl-3-(1-methyl-2-(S)-pyrrolidinylmethoxy)-pyridine from step 4a (70 mg, 0.26 mmol) in THF (3.0 mL) was added hydrogen chloride (1.0M in Et$_2$O, 0.56 mL, 0.56 mmol). The precipitate formed was filtered, washed (Et$_2$O) and vacuum-dried to afford the hydrochloride salt (69 mg, 75%). MS (CI/NH$_3$) m/z 273 (M+H)$^+$. $^1$H NMR (D$_2$O, 300 MHz) δ 0.93 (t, J=7.0 Hz, 3H), 1.43-1.68 (m, 4H), 2.02-2.31 (m, 3H), 2.34-2.47 (m, 1H), 2.48 (t, J=7.0 Hz, 2H), 3.03 (s, 3H), 3.20-3.33 (m, 1H), 3.70-3.84 (m, 1H), 3.86-4.00 (m, 1H), 4.30-4.38 (m, 1H), 4.47-4.55 (m, 1H), 7.48-7.53 (m, 1H), 8.22-8.28 (m, 2H). Anal. Calcd for C$_{17}$H$_{24}$N$_2$O·2.1 HCl·0.2 H20: C, 57.92; H, 7.58; N, 7.97. Found: C, 57.81; H, 7.59; N, 8.11. [α]$^{25}$D= 1.7° (c 0.35, MeOH).

Example 5

5-(2-Furanyl)-3-(1-methyl-2-(S)-pyrrolidinylmethoxy)pyridine dihydrochloride 5a. 5-(2-Furanyl)-3-(1-methyl-2-(S)-pyrrolidinylmethoxy) pyridine To a solution of furan (1.45 mL, 20.0 mmol) in THF (30.0 mL) was added sec-butyllithium (1.3M, 7.69 mL, 10.0 mmol) at −78° C. After half an hour at this temperature, trimethyl borate (2.27 mL, 20.0 mmol) was added. The reaction mixture was stirred at −78° C. for one hour and slowly warmed up to room temperature. Solvent was removed, and benzene (10.0 mL), sodium carbonate (2.0M, 5.0 mL), tetraids(triphenylphosphine)palladium(0) (175 mg) and 5-bromo-3-(1- methyl-2-(S)-pyrrolidinylmethoxy) pyridine (1.36 g, 5.0 mmol) were added. The reaction mixture was refluxed overnight, then cooled to room temperature. Water (2 mL) was added, and solid sodium bicarbonate was added until the aqueous layer was saturated. The mixture was extracted with EtOAc, which was dried over MgS04, filtered and concentrated. The residue was chromatographed on a silica gel column, eluting with NH$_4$OH/MeOH/EtOAc 0:1:9 and 1:10:90 to afford an oil (1.27 g, 99%). MS (CI/NH$_3$) m/z 259 (M+H)$^+$. $^1$H NMR (CDCl$_3$, 300 MHz) δ 1.70-2.22 (m, 4H), 2.28-2.40 (m, 1H), 2.51 (s, 3H), 2.66-2.75 (m, 1H), 3.10-3.18 (m, 1H), 3.97-4.11 (m, 2H), 6.51 (dd, J=4.8 Hz, J=3.6 Hz, 1H), 6.74 (d, J=4.9 Hz,, 1H), 7.47 (dd, J=3.0 Hz, J=2.1 Hz, 1H), 7.53 (d, J=3.6 Hz, 1H), 8.22 (d, J=3.0 Hz, 1H), 8.54 (d, J=2.1 Hz, 1H).

5b. 5-(2-Furanyl)-3-(1-methyl-2-pyrrolidinylmethoxy) pyridine dihydrochloride

To a solution of 5-(2-furanyl)-3-(1-methyl-2-(S)-pyrrolidinylmethoxy)-pyridine from step 5a (240 mg, 0.93 mmol) in THF (3.0 mL) was added hydrogen chloride (1.0M in Et$_2$O, 2.14 mL, 2.14 mmol). A precipitate formed which was filtered, washed (Et$_2$O) and vacuum-dried to afford the hydrochloride salt (278 mg, 20 90%). mp. 189–191° C. MS (CI/NH$_3$) m/z 259 (M+H)$^+$. $^1$H NMR (D$_2$O, 300 MHz) δ 2.08-2.23 (m, 3H), 2.35-2.47 (m, 1H), 3.05 (s, 3H), 3.21-3.32 (m, 1H), 3.74-3.86 (m, 1H), 3.90-4.02 (m, 1H), 4.37-4.44 (m, 1H), 4.55-4.63 (m, 1H), 6.64-6.68 (m, 1H), 6.97-7.01 (m, 1H), 7.68-7.71 (m, 1H), 7.77 (s, 1H), 8.21 (s, 1H), 8.58 (s, 1H). Anal. Calcd for C$_{15}$H$_{18}$N$_2$O$_2$·2.0 HCl·0.1 H$_2$O: C, 54.10; H, 6.11; N, 8.41. Found: C, 54.13; H, 5.92; N, 8.44. [α]$^{25}$D=6.7° (c 1.00, MeOH).

Example 6

5-(2-Thienyl)-3-(1-methyl-2-(S)-pyrrolidinylmethoxy)pyridine dihydrochloride 6a.5-(2-Thienyl)-3-(1-methyl-2-(S)-pyrrolidinylmethoxy) pyridine dihydrochloride To a solution of 5-bromo-3-(1-methyl-2-(S)-pyrrolidinylmethoxy)-pyridine (272 mg, 1.00 mmol) in benzene (2.0 mL), sodium carbonate (2.0M, 1.0 mL), tetrakis(triphenylphosphine)palladium(0) (35 mg, 0.03 mmol) and 2-thienylboronic acid (166 mg, 1.30 mmol) were added and the reaction mixture was refluxed overnight, and then cooled to room temperature. Water (2 mL) was added, and solid sodium bicarbonate was added until the aqueous layer was saturated. The mixture was extracted with EtOAc, which was dried over MgSO$_4$, filtered and concentrated. The residue was chromatographed on a silica gel column, eluting with NH$_4$OH/MeOH/EtOAc 0:1:9 and 1:10:90 to afford a light yellowish oil (171 mg, 62%). MS (CI/NH$_3$) m/z 275 (M+H)$^+$. $^1$H NMR (CDCl$_3$, 300 MHz) δ 1.75-1.97 (m, 3H), 2.02-2.15 (m, 1H), 2.30-2.50 (m, 1H), 2.57 (s, 3H), 2.67-2.86 (m, 1H), 3.13-3.28 (m, 1H), 3.98-4.12 (m, 2H), 7.12 (t, J=7.3 Hz, 1H), 7.37 (d, J=7.3 Hz, 2H), 7.39 (dd, J=3.0 Hz, J=2.1 Hz, 1H), 8.23 (d, J=3.0 Hz, 1H), 8.51 (d, J=2.1 Hz, 1H).

6b. 5-(2- Thienyl-3-(1-methyl-2-(S)-pyrrolidinylmethoxy) pyridine dihydrochloride To a solution of 5-(2-thienyl)-3-(1-methyl-2-(S)-pyrrolidinylmethoxy)-pyridine from step 6a (165 mg, 0.60 mmol) in THF (3.0 mL) was added hydrogen chloride (1.0M in Et$_2$O, 1.64 mL, 1.64 mmol). A precipitate formed which was filtered, washed (Et$_2$O) and vacuum-dried to afford the hydrochloride salt (177 mg, 73%). mp. 201–203° C. MS (CI/NH$_3$) m/z 275 (M+H)$^+$. $^1$H NMR (D$_2$O, 300 MHz) δ 2.07-2.24 (m, 3H), 2.32-2.46 (m, 1H), 3.07 (s, 3H), 3.18-3.31 (m, 1H), 3.73-3.84 (m, 1H), 3.90-4.01 (m, 1H), 4.5-4.45 (m, 1H), 4.52-4.61 (m, 1H), 7.22-7.25 (m, 1H), 7.55-7.60 (m, 2H), 7.72 (s, 1H), 8.23 (s, 1H), 8.54 (s, 1H). Anal. Calcd for C$_{16}$H$_{19}$N$_3$O·3.0 HCl·0.2 H$_2$O: C, 50.26; H, 5.91; N, 10.99. Found: C, 50.33; H, 5.97; N, 10.61. [α]$^{25}$D=6.1° (c 0.75, MeOH).

Example 7

5-(3-Pyridyl)-3-(1-methyl-2-(S)-pyrrolidinylmethoxy)pyridine dihydrochloride 7a. 5-(3-Pyridyl)-3-1-methyl-2-(S)-pyrrolidinylmethoxy) pyridine To a solution of 5-bromo-3-(1-methyl-2-(S)-pyrrolidinylmethoxy)-pyridine (272 mg, 1.0 mmol) in toluene (10.0 mL) was added 3-pyridinyltributyltin (442 mg, 1.2 mmol) and tetrakis(triphenylphosphine)palladium(0) (35 mg, 0.03 mmol). After being refluxed overnight, the resulting mixture was cooled to room temperature. Solvent was removed, and the residue was chromatographed on a silica gel column, eluting with NH$_{40}$H/MeOH/EtOAc 0:1:9 and 1:10:90 to afford an oil (127 mg, 48%). MS (CI/NH$_3$) m/z 270 (M+H)$^+$. $^1$H NMR (CDCl$_3$, 300 MHz) δ 1.70-1.93 (m, 3H), 2.00-2.12 (m, 1H), 2.28-2.39 (m, 1H), 2.52 (s, 3H), 2.67-2.76 (m, 1H), 3.11-3.18 (m, 1H), 3.98-4.13 (m, 2H), 7.38-7.44 (m, 2H), 7.86-7.92 (m, 1H), 8.37 (d, J=3.0 Hz, 1H), 8.46 (d, J=2.1 Hz, 1H), 8.67 (dd, J=6.0 Hz, J=1.8 Hz, 1H), 8.84 (d, J=2.1 Hz, 1H).

7b. 5-(3-Pyridinyl)-3-(1-methyl-2-(S)-pyrrolidinylmethoxy) pyridine dihydrochloride To a solution of 5-(3-pyridinyl)-3-(1-methyl-2-(S)-pyrrolidinylmethoxy)pyridine from step 7a (125 mg, 0.47 mmol) in THF (3.0 mL) was added hydrogen chloride (1.0M in Et$_2$O, 1.64 mL, 1.64 mmol). A precipitate formed which was filtered, washed (Et$_2$O) and vacuum-dried to afford the hydrochloride salt (130 mg, 73%). mp. 155–160° C. MS (CI/NH$_3$) m/z 270 (M+H)$^+$. $^1$H NMR (D$_2$O, 300 MHz) δ 2.08-2.25 (m, 3H), 2.32-2.44 (m, 1H), 3.08 (s, 3H), 3.17-3.28 (m, 1H), 3.71-3.82 (m, 1H), 3.90-4.03 (m, 1H), 4.38-4.47 (m, 1H), 4.55-4.66 (m, 1H), 7.64-7.71 (m, 1H), 7.79 (s, 1H), 8.23-8.26 (m, 1H), 8.38 (s, 1H), 8.53 (s, 1H), 8.58-8.65 (m, 1H), 8.84 (s, 1H). Anal. Calcd for C$_{16}$H$_{19}$N$_3$O·3.0 HCl·0.2 H$_2$O: C, 50.26; H, 5.91; N, 10.99. Found: C, 50.33; H, 5.97; N, 10.61. [α]$^{25}$D=6.1° (c 0.75, MeOH).

Example 8

5-Ethenyl-3-(1-methyl-2-(S)-pyrrolidinylmethoxy) pyridine dihydrochloride 8a. 5-Ethenyl-3-(1-methyl-2-(S)-pyrrolidinylmethoxy) pyridine dihydrochloride To a solution of 5-bromo-3-(1-methyl-2-(S)-pyrrolidinylmethoxy)-pyridine (272 mg, 1.0 mmol) in toluene (10.0 mL) was added vinyltributyltin (362 mL, 1.2 mmol) and tetrakis(triphenylphosphine)palladium(0) (35 mg, 0.03 mmol). After being refluxed overnight, the resulting mixture was cooled to room temperature. Solvent was removed and the residue was chromatographed on a silica gel column, eluting with NH$_4$OH/MeOH/EtOAc 0:1:9 and 1:10:90 to afford an oil (165 mg, 76%). MS (CI/NH$_3$) m/z 219 (M+H)$^+$. $^1$H NMR (CDCl$_3$, 300 MHz) δ 1.65-1.95 (m, 3H), 1.97-2.11 (m, 1H), 2.25-2.40 (m, 1H), 2.50 (s, 3H), 2.63-2.74 (m, 1H), 3.08-3.18 (m, 1H), 3.92-4.00 (m, 1H), 4.01-4.09 (m, 1H), 5.38 (d, J=11.4 Hz, 1H), 5.81 (d, J=17.6 Hz, 1H), 6.68 (dd, (d, J=11.4 Hz, J=17.6 Hz, 1H), 7.26 (dd, J=3.0 Hz, 1H), 8.21 (d, J=3.0 Hz, J=2.1 Hz, 1H), 8.22 (d, J=2.1 Hz, 1H).

8b. 5-Ethenyl-3-(1-methyl-2-(S)-pyrrolidinylmethoxy) pyridine dihydrochloride

To a solution of 5-ethenyl-3-(1-methyl-2-(S)-pyrrolidinylmethoxy)pyridine from step 8a (160 mg, 0.73 mmol) in THF (3.0 mL) was added hydrogen chloride (1.0M in Et$_2$O, 1.67 mL, 1.67 mmol). The precipitate formed was filtered, washed (Et$_2$O) and vacuum-dried to afford the hydrochloride salt (213 mg, 100%). mp. 152–156° C. MS (CI/NH$_3$) m/z 219 (M+H)$^+$. $^1$H NMR (D$_2$O, 300 MHz) δ 2.02-2.27 (m, 3H), 2.33-2.44 (m, 1H), 3.05 (s, 3H), 3.20-3.32 (m, 1H), 3.72-3.82 (m, 1H), 3.90-4.00 (m, 1H), 4.37-4.44 (m, 1H), 4.54-4.63 (m, 1H), 5.57 (d, J=11.4 Hz, 1H), 6.03 (d, J=17.6 Hz, 1H), 6.82 (dd, (d, J=11.4 Hz, J=17.6 Hz, 1H), 7.78 (s, 1H), 8.27 7.78 (s, 1H), 8.36 7.78 (s, 1H). Anal. Calcd for C$_{13}$H$_{18}$N$_2$O·2.2 HCl: C, 52.31; H, 6.82; N, 9.38. Found: C, 52.35; H, 6.76; N, 9.14. [α]$^{25}$D=-7.8° (c 1.00, MeOH).

Example 9

5-(1-Decynyl)-3-(1-methyl-2-(S)-pyrrolidinylmethoxy)pyridine dihydrochloride 9a. 5-(1-Decynyl)-3-(1-methyl-2-(S)-pyrrolidinylmethoxy) pyridine To a solution of 5-bromo-3-(1-methyl-2-(S)-pyrrolidinylmethoxy)-pyridine (544 mg, 2.00 mmol), bis (triphenylphosphine)palladium(II) chloride (28 mg, 0.038 mmol) and copper (I) iodide (5 mg, 0.038 mmol) in CH$_2$Cl$_2$ (3.0 mL) and NEt$_3$ (1.0 mL) was added 1-decyne (0.553 mL, 3.00 mmol). The mixture was refluxed overnight then cooled to room temperature. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with NH$_4$OH/MeOH/EtOAc 0:1:9 and 1:10:90 to afford an oil (543 mg, 85%). MS (CI/NH$_3$) m/z 329 (M+H)$^+$. $^1$H NMR (CDCl$_3$, 300 MHz) δ 0.90 (t, J=6.9 Hz, 3H), 1.23-2.10 (m, 14H), 2.25-2.41 (m, 1H), 2.41 (t, J=7.3 Hz, 2H), 2.50 (s, 3H), 2.60-2.75 (m, 1H), 3.08-3.21 (m, 1H),, 3.89-4.06 (m, 2H), 7.19 (s, 1H), 8.15-8.28 (m, 2H).

9b. 5-(1-Decynyl)-3-(1-methyl-2-(S)-pyrrolidinylmethoxy) pyridine dihydrochloride To a solution of 5-(1-decynyl)-3-(1-methyl-2-(S)-pyrrolidinylmethoxy)pyridine from step 9a (180 mg, 0.55 mmol) in THF (3.0 mL) was added hydrogen chloride (1.0M in Et$_2$O, 1.26 mL, 1.26 mmol). A precipitate formed which was filtered, washed (Et$_2$O) and vacuum-dried to afford the hydrochloride salt (163 mg, 74%). mp. 102–105° C. MS (CI/NH$_3$) m/z 329 (M+H)$^+$. $^1$H NMR (D$_2$O, 300 MHz) δ 0.95 (m, 3H), 1.33-1.70 (m, 11H), 1.92-2.28 (m, 2H), 2.36-2.46 (m, 2H), 3.034 (s, 3H), 3.20-3.33 (m, 1H), 3.70-3.93 (m, 2H), 4.30-4.55 (m, 2H), 7.32 (s, 1H), 8.00-8.20 (m, 2H). Anal. Calcd for C$_{21}$H$_{32}$N$_2$O·2.0 HCl·0.1 H$_2$O: C, 62.55; H, 8.55; N, 6.95. Found: C, 62.57; H, 8.67; N, 6.97. [α]$^{25}$D=-5.9° (c 1.28, MeOH).

Example 10

5-Acetyl-3-(1-methyl-2-(S)-pyrrolidinylmethoxy)pyridine dihydrochloride 10a. 5-(1-Ethoxyvinyl)-3-(1-methyl-2-(S)-pyrrolidinylmethoxy)pyridine dihydrochloride To a solution of 5-bromo-3-(1-methyl-2-(S)-pyrrolidinylmethoxy)-pyridine (272 mg, 1.0 mmol) in toluene (10.0 mL) was added (l-ethoxyvinyl)tributyltin (366 mL, 7.5 mmol) and tetrakis(triphenylphosphine)palladium (0) (35 mg). After being refluxed overnight, the resulting mixture was cooled to room temperature. Solvent was removed and the residue was chromatographed on a silica gel column, eluting with $NH_4OH/MeOH/EtOAc$ 0:1:9 and 1:10:90 to afford an oil (237 mg, 91%). MS ($CI/NH_3$) m/z 263 $(M+H)^+$. $^1H$ NMR ($CDCl_3$, 300 MHz) δ 1.43 (t, J=7.2 Hz, 3H), 1.71-1.93 (m, 3H), 1.98-2.11 (m, 1H), 2.50 (s, 3H), 2.63-2.73 (m, 1H), 3.08-3.17 (m, 1H), 3.93 (q, J=7.2 Hz, 2H), 3.93-3.99 (m, 1H), 4.02-4.08 (m, 1H), 4.28 (d, J=3.6 Hz, 1H), 4.69 (d, J=3.6 Hz, 1H), 7.43 (dd, J=3.0 Hz, J=2.1 Hz, 1H), 8.26 (d, J=3.0 Hz, 1H), 8.48 (d, J=2.1 Hz, 1H).

10b. 5-Acetyl-3-(1-methyl-2-(S)-pyrrolidinylmethoxy)pyridine dihydrochloride

To a solution of 5-(1-ethoxyvinyl)-3-(1-methyl-2-(S)-pyrrolidinylmethoxy)-pyridine (100 mg, 0.38 mmol) in MeOH (2.0 mL) was added hydrogen chloride (4.0M in 1,4-dioxane, 2.0 mL). A precipitate formed which was filtered, washed ($Et_2O$) and vacuum-dried to afford the hydrochloride salt (117 mg, 100%). MS ($CI/NH_3$) m/z 235 $(M+H)^+$. $^1H$ NMR ($D_2O$, 300 MHz) 6 2.04-2.47 (m, 4H), 2.68 (s, 3H), 3.05 (s, 3H), 3.22-3.32 (m, 1H), 3.73-4.01 (m, 2H), 4.37-4.46 (m, 1H), 4.55-4.63 (m, 1H), 7.93 (dd, J=3.0 Hz, J=2.1 Hz, 1H), 8.53 (d, J=3.0 Hz, 1H), 8.81 (d, J=2.1 Hz, 1H). Anal. Calcd for $C_{13}H_{20}N_2O_2·2.1$ HCl·0.3 $H_2O$: C, 49.37; H, 6.60; N, 8.86. Found: C, 49.46; H, 6.56; N, 8.61. $[α]^{25}D=7.0°$ (c 0.70, MeOH).

Example 11

5-(4-Fluorophenyl)-3-(1-methyl-2-(S)-pyrrolidinylmethoxy)pyridine dihydrochloride 11a. 5-(4-Fluorophenyl)-3-(1-methyl-2-(S)-pyrrolidinylmethoxy)pyridine To a solution of 5-bromo-3-(1-methyl-2-(S)-pyrrolidinylmethoxy)-pyridine (272 mg, 1.00 mmol) in benzene (2.0 mL) were added sodium carbonate (2.0M, 1.0 mL), tetrakis(triphenylphosphine)palladium(0) (35 mg, 0.03 mmol) and 4-fluorophenylboronic acid (210 mg, 1.50 mmol). The reaction mixture was refluxed overnight, then cooled to room temperature. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with $NH_4OH/MeOH/EtOAc$ 0:1:9 and 1:10:90 to afford a light yellowish oil (233 mg, 81%). MS ($CI/NH_3$) m/z 287 $(M+H)^+$. $^1H$ NMR ($CDCl_3$, 300 MHz) δ 1.75-2.15 (m, 4H), 2.31-2.48 (m, 1H), 2.57 (s, 3H), 2.70-2.75 (m, 1H), 3.14-3.28 (m, 1H), 3.99-4.25 (m, 2H), 7.13-7.21 (m, 2H), 7.37 (dd, J=3.0 Hz, J=2.1 Hz, 1H), 7.50-7.58 (m, 2H), 8.31 (d, J=3.0 Hz, 1H), 8.42 (d, J=2.1 Hz, 1H).

11b. 5-(4-Fluorophenyl)-3-(1-methyl-2-(S)-pyrrolidinylmethoxy)pyridine dihydrochloride To a solution of 5-(4-fluorophenyl)-3-(1-methyl-2-(S)-pyrrolidinylmethoxy)-pyridine from step 11a (230 mg, 0.80 mmol) in THF (5.0 mL) was added hydrogen chloride (1.0M in $Et_2O$, 1.85 mL, 1.85 mmol). A precipitate formed which was filtered, washed ($Et_2O$) and vacuum-dried to afford the hydrochloride salt (249 mg, 86%). MS ($CI/NH_3$) m/z 287 $(M+H)^+$. $^1H$ NMR ($D_2O$, 300 MHz) δ 2.08-2.28 (m, 3H), 2.32-2.47 (m, 1H), 3.06 (s, 3H), 3.18-3.30 (m, 1H), 3.72-3.84 (m, 1H), 3.90-4.04 (m, 1H), 4.36-4.46 (m, 1H), 4.55-4.65 (m, 1H), 7.26-7.35 (m, 2H), 7.68-7.74 (m, 3H), 8.31 (d, J=3.0 Hz, 1H), 8.48 (d, J=1.8 Hz, 1H). Anal. Calcd for $C_{17}H_{19}N_2OF·2.0$ HCl: C, 56.83; H, 5.89; N, 7.80. Found: C, 56.63; H, 5.85; N, 7.66. $[α]^{25}D=5.6°$ (c 1.40, MeOH).

Example 12

5-Hexenyl-3-(1-methyl-2-(S)-pyrrolidinylmethoxy)pyridine dihydrochloride 12a. 5-Hexenyl-3-(1-methyl-2-(S)-pyrrolidinylmethoxy)pyridine To a solution of 5-(1-hexynyl)-3-(1-methyl-2-(S)-pyrrolidinylmethoxy)-pyridine (from Example 4a, 100 mg, 0.37 mmol) in MeOH (3.0 mL) was added Lindlar's catalyst (10 mg). The mixture was stirred at room temperature overnight. The solvent was removed, and the residue was chromatographed on a silica gel column, eluting with $NH_4OH/MeOH/EtOAc$ 0:1:9 and 1:10:90 to afford a light yellowish oil (98 mg, 98%). MS ($CI/NH_3$) m/z 277 $(M+H)^+$. $^1H$ NMR ($CDCl_3$, 300 MHz) δ 0.88 (t, J=4.8 Hz, 3H), 1.23-1.37 (m, 6 H), 1.53-1.62 (m, 2H), 1.70-2.08 (m, 4H), 2.26-2.36 (m, 1H), 2.48 (s, 3H), 2.56 (t, J=7.7 Hz, 2H), 2.58-2.71 (m, 1H), 3.07-3.14 (m, 1H), 3.88-4.05 (m, 2H), 7.03 (dd, J=3.0 Hz, J=J=2.1 Hz, 1H), 8.06 (d, J=2.1 Hz, 1H), 8.13 (d, J=3.0 Hz, 1H).

12b. 5-Hexenyl-3-(1-methyl-2-(S)-pyrrolidinylmethoxy)pyridine dihydrochloride

To a solution of 5-hexenyl-3-(1-methyl-2-(S)-pyrrolidinylmethoxy)pyridine from step 12a (92 mg, 0.34 mmol) in THF (3.0 mL) was added hydrogen chloride (1.0M in $Et_2O$, 0.77 mL, 0.77 mmol). A precipitate formed which was filtered, washed ($Et_2O$) and vacuum-dried to afford the hydrochloride salt (113 mg, 84%). MS ($CI/NH_3$) m/z 277 $(M+H)^+$. $^1H$ NMR ($D_2O$, 300 MHz) δ 0.85 (t, J=4.8 Hz, 3H), 1.24-1.33 (m, 6 H), 1.60-1.70 (m, 2H), 2.03-2.44 (m, 4H), 2.72 (t, J=7.7 Hz, 2H), 3.04 (s, 3H), 3.15-3.30 (m, 1H), 3.72-3.86 (m, 1H), 3.88-4.00 (m, 1H), 4.34-4.43 (m, 1H), 4.52-4.58 (m, 1H), 7.61 (s, 1H), 8.17 (s, 1H), 8.22 (s, 1H). Anal. Calcd for $C_{17}H_{28}N_2O·2.0$ HCl·0.7 $H_2O$: C, 56.41; H, 8.74; N, 7.74. Found: C, 56.41; H, 8.77; N, 7.76. $[α]^{25}D=3.6°$ (c 1.05, MeOH).

Example 13

5-(2-(4-Pyridinyl)ethenyl)-3-(1-methyl-2-(S)-pyrrolidinylmethoxy)pyridine trihydrochloride 13a. 5-(2-(4-Pyridinyl)ethenyl)-3-(1-methyl-2-(S)-pyrrolidinylmethoxy)pyridine To a solution of 5-bromo-3-(1-methyl-2-(S)-pyrrolidinylmethoxy)pyridine (272.0 mg, 1.0 mmol) in acetonitrile (3.0 mL) and triethylamine (2.5 mL) was added 4-vinylpyridine (0.227.0 mL, 2.0 mmol), palladium acetate (23.0 mg, 0.1 mmol) and tri-o-tolylphosphine (122.0 mg). After being heated in a sealed tube at 100° C. overnight, the reaction mixture was cooled to room temperature. A minimum amount of saturated sodium bicarbonate was added to free the amine, and the mixture was extracted with EtOAc, dried (MgSO4), and concentrated. The residue was chromatographed on a silica gel column, eluting with $CHCl_3$/MeOH 10:1 to afford a light yellowish oil (259 mg, 88%). MS ($CI/NH_3$) m/z 295 $(M+H)^+$. $^1H$ NMR ($CDCl_3$, 300 MHz) δ 1.70-2.13 (m, 3H), 2.27-2.41 (m, 1H), 2.53 (s, 3H), 2.66-2.70 (m, 1H), 3.12-3.20 (m, 1H), 3.97-4.14 (m, 2H), 7.07 (d, J 16.6 Hz, 1H), 7.27 (d, J=16.6 Hz, 1H), 7.38 (d, J=5.5 Hz, 2H), 7.39 (dd, J=2.1 Hz, J=3.0 Hz, 1H), 8.28 (d, J=3.0 Hz, 1H), 8.36 (d, J=2.1 Hz, 1H), 8.62 (d, J=5.5 Hz, 2H).

13b. 5-(2-(4-Pyridinyl)ethenyl)-3-(1-methyl-2-(S)-pyrrolidinylmethoxy)pyridine trihydrochloride To a solution of 5-(2-(4-pyridinyl)ethenyl)-3-(1-methyl-2-(S)-pyrrolidinylmethoxy)pyridine from step 13a (125 mg, 0.42 mmol) in THF (3.0 mL) was added hydrogen chloride (1.0M in $Et_2O$, 0.97 mL, 0.97 mmol). The precipitate formed was filtered, washed ($Et_2O$) and vacuum-dried to afford the hydrochloride salt (151 mg, 97%). mp. 187–190° C. MS (CI/$NH_3$) m/z 296 (M+H)$^+$. $^1$H NMR ($D_2O$, 300 MHz) δ 2.05-2.50 (m, 4H), 3.08 (s, 3H), 3.21-3.37 (m, 2H), 3.93-4.03 (m, 1H), 4.46-4.56 (m, 1H), 4.63-4.70 (m, 1H), 7.57 (d, J=16.6 Hz, 1H), 7.83 (d, J=16.6 Hz, 1H), 8.12 (dd, J=2.1 Hz, J=3.0 Hz, 1H), 8.18 (d, J=5.5 Hz, 2H), 8.46 (d, J=3.0 Hz, 1H), 8.63 (d, J=2.1 Hz, 1H), 8.72 (d, J=5.5 Hz, 2H). Anal. Calcd for $C_{18}H_{21}N_3O$·3.0 HCl·0.2 $H_2O$: C, 52.94; H, 6.02; N, 10.29. Found: C, 53.04; H, 6.17; N, 10.07. [α]$^{25}$D=5.2° (c 1.0, MeOH).

Example 14

5-(5-Cyano-1-pentynyl)-3-(1-methyl-2-(S)-pyrrolidinylmethoxy)pyridine dihydrochloride 14a. 5-(5-Cyano-1-pentynyl)-3-(1-methyl-2-(S)-pyrrolidinylmethoxy)pyridine To a solution of 5-bromo-3-(1-methyl-2-(S)-pyrrolidinylmethoxy)-pyridine (816 mg, 3.00 mmol), bis(triphenylphosphine)palladium(II) chloride (42 mg, 0.06 mmol) and copper (I) iodide (10 mg, 0.06 mmol) in $CH_2C_{12}$ (6.0 mL) and NEt3 (2.0 mL) was added 5-cyanohexyne (0.481 mL, 4.5 mmol). The mixture was refluxed overnight then cooled to room temperature. Water (4 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with $NH_4OH$/MeOH/EtOAc 0:1:9 and 1:10:90 to afford a light yellowish oil (674 mg, 79%). MS (CI/$NH_3$) m/z 284 (M+H)$^+$. $^1$H NMR (CDCl$_3$, 300 MHz) δ 1.66-2.10 (m, 6H), 2.26-2.87 (m, 1H), 2.48 (s, 3H), 2.54-2.71 (m, 6H), 3.08-3.16 (m, 1H), 3.89-4.03 (m, 2H), 7.20 (dd, J=3.0 Hz, J=2.1 Hz, 1H), 8.23 (d, J=2.1 Hz, 1H), 8.24 (d, J=3.0 Hz, 1H).

14b. 5-(5-Cyano-1-pentynyl)-3-(1-2-(S)-pyrrolidinylmethoxy)pyridine dihydrochloride To a solution of 5-(5-cyano-1-pentynyl)-3-(1-methyl-2-(S)-pyrrolidinylmethoxy)pyridine from step 14a (100 mg, 0.35 mmol) in THF (3.0 mL) was added hydrogen chloride (1.0M in $Et_2O$, 0.81 mL, 0.81 mmol). A precipitate formed which was filtered, washed ($Et_2O$) and vacuum-dried to afford the hydrochloride salt (116 mg, 92%). mp. 165–167° C. MS (CI/$NH_3$) m/z 284 (M+H)$^+$. $^1$H NMR ($D_2O$, 300 MHz) δ 1.95-2.48 (m, 7H), 2.64-2.73 (m, 4H), 3.05 (s, 3H), 3.11-3.23 (m, 1H), 3.90-4.02 (m, 1H), 4.39-4.47 (m, 1H), 4.56-4.63 (m, 1H), 7.93 (S, 1H), 8.41 (S, 1H), 8.42 (S, 1H). Anal. Calcd for $C_{17}H_{21}N_3O$·2.0 HCl: C, 57.31; H, 6.51; N, 11.79. Found: C, 57.57; H, 6.36; N, 11.71. [α]$^{25}$D=3.8° (c 0.60, MeOH).

Example 15

5-(2-(Methoxycarbonyl)ethyl)-3-(1-methyl-2-(S)-pyrrolidinylmethoxy)pyridine dihydrochloride 15a. 5-(2-(Methoxycarbonyl)ethyl)-3-(1-methyl-2-(S)-pyrrolidinylmethoxy)pyridine dihydrochloride To a solution of 5-(2-(methoxycarbonyl)ethenyl)-3-(1-methyl-2-(S)-pyrrolidinylmethoxy)-pyridine (100 mg, 0.40 mmol) in MeOH (3.0 mL) was added palladium on charcoal (10%) (10 mg). The mixture was stirred at room temperature overnight. The solvent was removed and the residue was chromatographed on a silica gel column, eluting with $NH_4OH$/MeOH/EtOAc 0:1:9 and 1:10:90 to afford a light yellowish oil (90 mg, 90%). MS (CI/$NH_3$) m/z 279 (M+H)$^+$. $^1$H NMR (CDCl$_3$, 300 MHz) d 1.55-2.10 (m, 4H), 2.30-2.60 (m, 2H), 2.52 (s, 3H), 2.65 (t, J=6.3 Hz, 2H), 2.94 (t, J=6.3 Hz, 2H), 3.08-3.21 (m, 1H), 3.68 (s, 3H), 3.90-4.10 (m, 2H), 7.07 (dd, J=3.0, 2.1 Hz, 1H), 8.09 (d, J=2.1 Hz, 1H), 8.18 (d, J=3.0 Hz, 1H).

15b. 5-(2-(ethoxycarbonyl)ethyl)-3-(1-methyl-2-(S)-pyrrolidinylmethoxy)pyridine dihydrochloride To a solution of 5-(2-(methoxycarbonyl)ethyl)-3-(1-methyl-2-(S)-pyrrolidinylmethoxy)pyridine from step 15a (90 mg, 0.325 mmol) in THF (3.0 mL) was added hydrogen chloride (1.0M in $Et_2O$, 0.81 mL, 0.81 mmol). A precipitate formed which was filtered, washed ($Et_2O$) and vacuum-dried to afford the hydrochloride salt (114 mg, 100%). MS (CI/$NH_3$) m/z 279 (M+H)$^+$. $^1$H NMR ($D_2O$, 300 MHz) d 2.02-2.50 (m, 5H), 2.83 (t, J=6.3 Hz, 2H), 3.04 (s, 3H), 3.10 (t, J=6.3 Hz, 2H), 3.22-3.32 (m, 1H), 3.90-4.02 (m, 1H), 4.41-4.48 (m, 1H), 4.58-4.66 (m, 1H), 4.71 (s, 3H), 7.92 (dd, J=3.0, 2.1 Hz, 1H), 8.32 (d, J=2.1 Hz, 1H), 8.37 (d, J=3.0 Hz, 1H). Anal. Calcd for $C_{15}H_{22}N_2O_3$·2.1 HCl: C, 50.76; H, 6.84; N, 7.89. Found: C, 50.47; H, 6.78; N, 8.01. [α]$^{25}$D=+1.0° (c 0.60, MeOH).

Example 16

5-(2-(Methoxycarbonyl)ethenyl)-3-(1-methyl-2-(S)-pyrrolidinylmethoxy)pyridine dihydrochloride 16a. 5-(2-(Methoxycarbonyl)ethenyl)-3-(1-methyl-2-(S)-pyrrolidinylmethoxy)pyridine To a solution of 5-bromo-3-(1-methyl-2-(S)-pyrrolidinylmethoxy)pyridine (272.0 mg, 1.0 mmol) in acetonitrile (3.0 mL) and triethylamine (2.5 mL) was added methyl acyrate (0.360 mL, 4.0 mmol), palladium acetate (23.0 mg, 0.1 mmol) and tri-o-tolylphosphine (122.0 mg). After being heated in a sealed tube at 100° C. overnight, the resulting mixture was cooled to room temperature. A minimum amount of saturated sodium bicarbonate was added to free the amine, and the mixture was extracted with EtOAc, dried (MgSO4), and concentrated. The residue was chromatographed on a silica gel column, eluting with CHCl$_3$/MeOH 10:1 to afford a light yellowish oil (205 mg, 74%). MS (CI/$NH_3$) m/z 277 (M+H)$^+$. $^1$H NMR (CDCl$_3$, 300 MHz) δ 1.54-2.12 (m, 4H), 2.27-2.43 (m, 1H), 2.52 (s, 3H), 2.65-2.76 (m, 1H), 3.09-3.12 (m, 1H), 3.83 (s, 3H), 3.93-4.07 (m, 2H), 6.48 (d, J=16.2 Hz, 1H), 7.33 (dd, J=3.0, 2.1 Hz, 1H), 7.66 (d, J=16.2 Hz, 1H), 8.33 (d, J=3.0 Hz, 1H), 8.35 (d, J=2.1 Hz, 1H).

16b. 5-(2-(Methoxycarbonyl)ethenyl)-3-(1-methyl-2-(S)-pyrrolidinylmethoxy)pyridine dihydrochloride To a solution of 5-(2-(methoxycarbonyl)ethenyl)-3-(1-methyl-2-(S)-pyrrolidinylmethoxy)pyridine from step 16a (100 mg, 0.36 mmol) in THF (3.0 mL) was added hydrogen chloride (1.0M in $Et_2O$, 0.83 mL, 0.83 mmol). A precipitate formed which was filtered, washed ($Et_2O$) and vacuum-dried to afford the hydrochloride salt (121 mg, 96%). mp. 128–130° C. MS (CI/$NH_3$) m/z 277 (M+H)$^+$. $^1$H NMR ($D_2O$, 300 MHz) δ 2.04-2.30 (m, 4H), 2.36-2.48 (m, 1H), 3.05 (s, 3H), 3.22-3.32 (m, 1H), 3.92-4.02 (m, 1H), 4.46-4.53 (m, 1H), 4.62-4.68 (m, 1H), 4.71 (s, 3H), 6.78 (d, J=16.2 Hz, 1H), 7.75 (d, J=16.2 Hz, 1H), 8.16 (dd, J=3.0, 2.1 Hz, 1H), 8.49 (d, J=2.1 Hz, 1H), 8.61 (d, J=3.0 Hz, 1H). Anal. Calcd for $C_{15}H_{20}N_2O_3$·2.0 HCl: C, 51.59; H, 6.35; N, 8.02. Found: C, 51.44; H, 6.38; N, 7.96. [α]$^{25}$D=3.2° (c 0.65, MeOH).

Example 17

5-(5-Phenyl-1-pentynyl)-3-(1-methyl-2-(S)-pyrrolidinylmethoxy)pyridine dihydrochloride 17a. 5-(5-Phenyl-1-pentynyl)-3-(1-methyl-2-(S)-pyrrolidinylmethoxy)pyridine To a solution of 5-bromo-3-(1-methyl-2-(S)-pyrrolidinylmethoxy)-pyridine (408 mg, 1.50 mmol), bis(triphenylphosphine)palladium(II) chloride (21 mg, 0.029 mmol) and copper (I) iodide (5 mg, 0.029 mmol) in $CH_2Cl_2$ (3.0 mL) and $NEt_3$ (1.0 mL) was added 5-phenyl-1-pentyne (324 mg, 2.25 mmol). The mixture was refluxed overnight then cooled to room temperature. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with $NH_4OH/MeOH/EtOAc$ 0:1:9 and 1:10:90 to afford an oil (411 mg, 80%). MS ($CI/NH_3$) m/z 335 (M+H)$^+$. $^1H$ NMR ($CDCl_3$, 300 MHz) δ 1.65-2.10 (m, 6H), 2.26-2.37 (m, 1H), 2.41-2.47 (m, 2H), 2.48 (s, 3H), 2.61-2.73 (m, 1H), 2.76-2.83 (m, 2H), 3.07-3.16 (m, 1H), 3.89-4.03 (m, 2H), 7.17-7.36 (m, 6H), 8.21-8.26 (m, 2H).

17b. 5-(5-Phenyl-1-pentynyl)-3-(1-methyl-2-(S)-pyrrolidinylmethoxy)pyridine dihydrochloride To a solution of 5-(5-phenyl-1-pentynyl)-3-(1-methyl-2-(S)-pyrrolidinyl-methoxy)pyridine from step 17a (130 mg, 0.39 mmol) in THF (3.0 mL) was added hydrogen chloride (1.0M in $Et_2O$, 0.90 mL, 0.90 mmol). A precipitate formed which was filtered, washed ($Et_2O$) and vacuum-dried to afford the hydrochloride salt (150 mg, 94%). MS ($CI/NH_3$) m/z 335 (M+H)$^+$. $^1H$ NMR ($D_2O$, 300 MHz) δ 1.86-2.01 (m, 2H), 2.03-2.15 (m, 2H), 2.16-2.28 (m, 21H), 2.33-2.54 (m, 3H), 2.74-2.83 (m, 2H), 3.03 (s, 3H), 3.20-3.28 (m, 1H), 3.72-2.82 (m, 1H), 3.86-3.98 (m, 1H), 4.32-4.41 (m, 1H), 4.44-4.55 (m, 1H), 7.22-7.43 (m, 5H), 7.57-7.66 (s, 1H), 8.21-8.39 (m, 1H). Anal. Calcd for $C_{22}H_{26}N_2O \cdot 2.1\ HCl \cdot 0.3\ H_2O$: C, 63.45; H, 6.97; N, 6.56. Found: C, 63.53; H, 6.97; N, 6.56. $[\alpha]^{25}D=5.0°$ (c 1.1, MeOH).

Example 18

5-trans-(2-Phenylethenyl)-3-(1-methyl-2-(S)-pyrrolidinylmethoxy)pyridine dihydrochloride 18a. 5-trans-(2-Phenylethenyl)-3-(1-methyl-2-(S)-pyrrolidinylmethoxy)pyridine To a solution of 5-bromo-3-(1-methyl-2-(S)-pyrrolidinylmethoxy)pyridine (272.0 mg, 1.0 mmol) in acetonitrile (3.0 mL) and triethylamine (2.5 mL) was added styrene (231.0 uL, 2.0 mmol), palladium acetate (23.0 mg) and tri-o-tolylphosphine (122.0 mg). After being heated in a sealed tube at 100° C. overnight, the resulting mixture was cooled to room temperature. Minimum amount of saturated sodium bicarbonate was added to free the amine hydrochloride salt, and the mixture was extracted with EtOAc, dried ($MgSO_4$), and concentrated. The residue was chromatographed on a silica gel column, eluting with $CHCl_3/MeOH$ 10:1 to afford a light yellowish oil (210.0 mg, 71%). MS ($CI/NH_3$) m/z 295 (M+H)$^+$. $^1H$ NMR ($CDCl_3$, 300 MHz) δ 1.70-1.92 (m, 2H), 1.99-2.12 (m, 1H), 2.28-2.38 (m, 1H), 2.52 (s, 3H), 2.67-2.74 (m, 1H), 3.10-3.18 (m, 1H), 3.96-4.02 (m, 1H), 4.04-4.11 (m, 1H), 7.06 (d, J=16.0 Hz, 1H), 7.16 (d, =16.0 Hz, 1H), 7.27-7.42 (m, 4H), 7.50-7.54 (m, 2H), 8. 22 (d, J=1.2 Hz, 1H), 8.33 (d, J=0.9 Hz, 1H).

18b. 5-trans-(2-Phenylethenyl)-3-(1-methyl-2-(S)-pyrrolidinylmethoxy)pyridine dihydrochloride To a solution of 5-trans-(2-phenylethenyl)-3-(1-methyl-2-(S)-pyrrolidinylmethoxy)pyridine from step 18a (90 mg, 0.34 mmol) in THF (3.0 mL) was added hydrogen chloride (1.0M in $Et_2O$, 0.78 mL, 0.78 mmol). A precipitate formed which was filtered, washed ($Et_2O$) and vacuum-dried to afford the hydrochloride salt (93 mg, 75%). MS ($CI/NH_3$) m/z 295 (M+H)$^+$. $^1H$ NMR ($D_2O$, 300 MHz) δ 1.88-2.46 (m, 4H), 3.04 (s, 3H), 3.20-3.30 (m, 1H), 3. 3.71-3.82 (m, 1H), 3.84-3.99 (m, 1H), 4.35-4.44 (m, 1H), 4.52-4.60 (m, 1H), 7.17-7.53 (m, 5H), 7.62-7.68 (m, 2H), 7.82 (s, 1H), 8.23 (s, 1H), 8.40 (s, 1H). Anal. Calcd for $C_{19}H_{22}N_2O \cdot 2.0\ HCl \cdot 0.5\ H_2O$: C, 60.64; H, 6.70; N, 7.44. Found: C, 60.68; H, 6.78; N, 7.49. $[\alpha]^{25}D=4.0°$ (c 0.73, MeOH).

Example 19

5-(1-Pyrrolidinylcarbonyl)-3-(1-methyl-2-(S)-pyrrolidinylmethoxy)pyridine dihydrochloride 19a. 5-(1-Pyrrolidinylcarbonyl)-3-(1-methyl-2-(S)-pyrrolidinylmethoxy)pyridine To the ester obtained from Example 27 below was added pyrrolidine (6.0 mL), and the resulting mixture was refluxed for 20 hours. The mixture was concentrated and the residue was chromatographed on a silica gel column, eluting with $CHCl_3/MeOH/NH_3$, 1:10:89 to afford a light yellowish oil (712 mg, 62% for two steps. MS ($CI/NH_3$) m/z 290 (M+H)$^+$. $^1H$ NMR ($CDCl_3$, 300 MHz) δ 1.65-2.08 (m, 8H), 2.27-2.87 (m, 1H), 2.49 (s, 3H), 2.63-2.71 (m, 1H), 3.08-3.14 (m, 1H), 3.44-3.51 (m, 2H), 3.63-3.70 (m, 2H), 3.94-4.05 (m, 2H), 7.38 (dd, J=2.0, 3.0 Hz, 1H), 37 (d, J=2.0 Hz, 1H), 8.38 (d, J=3.0 Hz, 1H).

19b. 5-(1-Pyrrolidinylcarbonyl)-3-(1-methyl-2-(S)-pyrrolidinylmethoxy)pyridine dihydrochloride To the solution of 5-(1-pyrrolidinylcarbonyl)-3-(1-methyl-2-(S)-pyrrolidinylmethoxy)pyridine (100 mg, 0.35 mmol) in THF (3.0 mL) was added hydrogen chloride (1.0M in $Et_2O$, 0.80 mL, 0.80 mmol). The precipitate formed was filtered, washed ($Et_2O$) and vacuum-dried to afford the hydrochloride salt (128 mg, 100%). MS ($CI/NH_3$) m/z 290 (M+H)$^+$. $^1H$ NMR ($D_2O$, 300 MHz) δ 1.84-2.48 (m, 8H), 3.04 (s, 3H), 3.20-3.30 (m, 1H), 3. 42-3.50 (m, 2H), 3.55-3.62 (m, 2H), 3.73-3.81 (m, 1H), 3. 90-4.00 (m, 1H), 4.37-4.43 (m, 1H), 4.54-4.60 (m, 1H), 7.68 (dd, J=2.0 Hz, J=3.0 Hz, 1H), 8.37 (d, J=2.0 Hz, 1H), 8.46 (d, J=3.0 Hz, 1H). Anal. Calcd for $C_{16}H_{23}N_3O_2 \cdot 2.0\ HCl \cdot 0.8\ H_2O$: C, 51.10; H, 7.12; N, 11.71. Found: C, 51.06; H, 7.61; N, 10.71. $[\alpha]^{25}D=1.7°$ (c 1.2, MeOH).

Example 20

5-(4-chlorophenyl)-3-(2-(S)-pyrrolidinylmethoxy)pyridine dihydrochloride 20a. 5-(4-chlorophenyl)-3-(2-(R)-pyrrolidinylmethoxy)pyridine To a solution of 5-bromo-3-(1-BOC-2-(S)-pyrrolidinylmethoxy)pyridine (300 mg, 0.84 mmol) and 4-chlorophenylboronic acid (263 mg, 1.68 mmol, Lancaster Chemical Co.) in toluene (10 mL) was added Pd(0) (25 mg) and $Na_2CO_3$ (1 mL of a 2M solution), and the mixture was heated at reflux for 6 hours. The solvent was removed under vacuum, and the residue was chromatographed on a silica gel column, eluting with 1:5 to 1:2 EtOAc/hexane to afford the title compound (325 mg, 100% yield). MS ($CI/NH_3$) m/z 389 (M+H)$^+$. $^1H$ NMR ($CDCl_3$, 300 MHz) δ: 1.47 (s, 9h), 1.90 (m, 2H), 2.05 (br, 1H), 3.40 (br, 2H), 3.92 (br, 1H), 4.19 (br, 2H), 4.25 (br, 1H), 7.44 (m, 2H), 7.52 (m, 3H), 8.31 (m, 1H), 8.42 (s, 1H).

20b. 5-(4-chlorophenyl)-3-(2-(R)-pyrrolidinylmethoxy)pyridine hydrochloride

A sample of the compound from step 20a (325 mg, 0.84 mmol) was stirred in TFA (3 mL) and $CH_2Cl_2$ (3.0 mL) for 1/2 hour at 0° C. and ½ hour at room temperature. Saturated aqueous NaHCO$_3$ was added, and the mixture was extracted with CH$_2$Cl$_2$. The solution was dried over MgSO4 and concentrated. The residue was chromatographed on a silica gel column, eluting with MeOH/CH$_2$Cl$_2$ 5:100 to 10:100 containing 0.3% NH$_4$OH to give the free base (241 mg, 99% yield). MS (CI/NH$_3$) m/z 289 (M+H)$^+$. $^1$H NMR (CDCl$_3$, 300 MHz) δ: 1.82-2.22 (m, 4H), 3.24 (m, 2H), 3.90 (m, 1H), 4.23 (m, 2H), 7.36 (m, 1H), 7.45 (m, 4H), 8.27 (m, 1H), 8.42 (m, 1H). The free base was converted to the salt with HCl in THF to afford the title compound. mp 180–182° C. MS (CI/NH$_3$) m/z 289 (M+H)$^+$. $^1$H NMR (CDCl$_3$, 300 MHz) δ: 1.93-2.03 (m, 1H), 2.05-2.20 (m, 2H), 2.4 (m, 1H), 3.44 (t, J=7.4 Hz, 2H), 4.19 (m, 1H), 4.43 (dd, J=6.4, 10.7 Hz, 2H), 4.64 (dd, J=3.3, 10.7 Hz, 1H), 7.60 (m, 2H), 7.70 (m, 2H), 8.21 (m, 1H), 8.47 (d, J=2.6 Hz, 1H), 8.66 (d, J=1.8 Hz, 1H). Anal. Calcd for C$_{16}$H$_{17}$N$_2$OCl·2.5 HCl·1.0 H$_2$O: C, 48.29; H, 5.45; N, 7.04. Found: C, 48.28; H, 5.07; N, 6.87. [α]$^{25}$D=+8.02° (c 0.96, MeOH).

Example 21

5-(2-Phenylethyl))-3-(1-methyl-2-(S)-pyrrolidinylmethoxy)pyridine dihydrochloride 21a. 5-(2-Phenylethyl))-3-(1-methyl-2-(S)-pyrrolidinylmethoxy)pyridine dihydrochloride To a solution of 5-(2-phenylethenyl))-3-(1-methyl-2-(S)-pyrrolidinylmethoxy)-pyridine (100 mg, 0.40 mmol) in MeOH (3.0 mL) was added palladium on charcoal (10%) (10 mg). The mixture was stirred at room temperature overnight. The solvent was removed, and the residue was chromatographed on a silica gel column, eluting with NH$_4$OH/MeOH/EtOAc 0:1:9 and 1:10:90 to afford a light yellowish oil (95 mg, 95%). MS (CI/NH$_3$) m/z 297 (M+H)$^+$. $^1$H NMR (CDCl$_3$, 300 MHz) δ 1.55-2.09 (m, 4H), 2.25-2.36 (m, 1H), 2.48 (s, 3H), 2.59-2.70 (m, 1H), 2.91 (s, 4H), 3.08-3.15 (m, 1H), 3.84-4.00 (m, 4H), 6.96 (s, 1H), 7.13-7.32 (m, 5H), 8.04 (s, 1H), 8.16 (s, 1H).

21b. 5-(2-Phenylethyl))-3-(1-methyl-2-(S)-pyrrolidinylmethoxy)pyridine dihydrochloride To a solution of 5-(2-phenylethyl))-3-(1-methyl-2-(S)-pyrrolidinylmethoxy)-pyridine from step 21a (95 mg, 0.32 mmol) in THF (3.0 mL) was added hydrogen chloride (1.0M in Et$_2$O, 0.73 mL, 0.73 mmol). A precipitate formed which was filtered, washed (Et$_2$O) and vacuum-dried to afford the hydrochloride salt (86 mg, 73%). MS (CI/NH$_3$) m/z 297 (M+H)$^+$. $^1$H NMR (D2O, 300 MHz) δ 1.80-2.44 (m, 4H), 3.01 (s, 3H), 2.97-3.17 (m, 4H), 3.19-3.29 (m, 1H), 3.70-3.82 (m, 1H), 3.83-3.93 (m, 1H), 4.26-4.34 (m, 1H), 4.43-4.49 (m, 1H), 7.16-7.42 (m, 5H), 7.58 (s, 1H), 8.13 (s, 1H), 8.24 (s, 1H). Anal. Calcd for C$_{19}$H$_{24}$N$_2$O·2.6 HCl·0.3 H$_2$O: C, 57.54; H, 7.07; N, 7.06. Found: C, 57.50; H, 6.93; N, 7.11. [α]$^{25}$D=1.1° (c 0.70, MeOH).

Example 22

5-(3-oxo-1-hexenyl)-3-(1-methyl-2-(S)-pyrrolidinylmethoxy)pyridinine dihydrochloride 22a. 5-(3-oxo-1-hexenyl)-3-(1-methyl-2-(S)-pyrrolidinylmethoxy)pyridinine To a solution of 5-bromo-3-(1-methyl-2-(S)-pyrrolidinylmethoxy)pyridine (816 mg, 3.0 mmol) in acetonitrile (9.0 nm) and triethylamine (7.5 mL) was added hex-1-en-3-one (882 mg, 9.0 mmol), palladium acetate (69.0 mg, 1.2 mmol) and tri-o-tolylphosphine (366.0 mg). After being heated in a sealed tube at 100° C. overnight, the resulting mixture was cooled to room temperature. Minimum amount of saturated sodium bicarbonate was added to free the amine, and the mixture was extracted with EtOAc, dried (MgSO$_4$), and concentrated. The residue was chromatographed on a silica gel column, eluting with CHCl$_3$/MeOH 10:1 to afford a light yellowish oil (669 mg, 77%). MS (CI/NH$_3$) m/z 289 (M+H)$^+$. $^1$H NMR (CDCl$_3$, 300 MHz) δ 0.98 (t, J=7.4 Hz, 3H), 1.60-1.90 (m, 6H), 1.99-2.09 (m, 2H), 2.28-2.40 (m, 1H), 2.50 (S, 3H), 2.67 (t, J=7.4 Hz, 1H), 3.10-3.17 (m, 1H), 3.94-4.06 (m, 2H), 6.86 (d, J=16.1 HZ, 1H), 7.36 (dd, J=1.8, 2.9 Hz, 1H), 7.52 (d, J=16.1 Hz, 1H), 8.33 (d, J=2.9 Hz, 1H), 8.8.36 (d, J=1.8 Hz, 1H).

22b. 5-(3-oxo-1-hexenyl)-3-(1-methyl-2-(S)-pyrrolidinylmethoxy)pyridinine dihydrochloride To a solution of 5-(3-oxo-1-hexenyl)-3-(1-methyl-2-(S)-pyrrolidinylmethoxy)pyridinine from step 22a (120 mg, 0.42 mmol) in THF (3.0 mL) was added hydrogen chloride (1.0M in Et$_2$O, 0.90 mL, 0.90 mmol). A precipitate formed which was filtered, washed (Et$_2$O) and vacuum-dried to afford the hydrochloride salt (124 mg, 82%). MS (CI/NH$_3$) m/z 289 (M+H)$^+$. $^1$H NMR (D$_2$O, 300 MHz) δ 0.94 (t, J=7.4 Hz, 3H), 1.67 (p, J=7.4 Hz, 2 H), 2.04-2.47 (m, 4H), 2.81 (t, J=7.4 Hz, 2H), 3.07 (s, 3H), 3.20-3.32 (m, 1H), 3.72-3.81 (m, 1H), 3.90-4.02 (m, 1H), 4.42-4.49 (m, 1H), 4.56-4.65 (m, 1H), 7.01 (d, J=16.1 Hz, 1H), 7.70 (d, J=16.1 Hz, 1H), 8.02 (dd, J=1.8, 2.9 Hz, 1H), 8.45 (d, J=2.9 Hz, 1H), 8.55 (d, J=1.8 Hz, 1H). Anal. Calcd for C$_{17}$H$_{24}$N$_2$O$_2$·2.1 HCl: C, 55.95; H, 7.21; N, 7.68. Found: C, 55.77; H, 7.48; N, 7.68. [α]$^{25}$D=4.3° (c 0.80, MeOH).

Example 23

Intermediate Compound

5-Bromo-6-chloro-3-(2-(S)-pyrrolidinylmethoxy)pyridine dihydrochloride 23a. 5-Bromo-6-chloro-3-(1-BOC-2-(S)-pyrrolidinylmethoxy)pyridine To a solution of diethyl azodicarboxylate (1.89 mL, 12.0 mmol) in THF (30 mL) was added triphenylphosphine (3.15 g, 12.0 mmol) at 0° C., and the reaction mixture was stirred for half an hour. 1-BOC-(S)-pyrrolidinemethanol (2.41 g, 12.0 mmol) and 5-bromo-6-chloropyridine-3-ol (2.09 g, 10.0 mmol; V. Koch and S. Schnatterer, Synthesis 1990, 499–501)) were then added. The reaction mixture was slowly warmed up to room temperature overnight. Solvent was removed, and the residue was chromatographed on a silica gel column, eluting with EtOAc/hexane 1:5 and 1:2 to afford an oil (3.80 g, 97%). MS (CI/NH$_3$) m/z 391/393 (M+H)$^+$. $^1$H NMR (DMSO-d$_6$, 300 MHz) δ 01.65-2.05 (m, 4H), 3.20-3.35 (m, 2H), 3.95-4.15 (m, 3H), 7.98 (d, J=2.9 Hz, 1H), 8.21 (d, J=2.9 Hz, 1H).

23b. 5-Bromo-6-chloro-3-(2-(S)-pyrrolidinylmethoxy)pyridine dihydrochloride

To 5-bromo-6-chloro-3-(1-BOC-2-(S)-pyrrolidinylmethoxy)pyridine from step 23a (150 mg, 0.38 mmol) was added hydrogen chloride (4.0M in 1,4-dioxane, 3.0 mL), and the reaction mixture was allowed to stir at room temperature for two days. A precipitate formed which was filtered, washed (Et$_2$O) and vacuum-dried to afford the hydrochloride salt (119 mg, 94%). mp. 264–268° C. MS (CI/NH$_3$) m/z 291/293 (M+H)$^+$, 308/310 (M+NH$_4$)$^+$. $^1$H NMR (D2O, 300 MHz) δ 1.90-2.35 (m, 4H), 3.38-3.46 (m, 2H), 4.07-4.17 (m, 1H), 4.23-4.31 (m, 1H), 4.44-4.51 (m, 1H), 7.90 (d, J=2.9 Hz, 1H), 8.13 (d, J=2.9 Hz, 1H). Anal. Calcd for C$_{10}$H$_{12}$N$_2$OBrCl·1.0 HCl: C, 32.95; H, 3.87; N, 7.69. Found: C, 36.61; H, 3.95; N, 8.42. [α]$^{25}$D=+9.2° (c 0.90, MeOH).

Example 24

Intermediate Compound

5-Bromo-6-chloro-3-(1-methyl-2-(S)-pyrrolidinylmethoxy)pyridine dihydrochloride 24a 5-(Bromo-6-chloro-3-(1-methyl-2-(S)-pyrrolidinylmethoxy)pyridine To 5-bromo-6-chloro-3-(1-BOC-2-(S)-pyrrolidinylmethoxy)pyridine from Example 23a (300 mg, 0.77 mmol) was added formalin (38%, 3.0 mL) and formic acid (88%, 1.5 mL), and the mixture was refluxed for five hours and then cooled to room temperature. Hydrochloric acid (36%, 0.3 mL) was added, and the mixture was extracted with $Et_2O$ (3×8 mL). The aqueous layer was heated under vacuum to dryness. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with $CHCl_3$/MeOH 10:1 to afford an oil (214 mg, 91%). MS (CI/$NH_3$) m/z 305/307 $(M+H)^+$. $^1$H NMR ($CDCl_3$, 300 MHz) δ 1.60-2.11 (m, 4H), 2.27-2.38 (m, 1H), 2.48 (S, 3H), 2.63-2.72 (m, 1H), 3.07-3.15 (m, 1H), 3.89-4.02 (m, 2H), 7.52 (d, J=3.0 Hz, 1H), 8.04 (d, J=3.0 Hz, 1H).

24b. 5-Bromo-6-chloro-3-(1-methyl-2-(S)-pyrrolidinylmethoxy)pyridine dihydrochloride To 5-bromo-6-chloro-3-(1-methyl-2-(S)-pyrrolidinylmethoxy)pyridine from step 24a (100 mg, 0.33 mmol) in THF (3.0 mL) was added hydrogen chloride (1.0M in $Et_2O$, 0.75 mL, 0.75 mmol). A precipitate formed which was filtered, washed ($Et_2O$) and vacuum-dried to afford the hydrochloride salt (85 mg, 76%). mp. 189–191° C. MS (CI/$NH_3$) m/z 305/307 $(M+H)^+$. $^1$H NMR ($D_2O$, 300 MHz) δ 2.02-2.47 (m, 4H), 3.03 (S, 3H), 3.22-3.34 (m, 1H), 3.67-3.78 (m, 1H), 3.89-3.99 (m, 1H), 4.32-4.40 (m, 1H), 4.48-4.55 (m, 1H), 7.92 (d, J=3.0 Hz, 1H), 8.14 (d, J=3.0 Hz, 1H). Anal. Calcd for $C_{11}H_{14}N_2OBrCl·1.0$ HCl: C, 38.63; H, 4.51; N, 8.19. Found: C, 38.67; H, 4.49; N, 8.13. $[α]^{25}D=3.8°$ (c 0.50, MeOH).

Example 25

5-(5-Pyrimidinyl)-3-(1-methyl-2-(S)-pyrrolidinylmethoxy)pyridine dihydrochloride 25a. 5-tri-n-Butylstanyl-3-(1-methyl-2-(S)-pyrrolidinylmethoxy)-pyridine To a solution of 5-bromo-3-(1-methyl-2-(S)-pyrrolidinylmethoxy)-pyridine (1.36 g, 5.0 mmol) in toluene (10.0 mL) was added bis(tributyltin) (13.79 mL, 7.5 mmol) and tetrakis(triphenylphosphine)palladium(0) (58 mg, 0.05 mmol). After being refluxed overnight, the resulting mixture was cooled to room temperature. Solvent was removed and the residue was chromatographed on a silica gel column, eluting with $NH_4OH$/MeOH/EtOAc 0:1:9 and 1:10:90 to afford 5-tri-n-butylstanyl-3-(1-methyl-2-(S)-pyrrolidinylmethoxy)-pyridine as an oil (1.09 g, 45%). MS (CI/$NH_3$) m/z 271 $(M+2H-C_{12}H_{27}Sn)^+$. $^1$H NMR ($CDCl_3$, 300 MHz) δ 0.83-0.96 (m, 9H), 1.04-1.13 (m, 6H), 1.25-1.41 (m, 6H), 1.48-1.68 (m, 8H), 1.74-1.86 (m, 1H), 2.00-2.10 (m, 1H), 2.28-2.40 (m, 1H), 2.51 (s, 2H), 2.64-2.73 (m, 1H), 3.10-3.20 (m, 1H), 3.90-4.08 (m, 2H), 7.24-7.30 (m, 1H), 8.17-8.23 (m, 2H).

25b. 5-(5-Pyrimidinyl-3-(1-methyl-2-(S)-pyrrolidinylmethoxy)pyridine

To a solution of 5-tri-n-butylstanyl-3-(1-methyl-2-(S)-pyrrolidinylmethoxy)-pyridine from step 25a (241 mg, 0.5 mmol) in toluene (5.0 mL) was added 5-bromopyridine (159 mg, 1.0 mmol) and tetrakis(triphenylphosphine)palladium (0) (20 mg, 0.18 mmol). After being refluxed overnight, the resulting mixture was cooled to room temperature. Solvent was removed and the residue was chromatographed on a silica gel column, eluting with $NH_4OH$/MeOH/EtOAc 0:1:9 and 1:10:90 to afford an oil (64 mg, 47%). MS (CI/$NH_3$) m/z 271 $(M+H)^+$. $^1$H NMR ($CDCl_3$, 300 MHz) δ 1.68-2.12 (m, 4H), 2.28-2.40 (m, 1H), 2.51 (S, 3H), 2.67-2.77 (m, 1H), 3.10-3.18 (m, 1H), 4.00-4.13 (m, 2H), 7.39 (dd, J=2.1, 3.0 Hz), 8.43 (d, J=3.0 Hz, 1H), 8.45 (d, J=2.1 Hz, 1H), 8.97 (s, 1H), 9.28 (s, 1H).

25c. 5-(5-Pyrimidinyl)-3-(1-methyl-2-(S)-pyrrolidinylmethoxy)pyridine dihydrochloride To 5-(5-pyrimidinyl)-3-(1-methyl-2-(S)-pyrrolidinylmethoxy)pyridine from step 25b (60 mg, 0.22 mmol) was added hydrogen chloride (1.0M in $Et_2O$, 0.51 mL, 0.51 mmol). A precipitate formed which was filtered, washed ($Et_2O$) and vacuum-dried to afford the hydrochloride salt (76 mg, 100%). mp. 205–220° C. MS (CI/$NH_3$) m/z 271 $(M+H)^+$. $^1$H NMR ($D_2O$, 300 MHz) δ 2.06-2.50 (m, 4H), 3.08 (S, 3H), 3.23-3.33 (m, 1H), 3.72-3.83 (m, 1H), 3.93-4.04 (m, 1H), 4.47-4.55 (m, 1H), 4.64-4.73 (m, 1H), 8.12 (dd, J=2.1, 3.0 Hz), 8.54 (d, J=3.0 Hz, 1H), 8.68 (d, J=2.1 Hz, 1H), 9.13 (s, 1H), 9.24 (s, 1H). Anal. Calcd for $C_{15}H_{18}N_4O·2.0$ HCl·0.4 $H_2O·0.5$ MeOH: C, 50.55; H, 6.29; N, 15.21. Found: C, 50.72; H, 5.90; N, 14.97. $[α]^{25}D=4.0°$ (c 0.50, MeOH).

Example 26

5-Phenyl-6-chloro-3-(1-methyl-2-(S)-pyrrolidinylmethoxy)pyridine dihydrochloride 26a. 5-Phenyl-3-(1-methyl-1-(S)-pyrrolidinylmethoxy)pyridine To a solution of 5-phenyl-6-chloro-3-(1-methyl-2-(S)-pyrrolidinylmethoxy)-pyridine (110 mg, 0.36 mmol) in benzene (2.0 mL) were added sodium carbonate (2.0M, 1.0 mL), tetrakis(triphenylphosphine)palladium(0) (15 mg, 0.013 mmol) and phenylboronic acid (53 mg, 0.43 mmol). The reaction mixture was refluxed overnight, and then cooled to room temperature. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with $NH_4OH$/MeOH/EtOAc 0:1:9 and 1:10:90 to afford a light yellowish oil (74 mg, 67%). MS (CI/$NH_3$) m/z 303 $(M+H)^+$. $^1$H NMR ($CDCl_3$, 300 MHz) δ 1.65-2.10 (m, 4H), 2.27-2.38 (m, 1H), 2.49 (s, 3H), 2.63-2.72 (m, 1H), 3.08-3.16 (m, 1H), 3.93-4.05 (m, 2H), 7.24 (d, J=3.0 HZ, 1H), 7.44-7.48 (m, 5H), 8.09 (d, J 3.0 Hz, 1H).

26b. 5-Phenyl-3-(1-methyl-2-(S)-pyrrolidinylmethoxy)pyridine dihydrochloride

To a solution of 5-phenyl-3-(1-methyl-2-(S)-pyrrolidinylmethoxy)pyridine (70 mg, 0.23 mmol) in THF (3.0 mL) was added hydrogen chloride (1.0M in $Et_2O$, 0.53 mL, 0.53 mmol). A precipitate formed which was filtered, washed ($Et_2O$) and vacuum-dried to afford the hydrochloride salt (50 mg, 58%). mp. 180–183° C. MS (CI/$NH_3$) m/z 303 $(M+H)^+$. $^1$H NMR ($D_2O$, 300 MHz) δ 2.04-2.48 (m, 4H), 3.3 (s, 3H), 3.2-3.36 (m, 1H), 3.68-3.83 (m, 1H), 3.88-4.03 (m, 1H). 4.33-4.47 (m, 1H), 4.50-4.62 (m, 1H), 7.50-7.70 (m, 6H), 8.17 (s, 1H). Anal. Calcd for $C_{17}H_{19}N_2OCl·1.2$ HCl: C, 58.92; H, 5.87; N, 8.08. Found: C, 58.83; H, 5.74; N, 7.96. $[α]^{25}D=4.2°$ (c 0.45, MeOH).

Example 27

5-Methoxycarbonyl-3-(1-2-methyl-(S)-pyrrolidinylmethoxy)pyridine dihydrochloride 27a. 5-Methoxycarbonyl-3-(1-methyl-2-(S)-pyrrolidinylmethoxy)pyridine A reaction mixture of 5-bromo-3-(1-methyl-2-(S)-pyrrolidinylmethoxy)-pyridine (272 mg, 1.00 mmol), bis(triphenylphosphine)palladium(II) chloride (37 mg, 0.05 mmol) and triethylamine (219 mg) in MeOH (20 mL) was heated at 100° C. under CO (1100 psi) for 68 hours. The catalyst was filtered off and washed with EtOAc. The organics were concentrated and the residue was chromatographed on a silica gel column, eluting with $NH_4OH$/MeOH/EtOAc 0:1:9 and 1:10:90 to afford an oil (88 mg, 35%). MS (CI/$NH_3$) m/z 251 (M+H)$^+$. $^1$H NMR (CDCl$_3$, 300 MHz) δ 1.70-2.10 (m, 4H), 2.78-2.87 (m, 1H), 2.50 (s, 3H), 2.66-2.73 (m, 1H), 3.08-3.17 (m, 1H), 3.96 (s, 3H), 3.97-4.07 (m, 2H), 7.78 (d, J=3.0 Hz, J=2.1 Hz), 8.49 (d, J=3.0 Hz, 1H), 8.82 (d, J=2.1 Hz, 1H).

27b. 5-Methoxycarbonyl-3-(1-methyl-2-(S)-pyrrolidinylmethoxy)pyridine dihydrochloride (50722-94)

To a solution of 5-methoxycarbonyl-3-(1-methyl-2-(S)-pyrrolidinylmethoxy)-pyridine from stpe 27a (70 mg, 0.28 mmol) in EtOAc (3.0 mL) was added hydrogen chloride (1.0M in Et$_2$O, 0.64 mL, 0.64 mmol). A precipitate formed which was filtered, washed (Et$_2$O) and vacuum-dried to afford the hydrochloride salt (74 mg, 82%). mp. 165–167° C. MS (CI/$NH_3$) m/z 251 (M+H)$^+$. $^1$H NMR (D$_2$O, 300 MHz) δ 2.04-2.47 (m, 4H), 3.05 (s, 3H), 3.21-3.32 (m, 1H), 3.71-3.82 (m, 1H), 3.91-4.01 (m, 1H), 3.97 (s, 3H), 4.37-4.45 (m, 1H), 4.55-4.62 (m, 1H), 8.52 (d, J=3.0 HZ, 1H), 8.80 (d, J=2.1 Hz, 1H). Anal. Calcd for $C_{13}H_{18}N_2O_3Cl$·2.0 HCl: C, 48.29; H, 6.25; N, 8.67. Found: C, 48.33; H, 6.10; N, 8.51. $[\alpha]^{25}D$=2.5° (c 0.40, MeOH).

Example 28

5-(6-Hydroxy-1-hexynyl)-3-(1-methyl-2-(S)-pyrrolidinylmethoxy)pyridine dihydrochloride 28a. 5-(6-Hydroxy-1-hexynyl)-3-(1-methyl-2-(S)-pyrrolidinylmethoxy)pyridine To a solution of 5-bromo-3-(1-methyl-2-(S)-pyrrolidinylmethoxy)-pyridine (272 mg, 1.00 mmol), bis(triphenylphosphine)palladium(II) chloride (28 mg, 0.039 mmol), copper (I) iodide (5 mg, 0.039 mmol) and NEt3 (1.0 mL) in CH$_2$Cl$_2$ (3.0 mL) was added 5-hexyn-1-ol (0.172 mL, 1.5 mmol). The mixture was refluxed overnight and then cooled to room temperature. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with $NH_4OH$/MeOH/EtOAc 0:1:9 and 1:10:90 to afford a light yellowish oil (270 mg, 94%). MS (CI/$NH_3$) m/z 289 (M+H)$^+$. $^1$H NMR (CDCl$_3$, 300 MHz) δ 1.55-1.90 (m, 8H), 1.97-2.07 (m, 1H), 2.25-2.46 (m, 1H), 2.27 (s, 3H), 2.46-2.53 (m, 1H), 2.60-2.71 (m, 1H), 3.07-3.16 (m, 1H), 3.68-3.74 (m, 2H), 3.88-4.03 (m, 2H), 7.19 (dd, J=3.0, 1.8 Hz, 1H), 8.22 (d, J=3.0 Hz, 1H), 8.23 (d, J=1.8 Hz, 1H).

28b. 5-(6-Hydroxy-1-hexynyl)-3-(1-methyl-2-(S)-pyrrolidinylmethoxy)pyridine dihydrochloride To a solution of 5-(6-hydroxy-hex-1-ynyl)-3-(1-methyl-2-(S)-pyrrolidinylmethoxy)pyridine from step 28a (120 mg, 0.42 mmol) in THF (3.0 mL) was added hydrogen chloride (1.0M in Et$_2$O, 0.96 mL, 0.96 mmol). A precipitate formed was filtered, washed (Et$_2$O) and vacuum-dried to afford the hydrochloride salt (143 mg, 95%). MS (CI/$NH_3$) m/z 289 (M+H)$^+$. $^1$H NMR (D$_2$O, 300 MHz) δ 1.63-1.78 (m, 4H), 2.02-2.57 (m, 6H), 3.03 (s, 3H), 3.20-3.31 (m, 1H), 3.62-3.68 (m, 1H), 3.71-3.82 (m, 1H), 3.90-3.99 (m, 1H), 4.37-4.43 (m, 1H), 4.56-4.60 (m, 1H), 7.82 (s, 1H), 8.36 (s, 1H), 8.37 (s, 1H). Anal. Calcd for $C_{17}H_{24}N_2O_2$·2.3 HCl·0.7 H$_2$O: C, 53.06; H, 7.25; N, 7.28. Found: C, 52.94; H, 7.38; N, 7.96. $[\alpha]^{25}D$=4.0° (c 0.50, MeOH).

Example 29

5-(2-(4-Pyridinyl)ethyl)-3-(1-methyl-2-(S)-pyrrolidinylmethoxy)pyridine trihydrochloride 29a. 5-(2-(4-Pyridinyl)ethyl)-3-1-methyl-2-(S)-pyrrolidinylmethoxy)pyridine To a solution of 5-(2-(4-pyridinyl)ethyl)-3-(1-methyl-2-(S)-pyrrolidinylmethoxy)pyridine (100 mg, 0.34 mmol) in MeOH (3.0 mL) was added palladium(0) on charcoal (10%) (10 mg). The mixture was stirred at room temperature overnight. The solvent was removed and the residue was chromatographed on a silica gel column, eluting with $NH_4OH$/MeOH/EtOAc 0:1:9 and 1:10:90 to afford a light yellowish oil (87 mg, 87%). MS (CI/$NH_3$) m/z 298 (M+H)$^+$. $^1$H NMR (CDCl$_3$, 300 MHz) δ 1.65-2.07 (m, 4H), 2.27-2.36 (m, 1H), 2.49 (s, 3H), 2.59-2.61 (m, 1H), 2.93 (s, 3H), 3.08-3.18 (m, 1H), 3.86-4.02 (m, 2H), 6.96 (dd, J=3.0, 0.9 Hz, 1H), 7.08 (d, J=6.7 Hz, 1H), 8.04 (d, J=0.9 Hz, 1H), 8.19 (d, J=3.0 Hz, 1H), 8.50 (d, J=6.7 Hz, 1H).

29b. 5-(2-(4-pyridinyl)ethyl)-3-(1-methyl-2-(S)-pyrrolidinylmethoxy)pyridine trihydrochloride To a solution of 5-(2-(4-pyridinyl)ethyl)-3-(1-methyl-2-(S)-pyrrolidinylmethoxy)pyridine from step 29a (85 mg, 0.29 mmol) in THF (3.0 mL) was added hydrogen chloride (1.0M in Et$_2$O, 1.00 mL, 1.00 mmol). A precipitate formed was filtered, washed (Et$_2$O) and vacuum-dried to afford the hydrochloride salt (109 mg, 100%). mp. 148–150° C. MS (CI/$NH_3$) m/z 301 (M+H)$^+$. $^1$H NMR (D$_2$O, 300 MHz) δ 2.00-2.44 (m, 4H), 3.04 (s, 3H), 3.19-3.42 (m, 4H), 4.37-4.44 (m, 1H), 4.53-4.60 (m, 1H), 7.78 (dd, J=3.0 Hz, J=0.9 Hz, 1H), 7.87 (d, J=6.7 Hz, 1H), 8.17 (d, J=0.9 Hz, 1H), 8.32 (d, J=3.0 Hz, 1H), 8.63 (d, J=6.7 Hz, 1H). Anal. Calcd for $C_{18}H_{23}N_3O$·3.3 HCl·1.0 H$_2$O: C, 49.62; H, 6.55; N, 9.64. Found: C, 49.66; H, 6.52; N, 9.69. $[\alpha]^{25}D$=+1.7° (c 0.60, MeOH).

Example 30

5-(5,5-Dimethyl-1,3-hexadienyl)-3-(1-methyl-2-(S)-pyrrolidinylmethoxy)pyridine dihydrochloride 30a. 5-(5,5-Dimethyl-1,3-hexadienyl)-3-(1-methyl-2-(S)-pyrrolidinylmethoxy)pyridine To a solution of 5-bromo-3-(1-methyl-2-(S)-pyrrolidinylmethoxy)pyridine (272 mg, 3.0 mmol) in acetonitrile (3.0 mL) and triethylamine (2.5 mL) was added 5,5-dimethyl-1,3-hexadiene (0.50 mL), palladium acetate (23.0 mg, 0.1 mmol) and tri-o-tolylphosphine (122 mg, 0.1 mmol). After being heated in a sealed tube at 100° C. overnight, the resulting mixture was cooled to room temperature. Minimum amount of saturated sodium bicarbonate was added to free the amine hydrochloride salt, and the mixture was extracted with EtOAc, dried (MgSO$_4$), and concentrated. The residue was chromatographed on a silica gel column, eluting with CHCl$_3$/MeOH 10:1 to afford a light yellowish oil (225 mg, 75%). MS (CI/$NH_3$) m/z 301 (M+H)$^+$. $^1$H NMR (CDCl$_3$, 300 MHz) δ 1.08 (S, 9H), 1.55-1.77 (m, 3H), 1.98-2.10 (m, 1H), 2.37-2.47 (m, 1H), 2.50 (s, 3H), 2.64-2.73 (m, 1H), 3.07-3.17 (m, 1H), 3.90-4.06 (m, 2H), 5.93 (d, J=15.5 Hz, 1H), 6.16 (dd, J=15.5, 9.9 Hz, 1H), 6.42 (d, J=15.5 Hz, 1H), 6.78 (dd, J=9.9, 15.5 Hz, 1H), 7.21 (dd, J=3.0, 1.5 Hz, 1H), 8.14 (d, J=3.0 Hz, 1H), 8.19 (d, J=1.5 Hz, 1H).

30b. 5-(5,5-Dimethyl-1,3-hexadienyl)-3-(1-methyl-2-(S)-pyrrolidinylmethoxy)pyridine dihydrochloride To a solution of 5-(5,5-dimethyl-1,3-hexadienyl)-3-(1-methyl-2-(S)-pyrrolidinylmethoxy)pyridine from step 30a (140 mg, 0.47 mmol) in THF (3.0 mL) was added hydrogen chloride (1.0M in Et$_2$O, 1.07 mL, 1.07 mmol). A precipitate formed was filtered, washed (Et$_2$O) and vacuum-dried to afford the hydrochloride salt (137 mg, 78%). mp. 148–150° C. MS (CI/NH$_3$) m/z 301 (M+H)$^+$. $^1$H NMR (D$_2$O, 300 MHz) δ 1.07 (S, 9H), 2.03-2.47 (m, 4H), 3.05 (s, 3H), 3.22-3.32 (m, 1H), 3.71-3.83 (m, 1H), 3.92-4.01 (m, 1H), 4.43-4.49 (m, 1H), 4.57-4.84 (m, 1H), 6.19 (d, J=15.5 Hz, 1H), 6.34 (dd, J=15.5, 9.9 Hz, 1H), 6.59 (d, J=15.5 Hz, 1H), 7.50 (dd, J=9.9, 15.5 Hz, 1H), 7.93 (dd, J=3.0, 1.5 Hz, 1H), 8.25 (d, J=3.0 Hz, 1H), 8.38 (d, J=1.5 Hz, 1H). Anal. Calcd for C$_{19}$H$_{28}$N$_2$O·2.5 HCl·0.6 H$_2$O: C, 56.71; H, 7.94; N, 6.96. Found: C, 56.77; H, 7.96; N, 7.07. [α]$^{25}$D=4.4° (c 0.75, MeOH).

Example 31

5-(2-Naphthalenyl)-3-(1-methyl-2-(S)-pyrrolidinylmethoxy)pyridine dihydrochloride 31a. 5-(2-Naphthalenyl)-3-(1-methyl-2-(S)-pyrrolidinylmethoxy)pyridine To a solution of 2-bromonaphthalene (427 mg, 2.0 mmol) in THF (10.0 mL) was added sec-butyllithium (1.3M, 1.69 mL, 2.20 mmol) at −78° C. After half an hour at this temperature, trimethyl borate (0.341 mL, 2.20 mmol) was added. The reaction mixture was kept at the same temperature for one hour then slowly warmed up to room temperature. Solvent was removed, benzene (4.0 mL), sodium carbonate (2.0M, 2.0 mL), tetrakis(triphenylphosphine)palladium(0) (70 mg, 0.06 mmol) and 5-bromo-3-(1-methyl-2-(S)-pyrrolidinylmethoxy)pyridine (272.0 mg, 1.0 mmol) were added. The reaction mixture was refluxed overnight then cooled to room temperature. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with NH$_4$OH/MeOH/EtOAc 0:1:9 and 1:10:90 to afford an oil (242 mg, 76%). MS (CI/NH$_3$) m/z 319 (N+H)$^+$. $^1$H NMR (CDCl$_3$, 300 MHz) δ 1.75-2.12 (m, 4H), 2.28-2.40 (m, 1H), 2.53 (s, 3H), 2.67-2.77 (m, 1H), 3.11-3.18 (m, 1H), 4.02-4.15 (m, 2H), 7.50-7.56 (m, 3H), 7.68-7.73 (m, 1H), 7.86-7.96 (m, 3H), 8.04 (s, 1H), 8.33 (s, 1H), 8.59 (s, 1H).

31b. 5-(2-Naphthalenyl -3-(1-methyl-2-(S)-pyrrolidinylmethoxy)pyridine dihydrochloride To a solution of 5-(2-naphthalenyl)-3-(1-methyl-2-(S)-pyrrolidinylmethoxy)-pyridine from step 31b (282 mg, 0.77 mmol) in THF (3.0 mL) was added hydrogen chloride (1.0M in Et$_2$O, 1.91 mL, 1.91 mmol). A precipitate formed which was filtered, washed (Et$_2$O) and vacuum-dried to afford the hydrochloride salt (300 mg, 100%). mp. 248–251° C. MS (CI/NH$_3$) m/z 319 (M+H)$^+$. $^1$H NMR (D$_2$O, 300 MHz) δ 2.03-2.51 (m, 4H), 3.07 (s, 3H), 3.23-3.36 (m, 1H), 3.74-3.83 (m, 1H), 3.86-3.99 (m, 1H), 4.36-4.45 (m, 1H), 4.50-4.58 (m, 1H), 7.60-7.67 (m, 2H), 7.72-7.78 (m, 1H), 7.93-8.05 (m, 4H), 8.12 (s, 1H), 8.24 (s, 1H), 8.58 (s, 1H). Anal. Calcd for C$_{21}$H$_{22}$N$_2$O·2.1 HCl: C, 63.86; H, 6.15; N, 7.09. Found: C, 63.85; H, 6.06; N, 7.01. [α]$^{25}$D=5.8° (c 1.1, MeOH).

Example 32

5-Acetyl-6-chloro-3-(2-(S)-pyrrolidinylmethoxy)pyridine dihydrochloride 32a. 5-(1-Ethoxyvinyl)-6-chloro-3-(2-(S)-pyrrolidinylmethoxy)pyridine To a solution of 5-bromo-6-chloro-3-(1-BOC-2-(S)-pyrrolidinylmethoxy)pyridine (500 mg, 1.28 mmol) in toluene (10.0 mL) was added (1-ethoxyvinyl)tributyltin (489 mL, 1.41 mmol) and tetrakis(triphenylphosphine)palladium (0) (45 mg, 0.–45 mmol). After being refluxed overnight, the resulting mixture was cooled to room temperature. Solvent was removed and the residue was chromatographed on a silica gel column, eluting with hexane/EtOAc 2:1 and 1:1 to afford an oil (568 mg, >100%; some tin reagent contamination). MS (CI/NH$_3$) m/z 383 (M+H)$^+$. $^1$H NMR (CDCl$_3$, 300 MHz)δ 1.25-1.45 (m, 3H), 1.47 (s, 9H), 1.55-1.71 (m, 1H), 1.98-2.07 (m, 3H), 3.32-3.45 (m, 1H), 3.87-3.96 (m, 2H), 4.05-4.21 (m, 3H), 4.43-4.47 (m, 2H), 7.26-7.34 (m, 1H), 8.03-8.06 (m, 1H).

32b. 5-Acetyl-6-chloro-3-(2-(S)-pyrrolidinylmethoxy)pyridine dihydrochloride

To a solution of 5-(1-ethoxyvinyl)-6-chloro-3-(1-BOC-2-(S)-pyrrolidinylmethoxy)pyridine from step 32a (165 mg, 0.43 mmol) was added hydrogen chloride (4.0M in 1,4-dioxane, 4.0 mL), and the mixture was stirred at room temperature for two days. The precipitate formed was filtered, washed (Et$_2$O) and vacuum-dried to afford the hydrochloride salt (92 mg, 73%). mp 173–176° C. MS (CI/NH$_3$) m/z 255 (M+H)$^+$. $^1$H NMR (D$_2$O, 300 MHz) δ 1.90-2.36 (m, 4H), 2.71-2.75 (m, 1H), 3.39-3.46 (m, 2H), 4.09-4.20 (m, 1H), 4.25-4.33 (m, 1H), 4.50-5.56 (m, 1H), 4.75-5.86 (m, 2H), 7.76 (d, J=3.0 Hz, 1H), 8.26 (d, J=3.0 Hz, 1H). Anal. Calcd for C$_{12}$H$_{15}$N$_2$O$_2$C·1.2 HCl·0.1 H$_2$O: C, 47.97; H, 5.34; N, 9.04. Found: C, 48.00; H, 5.50; N, 9.30. [α]$^{25}$D=+12° (c 0.60, MeOH).

Example 33

5-(2-(4-Pyridinyl)ethenyl)-6-chloro-3-(2-(S)-pyrrolidinylmethoxy)pyridine dihydrochloride 33a. 5-(2-(4-Pyridinyl)ethenyl)-6-chloro-3-(1-BOC-2-(S)-pyrrolidinylmethoxy)pyridine To a solution of 5-bromo-6-chloro-3-(1-BOC-2-(S)-pyrrolidinylmethoxy)pyridine added 4-vinylpyridine (156 mg, 1.5 mmol), palladium acetate (29.0 mg, 0.12 mmol), tri-o-tolylphosphine (156 mg, 0.12 mmol) and triethylamine (3.2 mL). The reaction mixture was heated in a sealed tube at 100° C. overnight, then cooled to room temperature. Minimum amount of saturated sodium bicarbonate was added to free the amine hydrochloride salt, and the mixture was extracted with EtOAc, dried (MgSO$_4$), and concentrated. The residue was chromatographed on a silica gel column, eluting with 4 to 50% Et$_2$O in hexane) to give the title compound (282 mg). MS (CI/NH$_3$) m/z 416 (M+H)$^+$.

33b. 5-(2-(4-Pyridinyl)ethenyl)-6-chloro-3-(2-(S)-pyrrolidinylmethoxy)pyridine dihydrochloride To a solution of 5-(2-(4-Pyridinyl)ethenyl)-6-chloro-3-(1-BOC-2-(S)-pyrrolidinylmethoxy)pyridine from step 33a (100 mg) was added hydrogen chloride (4.0 M in 1,4-dioxane, 4.0 mL), and the mixture was stirred at room temperature for two days. The precipitate formed was filtered, washed (Et$_2$O) and vacuum-dried to afford the hydrochloride salt (92 mg, 73%). mp 235–240° C. MS (CI/NH$_3$) m/z 316 (M+H)$^{+·}$ $^1$H NMR (D$_2$O, 300 MHz) δ1.76–2.22 (m, 4H), 2.25–3.80 (m, 1H), 3.43 (t, J=7.2, 1H), 4.18 (dq, J=3.8, 8.0, 1H), 4.32 (dd, J=7.8, 10.8, 1H), 4.53 (dd, J=3.3, 10.5, 1H), 7.45 (d, J=16.3, 1H), 7.90 (d, J=3.0, 1H), 7.96 (d, J=16.3, 1H), 8.16 (d, J=2.7, 1H), 8.20 (d, J=7.2, 2H), 8.71 (d, J=7.0, 2H). Anal. Calcd for $C_{17}H_{18}N_3OCl \cdot 2.8$ HCl: C, 48.63; H, 5.47; N, 10.01. Found: C, 48.73; H, 5.47; N, 9.86. $[\alpha]^{25}D=+1.78°$ (c 0.45, MeOH).

Example 34

5-3-Pyridinyl)-6-chloro-3-(2-(S)-pyrrolidinylmethoxy) pyridine dihydrochloride 34a. 5-(3-Pyridinyl)-6-chloro-3-(1-BOC-2-(S)-pyrrolidinylmethoxy)pyridine To a solution of 5-bromo-6-chloro-3-(1-BOC-2-(S)-pyrrolidinylmethoxy)pyridine (from Example 23a, 500 mg, 1.28 mmol) in toluene (10.0 mL) was added 3-pyridinyltributyltin (564 mg, 1.5 mmol) and tetrakis (triphenylphosphine)palladium(0) (45 mg, 0.039 mmol). After being refluxed overnight, the resulting mixture was cooled to room temperature. Solvent was removed and the residue was chromatographed on a silica gel column, eluting with hexane/EtOAc 2:1 and 1:1 to afford an oil (428 mg, 86%). MS (CI/NH$_3$) m/z 390 (M+H)$^{+\cdot}$ $^1$H NMR (CDCl$_3$, 300 MHz) δ1.24–1.67 (m, 2H), 1.44 (s, 9H), 1.86– 2.10 (m, 2H), 3.32–3.45 (m, 2H), 3.95–4.27 (m, 3H), 7.28–7.44 (m, 2H), 7.81–7.86 (m, 1H), 8.14–8.17 (m, 1H), 8.65–8.73 (m, 2H).

34b. 5-(3-Pyridinyl)-6-chloro-3-(2-(S)-pyrrolidinylmethoxvy)pyridine dihydrochloride To a solution of 5-(3-pyridinyl)-6-chloro-3-(1-BOC-2-(S)-pyrrolidinylmethoxy)pyridine from step 34a (170 mg, 0.44 mmol) was added HCl (4.0 M in 1,4-dioxane, 3.0 mL), and the mixture was stirred at room temperature for two days. The precipitate formed was filtered, washed (Et$_2$O) and vacuum-dried to afford the hydrochloride salt (92 mg, 73%). mp 195–198° C. MS (CI/NH$_3$) m/z 290 (M+H)$^{+\cdot}$ $^1$H NMR (D$_2$O, 300 MHz) δ1.90–2.34 (m, 4H), 3.36–3.45 (m, 2H), 4.09–4.20 (m, 1H), 4.26–4.33 (m, 1H), 4.50–4.56 (m, 1H), 7.64–7.67 (m, 1H), 8.04–8.09 (m, 1H), 8.24–8.28 (m, 1H), 8.58–8.64 (m, 1H), 8.80–8.5 (m, 1H), 8.93–8.97 (m, 1H). Anal. Calcd for $C_{15}H_{16}N_3OCl \cdot 2.0$ HCl: C, 49.68; H, 5.00; N, 11.59. Found: C, 49.50; H, 4.99; N, 11.32. $[\alpha]^{25}D=+56°$ (c 1.00, MeOH).

Example 35

5-(3-Quinolinyl)-3-(1-methyl-2-(S)-pyrrolidinylmethoxy)pyridine trihydrochloride 35a. Ouinoline-3-boronic acid 3-Bromoquinoline (0.4 mL, 3 mmol) was dissolved in THF, and the solution was cooled to −78° C. To this solution was added t-butyllithium (4.1 mL, 7 mmol), and the reaction mixture was stirred for 20 minutes. Trimethyl borate (0.81 mL, 7.1 mmol) was added at −78° C., and the mixture was stirred and allowed to warm to room temperature. The reaction was quenched with water, and the solvents were removed under vacuum. The residue 180 mg was taken directly to the next step.

35b. 5-(3-Quinolinyl)-3-(1-methyl-(2-(S)-pyrrolidinylmethoxy)pyridine

To a solution of the compound from step 35a and 5-bromo-3-(1-methyl-2-(S)-pyrrolidinylmethoxy)-pyridine (271 mg, 1.0 mmol) in toluene (5.0 mL) was added Pd(0) (25 mg) and Na$_2$CO3 (1 mL of a 2 M solution), and the mixture was heated at reflux for 4 hours. The solvent was removed under vacuum, and the residue was purified by chromatography on silica gel, eluting with 2 to 5% MeOH in CH$_2$Cl$_2$ in a first column, followed by rechromatography, eluting with 0.1 to 1% Et$_2$O in hexane, to afford 120 mg of the title compound. MS (CI/NH$_3$) m/z 320 (M+H)$^{+\cdot}$ $^1$H NMR (CDCl$_3$, 300 MHz) δ1.82, (m, 3H), 2.06 (m, 1H), 2.34 (m, 1H), 2.52 (s, 3H), 2.73 (m, 1H), 3.13 (m, 1H), 4.09 (m, 2H), 7.52 (m, 1H), 7.62, (m, 1H), 7.76 (m, 1H), 7.90 (m, 1H), 8.16 (m, 1H), 8.32 (m, 1H), 8.40 (m, 1H), 8.58 (m, 1H).

35c. 5-(3-Quinolinyl)-3-(1-methyl2-(S)-pyrrolidinylmethoxy)pyridine trihydrochloride To a solution of 5-(3-Quinolinyl)-3-(2-(S)-pyrrolidinylmethoxy)pyridine from step 35b (117.2 mg) in THF/Et$_2$O (1.0 mL) was added hydrogen chloride (1.0 M in Et$_2$O, 0.90 mL). A precipitate formed which was filtered, washed (Et$_2$O) and vacuum-dried to afford the hydrochloride salt (133 mg). mp 184–186° C. MS (CI/NH$_3$) m/z 320 (M+H)$^{+\cdot}$ $^1$H NMR (D$_2$O, 300 MHz) δ9.47 (d, J=2.0 Hz, 1H), 9.36 (d, J=20 Hz, 1H), 8.85 (dd, J=1.7 Hz, 1H), 8.63 )d, J=2.7 Hz, 1H), 8.34 (m, 3H), 8.20 (m, 1H), 8.01 (m, 1H), 4.73 (m, 1H), 4.57 (dd, J=5.8, 11.2 Hz1H), 4.03 (m, 1H), 3.81 (m, 1H), 3.30 (m, 1H), 3.10 (s, 3H), 2.45 (m, 1H), 2.29–2.12 (br, 3H). Anal. Calcd for $C_{20}H_{21}N_3O \cdot 3.1$ HCl$\cdot 0.3$ H$_2$O: C, 54.87; H, 5.69; N, 9.59. Found: C, 55.22; H, 5.87; N, 9.14. $[\alpha]^{25}D=-8.15°$ (c 0.54, MeOH).

Example 36

5-(1-methyl-2-indolyl)-3-(1-methyl-2-(S)-pyrrolidinylmethoxy)pyridine hydrochloride 36a. 1-methylindol-2-boronic acid 1-Methylindole (0.38 mL, 3 mmol) was dissolved in THF (10 mL), and the solution was cooled to −78° C. To this solution was added sec-butyllithium (1.9 mL, 2.5 mmol), and the reaction mixture was stirred for 20 minutes. Trimethyl borate (0.34 mnL, 3 mmol) was added at −78° C., and the mixture was stirred and allowed to warm to room temperature. The reaction was quenched with water, and the solvents were removed under vacuum. The residue was taken directly to the next step.

36b. 5-(1-methyl-2-indolyl)-3-(1-methyl-2-(S)-pyrrolidinylmethoxy)pyridine

To a solution of the compound from step 36a and 5-bromo-3-(1-methyl-2-(S)-pyrrolidinylmethoxy)-pyridine (270 mg, 1.0 mmol) in toluene (5.0 mL) was added Pd(0) (25 mg) and Na$_2$CO3 (1 mL of a 2 M solution), and the mixture was heated at reflux for 60 hours. The solvent was removed under vacuum, and the residue was purified by chromatography on silica gel to afford 105 mg of the title compound. MS (CI/NH$_3$) m/z 322 (M+H)$^{+\cdot}$ $^1$H NMR (CDCl$_3$, 300 MHz) δ1.80 (m, 3H), 2.05 (m, 1H), 2.32 (m, 1H), 2.50 (s, 3H), 2.70 (m, 1H), 3.13 (m, 1H), 3.78 (s, 3H), 4.04 (m, 2H), 6.62 (s, 1H), 7.18 (m, 2H), 7.35 (m, 2H), 7.66 (m, 1H), 8.38 (m, 2H).

36c. 5(1-methyl-2-indolyl)-3-(1-methyl-2-(S)-pyrrolidinylmethoxy)pyridine hydrochloride To a solution of the compound from step 36b (117.2 mg) in THF/Et$_2$O was added hydrogen chloride (1.0 M in Et$_2$O). A precipitate formed which was filtered, washed (Et$_2$O) and vacuum-dried to afford the hydrochloride salt. mp 195–197° C. MS (CI/NH$_3$) m/z 322 (M+H)$^{+\cdot}$ $^1$H NMR (D$_2$O, 300 MHz) δ8.37 (d, J=1.6 Hz, 1H), 8.32 (d, J=2.8 Hz, 1H), 7.58 (m, 2H), 7.51 (d, J=8.4 Hz, 1H), 7.22 (m, 1H), 7.09 (m, 1H), 4.13 (m, 1H), 4.01 (m, 1H), 4.03 (m, 1H), 3.78 (s, 3H), 2.95 (m, 1H), 2.61 (m, 1H), 2.20 (m, 1H), 1.93 (m, 1H), 1.72–1.60 (m, 3H). Anal. Calcd for $C_{20}H_{23}N_3O \cdot 1.4$ HCl: C, 64.49; H, 6.60; N, 11.28. Found: C, 64.37; H, 6.71; N, 10.90. $[\alpha]^{25}D=-12.59°$ (c 1.00, MeOH).

Example 37

5-(3,5-bis(trifluoromethyl)phenyl)-3-(1-methyl-2-(S)-pyrrolidinylmethoxy)pyridine dihydrochloride 37a. 5-(3,5-bis(trifluoromethyl)phenyl)-3-(1-methyl-2-(S)-pyrrolidinylmethoxy)-pyridine To a solution of 3,5-bis(trifluoromethyl)phenylboronic acid (0.55 g, 2.0 mmol, Lancaster Chem Co.) and 5-bromo-3-(1-methyl-2-(S)-pyrrolidinylmethoxy)-pyridine (300 mg, 1.1 mmol) in toluene (5.0 mL) was added Pd(0) (25 mg) and Na$_2$CO3 (1 mL of a 2 M solution), and the mixture was heated at reflux. The solvent was removed under vacuum, and the residue was purified by chromatography on silica gel to afford 225 mg of the title compound. MS (CI/NH$_3$) m/z 405 (M+H)$^+$ $^1$H NMR (CDCl$_3$, 300 MHz) δ1.83 (m, 3H), 2.08 (m, 1H), 2.36 (m, 1H), 2.54 (s, 3H), 2.78 (m, 1H), 3.17 (m, 1H), 4.10 (m, 2H), 7.42 (m, 1H), 7.92 (s, 1H), 8.00 (s, 2H), 8.42 (m, 1H), 7.92 (s, 1H), 8.00 (s, 2H), 8.42 (m, 1H), 8.48 (m, 1H).

37b. 5-(3,5-bis(trifluoromethyl)phenyl-3-(1-methyl-2-(S)-pyrrolidinylmethoxy)-pyridine dihydrochloride To a solution of the compound from step 37a (225 mg) in THF/Et$_2$O was added hydrogen chloride (1.0 M in Et$_2$O). A precipitate formed which was filtered, washed (Et$_2$O) and vacuum-dried to afford the hydrochloride salt (195 mg). mp 68–70° C. MS (CI/NH$_3$) m/z 405 (M+H)$^+$ $^1$H NMR (D$_2$O, 300 MHz) δ8.66 (d, J=1.7 Hz, 1H), 8.50 (d, J=2.7 Hz, 1H), 8.28 (s, 2H), 8.22 (s, 1H), 8.06 (m, 1H), 4.67 (dd, J=3.8, J=11.9 Hz, 1H), 4.52 (dd, J=6.2, 11.2 Hz, 1H), 4.00 (m, 1H), 3.80 (m, 1H), 3.28 (m, 1H), 3.07 (s, 3H), 2.42 (m, 1H), 2.24 (m, 1H), 2.12 (m, 2H). Anal. Calcd for C$_{18}$H$_{19}$N$_3$OF$_6$·2 HCl: C, 47.82; H, 4.22; N, 5.87. Found: C, 47.60; H, 4.53; N, 5.86. [α]$^{25}$D=−6.60° (c 0.53, MeOH).

Example 38

5-(4-chlorophenyl)-3-(1-methyl-2-(S)-pyrrolidinylmethoxy)pyridine dihydrochloride Following the procedures of Example 37b, except substituting 4-chlorophenylboronic acid for the boronic acid reagent thereof and Pd(Ph$_3$P)$_4$ for the Pd(0), and carrying the product forward as in step 37c, the title compound was prepared (190 mg). mp 224–226° C. MS (CI/NH$_3$) m/z 302 (M+H)$^+$ $^1$H NMR (D$_2$O, 300 MHz) δ8.48 (d, J=1.7 Hz, 1H), 8.32 (d, J=2.7, 1H), 7.75 (t, J=2.4, 1H), 7.65 (m, 2H), 7.56 (m, 2H), 4.58 (dd, J=3.1, 11.2 Hz, 1H), 4.41 (dd, J=5.7, 11.1 Hz, 1H), 3.95 (m, 1H), 3.77 (m, 1H), 3.27 (m, 1H), 3.06 (s, 3H), 2.42 (m, 1H), 2.23 (m, 1H), 2.13 (m, 2H). Anal. Calcd for C$_{17}$H$_{19}$N$_2$OCl·2 HCl·0.1 H$_2$O: C, 54.09; H, 5.66; N, 7.42. Found: C, 53.75; H, 5.62; N. 7.07. [α]$^{25}$D=−5.07° (c 0.67, MeOH).

Example 39

5-(2,4-dichlorophenyl)-3-(1-methyl-2-(S)-pyrrolidinylmethoxy)pyridine dihydrochloride Following the procedures of Example 37b, except substituting 2,4-dichlorophenylboronic acid for the boronic acid reagent thereof and Pd(Ph$_3$P)$_4$ for the Pd(0), and carrying the product forward as in step 37c, the title compound was prepared (96 mg). mp 176–178° C. MS (CI/NH$_3$) m/z 337 (M+H)$^+$ $^1$H NMR (D$_2$O, 300 MHz) δ8.41 (d, J=2.5 Hz, 1H), 8.36 (d, J=1.4, 1H), 7.77 (m, 1H), 7.50 (dd, J=2.2, 8.5, 1H), 7.43 (d, J=8.1, 2H), 4.58 (dd, J=3.3, 11.4, 1H), 4.42 (dd, J=5.9, 11.0, 1H), 3.95 (m, 1H), 3.76 (m, 2H), 3.26 (m, 1H), 3.05 (s, 3H), 2.41 (m, 1H), 2.21 (m, 1H), 2.09 (m, 2H). Anal. Calcd for C$_{17}$H$_{18}$N$_2$OCl$_2$·2 HCl·0.6 MeO: C, 49.23; H, 5.26; N, 6.52. Found: C, 49.38; H, 5.47; N, 6.17. [α]$^{25}$D=−7.67° (c 0.86, MeOH).

Example 40

5-(2-phenylethynyl)-3-(1-methyl-2-(S)-pyrrolidinylmethoxy)pyridine dihydrochloride To a solution of 5-bromo-3-(1-methyl-2-(S)-pyrrolidinylmethoxy)pyridine (272 mg, 1 mmol) in 6 mL of CH$_2$Cl$_2$ was added triethylamine (0.5 mL), Pd(II) (19 mg), CuI (a catalytic amount) and 0.22 mL of phenylacetylene (2 mmol). The reaction mixture was heated at reflux for 40 hours. The solvent was removed under reduced pressure, and the free base was purified by chromatography, eluting with 2 to 6% MeOH in CH$_2$Cl$_2$. MS (CI/NH$_3$) m/z 293 (M+H)$^+$ $^1$H NMR (CDCl$_3$, 300 MHz) δ2.07 (m, 2H), 2.25 (m, 2H), 2.81 (m, 1H), 2.88 (s, 3H), 3.47 (m, 1H), 3.67 (m, 1H), 4.23 (m, 1H), 4.64 (m, 1H), 7.38 (m, 4H), 7.54 (m, 2H), 8.28 (m, 1H), 8.42 (m, 1H). The salt was prepared by treatment with HCl in Et$_2$O, as described above to give 90 mg of the title compound. mp 190–192° C. MS (CI/NH$_3$) m/z 293 (M+H)$^+$ $^1$H NMR (D$_2$O, 300 MHz) δ8.39 (d, J=1.5, 1H), 8.30 (d, J=2.6, 1H), 7.65 (m, 3H), 7.48 (m, 3H), 4.54 (dd, J=3.3, 11.0, 1H), 4.38 (dd, J=5.9, 11.4, 1H), 3.94 (br, 1H), 3.26 (br, 1H), 3.05 (s, 3H), 2.41 (m, 1H), 21.4 (m, 1H), 2.09 (m, 2H). Anal. Calcd for C$_{19}$H$_{20}$N$_2$O·2.2 HCl: C, 61.25; H, 6.01; N, 7.52. Found: C, 61.14; H, 5.84; N, 7.52. [α]$^{25}$D=−10.00° (c 0.22, MeOH).

Example 41

5-(4-methylphenyl)-3-(1-methyl-2-(S)-pyrrolidinylmethoxy)pyridine dihydrochloride Following the procedures of Example 37b, except substituting 4-methylphenylboronic acid for the boronic acid reagent thereof and Pd(Ph$_3$P)$_4$ for the Pd(0), then carrying the product forward as in step 37c, the title compound was prepared (100 mg). mp 204–206° C. MS (CI/NH$_3$) m/z 283 (M+H)$^+$ $^1$H NMR (D$_2$O, 300 MHz) δ8.52 (s, 1H), 8.32 (d, J=2.7, 1H), 7.83 (m, 1H), 7.63 (d, J=8.1, 2H), 7.42 (d, J=8.2, 2H), 4.60 (dd, J=4.5, 11.1, 1H), 4.43 (dd, J=6.1, 11.5, 1H), 3.95 (m, 1H), 3.76 (m, 1H), 3.27 (m, 1H), 3.06 (s, 3H), 2.42 (m, 1H), 2.41 (s, 3H), 2.23 (m, 1H), 2.12 (m, 2H). Anal. Calcd for C$_{18}$H$_{22}$N$_2$O·2.5 HCl·0.5 H$_2$O: C, 56.52; H, 6.72; N, 7.32. Found: C, 56.22; H, 6.85; N, 6.94. [α]$^{25}$D=−5.48° (c 0.42, MeOH).

Example 42

5-(3-chloro-4-fluorophenoyl)-3-(1-methyl-2-(S)-pyrrolidinylmethoxy)pyridine dihydrochloride Following the procedures of Example 37b, except substituting 3-chloro-4-fluorophenylboronic acid for the boronic acid reagent thereof and Pd(Ph$_3$P)$_4$ for the Pd(0), then carrying the product forward as in step 37c, the title compound was prepared (120 mg). mp 202–204° C. MS (CI/NH$_3$) m/z 321 (M+H)$^+$ $^1$H NMR (D$_2$O, 300 MHz) δ8.54 (s, 1H), 8.41 (d, J=2.4, 1H), 7.95 (s, 1H), 7.84 (dd, J=2.4, 6.8, 1H), 7.63 (m, 1H), 7.41 (t, J=8.8, 1H), 4.64 (dd, J=3.0, 11.2, 1H), 4.47 (dd, J=6.2, 11.2, 1H), 3.98 (m, 1H), 3.78 (m, 1H), 3.28 (m, 1H), 3.07 (s, 3H), 2.42 (m, 1H), 2.23 (m, 1H), 2.13 (m, 2H). Anal. Calcd for C$_{17}$H$_{18}$N$_2$OClF·2 HCl·0.5 MeO·0.4 H$_2$O: C, 50.41; H, 5.51; N, 6.72. Found: C, 50.41; H, 5.43; N, 6.37. [α]$^{25}$D=−4.64° (c 0.69, MeOH).

Example 43

5-(3-aminophenyl-3-(1-methyl-2-(S)-pyrrolidinylmethoxy)pyridine dihydrochloride Following the procedures of Example 37b, except substituting 3-aminophenylboronic acid for the boronic acid reagent thereof and Pd(Ph$_3$P)$_4$ for the Pd(0), then carrying the product forward as in step 37c, the title compound was prepared (250 mg). mp 80–82° C. MS (CI/NH$_3$) m/z 283 (M+H)$^+$ $^1$H NMR (D$_2$O, 300 MHz) δ8.58 (m, 1H), 8.40 (m, 1H), 7.98 (m, 1H), 7.53 (m, 1H), 7.44 (m, 1H), 7.37 (m, 1H), 7.21 (m, 1H), 4.64 (dd, J=3.1, 11.2, 1H), 4.48 (dd, J=6.1, 11.2, 1H), 3.98 (m, 1H), 3.78 (m, 1H), 3.28 (m, 1H), 3.07 (s, 3H), 2.43 (m, 1H), 2.24–2.08 (m, 3H). Anal. Calcd for C$_{17}$H$_{21}$N$_3$O·2.2 HCl·0.8 H$_2$O: C, 54.02; H, 6.61; N,11.12. Found: C, 53.96; H, 6.62; N, 10.82. [α]$^{25}$D=−7.50° (c 1.00, MeOH).

Example 44

5-(2-formylphenyl)-3-(1methyl-2-(S)-pyrrolidinylmethoxy)pyridine dihydrochloride Following the procedures of Example 37b, except substituting 2-formylphenylboronic acid for the boronic acid reagent thereof and Pd(Ph$_3$P)$_4$ for the Pd(0), then carrying the product forward as in step 37c, the title compound was prepared (250 mg). MS (CI/NH$_3$) m/z 297 (M+H)$^+$ $^1$H NMR (D$_2$O, 300 MHz) δ9.89 (s, 1H), 8.44 (m, 1H), 8.31 (m, 1H), 8.07 (m, 1H), 7.85 (m, 1H), 7.73 (m, 2H), 7.54 (m, 1H), 4.58 (dd, J=3.0, 11.1, 1H), 4.42 (dd, J=5.9, 11.0, 1H), 3.95 (m, 1H), 3.75 (m, 1H), 3.27 (m, 1H), 3.06 (s, 3H), 2.42 (m, 1H), 2.23 (m, 1H), 2.13 (m, 2H). Anal. Calcd for C$_{18}$H$_{20}$N$_2$O·2 HCl: C, 58.54; H, 6.00; N, 7.59. Found: C, 58.61; H, 6.16; N, 7.62. [α]$^{25}$D=−7.06° (c 0.42, MeOH).

Example 45

5-(2methylphenyl)-3-(1-methyl-2-(S)-pyrrolidinylmethoxy)pyridine dihydrochloride Following the procedures of Example 37b, except substituting 2-methylphenylboronic acid for the boronic acid reagent thereof and Pd(Ph$_3$P)4 for the Pd(0), then carrying the product forward as in step 37c, the title compound was prepared (140 mg). MS (CI/NH$_3$) m/z 283 (M+H)$^+$ $^1$H NMR (D$_2$O, 300 MHz) δ9.89 (s, 1H), 8.57 (s, br, 1H), 8.40 (s, br, 1H), 7.94 (s, br, 1H), 7.37 (m, 2H), 7.31 (m, 2H), 4.63 (dd, J=3.4, 11.2, 1H), 3.97 (m, 1H), 3.29–3.22 (m, 1H), 3.09 (s, 3H), 2.44 (m, 1H), 2.31 (s, 3H), 2.24 (m, 1H), 2.18–2.09 (m, 2H). Anal. Calcd for C$_{18}$H$_{22}$N$_2$O·2 HCl: C, 60.85; H, 6.81; N, 7.88. Found: C, 61.06; H, 6.96; N, 7.85. [α]$^{25}$D=−13.80° (c 0.36, MeOH).

Example 46

5-(4-(trifluoromethyl)phenyl)-3-1-methyl-2-(S)-pyrrolidinylmethoxy)pyridine dihydrochloride Following the procedures of Example 37b, except substituting 4-(trifluoromethyl)phenylboronic acid for the boronic acid reagent thereof and Pd(Ph$_3$P)$_4$ for the Pd(0), then carrying the product forward as in step 37c, the title compound was prepared (200 mg). MS (CI/NH$_3$) m/z 337 (M+H)$^+$ $^1$H NMR (D$_2$O, 300 MHz) ε8.52 (d, J=1.5, 1H), 8.35 (d, J=2.6, 1H), 7.84 (s, 4H), 7.78 (m, 1H), 4.59 (dd, J=2.9, 11.0, IH), 4.42 (dd, J=6.3, 11.4, 1H), 3.96 (m, 1H), 3.78 (m, 1H), 3.28 (m, 1H), 3.07 (s, 3H), 2.43 (m, 1H), 2.25 (m, 1H), 2.14 (m, 2H). Anal. Calcd for C$_{18}$H$_{19}$N$_2$OF$_3$·2.2 HCl·0.2 H$_2$O: C, 51.45; H, 5.18; N, 6.70. Found: C, 51.41; H, 5.15; N, 6.36. [α]$^{25}$D=−4.70° (c 0.60, MeOH).

Example 47

5-(3,3-dimethylbutynyl)-3-(1-methyl-2(S)-pyrrolidinylmethoxy)pyridine dihydrochloride To a solution of 5-bromo-3-(1-methyl-2-(S)-pyrrolidinylmethoxy)pyridine 270 mg, 1 mmol) in 5 mL of CH$_2$Cl$_2$ was added triethylamine (0.5 mL), Pd(II) (19 mg), CuI (a catalytic amount) and 0.3 mL of 3,3-dimethyl-1-butyne (2 mmol). The reaction mixture was heated at reflux for 40 hours. The mixture was diluted with CH$_2$Cl$_2$, and 2 mL of 10% NaOH were added. The organic layer was separated and dried, and the solvent was removed under reduced pressure. The free base was purified by chromatography, eluting with 1 to 2% MeOH in CH$_2$Cl$_2$. MS (CI/NH$_3$) m/z 273 (M+H)$^+$ $^1$H NMR (CDCl$_3$, 300 MHz) δ1.32 (s, 9H), 1.80 (br m, 3H), 2.05 (m, 1H), 2.36 (m, 1H), 2.52 (s, 3H), 2.73 (m, 1H), 3.17 (m, 1H), 3.95 (m, 1H), 4.05 (m, 1H), 7.18 (m, 1H), 8.20 (m, 2H). The salt was prepared by treatment with HCl in Et$_2$O, as described above, to give 100 mg of the title compound. MS (CI/NH$_3$) m/z 273 (M+H)$^+$ $^1$H NMR (D$_2$O, 300 MHz) δ8.44 (d, J=2.2, 1H), 8.40 (s, 1H), 8.01 (m, 1H), 4.61 (dd, J=2.9, 11.1, 1H), 4.54 (dd, J=5.5, 11.0, 1H), 3.96 (m, 1H), 3.26 (m, 1H), 3.05 (s, 3H), 2.41 (m, 1H), 2.22 (m, 1H), 2.10 (m, 2H). Anal. Calcd for C$_{17}$H$_{24}$N$_2$O·2.0 HCl·0.4 H$_2$O: C, 57.92; H, 7.66; N, 7.95. Found: C, 58.10; H, 7.74; N, 7.57. [α]$^{25}$D=−7.70° (c 1.46, MeOH).

Example 48

5-(2-(4-methylphenyl)ethynyl)-3-(1-methyl-2-(S)-pyrrolidinylimethoxy)pyridine dihydrochloride To a solution of 5-bromo-3-(1-methyl-2-(S)-pyrrolidinylmethoxy)pyridine (200 mg, 0.7 mmol) in 5 mL of CH$_2$Cl$_2$ was added triethylamine (0.4 mL), Pd(ll) (12 mg), CuI (a catalytic amount) and 0.15 mL of 2-methyl-5-ethynylpyridine (0.14 mmol). The reaction mixture was heated at reflux for 40 hours. The mixture was diluted with CH$_2$Cl$_2$, and 2 mL of 10% NaOH were added. The organic layer was separated and dried, and the solvent was removed under reduced pressure. The free base was purified by chromatography, eluting with 1 to 2% MeOH in CH$_2$Cl$_s$. MS (CI/NH$_3$) m/z 307 (M+H)$^+$ $^1$H NMR (CDCl$_3$, 300 MHz) δ1.50 (m, 3H), 1.79 (m, 3H), 2.04 (m, 1H), 2.30 (m, 1H), 2.50 (s, 3H), 2.67 (m, 1H), 3.12 (m, 1H), 3.98 (m, 2H), 7.18 (m, 2H), 7.32 (m, 1H), 7.43 (m, 2H), 8.26 (m, 1H). The salt was prepared by treatment with HCl in Et$_2$O, as described above, to give 120 mg of the title compound. mp 197–199° C. MS (CI/NH$_3$) m/z 307 (M+H)$^+$ $^1$H NMR (D$_2$O, 300 MHz) δ8.49 (d, J=1.5, 1H), 8.42 (d, J=2.6, 1H), 7.98 (m, 1H), 7.55 (d, J=8.1 (2H), 7.32 (d, J=7.7, 2H), 4.60 (dd, J=3.0, 11.1, 1H), 4.44 (dd, J=5.9, 11.4, 1H), 3.96 (m, 1H), 3.77 (m, 1H), 3.26 (m, 1H), 3.05 (s, 3H), 2.41 (m, 1H), 2.38 (s, 3H), 2.23 (m, 1H), 2.12 (m, 2H). Anal. Calcd for C$_{22}$H$_{24}$N$_2$O·2.0 HCl·1.1 H$_2$O: C, 60.18; H, 6.62; N, 7.02. Found: C, 59.98; H, 6.58; N, 6.77. [α]$^{25}$D=−3.70° (c 0.54, MeOH).

Example 49

5-octynyl-3-(1-methyl-2-(S)-pyrrolidinylmethoxy) pyridine dihydrochloride

To a solution of 5-bromo-3-(1-methyl-2-(S)-pyrrolidinylmethoxy)pyridine (272 mg, 0.1 mmol) in 6 mL of CH$_2$Cl$_2$ was added triethylamine (0.4 mL), Pd(II) (18 mg), CuI (a catalytic amount) and 0.3 mL of 1-octyne (0.2 mmol). The reaction mixture was heated at reflux for 40 hours. The mixture was diluted with CH$_2$Cl$_2$, and 2 mL of 10% NaOH were added. The organic layer was separated and dried, and the solvent was removed under reduced pressure. The free was purified by chromatography, eluting with 1 to 2% MeOH in CH$_2$Cl$_2$. MS (CI/NH$_3$) m/z 301 (M+H)$^+$ $^1$H NMR (CDCl$_3$, 300 MHz) δ0.91 (m, 3H), 1.32 (m, 4H), 1.60 (m, 2H), 1.90 (m, 3H), 2.15 (m, 1H), 2.42 (m, 2H), 2.64 (s, 3H), 2.98 (br s, 1H), 3.34 (br s, 1H), 4.04 (m, 1H), 4.25 (m, 1H), 7.22 (m, 1H), 8.22 (m, 2H). The salt was prepared by treatment with HCl in Et$_2$O, as described above, to give 110 mg of the title compound. MS (CI/NH$_3$) m/z 301 (M+H)$^+$. $^1$H NMR (D$_2$O, 300 MHz) δ8.45 (d, J=2.6, 1H), 8.42 (d, J=1.1, 1H), 8.07 (m, 1H), 4.63 (dd, J=3.0, 11.1, 1H), 4.47 (dd, J=5.9, 11.4, 1H), 3.97 (m, 1H), 3.78 (m, 1H), 3.27 (m, 1H), 3.05 (s, 3H), 2.51 (t, J=7.0, 2H), 2.42 (m, 1H), 2.23 (m, 1H), 2.10 (m, 2H), 1.63 (m, 2H), 1.44 (m, 2H), 1.33 (m, 4H), 0.88 (m, 3H). Anal. Calcd for C$_{19}$H$_{28}$N$_2$O·2.0 HCl: C, 61.12; H, 8.10; N, 7.50. Found: C, 60.99; H, 7.89; N, 7.28. [α]$^{25}$D=−4.00° (c 1.75, MeOH).

Example 50

5-(2-(4-Pyridinyl)ethenyl)-6-chloro-3-(1-methyl-2-(S)-pyrrolidinylmethoxy)pyrdine dihydrochloride 50a. 5-(2-(4-Pyridinyl)ethenyl)-6-chloro-3(1-methyl-2-(S)-pyrrolidinylmethoxy)pyridine To 5-(2-(4-pyridinyl)ethenyl)-6-chloro-3-(2-(S)-pyrrolidinyl-methoxy)pyridine from Example 33 (110 mg, 0.27 mmol) was added formalin (38%, 3.0 mL) and formic acid (88%, 1.5 mL). The mixture was refluxed for five hours then cooled to room temperature. Hydrochloric acid (36%, 0.3 mL) was added, and the mixture was extracted with Et$_2$O (3×8 mL). The aqueous layer was heated under vacuum to dryness. Water (2 mL) was added, and solid sodium bicarbonate was added until the aqueous layer was saturated. The mixture was extracted with EtOAc, which was dried over MgSO4, filtered and concentrated. The residue was chromatographed on a silica gel column, eluting with CHCl$_3$/MeOH 10:1 to afford an oil (72 mg, 83%). MS (CI/NH$_3$) m/z 330 (M+H)$^+$. $^1$H NMR (CDCl$_3$, 300 MHz) δ1.70–2.10 (m, 4H), 2.38–2.40 (m, 1H), 2.51 (s, 3H), 2.65–2.76 (m, 1H), 3.10–3.19 (m, 1H), 3.96–4.10 (m, 2H), 6.96–7.04 (m, 1H), 7.39–7.44 (m, 2H), 7.53 (s, 1H), 7.52–7.60 (m, 1H), 8.05–8.08 (m, 1H), 8.63–8.67 (m, 1H).

50b. 5-(2-(4-Pyridinyl)ethenyl)-6-chloro-3-(2-(S)-pyrrolidinylmethoxy)pyridine dihydrochloride To a solution of 5-(2-(4-pyridinyl)ethenyl)-6-chloro-3-(1-methyl-2-(S)-pyrrolidinylmethoxy)pyridine (70 mg, 0.21 mmol) in THF (3.0 mL) was added hydrogen chloride (1.0 M in Et$_2$O, 0.70 mL, 0.70 mmol). The precipitate formed was filtered, washed (Et$_2$O) and vacuum-dried to afford the hydrochloride salt (79 mg, 94%). mp. 218–222° C. MS (CI/NH$_3$) m/z 330 (M+H)$^+$. $^1$H NMR (D$_2$O, 300 MHz, presumed to be two rotomers, tentative assignment of one) δ1.85–2.48 (m, 4H), 2.97 (s, 3H), 3.15–3.32 (m, 1H), 3.65–4.01 (m, 2H), 4.16–4.43 (m, 2H), 7.05–7.11 (m, 1H), 7.18–7.23 (m, 1H), 7.36–7.38 (m, 1H), 7.74–7.79 (m, 1H), 8.13–8.19 (m, 2H), 8.55–8.5 (m, 2H). Anal. Calcd for C$_{18}$H$_{20}$N$_3$OCl·2.2 HCl·1.0 MeOH: C, 51.62; H, 5.97; N, 9.51. Found: C, 51.60; H, 5.67; N, 9.24. [α]$^{25}$D=−5.7° (c 0.65, MeOH).

Example 51

5-phenyl-3-(2-(S)-pyrrolidinylmethoxy)pyridine dihydrochloride 51a. 1-Tosyl-(S)-pyrrolidinemethanol (S)-Prolinol (Aldrich Chem. Co., 5.10 g, 0.05 mmol) p-toluenesulfonyl chloride (9.63 g, 0.05 mmol) and triethylamine (8.5 mL, 0.06 mmol) were dissolved in chlorform (50 mL), and the reaction mixture was stirred for 20 hours at room temperature. To the mixture was added water and aqueous saturated NaCO$_3$ to give a pH 8–9. This mixture was extracted with ethyl acetate, which was dried over MgSO4, filtered and concentrated. The residue was chromatographed on a silica gel column, eluting with EtOAc:hexane 1:1 to afford the title compound. MS (CI/NH$_3$) m/z 256 (M+H)$^+$, 273 (M+NH$_4$)$^+$. $^1$H NMR (CDCl$_3$, 300 MHz) δ7.75 (d, J=2.5, 2H), 7.33 (d, J=2.5, 2H), 7.27 (s, 1H), 3.7–3.6 (m, 3H), 3.5–3.4 (m, 1H), 3.3–3.2 (m, 1H), 2.8–2.7 (m, 1H), 2.42 (s, 3H), 1.85–1.65 (m, 3H), 1.5–1.4 (m, 1H), 1.33–1.26 (m, 1H).

51b. 5-bromo-3-(1-tosyl-2-(S)-pyrrolidinylmethoxy)pyridine

To a suspension of 3,5-dibromopyridine (1.5 g, 6.05 mmol) and 60% NaH (307 mg, 7.7 mmol) in DMF (6 mL) was added 1-tosyl-2-(S)-pyrrolidinemethanol (1.4 g, 5.5 mmol), and the reaction mixture was stirred for 4 hours at room temperature and 1 hour at 60° C. The DMF was removed under reduced pressure, and the residue was chromatographed on a silica gel column, eluting with EtOAc/hexane 6:1 to afford the title compound (1.2 g).

51c. 5-phenyl-3-(2-tosyl-2-(S)-pyrrolidinylmethoxy)pyridine 5-bromo-3-(1-tosyl-2-(S)-pyrrolidinylmethoxy)pyridine from step 51b (300 mg, 10.73 mmol), boric acid (107 mg, 10.88 mmol) and Pd(0) (26 mg) were mixed together in benzene (2 mL), and the mixture was heated at reflux for 16 hours. NaHCO$_3$ solution (2%, 1mL) was added, and the mixture was extracted with CHCl$_3$. The CHCl$_3$ was removed under reduced pressure, and the residue was chromatographed on a silica gel column, eluting with EtOAc/hexane 1:1 to afford the title compound (300 mg).

51d. 5-phenyl-3-(2-(S)-pyrrolidinlmethoxy)pyridine

The 5-phenyl-3-(1-tosyl-2-(S)-pyrrolidinylmethoxy)pyridine from the previous step was dissolved in HBr/HOAc, and the reaction was stirred at room temperature for 16 hours and at 40° C. for 4 hours. The volatiles were removed under vacuum, and the residue was chromatographed on a silica gel column, eluting with CHCl$_3$/MeOH 10/1.5 to afford the title compound (57 mg). MS (CI/NH$_3$) m/z 255 (M+H)$^+$. $^1$H NMR (CDCl$_3$, 300 MHz) δ1.54–2.12 (m, 5H), 2.95–3.13 (m, 2H), 3.54–3.66 (m, 1H), 3.94–4.08 (m, 2H), 7.36–7.52 (m, 4H), 7.54–7.62 (m, 2H), 8.29 (d, J=3, 1H), 8.46 (d, J=2, 1H).

51e. 5-phenyl-3-(2-(S)-pyrrolidinylmethoxy)pyridine dihydrochloride

The salt was prepared by treatment with HCl in Et$_2$O, as described above, to give the title compound. mp. 134–136° C. MS (CI/NH$_3$) m/z 255 (M+H)$^+$. $^1$H NMR (D$_2$O, 300 MHz) δ1.92–2.35 (m, 4H), 3.41–3.66 (m, 2H), 4.11–4.20 (m, 1H), 4.33 (dd, J=7.5, 10.5, 1H), 4.54 (dd, J=3.4, 10.6, 1H), 7.50–7.61 (m, 5H), 7.70–7.78 (m, 3H), 8.30 (d, J=2.7, 1H), 8.51 (d, J=1.7, 1H). Anal. Calcd for C$_{16}$H$_{18}$N$_2$OCl·2 HCl: C, 58.72; H, 6.16; N, 8.56. Found: C, 58.62; H, 6.16; N, 8.88. [α]$^{25}$D=+13.67° (c 0.2, MeOH).

Example 52

5-phenyl-3-(2)-(R)-pyrrolidinylmethoxy)pyridine dihydrochloride

Following the procedures of Example 51, except starting with the (R)-prolinol instead of the (S)-prolinol, the title compound was prepared. mp. 129–131° C. MS (CI/NH$_3$) m/z 255 (M+H)$^+$. $^1$H NMR (D$_2$O, 300 MHz) δ1.92–2.37 (m, 5H), 3.44 (t, J=18, 2H), 4.13–4.22 (m, 1H), 4.37 (dd, J=7.4, 10.5, 1H), 4.59 (dd, J=3.4, 10.6, 1H), 7.56–7.63 (m, 5H), 7.71–7.75 (m, 2H), 8.05 (t, J=2.0, 1H), 8.39 (d, J=2.7, 1H), 8.60 (d, J=1.7, 1H). Anal. Calcd for C$_{16}$H$_{18}$N$_2$OCl·2HCl: C, 58.72; H, 6.16; N, 8.56. Found: C, 58.45; H, 6.24; N, 8.49. [α]$^{25}$D=−2.7° (c 0.3, MeOH).

Example 53

5-phenyl-3-(1-methyl-2-(R)-pyrrolidinylmethoxy) pyridine dihydrochloride

To 5-phenyl-3-(2-(R)-pyrrolidinylmethoxy)pyridine from Example 52 (150 mg, 0.59 mmol) was added formalin (38%, 5.0 mL) and formic acid (88%, 2.5 mL), and the mixture was refluxed for 16 hours. The reaction was quenched by the addition of saturated aqueous NaHCO$_3$. The mixture was extracted with CHCl$_3$, which was dried over MgSO4, filtered and concentrated. The residue was chromatographed on a silica gel column, eluting with CHCl$_3$/MeOH 10:1.5 to afford the base. The salt was prepared by treatment with HCl in Et$_2$O, as described above, to give the title compound. mp. 89–90° C. MS (CI/NH$_3$) m/z 269 (M+H)$^+$. $^1$H NMR (D$_2$O, 300 MHz) δ2.05–2.29 (m, 2H), 2.38–2.47 (m, 1H), 3.07 (s, 3H), 3.23–3.32 (m, 1H), 3.64–3.82 (m, 1H), 3.92–4.00 (m, 1H), 4.44 (dd, J=7.7, 11.0 (1H), 4.61 (dd, J=3.0, 11.2, 1H), 7.51–7.62 (m, 3H), 7.70–7.74 (m, 2H), 7.88 (s, 1H), 8.36 (br s, 1H), 8.56 (br s, 1H). Anal. Calcd for C$_{17}$H$_{20}$N$_2$O·Cl·2 HCl·0.5 H$_2$O: C, 58.29; H, 6.62; N, 8.00. Found: C, 58.16; H, 6.76; N, 8.18. [α]$^{25}$D=+9.2° (c 0.39, MeOH).

Example 54

Intermediate Compound 5-bromo-3-1-(BOC-2-(S)-azetidinylmethoxy)pyridine 54a. 1-BOC-2-(S)-azetidinemethanol (S)-Azeditinecarboxylic acid (Aldrich) was treated with di-t-butyl dicarbonate to give the 1-BOC-(S)-azeditinecarboxylic acid. This compound in turn was was dissolved in anhydrous THF and brought to 0° C. with stiring. Borane/THF complex was added dropwise via syringe over a 10 minute period. The reaction mixture was stirred at room temperature for 1 hour, then the reaction was quenched slowly with saturated NaHCO$_3$ and stirred for an additional hour. The solvent was removed in vacuo, and the residue was diluted with H$_2$O. The desired compound was extracted from the aqueous phase with Et$_2$O (3X). The organic layer was then washed with brine (2X) dried (MgSO$_4$) and evaporated to afford the title compound.

54b. 5-bromo-3-(1-BOC-2-(S)-azetidinylmethoxy) pyridine

Triphenylphosphine (4.01 g, 15.3 mmol) and DEAD (2.43 mL, 15.3 mmol) were dissolved in 30 mL of THF at 0° C., and the mixture was stirred for for 10 minutes. Samples of 1-BOC-2-(S)-azetidinemethanol (2.86 g, 15.3 mmol), prepared as described above, and 5-bromo-3-hydroxypyridine (1.505 g, 10.2 mmol) were added, and the reaction rnixture was stirred for 40 hours at room temperature. The volatiles were removed under vacuum, and the residue was triturated with hexane. The hexane was removed, and the residue was chromatographed on a silica gel column, eluting with hexane:Et$_2$O 10:1 to 10:2 to afford the title compound as a colorless oil (1.669 g). MS (CI/NH$_3$) m/z 344 (M+H)$^+$. $^1$H NMR (CDCl$_3$, 300 MHz) δ1.42 (s, 9H), 2.31 (m, 2H), 3.89 (m, 2H), 4.12 (m, 1H), 4.322 (m, 1H), 4.52 (m, 1H), 7.43 (m, 1H), 8.29 (m, 2H).

Example 55

5-(5,5-Dimethyl-1,3-hexadienyl-6-chloro-3-(2-(R)-pyrrolidinylmethoxy)pyridine citric acid salt 55a. 5-(5,5-Dimethyl-1,3-hexadienyl)-3-(1-BOC-2-(R)-pyrrolidinylmethoxy)pyridine To a solution of 5-bromo-6-chloro-3-(1-BOC-2-(R)-pyrrolidinylmethoxy)pyridine (600 mg, 1.59 mmol) in acetonitrile (5.0 mL) and triethylamine (4.5 mL) was added 5,5-dimethyl-1,3-hexadiene (228 mg), palladium acetate (39 mg) and tri-o-tolylphosphine (205 mg). After being heated in a sealed tube at 100° C. overnight, the resulting mixture was cooled to room temperature. Minimum amount of saturated sodium bicarbonate was added to free the amine hydrochloride salt, and the mixture was extracted with EtOAc, dried (MgSO$_4$), and concentrated. The residue was chromatographed on a silica gel column, eluting with EtOAc:hexane 1:3 to afford the title compound (126 mg, 42% yield). MS (CI/NH$_3$) m/z 307 (M+H)$^+$. $^1$H NMR (CDCl$_3$, 300 MHz) δ1.42 (s, 9H), 1.55 (s, 9H), 2.24–2.42 (m, 2H), 3.88 (t, J=7.5, 2H), 4.13 (dd, J=3, 7.5, 1H), 4.29–4.41 (m, 1H), 5.97 (d, J=15, 1H), 6.22 (dd, J=9, 15, 1H), 6.67–6.78 (m, 2H), 7.45 (br s, 1H), 8.95 (d, J=3.0, 1H).

55b. 5-(5,5-Dimethyl-1,3-hexadienyl -6-chloro-3-(2-(R)-pyrrolidinylmethoxy)pyridine citrate To a solution of the compound from step 55a (126 mg) in CH$_2$Cl$_2$ (1.5 mL) was added TFA (1.5 mL), and the mixture was stirred for 4 hours at room temperature. The solvent was removed, and the residue was chromatographed on a silica gel column, eluting with CH$_2$Cl$_2$:MeOH 10:1 to afford the free base of the title compound (75 mg, 79% yield). MS (CI/NH$_3$) m/z 307 (M+H)$^+$. $^1$H NMR (CDCl$_3$, 300 MHz) δ2.22–2.51 (m, 3H), 3.50–3.60 (m, 1H), 3.68–3.83 (m, 1H), 4.01–4.14 (m, 2H), 4.27–4.42 (m, 1H), 5.96 (d, J=15 Hz, 1H), 6.22 (ddd, J=3.0, 7.5, 15 Hz, 1H), 6.70–6.75 (m, 2H), 7.41 (d, J=3.0 Hz, 1H), 7.94 (d, J=3.0 Hz, 1H). This material was converted to the title compound by treatment with citric acid in EtOH. mp. 100–102° C. MS (CI/NH$_3$) m/z 307 (M+H)$^+$. $^1$H NMR (D$_2$O, 300 MHz) δ2.54–2.86 (m, 7h), 3.98–4.18 (m, 3H), 4.40–4.44 (m, 2H), 6.04 (d, J=15.4, 1H), 6.23–6.32 (m, 1H), 6.73 (d, J=15.8, 1H), 6.98 (dd, J=10.3, 15.1, 1H), 7.73 (d, J=3.0, 1H), 8.01 (d, J=3.0, 1H). Anal. Calcd for C$_{17}$H$_{23}$N$_2$O·1.1 C$_6$H$_8$O$_7$: C, 54.70; H, 6.19; N, 5.41. Found: C, 54.59; H, 5.93; N, 5.20. [α]$^{25}$D=+4.33° (c 0.1, MeOH).

Example 56

5-Phenyl-3-(2-(S)-azetidinylmethoxy)pyridine dihydrochloride 56a. 5-Phenyl-3-(1-BOC-2-(S)-azetidinylmethoxy) pyridine The 5-bromo-3-(1-BOC-2-(S)-azetidinylmethoxy) pyridine from Example 54b (1.03 g, 3 mmol), phenylboronic acid (920 mg, 7.5 mmol), Pd(0) (100 mg) and Na$_2$CO3 (4 mL of a 2 M solution) were mixed in 20 mL of toluene, and the mixture was stirred at reflux for 3 hours. The solvent was removed under vacuum, and the residue was purified by chromatography on silica gel, eluting with CHCl$_3$:MeOH 100:2, to afford 1.39 g of the title compound. MS (CI/NH$_3$) m/z 341 (M+H)$^+$. $^1$H NMR (CDCl$_3$, 300 MHz) δ1.38 (s, 9H), 2.32 (m, 2H), 3.89 (m, 2H), 4.21 (m, 1H), 4.41 (m, 1H), 4.54 (m, 1H), 7.40 (m, 3H), 7.50 (m, 2H), 8.10 (m, 1H), 8.54 (m, 1H), 8.20 (m, 1H).

56b. 5-Phenyl-3-(2-(S)-azetidinylmethoxy)pyridine dihydrochloride

The BOC group was removed from the compound of step a by treatment with TFA in CH$_2$Cl$_2$ at 0° C. for 30 minutes to give the free base of the title compound. The volatiles were then removed under vacuum. The residue was neutralized with NaHCO$_3$ to p[H 8, then extracted with CH$_2$Cl$_2$, which was dried over MgSO$_4$ and concentrated. The free base was chromatographed on a silica gel column, eluting with MeOH:CH$_2$Cl$_2$:NH$_4$OH 10:100:0.5 to afford the title compound (550 mg). MS (CI/NH$_3$) m/z 241 (M+H)$^+$. $^1$H NMR (CDCl$_3$, 300 MHz) δ2.47 (m, 2H), 3.68 (m, 1H), 3.87 (m, 1H), 4.18 (m, 2H), 4.52 (m, 1H), 7.45 (m, 4H), 7.56 (m, 2H), 8.28 (m, H), 8.47 (s, 1H). The base (111 mg) was converted to the salt by treatment with hydrogen chloride saturated EtOH to give the title compound (82.9 mg). MS (CI/NH$_3$) m/z 241 (M+H)$^+$. $^1$H NMR (D$_2$O, 300 MHz) δ2.68–2.77 (m, 2H), 4.08–4.29 (m, 2H), 4.42 (d, J=4.1 Hz, 1H), 4.98 (m, 1H), 7.45–7.56 (m, 3H), 7.57–7.68 (m, 3H), 8.28 (d, J=2.5 Hz, 1H), 8.43 (d, J=1.5 Hz, 1H). Anal. Calcd for C$_{15}$H$_{16}$N$_2$O·2 HCl·0.5 H$_2$O: C, 55.91; H, 5.94; N. 8.69. Found: C, 55.83; H, 5.72; N. 8.80. [α]$^{25}$D=–6.00° (c 0.60, MeOH).

Example 57

5-Phenyl-3-(1-methyl-2-(S)-(azetidinylmethoxy)pyridine dihydrochloride

To 5-phenyl-3-(2-(S)-azetidinylmethoxy)pyridine HCl from Example 56 (440 mg, 1.8 mmol) in water (7 mL) was added formalin (37%, 0.5 mL), formic acid (0.6 mL), and the pH was adjusted to 5. Then NaCNBH$_3$ (37 mg, 6.2 mmol) was added, and the mixture was stirred at room temperature for 1 hour. The pH was adjusted to 9 with 10% NaOH, and the mixture was extracted with CH$_2$Cl$_2$. The solvent was dried over MgSO4, filtered and concentrated. The residue was chromatographed on a silica gel column, eluting with CH$_2$Cl$_2$:MeOH 100:2–10 to afford the base (175 mg). MS (CI/NH$_3$) m/z 255 (M+H)$^+$. $^1$H NMR (CDCl$_3$, 300 MHz) δ2.12 (m, 2H), 2.44 (s, 3H), 2.90 (m, 1H), 3.48 (m, 2H), 4.11 (m, 2H), 7.44 (m, 4H), 7.58 (m, 2H), 8.29 (m, 1H), 8.47 (m, 1H). The salt was prepared by treatment with HCl in Et$_2$O, as described above, to give the title compound (47 mg). mp. 120–122° C. MS (CI/NH$_3$) m/z 255 (M+H)$^+$. $^1$H NMR (D$_2$O, 300 MHz) δ2.61–2.79 (m, 2H), 3.02 (s, 3H), 4.31 (m, 1H), 4.51–4.64 (m, 2H), 4.80 (m, 2H), 7.60 (m, 3H), 7.74 (m, 2H), 8.00 (m, 1H), 8.41 (d, J=2.4, 1H), 8.60 (d, J=1.6, 1H). Anal. Calcd for C$_{16}$H$_{18}$N$_2$O·2 HCl 0.4 H$_2$O: C, 57.46; H, 6.27; N, 8.38. Found: C, 57.28; H, 6.41; N, 8.18. [α]$^{25}$D=–24.88° (c 0.44, MeOH).

Example 58

5-Hexynyl-3-(2-(S)-azetidinylmethoxy)pyridine dihydrochloride 58a. 5-Hexynyl-3-(1-BOC-2-(S-azetidinylmethoxy)pyridine (47752-235)

To a solution of 5-bromo-3-(1-BOC-2-(S)-azetidinylmethoxy)pyridine from Example 54b (180 mg, 0.48 mmol), bis(triphenylphosphine)palladium(II) chloride (7 mg, 0.05 mmol), copper (I) iodide (2 mg) and triethylamine (1.0 mL) in CH$_2$Cl$_2$ (3 mL) was added 1-hexyne (8.3 mL, 0.72 mmol). The mixture was refluxed overnight and cooled to room temperature. The solvent was removed, and the residue was chromatographed on a silica gel column, eluting with EtOAc:hexane 1:1 to afford the title compound (102 mg, 56% yield). MS (CI/NH$_3$) m/z 379 (M+H)$^+$. $^1$H NMR (CDCl$_3$, 300 MHz) δ0.96 (t, J=6.6 Hz, 3H), 1.43 (s, 9H), 1.46–1.69 (m, 4H), 2.20–2.40 (m, 2H), 2.44–2.56 (m, 2H), 3.83–3.92 (m, 2H), 4.06–4.15 (m, 1H), 4.26–4.38 (m, 2H), 4.45–4.57 (m, 1H), 7.34 (br s, 1H), 7.51–7.58 (m, 1H).

58b. 5-Hexynyl-3-(2-(S)-azetidinylmethoxy)pyridine dihydrochloride (47752-250)

A solution of 5-hexynyl-3-(1-BOC-2-(S)-azetidinylmethoxy)pyridine from step 58a (102 mg, 0.26 mmol) in CH$_2$Cl$_2$ (2 mL) and TFA (1 mL) was stirred at room temperature for 3 hours. The solvent was removed, and the residue was chromatographed on a silica gel column, eluting with CHCl$_3$:MeOH:NH$_4$OH 10:1:0.1 to afford the free base of the title compound(73 mg, 96% yield). MS (CI/NH$_3$) m/z 279 (M+H)$^+$. $^1$H NMR (CDCl$_3$, 300 MHz) δ0.96 (t, J=7.0 Hz, 3H), 1.43–1.61 (m, 2H), 2.21–2.44 (m, 4H), 2.48 (t, J=7.5 Hz, 2H), 3.44–3.52 (m, 1H), 3.68–3.80 (m, 1H), 3.96–4.09 (m, 2H), 4.25–4.35 (m, 1H), 7.28 (d, J=3.0 Hz, 1H, 7.99 (d, J=3.0 Hz, 1H). The base was treated with HCl in EtOH to afford the hydrochloride salt (73 mg). mp 103–105° C. MS (CI/NH$_3$) m/z 279 (M+H)$^+$. $^1$H NMR (D$_2$O, 300 MHz) δ0.98 (t, J=7.4, 3H), 1.48–1.72 (m, 4H), 2.55–2.60 (m, 2H), 2.68–2.77 (m, 2H), 4.07–4.24 (m, 2H), 4.44–4.48 (m, 2H), 4.80–4.99 (m, 1H), 7.66 (d, J=2.7, 1H), 8.14 (d, J=3.1, 1H). Anal. Calcd for C$_{15}$H$_{19}$N$_2$O·1.6 HCl: C, 53.44; H, 6.16; N, 8.31. Found: C, 53.81; H, 5.77; N, 8.43. [α]$^{25}$D=–7.5° (c 0.2, MeOH).

Example 59

5-(2-(4-Pridinyl)ethenyl)-3-(2-(S)-azetidinylmethoxy(pyridine trihydrochloride 59a. 5-(2-(4-Pyridinyl)ethenyl)-3-(1-BOC-2-(S)-azetidinylmethoxy)pyridine To a solution of 5-bromo-3-(1-BOC-2-(S)-azetidinylmethoxy)pyridine from step 54b (1.03 g, 3.0 mmol) in acetonitrile (20 mL) and triethylamine (12.5 mL) was added 4-vinylpyridine (0.65 mL, 6 mmol), palladium acetate (125 mg, 0.56 mmol) and tri-o-tolylphosphine (625 mg). The mixture was heated at reflux for 16 hours. The solvent was removed, and the residue was washed with saturated sodium bicarbonate was added to free the amine, and the mixture was extracted with EtOAc, dried (MgSO$_4$), and concentrated. The residue was chromatographed on a silica gel column, eluting with hexane:Et$_2$O 1:2 to 0:1 to afford the title compound (760 mg, 69%). MS (CI/NH$_3$) m/z 368 (M+H)$^+$. $^1$H NMR (CDCl$_3$, 300 MHz) δ1.43 (s, 9H), 2.35 (m, 2H), 3.90 (m, 2H), 4.20 (m, 1H), 4.40 (m, 1H), 4.55 (m, 1H), 7.10 (m, 1H), 7.2 (m, 1H), 7.38 (m, 2H), 7.45 (br s, 1H), 8.29 (m, 1H), 8.37 (s, 1H), 8.61 (m, 2H).

59b. 5-(2-(4-Pyridinyl)ethenyl)-3-(2-(S)-azetidinylmethoxy)pyryidine trihydrochloride A solution of the compound from step 59a (130 mg, 0.35 mmol) in CH$_2$Cl$_2$ (2 mL) and TFA (0.9 mL) was stirred for 30 minutes at 0° C. The residue was neutralized with NaHCO$_3$ to pH 8, then extracted with CH$_2$Cl$_2$, which was dried over MgSO$_4$ and concentrated. The free base was chromatographed on a silica gel column, eluting with CH$_2$Cl$_2$:MeOH:NH$_4$OH 10:1:0 to 10:1:0.3 to afford the pure compound (75 mg). MS (CI/NH$_3$) m/z 268 (M+H)$^+$. $^1$H NMR (CDCl$_3$, 300 MHz) δ2.54 (m, 2H), 3.56 (m, 1H), 3.76 (m, 1H), 4.14 (m, 2H), 4.38 (m, 1H), 7.04 (m, 1H), 7.22 (m, 1H), 7.40 (m, 3H), 8.25 (m, 1H), 8.36 (s, 1H), 8.63 (m, 2H). The base was converted to the salt by treatment with hydrogen chloride saturated EtOH to give the title compound (50 mg). mp. 98–100° C. MS (CI/NH$_3$) m/z 268 (M+H)$^+$. $^1$H NMR (D$_2$O, 300 MHz) δ2.65 (m, 2H), 4.12 (m, 2H), 4.40 (d, J=4.4 Hz, 1H), 4.78 (m, 1H), 4.95 (m, 1H), 7.20 (d, J=16.2 Hz, 1H), 7.38 (d, J=16.2 Hz, 1H), 7.51 (d, J=6.4 Hz, 2H), 7.62 (m, 1H), 8.21 (m, 1H), 8.32 (m, 1H), 8.45 (d, J=5.8 Hz, 2H). Anal. Calcd for C$_{16}$H$_{17}$N$_3$O·0.8 HCl·0.1 H$_2$O: C, 64.42; H, 6.08; N, 14.09. Found: C, 64.68; H, 5.98; N, 13.70. [α]$^{25}$D=–18.38° (c 0.98, MeOH).

Example 60

5-(2-(4-Pyridinyl)ethyl)-3-(2-(S)-azetidinylmethoxy)pyridine dihydrochloride

60a. 5-(2-(4-Pyridinyl)ethyl)-3-(1-BOC-2-(S)-azetidinylmethoxy)pyridine

To a solution of 5-(2-(4-pyridinyl)ethenyl)-3-(1-BOC-2-(S)-azetidinylmethoxy)pyridine from Example 59a (188 mg, 0.51 mmol) in MeOH (10 mL) was added Pd/C (20 mg), and the mixture was stirred at room temperature for 40 hours. The catalyst was filtered off, and the solvent was removed under vacuum. The residue was chromatographed on a silica gel column, eluting with $CH_2Cl_2$:MeOH 10:2 to 10:5 to afford the title compound (154 mg). MS ($CI/NH_3$) m/z 370 $(M+H)^+$. $^1H$ NMR ($CDCl_3$, 300 MHz) δ1.42 (s, 9H), 2.32 (m, 2H), 3.89 (m, 2H), 4.10 (m, 1H), 4.28 (m, 1H), 4.50 (m, 1H), 7.02 (m, 1H), 7.02 (m, 1H), 7.08 (m, 2H), 8.06 (m, 1H), 8.20 (m, 1H), 8.51 (m, 2H).

60b. 5-(2-(4-Pyridinyl)-3-(1-2(S)-azetidinylmethoxy)pyridine

A solution of the compound from step 60a (154 mg, 0.42 mmol) in $CH_2Cl_2$ (2 mL) and TFA (1.2 mL) was stirred for 30 minutes at 0° C. The residue was neutralized with $NaHCO_3$ to pH 8, then extracted with $CH_2Cl_2$, which was dried over $MgSO_4$ and concentrated. The residue was chromatographed on a silica gel column, eluting with $CH_2Cl_2$:MeOH:$NH_4OH$ 10:1:0 to 10:1:0.3 to afford the free base of the title compound. MS ($CI/NH_3$) m/z 270 $(M+H)^+$. $^1H$ NMR ($CDCl_3$, 300 MHz) δ2.42 (br s, 2H), 2.92 (s, 4H), 3.62 (m, 1H), 3.83 (m, 1H), 4.09 (m, 2H), 4.44 (m, 1H), 6.96 (s, 1H), 7.08 (m, 2H), 8.08 (br, 1H), 8.18 (m, 1H), 8.50 (br, 1H). The base was converted to the salt by treatment with hydrogen chloride saturated EtOH to give the title compound. MS ($CI/NH_3$) m/z 270 $(M+H)^+$. $^1H$ NMR ($D_2O$, 300 MHz) δ2.65 (m, 2H), 3.05 (m, 4H), 4.10 (m, 2H), 4.33 (d, J=4.1 Hz, 2H), 4.91 (m, 1H), 7.23 (m, 3H), 7.99 (s, 1H), 8.15 (s, 1H), 8.37 (m, 2H). Anal. Calcd for $C_{16}H_{19}N_3O·1.5$ HCl·0.1 EtOH·0.1 $H_2O$: C, 59.11; H, 6.56; N, 12.60. Found: C, 59.37; H, 6.25; N, 12.60. $[α]^{25}D=-4.13°$ (c 0.92, MeOH).

Example 61

5-(2-(4-Pyridinyl)ethenyl)-3-(1-methyl-2-(S)-azetidinylmethoxy)pyridine trihydrochloride

A sample of 5-bromo-3-(1-BOC-2-(S)-azetidinylmethoxy)pyridine from step 54b (130 mg, 0.35 mmol) was dissolved in 2 mL of formic acid and 4 mL of formalin, and the mixture was heated at 70° C. for 16 hours. The mixture was basified with saturated saturated sodium bicarbonate, then extracted with $CH_2Cl_2$. The organic layer was dried over $MgSO_4$ and concentrated. The residue was chromatographed on a silica gel column, eluting with methelene chloride:MeOH 10:1 to afford the free base of the title compound (58 mg). MS ($CI/NH_3$) m/z 368 $(M+H)^+$. $^1H$ NMR ($CDCl_3$, 300 MHz) δ1.42 (s, 8H), 2.35 (m, 2H), 3.91 (m, 2H), 4.20 (m, 1H), 4.42 (m, 1H), 4.55 (m, 1H), 7.10 (m, 1H), 7.26 (m, 1H), 7.38 (m, 2H), 7.45 (s, 1H), 8.29 (m, 1H), 8.37 (s, 1H), 8.62 (m, 2H). The base was converted to the salt by treatment with hydrogen chloride saturated EtOH to give the title compound. MS ($CI/NH_3$) m/z 282 $(M+H)^+$. $^1H$ NMR ($D_2O$, 300 MHz) 3 2.64–2.78 (m, 2H), 3.02 (s, 3H), 4.04 (m, 1H), 4.31 (m, 1H), 4.56–4.69 (m, 2H), 7.61 (d, J=16.3 Hz, 1H), 7.85 (d, J=16.3 Hz, 1H), 8.20 (d, J=6.8 Hz, 2H), 8.27 (s, 1H), 8.53 (d, J=2.4 Hz, 1H), 8.68 (s, 1H), 8.73 (d, J=6.4 Hz, 2H). Anal. Calcd for $C_{17}H_{19}N_3O·3.7$ HCl·0.3 EtOH: C, 49.85; H, 5.91; N, 9.58. Found: C, 50.11; H, 6.09; N, 9.24. $[α]^{25}D=-16.83°$ (c 0.60, MeOH).

Example 62

5-(2-(4-Pyridinyl)ethyl)-3-(1-methyl-2-(S)-azetidinylmethoxy)pyridine dihydrochloride

A sample of 5-(2-(4-Pyridinyl)ethyl)-3-(1-BOC-2-(S)-azetidinylmethoxy)pyridine from Example 60a (220 mg, 0.60 mmol) was dissolved in 4 mL of formic acid and 8 mL of formalin, and the mixture was heated at 70° C. for 16 hours. The mixture was basified with saturated saturated sodium bicarbonate, then extracted with $CH_2Cl_2$. The organic layer was dried over $MgSO_4$ and concentrated. The residue was chromatographed on a silica gel column, eluting with $CH_2Cl_2$:MeOH 10:1 to afford the free base of the title compound (71 mg). MS ($CI/NH_3$) m/z 284 $(M+H)^+$. $^1H$ NMR ($CDCl_3$, 300 MHz) δ2.08 (m, 2H), 2.40 (s, 3H), 2.88 (m, 1H), 3.36 (m, 1H), 3.46 (m, 1H), 3.98 (m, 2H), 6.98 (m, 1H), 7.08 (m, 2H), 8.04 (s, 1H), 8.17 (m, 1H), 8.49 (m, 2H). The base was converted to the salt by treatment with hydrogen chloride saturated EtOH to give the title compound. mp 105–107° C. MS ($CI/NH_3$) m/z 284 $(M+H)^+$. $^1H$ NMR ($D_2O$, 300 MHz) δ2.67 (m, 2H), 2.99 (s, 3H), 3.15 (t, J=7.2 Hz, 2H), 3.28 (t, J=7.1 Hz, 2H), 4.00 (m, 1H), 4.28 (m, 1H), 4.36–4.49 (m, 2H), 4.80 ((m, 1H), 7.46 (s, 1H), 7.74 (d, J=6.1 Hz, 1H), 8.02 (s, 1H), 8.20 (d, J=2.3 Hz, 1H), 8.57 (d, J=6.2 Hz, 2H). Anal. Calcd for $C_{17}H_{21}N_3O·2.4$ HCl·0.1 EtOH: C, 55.25; H, 6.50; N,11.11. Found: C, 55.27; H, 6.43; N, 10.76. $[α]^{25}D=-8.32°$ (c 0.62, MeOH).

Example 63

5-octynyl-3-(2-(S)-azetidinalmethoxy)pyridine dihydrochloride

63a. 5-octynyl-3-(BOC-2-(S)-azetidinylmethoxy)pyridine

To a solution of 5-bromo-3-(1-BOC-2-(S)-azetidinylmethoxy)pyridine from step 54b (450 mg, 1.3 mmol) in 10 mL of $CH_2Cl_2$ was added triethylamine (0.6 mL), $Pd(PPh_3)_2Cl_2$ (25 mg), CuI (a catalytic amount) and 1-octyne (0.37 mL, 0.26 mmol). The reaction mixture was heated at reflux for 40 hours. The mixture was diluted with $CH_2Cl_2$, and 2 mL of 10% NaOH were added. The organic layer was separated and dried, and the solvent was removed under reduced pressure. The residue was purified by chromatography, eluting with 1 to 2% MeOH in $CH_2Cl_2$ to afford the title compound (438 mg). MS ($CI/NH_3$) m/z 373 $(M+H)^+$. $^1H$ NMR ($CDCl_3$, 300 MHz) δ0.91 (m, 3H), 1.32 (m, 2H), 1.41 (s, 9H), 1.44 (m, 2H), 1.61 (m, 2H), 2.30 (m, 2H), 2.41 (m, 2H), 3.88 (m, 2H), 4.11 (m, 1H), 4.30 (m, 1H), 4.50 (m, 1H), 7.23 (m, 1H), 8.23 (br s, 2H).

63b. 5-octynyl-3-(2-(S)-azetidinylmethoxy)pyridine dihydrochloride

A sample of 5-octynyl-3-(1-BOC-2-(S)-azetidinylmethoxy)pyridine from step 63a in $CH_2Cl_2$ (3 mL) and TFA (2 mL) was stirred for 30 minutes at 0° C. The residue was neutralized with $NaHCO_3$ to pH 8, then extracted with $CH_2Cl_2$, which was dried over $MgSO_4$ and concentrated. The residue was chromatographed on a silica gel column, eluting with $CH_2Cl_2$:MeOH 10:5 to 10:11 to afford the free base of the title compound (178 mg). MS ($CI/NH_3$) m/z 273 $(M+H)^+$. $^1H$ NMR ($CDCl_3$, 300 MHz) δ0.90 (m, 3H), 1.32 (m, 4H), 1.45 (m, 2H), 1.62 (m, 2H), 2.40 (m, 2H), 2.53 (m, 2H), 3.80 (m, 1H), 3.96 (m, 1H), 4.19 (m, 2H), 4.62 (m, 1H), 7.22 (m, 1H), 8.20 (m, 2H). The base was converted to the salt by treatment with hydrogen chloride saturated EtOH to give the title compound. mp 88–90° C. MS ($CI/NH_3$) m/z 273 $(M+H)^+$. $^1H$ NMR ($D_2O$, 300 MHz) δ0.90 (m, 3H), 1.33 (m, 4H), 1.46 (m, 2H), 1.64

(m, 2H), 2.50 (t, J=2.9 Hz, 2H), 2.71 (m, 2H), 4.05–4.22 (m, 2H), 4.49 (d, J=4.4 Hz, 2H), 4.98 (m, 1H), 7.99 (m, 1H), 8.34 (s, 1H), 8.39 (d, J=2.6 Hz, 1H). Anal. Calcd for $C_{17}H_{24}N_2O \cdot 2.8$ HCl: C, 54.53; H, 7.21; N, 7.48. Found: C, 54.25; H, 7.12; N, 7.63. $[\alpha]^{25}D=-9.64°$ (c 2.08, MeOH).

Example 64

5-octynyl-3-(1-methyl-2-(S)-azetidinylmethoxy)pyridine dihydrochloride

A sample of 5-octynyl-3-(1-BOC-2-(S)-azetidinylmethoxy)pyridine from Example 63a (175 mg, 0.47 mmol) was dissolved in 3.5 mL of formic acid and 7 mL of formalin, and the mixture was heated at 70° C. for 16 hours. The mixture was basified with saturated saturated sodium bicarbonate, then extracted with $CH_2Cl_2$. The organic layer was dried over $MgSO_4$ and concentrated. The residue was chromatographed on a silica gel column, eluting with methelene chloride:MeOH 10:3 to 10:8 to afford the free base of the title compound (54.2 mg). MS ($CI/NH_3$) m/z 287 (M+H)$^+$. $^1$H NMR ($CDCl_3$, 300 MHz) δ0.90 (m, 3H), 1.32 (m, 4H), 1.44 (m, 2H), 1.61 (m, 2H), 2.08 (m, 2H), 2.39 (s, 3H), 2.42 (m, 2H), 2.88 (m, 1H), 3.42 (m, 2H), 4.00 (m, 2H), 7.18 (m, 1H), 8.20 (m, 2H). The base was converted to the salt by treatment with hydrogen chloride saturated EtOH to give the title compound. MS ($CI/NH_3$) m/z 287 (M+H)$^+$. $^1$H NMR ($D_2O$, 300 MHz) δ0.86 (m, 2H), 1.32 (m, 3H), 1.46 (m, 2H), 1.63 (m, 2H), 2.50 (t, J=6.9 Hz, 2H), 2.63–2.74 (m, 2H), 2.99 (s, 3H), 4.03 (m, 1H), 4.27 (m, 1H), 4.53 (m, 2H), 4.80 (m, 1H), 7.98 (s, 1H), 8.39 (s, 1H), 8.43 (d, J=2.4 Hz, 1H). Anal. Calcd for $C_{18}H_{26}N_2O \cdot 2.1$ HCl: C, 59.56; H, 7.80; N, 7.72. Found: C, 59.36; H, 7.83; N, 7.72. $[\alpha]^{25}D=-16.16°$ (c 0.76, MeOH).

Example 65

5-(3-aminophenyl)-3-(2-(S)-azetidinylmethoxy)pyridine hydrochloride 65a. 5-(3-aminophenyl)-3-(1-BOC-2-(S)-azetidinylmethoxy)pyridine The 5-bromo-3-(1-BOC-2-(S)-azetidinylmethoxy)pyridine from Example 54b (400 mg, 1.2 mmol), 3-aminophenylboronic acid (361 mg, 2.3 mmol, Aldrich Chem. Co.), Pd(0) (35 mg) and $Na_2CO3$ (1.5 mL of a 2 M solution) were mixed in 8 mL of toluene, and the mixture was stirred at reflux for 16 hours. The solvent was removed under vacuum, and the residue was purified by chromatography on silica gel, eluting with exane:$Et_2O$ 1:1, to afford 178 mg of the title compound. MS ($CI/NH_3$) m/z 356 (M+H)$^+$. $^1$H NMR ($CDCl_3$, 300 MHz) δ1.42 (s, 9H), 2.33 (m, 2H), 3.92 (m, 2H), 4.20 (m, 1H), 4.38 (m, 1H), 4.55 (m, 1H), 6.72 (m, 1H), 6.88 (s, 1H), 6.97 (m, 1H), 7.44 (m, 2H), 8.31 (m, 1H), 8.44 (m, 1H).

65b. 5-(3-aminophenyl)-3-(2-(S)-azetidinylmethoxy)pyridine hydrochloride

The BOC group was removed from the compound of step 65a (157 mg) by treatment with TFA in $CH_2Cl_2$ at 0° C. for 30 minutes to give the free base of the title compound. The volatiles were then removed under vacuum. The residue was neutralized with $NaHCO_3$ to p[H 8, then extracted with $CH_2Cl_2$, which was dried over $MgSO_4$ and concentrated. The residue was chromatographed on a silica gel column, eluting with $CH_2Cl_2$:MeOH:$NH_4OH$ 10:1:0.03 to afford the free base of the title compound (75 mg, 67% yield). MS ($CI/NH_3$) m/z 256 (M+H)$^+$. $^1$H NMR ($CDCl_3$, 300 MHz) δ2.30 (m, 1H), 2.42 (m, 1H), 3.79 (m, 2H), 4.10 (m, 2H), 4.32 (m, 1H), 6.88 (m, 1H), 6.97 (m, 1H), 7.23 (m, 1H), 7.48 (s, 1H), 8.28 (m, 1H), 8.43 (m, 1H). The base was converted to the salt by treatment with hydrogen chloride saturated EtOH to give the title compound. mp 85–87° C. MS ($CI/NH_3$) m/z 256 (M+H)$^+$. $^1$H NMR ($D_2O$, 300 MHz) δ2.56 (m, 2H), 3.84 (m, 1H), 4.34 (d, J=5.1 Hz, 1H), 4.72 (m, 2H), 6.93 (m, 1H), 7.10 (m, 2H), 7.36 (m, 1H), 7.61 (m, 1H), 8.25 (m, 1H), 8.39 (m, 1H). Anal. Calcd for $C_{15}H_{17}N_3O \cdot 0.5$ HCl: C, 65.86; H, 6.45; N, 15.36. Found: C,65.84; H, 6.26; N, 15.32. $[\alpha]^{25}D=-12.36°$ (c 0.96, MeOH).

Example 66

Intermediate Compound

5-Bromo-6-chloro-3-(2-(S)-azetidinylmethoxy)pyridine hydrochloride 66a. 5-Bromo-6-chloro-3-(1-BOC-2-(S)-azetidinvlmethoxy)pyridine (50722-136)

To a solution of diethyl azodicarboxylate (1.52 mL, 9.6 mmol) in THF (56 mL) was added triphenylphosphine (2.52 g, 9.6 mmol) at 0° C., and the reaction mixture was stirred for half an hour. 1-BOC-2-(S)-azetidinemethanol (1.44 g, 7.7 mmol) and 5-bromo-6-chloropyridine-3-ol (1.4 g, 6.4 mmol; prepared according to V. Koch and S. Schnatterer, Synthesis 1990, 499–501)) were then added. The reaction mixture was slowly warmed up to room temperature overnight. Solvent was removed, and the residue was chromatographed on a silica gel column, eluting with $CHCl_3$:MeOH 100:1 to afford the title compound. MS ($CI/NH_3$) m/z 377/379 (M+H)$^+$.

66b. 5-Bromo-6-chloro-3-(2-(S)-azetidinylmethoxy)pyridine hydrochloride (50722-141)

To 5-bromo-6-chloro-3-(1-BOC-2-(S)-azetidinylmethoxy)pyridine from step 66a (360 mg, 0.95 mmol) was added TFA in $CH_2Cl_2$ at 0° C., and the mixture was stirred for 30 minutes. The volatiles were then removed under vacuum. The residue was neutralized with $NaHCO_3$ to pH 8, then extracted with $CH_2Cl_2$, which was dried over $MgSO_4$ and concentrated. The residue was chromatographed on a silica gel column, eluting with $CH_2Cl_2$:MeOH:$NH_4OH$ 10:1:0.1 to afford to give the free base of the title compound. The base was converted to the salt by treatment with hydrogen chloride saturated EtOH to give the title compound (224 mg). mp 168–169° C. MS ($CI/NH_3$) m/z 277/279 (M+H)$^+$. $^1$H NMR ($D_2O$, 300 MHz) δ2.69 (dd, J=7.0, 8.5, 2H), 4.06–4.20 (m, 3H), 4.43 (d, J=4.5, 2H), 4.91–4.99 (m, 1H), 7.94 (d, J=3.0, 1H), 8.17 (d, J=3.0, 1H). Anal. Calcd for $C_9H_{10}N_2OBrCl \cdot 0.9$ HCl: C, 34.83; H, 3.54; N, 9.03. Found: C, 34.85; H, 3.56; N, 8.82. $[\alpha:]^{25}D=-4.81°$ (c 0.13, MeOH).

Example 67

5-Phenyl-6-chloro-3-(2-(S)-azetidinylmethoxy)pyridine hydrochloride 67a. 5-Phenyl-6-chloro-3-(1-BOC-2-(S)-azetidinylmethoxy)pyridine 5-bromo-6-chloro-3-(1-BOC-2-(S)-azetidinylmethoxy)pyridine from Example 66a (375 mg, 1 mmol), phenylboronic acid (146 mg, 1.2 mmol) and Pd(0) (35 mg) were mixed together in toluene (2 mL), and the mixture was heated at reflux for 16 hours. $NaHCO_3$ solution (2%, mL) was added, and the mixture was extracted with $CHCl_3$. The $CHCl_3$ was removed under reduced pressure, and the residue was chromatographed on a silica gel column, eluting with EtOAc/hexane 1:1 to afford the title compound (280 mg).

MS (CI/NH$_3$) m/z 375 (M+H)$^+$. $^1$H NMR (CDCl$_3$, 300 MHz) δ1.40 (s, 9H), 2.33–2.43 (m, 2H), 3.29 (t, J=7.5 Hz, 2H), 4.15 (dd, J=2.5, 7.5 Hz, 1H), 4.32–4.42 (m, 1H), 4.48–4.57 (m, 1H), 7.25–7.29 (m, 4H), 7.28 (d, J=2 Hz, 1H), 7.42–7.48 (m, 5H), 8.12 (d, J=3 Hz, 1H).

67b. 5-Phenyl-6-chloro-3-(2-(S)-azetidinylmethoxy)pyridine hydrochloride

To 5-phenyl-6-chloro-3-(1-BOC-2-(S)-azetidinylmethoxy)pyridine from step 67a (380 mg) was added TFA in CH$_2$Cl$_2$ at 0° C., and the mixture was stirred for 30 minutes. The volatiles were then removed under vacuum. The residue was neutralized with NaHCO$_3$ to pH 8, then extracted with CH$_2$Cl$_2$, which was dried over MgSO$_4$ and concentrated. The residue was chromatographed on a silica gel column, eluting with CH$_2$Cl$_2$:MeOH:NH$_4$OH 10:1:0.1 to afford to give the free base of the title compound. MS (CI/NH$_3$) m/z 275 (M+H)$^+$, 277 (M+2H)$^+$. $^1$H NMR (CDCl$_3$, 300 MHz) δ2.21–2.46 (m, 2H), 3.41–3.50 (m, 1H), 3.73 (dd, J=7.5, 8.0 Hz, 1H), 4.0–4.12 (m, 2H), 4.25–4.35 (m, 1H), 7.26 (d, J=3 Hz, 1H), 7.41–7.48 (m, 5H), 8.09 (d, J=3 Hz, 1H). The base was converted to the salt by treatment with hydrogen chloride saturated EtOH to give the title compound (256 mg). mp 148–150° C. MS (CI/NH$_3$) m/z 275 (M+H)$^+$. $^1$H NMR (D$_2$O, 300 MHz) δ2.66–274 (m, 2H), 4.06–4.21 (m, 3H), 4.46 (d, J=4.1, 2H), 4.92–5.01 (m, 1H), 7.50–7.59 (m, 5H), 7.60 (d, J=3.0, 1H), 8.20 (d, J=3.0, 1H). Anal. Calcd for C$_{15}$H$_{15}$N$_2$OCl·2 HCl: C, 51.82; H, 4.93; N, 8.06. Found: C, 52.10; H, 5.29; N, 7.70. [α]$^{25}$D=+7.5° (c 0.16, MeOH).

Example 68

5-Phenyl-6-chloro-3(1-methyl-2-(S)-azetidinylmethoxy)pyridine hydrochloride

To 5-phenyl-6-chloro-3-(2-(S)-azetidinylmethoxy)pyridine from Example 67 (100 mg, 0.36 mmol) in EtOH (3 mL) was added formalin (37%, 0.5 mL) and formic acid (0.25 mL), and the pH was adjusted to 6. Then NaCNBH$_3$ (70 mg) was added, and the mixture was stirred at room temperature for 16 hours. The mixture was diluted with water and saturated with K2CO3. The mixture was extracted with CHCl$_3$. The solvent was dried over MgSO4, filtered and concentrated. The residue was chromatographed on a silica gel column, eluting with CH$_2$Cl$_2$:MeOH 10:1 to afford the free base of the title compound. MS (CI/NH$_3$) m/z 289 (M+H)$^{+\cdot}$ $^1$H NMR (CDCl$_3$, 300 MHz) δ2.05–2.14 (m, 2H), 2.40 (s, 3H), 2.32–2.44 (m, 1H), 3.34–3.51 (m, 2H), 4.44 (d, J=7.5 Hz, 2H), 7.26 (d, J=3 Hz, 1H), 8.09 (d, J=3 Hz, 1H). The salt was prepared by treatment with HCl in Et$_2$O, as described above, to give the title compound. mp 187–188° C. MS (CNH) m/z 289 (M+H)$^{+\cdot}$ $^1$H NMR (D$_2$O, 300 MHz) δ2.60–2.71 (m, 2H), 2.99 (s, 3H), 3.94–4.12 (m, 1H), 4.18–4/33 (m, 1H), 4.47–4.55 (m, 3H), 7.57 (m, 5H), 7.60 (d, J=3.0 Hz, 1H), 8.18 (d, J=3.0 Hz, 1H). Anal. Calcd for C$_{16}$H$_{17}$N$_2$OCl·HCl·0.5 H$_2$O: C, 57.50; H, 5.73; N, 8.38. Found: C, 57.38; H, 5.53; N, 8.35. [α]$^{25}$D=+15° (c 0.11, MeOH).

Example 69

5-Phenyl-6-chloro-3-(1-methyl-2-(R)-pyrrolidinylmethoxy)pyridine dihydrochloride 69a. 5-Bromo-6-chloro-3-(1-BOC-2-(R)-pyrrolidinylmethoxy)pyridine Following the procedure of Example 23, except substituting 1-BOC-(R)-pyrrolidinemethanol for the 1-BOC-(S)-pyrrolidinemethanol the thereof, the title compound was prepared. MS (CI/NH$_3$) m/z 391/393 (M+H)$^{+\cdot}$ $^1$H NMR (DMSO-d$_6$, 300 MHz) δ01.65–2.05 (m, 4H), 3.20–3.35 (m, 2H), 3.95–4.15 (m, 3H), 7.98 (d, J=2.9 Hz, 1H), 8.21 (d, J=2.9 Hz, 1H).

69b. 5-Phenyl-6-chloro-3-(1-BOC-2-(R)-pyrrolidinylmethoxy)pyridine and 5-,6-diphenyl-3-(1-BOC-2-(R -pyrrolidiniylmethoxy)pyrdine 5-bromo-6-chloro-3-(1-BOC-2-(R)-pyrrolidinylmethoxy)pyridine from step 69a (784 mg, 2 mmol), phenylboronic acid (610 mg, 5 mmol), Na$_2$CO$_3$ (3 mL) and Pd(0) (70 mg) were mixed together in toluene (20 mL), and the mixture was heated at reflux for 4 hours. The mixture was extracted with CHCl$_3$. The CHCl$_3$ was removed under reduced pressure, and the residue was chromatographed on a silica gel column, eluting with hexane/EtOAc 100:5 to 100:25 to afford the title compounds. For the mono-phenyl compound: MS (CI/NH$_3$) m/z 390 (M+H)$^{+\cdot}$ $^1$H NMR (CDCl$_3$, 300 MHz) δ1.43 (s, 9H), 1.88 (m, 1H), 2.04 (m, 2H), 3.37 (m, 2H), 3.37 (m, 2H), 3.89 (br s, 1H), 4.01 (br s, 1H), 4.15 (m, 2H), 7.46 (s, 5H), 7.47 (m, 1H), 8.09 (m, 1H). For the diphenyl compound: MS (CI/NH$_3$) m/z 431 (M+H)$^{+1}$H NMR (CDCl$_3$, 300 MHz) δ1.46 (s, 9H), 1.89 (m, 1H), 2.07 (m, 2H), 34.2 (br s, 2H), 3.93 (br s, 1H), 4.07 (br s, 1H), 4.23 (m, 2H), 7.20 (m, 5H), 7.28 (m, 6H), 8.40 (m, 1H).

69c. 5-Phenyl-6-chloro-3-(1-methyl-2-(R)-pyrrolidinylmethoxy)pyridine hydrochloride To the 5-phenyl-6-chloro-3-(1-BOC-2-(R)-pyrrolidinylmethoxy)pyridine compound from step 69b (262 mg) was added formalin (37%, 0.5 mL) and formic acid (0.25 mL), and the mixture was heated at 70° C. for 3 hours. The solvent was removed, and to the residue was added solid NaHCO$_3$. When pH 7–8 was achieved, the mixture was extracted with CH$_2$Cl$_2$, which was dried over MgSO$_4$ and concentrated. The residue was chromatographed on a silica gel column, eluting with CH$_2$Cl$_2$:MeOH:NH$_4$OH 100:10:0.04 to afford to give the free base of the title compound (200 mg). MS (CI/NH$_3$) m/z 303 (M+H)$^{+\cdot}$ $^1$H NMR (CDCl$_3$, 300 MHz) δ1.98 (m, 2H), 2.10 (m, 1H), 2.22 (m, 1H), 2.71 (m, 1H), 2.78 (s, 3H), 3.27 (m, 1H), 3.60 (m, 1H), 4.18 (m, 1H), 4.47 (m, 1H), 7.46 (m, 5H), 8.10 (m, 1H), 8.30 (br s, 1H). The base was converted to the salt by treatment with HCl in THF to give the title compound. MS (CI/NH$_3$) m/z 303 (M+H)$^{+\cdot}$ $^1$H NMR (D$_2$O, 300 MHz) δ2.05–2.17 (m, 2H), 2.19–2.27 (m, 1H), 2.35–2.45 (m, 1H), 3.04 (s, 3H), 3.30 (m, 1H), 3.74 (m, 1H), 3.94 (m, 1H), 4.37 (dd, J=6.1, 11.2 Hz, 1H), 4.54 (dd, J=3.3, 11.2 Hz, 1H), 7.56 (m, 6H), 8.15 (d, J=3.0 Hz, 1H). Anal. Calcd for C$_{17}$H$_{19}$N$_2$OCl·1.1 HCl: C, 59.55; H, 5.91; N, 8.17. Found: C, 59.74; H, 6.04; N, 8.14. [α]$^{25}$D=+7.17° (c 1.11, MeOH).

Example 70

5-Phenyl-6-chloro-3-(2-(R)-pyrrolidinylmethoxy)pyridine hydrochloride

To the 5-phenyl-6-chloro-3-(1-BOC-2-(R)-pyrrolidinylmethoxy)pyridine compound from Example 69b (164 mg) was added HCl in dioxane (3 mL). The mixture was stirred at room temperature for 40 hours. The solvent was removed under vacuum at 50° C., and the residue was triturated with Et$_2$O. The solid was dried under high vacuum to afford the title compound. mp 178–180° C. MS (CI/NH$_3$) m/z 289 (M+H)$^{+\cdot}$ $^1$H NMR (D$_2$O, 300 MHz) δ1.27–2.10 (m, 1H), 2.03–2.18 (m, 2H), 2.22–2.31 (m, 1H), 3.41 (t, J=7.5 Hz, 2H), 4.13 (m, 1H), 4.26 (m, 1H), 4.46 (dd, J=3.4, 10.8 Hz, 1H), 7.54 (m, 6H), 8.12 (d, J=3.0 Hz, 1H). Anal. Calcd for C$_{16}$H$_{17}$N$_2$OCl·1.2 HCl: C, 57.79; H, 5.52; N, 8.42. Found: C, 57.73; H, 6.5.58; N, 8.27. [α]$^{25}$D=−10.94° (c 0.64, MeOH).

Example 71

5,6-Diphenyyl-3-(2-(R)-pyrroidinylmethoxy)pyridine dihydrochloride

To the 5,6-diphenyl-3-(1-BOC-2-(R)-pyrrolidinylmethoxy)pyridine compound from Example 69b (140 mg) was added HCl in dioxane (3 mL). The mixture was stirred at room temperature for 40 hours. The solvent was removed under vacuum at 50° C., and the residue was triturated with Et$_2$O. The solid was dried under high vacuum to afford the title compound. MS (CI/NH$_3$) m/z 331 (M+H)$^+$. $^1$H NMR (D$_2$O, 300 MHz) δ1.97–2.20 (m, 3H), 2.33 (m, 1H), 3.43 (t, J=7.2 Hz, 1H), 3.74 (m, 1H), 4.21 (m, 1H), 4.48 (m, 1H), 4.68 (dd, J=3.4, 10.5 Hz, 1H), 7.27–7.55 (m, 10H), 8.23 (d, J=2.7 Hz, 1H), 8.55 (d, J=2.7 Hz, 1H). Anal. Calcd for C$_{22}$H$_{22}$N$_2$O·2.4 HCl·0.5 H$_2$O: C, 61.89; H, 6.00; N, 6.56. Found: C, 62.04; H, 6.17; N, 6.03. [α]$^{25}$D=–2.36° (c 1.95, MeOH).

Example 72

5,6-Diphenyl-3-(1-methyl-2-(R)-pyrrolidinylmethoxy)pyridine dihydrochloride

To the 5,6-diphenyl-3-(1-BOC-2-(S)-pyrrolidinylmethoxy)pyridine compound from Example 69b (195 mg) was added formalin (37%, 6 mL) and formic acid (3 mL), and the mixture was heated at 70° C. for 4 hours. The solvent was concentrated, and to the residue was added solid NaHCO$_3$. When pH 7–8 was achieved, the mixture was extracted with CH$_2$Cl$_2$, which was dried over MgSO$_4$ and concentrated. The residue was chromatographed on a silica gel column, eluting with CH$_2$Cl$_2$:MeOH:NH$_4$OH 100:15:0.04 to afford to give the free base of the title compound (144 mg, 93% yield). MS (CI/NH$_3$) m/z 345 (M+H)$^+$. $^1$H NMR (CDCl$_3$, 300 MHz) δ2.02 (m, 3H), 2.19 (m, 1H), 2.67 (m, 1H), 2.76 (s, 3H), 3.17 (m, 1H), 3.50 (m, 1H), 4.19 (m, 1H), 4.42 (m, 1H), 7.19 (m, 5H), 7.28 (m, 5H), 8.32 (s, 1H). The base was converted to the salt by treatment with hydrogen chloride in THF to give the title compound. MS (CI/NH$_3$) m/z 345 (M+H)$^+$. $^1$H NMR (D$_2$O, 300 MHz) δ2.08–2.20 (m, 2H), 2.20–2.26 (m, 1H), 2.45–2.47 (m, 1H), 3.09 (s, 3H), 3.29 (m, 1H), 3.74 (m, 1H), 4.02 (m, 1H), 4.73 (m, 1H), 7.27–7.55 (m, 10H), 8.23 (d, J=2.7 Hz, 1H), 8.56 (d, J=2.7 Hz, 1H). Anal. Calcd for C$_{23}$H$_{24}$N$_2$O·2.2 HCl·0.5 H$_2$O: C, 63.70; H, 6.32; N, 6.46. Found: C, 63.68; H, 6.13; N, 6.68. [α]$^{25}$D=+12.31° (c 3.25, MeOH).

Example 73

Intermediate Compound

5-bromo-6-chloro-3-(2-(R)-pyrrolidinylmethoxy)pyridine dihydrochloride

5-bromo-6-chloro-3-(1-BOC-2-(R)-pyrrolidinylmethoxy)pyridine from step 69a (150 mg) was stirred with HCl in dioxane (3 mL) at room temperature for 16 hours. The precipitate formed was triturated with Et$_2$O, and the solid was dried under high vacuum to afford the title compound (99.2 mg). mp 230° C. MS (CI/NH$_3$) m/z 291/293 (M+H)$^+$. $^1$H NMR (D$_2$O, 300 MHz) δ1.89–2.02 (m, 1h), 2.05–2.21 (m, 2H), 2.21–2.35 (m, 1H), 3.42 (t, J=7.2 Hz, 2H), 4/12 (m, 1H)), 4.25 (dd, J=7.8, 10.5 Hz, 1H), 4.47 (dd, J=3.2, 10.5 Hz, 1H), 7.90 (d, J=2.7 Hz, 1H), 8.13 (d, J=2.7 Hz, 1H). Anal. Calcd for C$_{10}$H$_{12}$N$_2$OBrCl·2 HCl: C, 36.61; H, 3.99; N, 8.54. Found: C, 36.69; H, 3.91; N, 8.41. [α]$^{25}$D=–14.80° (c 0.25, MeOH).

Example 74

Intermediate Compound

5-bromo-6-chloro-3-(1-methyl-2-(R)-pyrrolidinylmethoxy)pyridine hydrochloride

To 5-bromo-6-chloro-3-(1-BOC-2-(R)-pyrrolidinylmethoxy)pyridine from step 69a (210 mg, 0.54 mmol) was added formalin (37%, 7 mL) and formic acid (3.5 mL), and the mixture was heated at 70° C. for 2.5 hours. The solvent was concentrated, and solid NaHCO$_3$ was added to the residue. At pH 8 the mixture was extracted with CH$_2$Cl$_2$, which was dried over MgSO$_4$ and concentrated. The residue was chromatographed on a silica gel column, eluting with CH$_2$Cl$_2$:MeOH 100:5–100:10 to afford to give the free base of the title compound (110 mg, 67% yield). MS (CI/NH$_3$) m/z 305/307 (M+H)$^+$. $^1$H NMR (CDCl$_3$, 300 MHz) δ1.68 (m, 3H), 2.02 (m, 1H), 2.32 (m, 1H), 2.48 (s, 3H), 2.67 (m, 1H), 3.12 (m, 1H), 3.96 (m, 2H), 7.52 (m, 1H), 8.06 (m, 1H). The base was converted to the salt by treatment with hydrogen chloride in THF to give the title compound. MS (C NH$_3$) m/z 305/307 (M+H)$^+$. $^1$H NMR (D$_2$O, 300 MHz) δ2.20–2.17 (m, 2H), 2.18–2.31 (m, 1H), 2.32–2.47 (m, 1H), 3.03 (s, 3H), 3.27 (m, 1H), 3.73 (m, 1H), 3.96 (m, 1H), 4.36 (dd, J=6.1, 11.2 Hz, 1H), 4.53 (dd, J=3.1, 11.2 Hz, 1H), 7.91 (d, J=2.7 Hz, 1H), 8.13 (d, J=2.7 Hz, 1H). Anal. Calcd for C$_{11}$H$_{14}$N$_2$OBrCl·1.1 HCl: C, 38.22; H, 4.40; N, 8.10. Found: C, 37.95; H, 4.81; N, 7.76. [α]$^{25}$D=+11.06° (c 0.24, MeOH).

Example 75

5-(3-aminophenyl)-6-chloro-3-(2-(R)-pyrrolidinylmethoxy)pyridine dihydrochloride

75a. 5-(3-aminophenyl)-6-chloro-3-(1-BOC-2-(R)-pyrrolidinylmethoxy)pyridine

To a solution of 5-bromo-6-chloro-3-(1-BOC-2-(R)-pyrrolidinylmethoxy)pyridine from Example 69a (520 mg, 1.33 mmol) and 3-aminophenylboronic acid (310 mg, 2.0 mmol) in toluene (8 mL) was added Pd(0) (50 mg) and Na$_2$CO3 (2.5 mL of a 2 M solution), and the mixture was heated at reflux for 16 hours. The solvent was removed under vacuum, and the residue was purified by chromatography on a silica gel column, eluting with CHCl$_3$:Et$_2$O 100:5–100:40 to afford 160 mg of the title compound. MS (CI/NH$_3$) m/z 404 (M+H)$^+$. $^1$H NMR (CDCl$_3$, 300 MHz) δ1.44 (s, 9H), 1.88 (m, 1H), 2.03 (m, 2H), 3.37 (m, 2H), 3.76 (m, 2H), 4.16 (m, 2H), 6.75 (m, 2H), 6.82 (m, 1H), 7.22 (m, 2H), 8.08 (m, 1H).

75b. 5-(3-aminophenyl)-6-chloro-3-(2-(R-pyrrolidinylmethoxy)pyridine dihydrochloride The compound from step 75a was stirred with HCl in dioxane at room temperature. The precipitate formed was triturated with Et$_2$O, and the solid was dried under high vacuum to afford the title compound. MS (CI/NH$_3$) m/z 304 (M+H)$^+$. $^1$H NMR (D$_2$O, 300 MHz) δ1.92–2.02 (m, 1H), 2.07–2.18 (m, 2H), 2.25–2.34 (m, 1H), 3.42 (t, J=7.3 Hz, 2H), 4.13 (m, 1H), 4.28 (dd, J=7.6, 10.8 Hz, 1H), 4.51 (dd, J=3.4, 10.5 Hz, 1H), 7.51–7.71 (m, 5H), 8.17 (d, J=3.1 Hz, 1H). Anal. Calcd for C$_{16}$H$_{18}$N$_3$OCl·2 HCl·1.7 H$_2$O: C, 51.01; H, 5.35; N, 11.15. Found: C, 50.75; H. 5.28; N, 10.95. [α]$^{25}$D=–13.95° (c 0.38, MeOH).

Example 76

5-4-chlorophenyl)-6-chloro-3-(1-methyl-2(R)-pyrrolidinylmethoxy)pyridine hydrochloride 76a. 5-(4-chlorophenyl)-6-chloro-3-(1-BOC-2-(R)-pyrrolidinylmethoxy)pyridine To a solution of 5-bromo-6-chloro-3-(1-BOC-2-(R)-pyrrolidinylmethoxy)pyridine from Example 69a (460 mg, 1.2 mmol) and 4-chlorophenylboronic acid (225 mg, 1.44 mmol) in toluene (10 mL) was added Pd(0) (40 mg) and $Na_2CO_3$ (1.2 mL of a 2 M solution), and the mixture was heated at reflux for 1.5 hours. The solvent was removed under vacuum, and the residue was purified by chromatography on a silica gel column, eluting with hexane:$Et_2O$ 100:10–100:30 to afford of the title compound (345 mg, 68% yield). MS (CI/NH3) m/z 423 (M+H)$^+$ $^1$H NMR (CDCl$_3$, 300 MHz) δ1.45 (s, 9H), 1.89 (m, 2H), 2.03 (m, 2H), 3.37 (m, 2H), 4.00 (m, 1H), 4.15 (m, 2H), 7.42 (m, 6H), 8.10 (m, 2H).

76b. 5-(4-chlorophenyl)-6-chloro-3-(1-methyl-2-(R)-pyrrolidinylmethoxy)pyridine

To 5-(4-chlorophenyl)-6-chloro-3-(1-BOC-2-(R)-pyrrolidinylmethoxy)pyridine from step 76aa (340 mg, 0.8 mmol) was added formalin (37%, 10 mL) and formic acid (5 mL), and the mixture was heated at 70° C. for 2.5 hours. The solvent was concentrated, and solid NaHCO$_3$ was added to the residue. At pH 8 the mixture was extracted with CH$_2$Cl$_2$, which was dried over MgSO$_4$ and concentrated. The residue was chromatographed on a silica gel column, eluting with CH$_2$Cl$_2$:MeOH 100:5–100:10 to afford to give the free base of the title compound (255 mg, 94% yield). MS (CI/NH$_3$) m/z 337 (M+H)$^+$ $^1$H NMR (CDCl$_3$, 300 MHz) δ1.80–2.40 (m, 4H), 2.52 (m, 1H), 2.65 (s, 3H), 2.98 (m, 1H), 3.38 (m, 1H), 4.08 (m, 1H), 4.28 (m, 1H), 7.23 (m, 1H), 7.42 (m, 4H), 8.10 (m, 1H). The base was converted to the salt by treatment with hydrogen chloride in Et$_2$O/THF to give the title compound. mp 176–178° C. MS (CI/NH$_3$) m/z 337 (M+H)$^+$ $^1$H NMR (D$_2$O, 300 MHz) δ2.06–2.16 (m, 2H), 2.19–2.23 (m, 1H), 2.38–2.41 (m, 1H), 3.03 (s, 3H), 3.24 (m, 1H), 3.74 (m, 1H), 3.91 (m, 1H), 4.36 (dd, J=6.1, 11.2 Hz, 1H), 4.54 (dd, J=3.1, 11.2 Hz, 1H), 7.49–7.57 (m, 5H), 8.14 (d, J=3.0 Hz, 1H). Anal. Calcd for C$_{17}$H$_{18}$N$_2$OCl$_2$·1.3 HCl: C, 53.08; H, 5.06; N, 7.28. Found: C, 52.93; H, 5.17; N, 7.33. [α]$^{25}$D=+7.33° (c 2.25, MeOH).

Example 77

5-(5,5-dimethyl-1,3-hexadienyl)-6-chloro-3-(2-(R)-pyrrolidinylmethoxy)pyridine dihydrochloride 77a. 5-(5,5-dimethyl-1,3-hexadienyl)-6-chloro-3-(1-BOC-2-(R)-pyrrolidinylmethoxy)pyridine A solution of 5-bromo-6-chloro-3-(1-BOC-2-(R)-pyrrolidinylmethoxy)pyridine from Example 69a (480 mg, 1.2 mmol), 5-(5,5-dimethyl-1,3-hexadiene (200 mg, 1.8 mmol), Pd(OAc)$_4$ (25 mg), tris(o-tolyl)phosphine (125 mg), and triethylamnine (2.5 mL) in acetonitrile (5 mL) was sealed in a tube and headed at 100° C. for 4 days. The solution was then diluted with EtOAc, and the mixture was extracted with water and aqueous NaHCO3 solution. The organic layer was dried and concentrated. The residue was chromatographed on a silica gel column, eluting with hexane:Et$_2$O 100:5–100:15 to afford the title compound (135 mg, 43% yield). MS (CI/NH$_3$) m/z 421 (M+H)$^+$. $^1$H NMR (CDCl$_3$, 300 MHz) δ1.08 (s, 9H), 1.48 (s, 9H), 1.89 (m, 2H), 2.00 (m, 2H), 3.38 (m, 2H), 3.95 (m, 1H), 4.13 (m, 1H), 4.23 (m, 1H), 5.99 (m, 1H), 6.22 (m, 1H), 6.71 (m, 1H), 6.95 (m, 1H), 7.74 (br s, 1H).

77b. 5-(5,5-dimethyl-1,3-hexadienyl)-6-chloro-3-(1-BOC-2-(R)-pyrrolidinylmethoxy)pyridine dihydrochloride This compound from step 77a was deprotected and converted to the salt by treatment with hydrogen chloride in Et$_2$O/THF to afford the title compound. mp 190–192° C. MS (CI/NH$_3$) m/z 321 (M+H)$^+$. $^1$H NMR (D$_2$O, 300 MHz) δ1.08 (s, 9H), 1.92–2.02 (m, 1H), 2.06–2.19 (m, 2H), 2.22–2.32 (m, 1H), 3.39 (m, 2H), 4.13 (m, 1H), 4.25 (m, 1H), 4.47 (m, 1H), 6.13 (d, J=15.2 Hz, 1H), 6.37 (dd, J=10.2, 15.1 Hz, 1H), 6.77 (d, J=14.9 Hz, 1H), 6.96 (dd, J=10.2, 15.3 Hz, 1H), 7.65 (d, J=2.8 Hz, 1H), 7.95 (d, J=2.7 Hz, 1H). Anal. Calcd for C$_{18}$H$_{25}$N$_2$OCl·2 HCl: C, 55.90; H, 6.91; N, 7.11. Found: C, 54.87; H, 7.12; N, 6.85. [α]$^{25}$D=−6.67° (c 0.40, MeOH).

Example 78

5-(5,5-dimethyl-1,3-hexadienyl)-6-chloro-3-(1-methyl-2-(R)-pyrrolidinylmethoxyy)pyridine dihydrochloride To 5-(5,5-dimethyl-1,3-hexadienyl)-6-chloro-3-(1-BOC-2-(R)-pyrrolidinylmethoxy)pyridine from step 77a (145 mg, 0.34 mmol) was added formalin (37%, 4 mL) and formic acid (2 mL), and the mixture was heated at 70° C. for 3 hours. The solvent was concentrated, and solid NaHCO$_3$ was added to the residue. At pH 8 the mixture was extracted with CH$_2$Cl$_2$, which was dried over MgSO$_4$ and concentrated. The residue was chromatographed on a silica gel column, eluting with CH$_2$Cl$_2$:MeOH 100:4 to afford to give the free base of the title compound (72.5 mg, 66% yield). MS (CI/NH$_3$) m/z 335 (+H)$^+$. $^1$H NMR (CDCl$_3$, 300 MHz) δ1.10 (s, 9H), 1.77 (m, 2H), 2.00 (m, 1H), 2.28 (m, 1H), 2.45 (m, 3H), 2.70 (m, 1H), 3.10 (m, 1H), 3.43 (m, 1H), 4.00 (m, 1H), 4.38 (m, 1H), 5.95 (m, 1H), 6.20 (m, 1H), 6.70 (m, 2H), 7.38 (m, 1H), 7.93 (m, 1H). The base was converted to the salt by treatment with hydrogen chloride in Et$_2$O/THF to give the title compound. mp 194° C. (dec). MS (CI/NH$_3$) m/z 335 (M+H)$^+$. $^1$H NMR (D$_2$O, 300 MHz) δ1.07 (s, 9H), 1.78–2.05 (m, 2H) 2.17–2.28 (m, 1H), 2.90 (dd, J=5.1, 31.9 Hz, 3H), 3.12 (m, 1H), 3.50 (m, 3H), 4.41 (m, 2H), 6.04 (d, J=15.6 Hz, 1H), 6.30 (dd, J=10.2, 15.2 Hz, 1H), 6.70 (d, J-15.6 Hz, 1H), 7.10 (ss, J=10.2, 15.6 Hz, 1H), 7,.84 (d, J=3.0 Hz, 1H), 8.06 (d, J=3.1 Hz, 1H). Anal. Calcd for C$_{19}$H$_{27}$N$_2$OCl·1.7 HCl·0.8 Et$_2$O: C, 58.45; H, 8.11; N, 6.14. Found: C, 58.58; H, 8.11; N, 5.85. [α]$^{25}$D=+6.95° (c 0.71, MeOH).

Example 79

5-(1-octynyl)-6-chloro-3-(2-(R)-pyrrolidinylmethoxy)pyridine dihydrochloride 79a. 5-(1-octynyl)-6-chloro-3-(1-BOC-2-(R)-pyrrolidinylmethoxy)pyridine A mixture of 5-bromo-6-chloro-3-(1-BOC-2-(R)-pyrrolidinylmethoxy)pyridine from Example 69a (425 mg, 1.1 mmol), 1-octyne (0.2 mL, 1.4 mmol), Pd(PPh)$_3$Cl$_2$ (20 mg), CuI (catalytic amount) and triethylamine (0.5 mL) in CH$_2$Cl$_2$ (8 mL) was heated at reflux for 16 hours. Heating was continued until no starting material remained. The solvent was removed, and the residue was washed with 10% NaOH then extracted with CH$_2$Cl$_2$. The organic extract was dried over MgSO$_4$ and concentrated. The residue was chromatographed on a silica gel column, eluting with hexane:Et$_2$O 100:6–100:15 to afford to give the title compound (335 mg, 72% yield). MS (CI/NH$_3$) m/z 421 (M+H)$^+$. $^1$H NMR (CDCl$_3$, 300 MHz) δ0.90 (m, 3H), 1.32 (m, 4H), 1.48 (s, 9H), 1.49 (m, 2H), 1.62 (m, 2H), 1.88 (m, 2H), 2.00 (m, 2H), 2.48 (m, 2H), 3.34 (m, 2H), 3.90 (m, 1H), 4.12 (m, 2H), 7.30 (br s, 1H), 7.98 (m, 1H).

79b. 5-(1-octynyl)-6-chloro-3-(2-(R)-pyrrolidinylmethoxy)pyridine dihydrochloride The compound from step 79a was dissolved in TFA (1 mL) and $CH_2Cl_2$ (2 mL), and the solution was stirred at 0° C. for 25 minutes. The solution was warmed to room temperature and made basic with saturated aqueous $NaHCO_3$. The basic mixture was extracted with $CH_2Cl_2$, which was dried over $MgSO_4$ and concentrated. The residue was chromatographed on a silica gel column, eluting with $CH_2Cl_2$:MeOH 100:5–100:15 to afford to give the free base of the title compound (126 mg). MS (CI/$NH_3$) m/z 321 (M+H)$^+$. $^1$H NMR (CDCl$_3$, 300 MHz) δ0.92 (m, 3H), 1.30 (m, 4H), 2.00 (m, 2H), 2.15 (m, 1H), 2.46 (m, 2H), 2.62 (m, 2H), 2.82 (m, 1H), 3.20 (m, 2H), 3.80 (m, 1H), 4.12 (m, 2H), 7.36 (m, 1H), 7.95 (m, 1H). The base was converted to the salt by treatment with HCl in $Et_2O$/THF to give the title compound. MS (CI/$NH_3$) m/z 321 (M+H)$^+$. $^1$H NMR (D$_2$O, 300 MHz) δ: 0.93 (m, 3H), 1.26–1.41 (m, 4H), 1.48 (m, 2H), 1.61 (m, 2H), 1.90 (m, 1H), 2.10 (m, 1H), 2.24 (m, 1H), 2.45 (t, J=7.0 Hz, 2H), 3.43 (t, J=7.0 Hz, 2H), 4.09 (m, 1H), 4.21 (m, 1H), 4.34 (dd, J=3.8, 10.3 Hz, 1H), 7.38 (d, J=3.0 Hz, 1H), 8.01 (d, J=2.9 Hz, 1H). Anal. Calcd for $C_{18}H_{25}N_2OCl·1.8$ HCl: C, 55.94; H, 6.99; N, 7.25. Found: C, 56.05; H, 6.99; N, 6.85. $[α]^{25}D=-3.03°$ (c 0.76, MeOH).

Example 80

5-(1-octynyl)-6-chloro-3- 1-methyl-2-(R)-pyrrolidinylmethoxy)pyridine dihydrochloride To 5-(1-octynyl)-6-chloro-3-(1-BOC-2-(R)-pyrrolidinylmethoxy)pyridine from Example 79a (330 mg, 0.78 mmol) was added formalin (37%, 9 mL) and formic acid (4.5 mL), and the mixture was heated at 70° C. for 2 hours. The solvent was concentrated, and solid $NaHCO_3$ was added to the residue. At pH 8 the mixture was extracted with $CH_2Cl_2$, which was dried over $MgSO_4$ and concentrated. The residue was chromatographed on a silica gel column, eluting with $CH_2Cl_2$:MeOH 100:1–100:3 to afford to give the free base of the title compound (166.5 mg, 64% yield). MS (CI/$NH_3$) m/z 335 (M+H)$^+$. $^1$H NMR (CDCl$_3$, 300 MHz) δ0.92 (m, 3H), 1.32 (m, 4H), 1.48 (m, 2H), 1.62 (m, 2H), 1.80 (m, 4H), 2.02 (m, 1H), 2.30 (m, 1H), 2.45 (m, 1H), 2.47 (s, 3H), 2.66 (m, 1H), 3.12 (m, 1H), 3.93 (m, 2H), 7.27 (m, 1H), 7.98 (m, 1H). The base was converted to the salt by treatment with HCl in $Et_2O$ to give the title compound. mp 114–116° C. (dec). MS (CI/$NH_3$) m/z 335 (M+H)$^+$. $^1$H NMR (D$_2$O, 300 MHz) δ1.02 (t, J=6.7 Hz, 3H), 1.43 (m, 4H), 1.58 (m, 2H), 1.71 (m, 2H), 2.06 (m, 2H), 2.21 (m, 2H), 2.42 (m, 1H), 2.56 (t, J=6.7 Hz, 2H), 3.06 (s, 3H), 3.28 (m, 1H), 3.77 (m, 1H), 3.87 (m, 1H), 4.41 (m, 2H), 7.50 (m, 1H), 8.12 (d, J=2.4 Hz, 1H). Anal. Calcd for $C_{19}H_{27}N_2OCl·1.5$ HCl: C, 58.58; H, 7.37; N, 7.19. Found: C, 58.64; H, 7.39; N, 7.20. $[α]^{25}D=+8.99°$ (c 0.64, MeOH).

Example 81

5-(2-(4-pyridinyl)ethenyl)-6-chloro-3-(2-(R)-pyrrolidinylmethoxy)pyridine dihydrochloride 80a. 5-(2-(4-pyridinyl)ethenyl)-6-chloro-3-(1-BOC-2-(R)-pyrrolidinylmethoxy)pyridine A mixture of 5-bromo-6-chloro-3-(1-BOC-2-(R)-pyrrolidinyimethoxy)pyridine from Example 69a (1.18 g, 3 mmol), 4-ethenylpyridine (0.39 mL, 3.6 mmol), Pd(OAc)$_4$ (62.5 mg), tris(o-tolyl)phosphine (312.5 mg), and triethylamine (6.25 mL) in acetonitrile (15 mL) was heated at reflux for 16 hours. The solution was then concentrated, and the residue was washed with water and aqueous $NaHCO_3$ solution. The organic layer was dried and concentrated. The residue was chromatographed on a silica gel column, eluting with hexane:$Et_2O$ 100:5–100:15 to afford the title compound (852 mg, 69% yield). MS (CI/$NH_3$) m/z 416 (M+H)$^+$. $^1$H NMR (CDCl$_3$, 300 MHz) δ1.48 (s, 9H), 1.92 (m, 2H), 2.02 (m, 2H), 3.42 (m, 2H), 3.97 (m, 1H), 4.13 (m, 2H), 7.43 (m, 2H), 7.56 (m, 1H), 8.05 (m, 1H), 8.62 (m, 2H).

80b. 5-(2-4-pyridinyl)ethenyl)-6-chloro-3-(2-(R)-pyrrolidinylmethoxy)pyridine dihydrochloride The compound from step 81a was deprotected and converted to the salt by treatment with HCl in dioxane to give the title compound. MS (CI/$NH_3$) m/z 316 (M+H)$^+$. $^1$H NMR (D$_2$O, 300 MHz) δ1.92–2.07 (m, 1H), 2.09–2.21 (m, 2H), 2.22–2.37 (m, 1H), 3.44 (t, J=6.4 Hz, 2H), 4.15 (m, 1H), 4.31 (dd, J=7.5, 10.6Hz, 1H), 7.40 (d, J=16.2 Hz, 1H), 7.88 (m, 2H), 8.12 (m, 3H), 8.67 (d, J=7.1 Hz, 2H). Anal. Calcd for $C_{17}H_{18}N_3OCl·1.8$ HCl: C, 55.94; H, 6.99; N, 7.25. Found: C, 56.05; H, 6.99; N, 6.85. $[α]^{25}D=-2.47°$ (c 0.77, MeOH).

Example 82

5-(2-(4-pyridinyl)ethenyl)-6-chloro-3-(1-methyl-2-(R)-pyrrolidinylmethoxy)pyridine dihydrochloride To 5-(2-(4-pyridinyl)ethenyl))-6-chloro-3-(1-BOC-2-(R)-pyrrolidinylmethoxy)pyridine from Example 81a (760 mg, 1.8 mmol) was added formalin (37%, 20 mL) and formic acid (10 mL), and the mixture was heated at 100° C. for 1 hours. The solvent was concentrated, and saturated aqueous $NaHCO_3$ was added to the residue. At pH 8 the mixture was extracted with $CH_2Cl_2$, which was dried over $MgSO_4$ and concentrated. The residue was chromatographed on a silica gel column, eluting with $CH_2Cl_2$:MeOH 100:2–100:15 to afford to give the free base of the title compound (327 mg, 55% yield). MS (CI/$NH_3$) m/z 330 (M+H)$^+$. $^1$H NMR (CDCl$_3$, 300 MHz) δ1.80 (m, 3H), 2.07 (m, 1H), 2.35 (m, 1H), 2.52 (s, 3H), 2.72 (m, 1H), 3.16 (m, 1H), 4.00 (m, 1H), 4.07 (m, 1H), 7.0 (m, 1H), 7.40 (m, 2H), 7.53 (m, 2H), 8.06 (m, 1H), 8.63 (m, 2H). The base was converted to the salt by treatment with HCl in $Et_2O$ to give the title compound. mp 220–222° C. (dec). MS (CI/$NH_3$) m/z 330 (M+H)$^+$. $^1$H NMR (D$_2$O, 300 MHz) δ2.06–2.37 (m, 3H), 2.44 (m, 1H), 3.07 (s, 3H), 3.30 (m, 1H), 3.78 (m, 1H), 3.98 (m, 1H), 4.42 (dd, J=6.1, 11.2 Hz, 1H), 4.58 (dd, J=3.0, 11.2 Hz, 1H), 7.36 (d, J=16.3 Hz, 1H), 7.82 (d, J=16.6 Hz, 1H), 7.87 (d, J=3.1 Hz, 1H), 8.03 (d, J=6.8 Hz, 2H), 8.11 (d, J=2.7 Hz, 1H), 8.63 (d, J=6.8 Hz, 2H). Anal. Calcd for $C_{18}H_{20}N_3OCl·2.2$ HCl: C, 52.73; H, 5.46; N, 10.23. Found: C, 52.98; H, 5.56; N, 9.90. $[α]^{25}D=+11.48°$ (c 0.30, MeOH).

Example 83

5-(2-(4-pyridinyl)ethyl)-6-chloro-3-(1-methyl-2-(R)-pyrrolidinylmethoxy)pyrdine trihydrochloride A sample of 5-(2-(4-pyridinyl)ethenyl)-6-chloro-3-(1-methyl-2-(R)-pyrrolidinylmethoxy)pyridine from Example 82 (85 mg) was dissolved in MeOH. To this solution was added Pd/C (9.5 mg), and the mixture was stirred under $H_2$ for 16 hours at room temperature. The catalyst was filtered off, and the solvent was removed under vacuum. The residue was chromatographed on a silica gel column, eluting with $CH_2Cl_2$:MeOH 100:3–100:10 to afford to give the free base of the title compound (30 mg). MS (CI/$NH_3$) m/z 332 (M+H)$^+$. $^1$H NMR (CDCl$_3$, 300 MHz) δ1.65 (m, 2H), 1.80 (m, 1H), 2.0 (m, 1H), 2.32 (m, 1H), 2.47 (s, 3H), 2.64 (m, 1H), 2.96 (m, 4H), 3.12 (m, 1H), 3.90 (m, 2H), 6.98 (m, 1H), 7.12 (m, 2H), 7.96 (m, 1H), 8.50 (m, 2H). The base was converted to the salt by treatment with HCl in $Et_2O$ to give the title compound. mp 236–238° C. MS (CI/$NH_3$) m/z 332

(M+H)+. 1H NMR (D2O, 300 MHz) δ1.98–2.23 (m, 3H), 2.38 (m, 1H), 3.01 (s, 3H), 3.17 (m, 2H), 3.25 (m, 3H), 3.74 (m, 1H), 3.90 (m, 1H), 4.27 (dd, J=7.1, 11.2, 1H), 4.44 (dd, J=3.10, 11.2, 1H), 7.36 (d, J=3.0, 1H), 7.70 (d, J=8.4, 2H), 8.01 (d, J=3.0, 1H), 8.56 (d, J=6.1, 2H). Anal. Calcd for C18H22N3OCl·3 HCl: C, 49.00; H, 5.71; N, 9.52. Found: C, 48.94; H, 5.85; N, 9.23. [α]25D=+8.64° (c 0.94, MeOH).

Example 84

5-Phenyl-6-chloro-3-(2-(S)-pyrrolidinylmethoxy) pyridine dihydrochloride 84a. 5-Phenyl-6-chloro-3-(1-BOC-2-(S)-pyrrodinylmethoxy)pyridine Following the procedure of Example 69b, except substituting 5-bromo-6-chloro-3-(1-BOC-2-(S)-pyrrolidinylmethoxy)pyridine from Example 23a for the 5-bromo-6-chloro-3-(1-BOC-2-(R)-pyrrolidinylmethoxy) pyridine of step 69b, the title compound was prepared. MS (CI/NH3) m/z 390 (M+H)+.

84b. 5-Phenyl-6-chloro-3-(2-(S)-pyrrolidinylmethoxy) pyridine

The compound from step 84a was deprotected and converted to the salt by treatment with HCl in EtOH to give the title compound (189 mg, 83% yield). mp 75– 80° C. MS (CI/NH3) m/z 289 (M+H)+. 1H NMR (D2O, 300 MHz) δ1.27–2.10 (m, 1H), 2.03–2.18 (m, 2H), 2.22–2.31 (m, 1H), 3.41 (t, J=7.5 Hz, 2H), 4.13 (m, 1H), 4.26 (m, 1H), 4.46 (dd, J=3.4, 10.8 Hz, 1H), 7.54 (m, 6H), 8.12 (d, J=3.0 Hz, 1H). Anal. Calcd for C16H17N2OCl·1.6 HCl: C, 55.53; H, 5.25; N, 7.96. Found: C, 55.53; H, 5.40; N, 8.07. [α]25D=+9.88° (c 0.27, MeOH).

Example 85

5-(2-thienyl)-6-chloro-3-(2-(R)-pyrrolidinylmethoxy) pyridine dihydrochloride 85a. 5-(2-thienyl-6-chloro-3-(1-BOC-2-(R)-pyrrolidinylmethoxy)pyridine A mixture of 5-bromo-6-chloro-3-(1-BOC-2-(R)-pyrrolidinylmethoxy)pyridine from Example 69a (310 mg, 0.87 mmol), 2-thienylboronic acid (167 mg, 1.3 mmol), 2 M Na2CO3 (3 mL) and Pd(0) (32 mg) were mixed together in toluene (6 mL), and the mixture was heated at reflux for 4 hours. The mixture was cooled and extracted with CHCl3. The CHCl3 was removed under reduced pressure, and the residue was chromatographed on a silica gel column, eluting with hexane/EtOAc 1:1 to afford the title compound (64 mg, 20% yield). MS (CI/NH3) m/z 287 (M+H)+. 1H NMR (CDCl3, 300 MHz) 1.47 (s, 9H), 1.84–2.11 (m, 3H), 3.31–3.48 (m, 2H), 3.82–4.30 (m, 3H), 7.12 (dd, J=4.5, 6, 1H), 7.34–7.42 (m, 3H), 7.46–7.57 (m, 1H), 8.23 (d, J=3, 1H).

85b. 5-(2-thienyl-6-chloro-3-(2-(R)-pyrrolidinylmethoxy)pyridine dihydrochloride The compound from step 81a was deprotected by treatment with TFA in CH2Cl2 to give the free base. MS (CI/NH3) m/z 261 (M+H)+. 1H NMR (CDCl3, 300 MHz) δ1.79–2.06 (m, 4H), 2.96–2.22 (m, 2H), 3.55–3.64 (m, 1H), 3.94–4.08 (m, 2H), 7.08–7.13 (m, 1H), 7.32–7.44 (m, 3H), 8.23 (d, J=2 Hz, 1H), 8.49 (m, 1.5 Hz). The free base was converted to the salt with HCl in EtOH to give the title compound (46 mg). mp 178–180° C. MS (CI/NH3) m/z 261 (M+H)+. 1H NMR (D2O, 300 MHz) δ1.91–2.06 (m, 1H), 2.07–2.22 (m, 2H), 2.25–2.37 (m; 1H), 3.41–3.46 (m, 2H), 4.14–4.17 (m, 1H), 4.30 (dd, J=2.0, 7.5 Hz, 1H), 4.53 (dd, J=2.4, 10.5 Hz, 1H), 7.23 (dd, J=3.7, 5.1 Hz, 1H), 7.56–7.59 (m, 2H), 7.70–7.71 (m, 1H), 8.21 (d, J=2.7 Hz, 1H), 8.53 (d, J=2 Hz, 1H). Anal. Calcd for C14H16N2OS ·2 HCl·1 H2O: C, 47.87; H, 5.74; N, 7.97. Found: C, 47.78; H, 6.13; N, 8.23. [α]25D=+4.0° (c 0.05, MeOH).

Example 86

5-(2-(4-pyridinyl)ethenyl -3-(2-(R)-pyrrolidinylmethoxy) pyridine trihydrochloride 86a. 5-(2-(4-pyridinyl)ethenyl)-3-(1-BOC-2(R)-pyrrolidinylmethoxy)pyridine A mixture of 5-bromo-3-(1-BOC-2-(R)-pyrrolidinylmethoxy)pyridine (440 mg, 1.25 mmol), 4-vinylpyridine (0.267 mL), Pd(OAc)4 (30 mg), tris(o-tolyl)phosphine (160 mg), and triethylamine (3.5 mL) in acetonitrile (4 mL) was heated at reflux for 16 hours. The solution was then concentrated, and the residue was washed with water and aqueous NaHCO3 solution. The organic layer was dried and concentrated. The residue was chromatographed on a silica gel column, eluting with hexane:EtOAc 1:3 to afford the title compound (440 mg, 79% yield). MS (CI/NH3) m/z 382 (M+H)+. 1H NMR (CDCl3, 300 MHz) δ1.49 (s, 3H), 1.85–2.12 (m, 4H), 3/26 –3.55 (m, 2H), 3.86–4.08 (m, 1H), 4.08—4.34 (m, 1H), 7.20–7.30 (m, 2H), 7.36–7.42 (m, 2H), 7.71 (br s, 0.5 H), 8.22–8.42 (m, 1.5 H), 8.58–8.69 (m, 2H).

86b. 5-(2-(4-pyridinyl)ethenyl)-3-(2-(R)-pyrrolidinylmethoxy)pyridine dihydrochloride The compound from step 86a (96 mg) was deprotected to give the free base and the free base was converted to the salt by treatment with HCl in EtOH to give the title compound (75 mg, 77% yield). mp 250–252° C. MS (CI/NH3) m/z 282 (M+H)+. 1H NMR (D2O, 300 MHz) δ1.94–2.40 (m, 3H), 3.15–3.24 (m, 1H), 3.46 (t, J=7.5 Hz, 2H), 4.11–4.24 (m, 1H), 4.36–4.44 (m, 1H), 4.58–4.63 (m, 1H), 7.51 (d, J=15.9 Hz, 1H), 7.83 (d, J=16.2 Hz, 1H), 8.10 (br s, 1H), 8.17 (d, J=6.8 Hz, 2H), 8.43 (d, J=3 Hz, 1H), 8.61 (br s, 1H), 8.71 (d, J=6.5 Hz, 1H). Anal. Calcd for C17H19N3O·3 HCl: C, 52.26; H, 5.67; N, 10.75. Found: C, 51.99; H, 6.00; N, 10.50. [α]25D=+6.96° (c 0.12, MeOH).

Example 87

5-(2-(4-pyridinyl)ethyl)-3-(2-(R)-pyrrolidinylmethoxy) pyridine trihydrochloride A sample of 5-(2-(4-pyridinyl)ethenyl)-3-(1-BOC-2-(R)-pyrrolidinylmethoxy)pyridine from Example 86a (220 mg) was dissolved in MeOH. To this solution was added Pd/C (22 mg), and the mixture was stirred under H2 for 16 hours at room temperature. The catalyst was filtered off, and the solvent was removed under vacuum. The residue was chromatographed on a silica gel column, eluting with CH2Cl2:MeOH 100:3–100:10 to afford to give the free base of the title compound (220 mg). The base was converted to the salt by treatment with HCl in Et2O to give the title compound. mp 178–180° C. MS (CI/NH3) m/z 284 (M+H)+. 1H NMR (D2O, 300 MHz) δ1.92–2.09 (m, 1H), 2.10–2.17 (m, 2H), 2.20–2.37 (m, 1H), 3.22–3.40 (m, 3H), 3.42 (t, J=7 Hz, 1H), 4.13–4.20 (m, 1H), 4.33 (dd, J=7.4, 10.3 Hz, 1H), 4.53 (dd, J=3.6, 10.6 Hz, 1H), 7.84 (br s, 1H), 7.89 (d, J=6.3 Hz, 2H), 8.20 (br s, 1H), 8.33 (br s, 1H), 8.64 (d, J=6.6 Hz, 2H). Anal. Calcd for C17H21N3O·3.5 HCl: C, 49.68; H, 6.01; N, 10.22. Found: C, 49.67; H, 6.25; N, 10.03. [α]25D=−2.05° (c 0.26, MeOH).

Example 88

5-(3-aminophenyl)-3-(2-(R)-pyrrolidinylmethoxy)pyridine trihydrochloride 88a. 5-(3-aminophenyl)-3-(1-BOC-2-(R)-pyrrolidinyl)methoxy)pyridine To a solution of 3-aminophenylboronic acid (366 mg, 2.36 mmol, Aldrich Chem. Co.) and 5-bromo-3-(1-BOC-2-(R)-pyrrolidinylmethoxy)-pyridine (560 mg, 1.57 mmol) in toluene (10 mL) was added Pd(0) (58 mg) and $Na_2CO3$ (5 mL of a 2 M solution), and the mnixture was heated at reflux. The solvent was removed under vacuum, and the residue was extracted with EtOAc and $CHCl_3$. The organic extracts were dried over $MgSO_4$ and concentrated. The residue was chromatographed on a silica gel column, eluting with EtOAc hexane 1:1 to afford to give the title compound (860 mg, 100% yield). MS ($CI/NH_3$) m/z 370 (M+H)$^+$. $^1$H NMR ($CDCl_3$, 300 MHz) δ1.48 (s, 9h), 1.84–2.13 (m, 4H), 3.28–3.51 (m, 2H), 3.70–4.08 (m, 4H), 4.08–4.29 (m, 2H), 6.70–6.75 (m, 1H), 6.85–7.03 (m, 2H), 7.31–7.50 (m, 2H), 7.50–7.72 (m, 1H), 8.29 (d, J=3.0, 1H), 8.443 (br s, 1H).

88b. 5-(3-aminophenyl)-3-(2-(R)-pyrrolidinylmethoxy)pyridine

A sample of the compound from step 88a (300 mg) was stirred in TFA (1.5 mL) and $CH_2Cl_2$ (3.0 mL) for 5 hours at room temperature. The solvent was removed, and the residue was extracted with EtOAc. The solution was dried over $MgSO_4$ and concentrated. The residue was chromatographed on a silica gel column, eluting with EtOAc hexane 1:1) to give the free base, and the free base was converted to the salt with HCl in EtOH to afford the title compound (141 mg, 64% yield). mp 240–242° C. MS ($CI/NH_3$) m/z 270 (M+H)+. $^1$H NMR ($D_2O$, 300 MHz) δ1.97–2.22 (m, 2H), 2.28–2.36 (m, 1H), 3.45 (t, J=7.0, 2H), 4.18–4.22 (m, 1H), 4.46 (dd, J=7.4, 10.7, 1H), 4.67 (dd, J=3.3, 10.7, 1H), 7.47–7.51 (m, 1H), 7.65–7.75 (m, 4H), 8.32 (dd, J=1.5, 2.6, 1H), 8.54 (d, J=2.5, 1H), 8.72 (d, J=1.5, 1H). Anal. Calcd for $C_{16}H_{19}N_3O \cdot 3.0$ HCl: C, 50.74; H, 5.85; N, 11.10. Found: C, 50.80; H, 5.82; N, 10.88. $[\alpha]^{25}D$=+1.38° (c 0.15, MeOH).

Example 89

5-(2-(4-Pyridinyl)ethenyl)-6-chloro-3-(2-(S)-azetidinylmethoxy)pyridine citric acid salt 89a. 5-(2-4-Pyridinyl)ethenyl)-6-chloro-3-(1-BOC-2-(S)-azetidinylmethoxy)pyridine To a solution of 5-bromo-6-chloro-3-(1-BOC-2-(S)-azetidinylmethoxy)pyridine from Example 66a (470 mg, 1.25 mmol) in acetonitrile (6.2 mL) was added 4-vinylpyridine (0.17 mL, 1.57 mmol), palladium acetate (26.0 mg, 0.11 mmol), tri-o-tolylphosphine (130 mg, 0.1 mmol) and triethylamine (2.6 mL). The reaction mixture was heated at reflux overnight, then cooled to room temperature. The solvent was removed, and the residue was chromatographed on a silica gel column, eluting with EtOAc:hexane 1:1 to 3:1 to afford the title compound (176 mg, 35% yield). MS ($CI/NH_3$) m/z 402 (M+H)$^+$. $^1$H NMR ($CDCl_3$, 300 MHz) δ1.42 (s, 9H), 2.27–2.43 (m, 2H), 3.86–3.95 (m, 2H), 4.27–4.24 (m, 1H), 4.36–4.67 (m, 1H), 4.50–4.60 (m, 1H), 7.07 (d, J=ll, 1H), 7.41–7.47 (m, 4H), 7.57 (d, J=11, 1H), 7.58–7.65 (m, 1H), 8.09 (d, J=2, 1H), 8.61–8.68 (m, 2H).

89b. 5-(2-(4-Pyridinyl)ethenyl)-6-chloro-3-(2-(S)-azetidinylmethoxy)pyridine dihydrochloride To a solution of 5-(2-(4-Pyridinyl)ethenyl)-6-chloro-3-(1-BOC-2-(S)-azetidinylmethoxy)pyridine from step 89a (176 mg) in $CH_2Cl_2$ (3 mL) and TFA (1.5 mL) was stirred at room temperature for 3 hours. The solvent was removed, and the residue was chromatographed on a silica gel column, eluting with $CHCl_3$:MeOH:$NH_4OH$ 10:1:0.1 to afford the free base of the title compound (102 mg, 79% yield). MS ($CI/NH_3$) m/z 302 (M+H)$^+$. $^1$H NMR ($CDCl_3$, 300 MHz) δ2.24–2.48 (m, 2H), 3.42–2.54 (m, 1H), 3.76 (q, J=7.5 Hz, 1H), 4.02–4.17 (m, 2H), 4.26–4.39 (m, 1H), 7.0 (d, J1=1.0 Hz, 1H), 7.36–7.44 (m, 2H), 7.52–7.62 (m, 2H), 8.05 (d, J=3.0 Hz, 1H), 8.58–8.73 (m, 2H). The base was treated with HCl in EtOH to afford the hydrochloride salt. mp 195–197° C. MS ($CI/NH_3$) m/z 302 (M+H)$^+$. $^1$H NMR ($D_2O$, 300 MHz) δ1.17 (d, J=6, 1H), 2.52–2.66 (m, 2H), 2.68–2.89 (m, 4H), 4.96–5.25 (m, SH), 6.97–7.12 (m, 1H), 7.33 (d, J=3, 1H), 7.48–7.54 (m, 1H), 7.86–7.95 (m, 1H), 8.04–8.22 (m, 2H), 8.44–8.53 (m, 1H), 8.63–8.71 (m, 1H). Anal. Calcd for $C_{16}H_{16}N_3OCl \cdot 1.5$ $C_6H_8O_7 \cdot 0.5$ $H_2O$: C, 50.13; H, 4.88; N, 7.01. Found: C, 49.95; H, 4.80; N, 7.31. $[\alpha]^{25}D$=–1.14° (c 0.18, MeOH).

Example 90

5-phenyl-3-(1-methyl-2-(S)-pyrrolidinylmethoxy)pyridine dihydrochloride

To a solution of 5-bromo-3-(1-methyl-2-(S)-pyrrolidinylmethoxy)pyridine (370 mg, 1.4 mmol) in 15 mL of THF at 0° C. was added phenylmagnesium bromide (2.8 mL, 2.8 mmol) and (dppp)NiCl2 (4.4 mg, 0.0082 mmol). The mixture was stirred at reflux for 2.5 hours, the quenched by the addition of aqueous ammonium chloride. The aqueous layer was extracted with $CHCl_3$. The organic solution was dried, concentrated, and the residue was was purified by chromatography, eluting with 1.5 to 5% MeOH in $CHCl_3$ to afford the free base of the title compound (100 mg, 29% yield). MS ($CI/NH_3$) m/z 269 (M+H)$^+$. $^1$H NMR ($CDCl_3$, 300 MHz) δ1.84 (m, 3H), 2.05 (m, 1H), 2.34 (m, 1H), 2.52 (s, 3H), 2.72 (m, 1H), 3.13 (m, 1H), 4.06 (m, 2H), 7.45 (m, 4H), 7.58 (m, 2H), 8.30 (m, 1H), 8.45 (m, 1H). The salt was prepared by treatment with HCl in $Et_2O$, as described above, to give 55 mg of the title compound. mp 88–90° C. MS ($CI/NH_3$) m/z 269 (M+H)$^+$. $^1$H NMR ($D_2O$, 300 MHz) δ2.05–2.26 (m, 3H), 2.44 (m, 1H), 3.28 (m, 1H), 3.78 (m, 1H), 3.95 (m, 1H), 4.45 (dd, J=5.9, 11.0 Hz, 1H), 4.62 (dd, J=2.9, 11.4 Hz, 1H), 7.58 (m, 3H), 7.72 (m, 2H), 7.91 (m, 1H), 8.35 (d, J=2.6 Hz, 1H), 8.56 (d, J=1.5 Hz, 1H), Anal. Calcd for $C_{17}H_{20}N_2O \cdot 1.9$ HCl $\cdot 0.2Et_2O$: C, 60.66; H, 6.83; N, 7.95. Found: C, 60.73; H, 6.74; N, 7.63. $[\alpha]^{25}$ D=–10.6° (c 0.66, MeOH).

Example 91

5-(3-thienyl)-3-(1-methyl-2-(R)-azetdinylmethoxy)pyridine dihydrochloride 91a. 5-(3-thienyl)-3-(1-BOC-2-(R)-azetdinylmethoxy)pyridine To a solution of 2-thienylboronic acid (384 mg, 3.0 mmol, Aldrich Chem. Co.) and 5-bromo-3-(1-BOC-2-(R)-azetdinylmethoxy)pyridine (420 mg, 1.2 mmol) in toluene (10 mL) was added Pd(0) (40 mg) and $Na_2CO3$ (2 mL of a 2 M solution), and the mixture was heated at reflux for 16 hours. The solvent was removed under vacuum, and the residue was extracted with EtOAc and $CHCl_3$. The organic extracts were dried over MgSO4 and concentrated. The residue was chromatographed on a silica gel column, eluting with hexane:EtOAc 10:1–2:1 to afford to give the title compound (236 mg, 57% yield). MS ($CI/NH_3$) m/z 347 (M+H)$^+$. $^1$H NMR ($CDCl_3$, 300 MHz) δ1.42 (s, 9H), 2.35 (m, 2H), 3.92 (m, 2H), 4.19 (m, 1H), 4.38 (m, 1H), 4.55 (m, 1H), 7.12 (m, 1H), 7.38 (m, 2H), 7.44 (m 1H), 8.26 (m, 1H), 8.51 (s, 1H).

91 b. 5-(3-thienyl)-3-(1-methyl-2-(R)-azetdinylmethoxy)pyridine dihydrochloride

To a sample of the compound from step 91a (122 mg, 0.35 mmol) was added formalin (37%, 4 mL) and formic acid (2 mL), and the mixture was heated at 70° C. for 16 hours. The solvent was concentrated, and saturated aqueous $NaHCO_3$ was added to the residue. At pH 8–9 the mixture was extracted with $CH_2Cl_2$, which was dried over $MgSO_4$ and concentrated. The residue was chromatographed on a silica gel column, eluting with $CH_2Cl_2$:MeOH 100:5–100:10 to afford to give the free base of the title compound (56 mg, 62% yield). MS ($CI/NH_3$) m/z 261 (M+H)$^+$. $^1$H NMR ($CDCl_3$, 300 MHz) δ2.11 (m, 2H), 2.42 (s, 3H), 2.90 (m, 1H), 3.46 (m, 2H), 4.08 (m, 2H), 7.12 (m, 1H), 7.38 (m, 3H), 8.22 (m, 1H), 8.49 (m, 1H). The base was converted to the salt by treatment with HCl in $Et_2O$ to give the title compound. mp 112–114° C. MS ($CI/NH_3$) m/z 261 (M+H)$^+$. $^1$H NMR ($D_2O$, 300 MHz) δ2.69 (m, 2H), 3.04 (s, 3H), 4.04 (m, 1H), 4.30 (m, 1H), 4.57 (m, 2H), 4.86 (m, 1H), 7.25 (m, 1H), 7.66 (m, 2H), 8.09 (m, 1H), 8.36 (d, J=2.5 Hz, 1H), 8.67 (d, J=1.5 Hz, 1H). Anal. Calcd for $C_{14}H_{16}N_2OS \cdot 2.5$ HCl·0.8 $H_2O$: C,45.95; H, 5.54; N, 7.66. Found: C, 45.62; H, 5.93; N, 7.88. $[\alpha]^{25}D$=–23.94° (c 0.36, MeOH).

Example 92

3-(2-(S)-Azetidinylmethoxy)-5-(N-benzoylamino)methyl-6-chloropyridine hydrochloride 92a. 3-(1-BOC-2-(S)-azetidinylmethoxy)-6-chloro-5-cyanopyridine To a flamed dried flask purged with nitrogen was added 5-bromo-6-chloro-3-(1-BOC-2-(S)-azetidinylmethoxy)pyridine from Example 66a (1.84 g, 4.90 mmol) zinc cyanide (0.32 g, 2.70 mmol) and tetrakis(triphenylphosphine)-palladium(0) (0.340 g, 0.30 mmol). To the mixture was added degassed DMF (20 mL), and the mixture was heated to 80° C. for 16 hours. The mixture was poured into saturated $NaHCO_3$ (200 mL), and this mixture was extracted with EtOAc (450 mL), which was dried ($MgSO_4$) and concentrated. The residue was chromatographed (silica gel; EtOAc/Hexane, 1/4) to afford a colorless oil (0.608 g, 39%). MS ($CI/NH_3$) m/z 315 (M+H$^+$), 332 (M+$NH_4^+$). $^1$H NMR ($CDCl_3$, 300 MHz): 1.56 (s, 9H), 2.27–2.32 (m, 2H), 3.80–3.94 (m, 2H), 4.16 (dd, J=2.7, 9.5 Hz, 1H), 4.35–4.42 (m, 1H), 4.49–4.53 (m, 1H), 7.56 (d, J=2.9 Hz, 1H), 8.32 (d, J=2.6 Hz, 1H).

92b. 5-Aminomethyl-3(1-BOC-2-(S)-azetidinylmethoxy)-6-chloropyridine 3-(1-BOC-2-(S)-azetidinylmetioxy)-6-chloro-5-cyanopyridine (0.26 g, 0.80 mmol) from step 92a was stirred in the presence of Raney nickel (0.047 g, 0.80 mmol) under 1 atm of hydrogen at room temperature for 2 hours. The mixture was filtered, and the solvent was removed to give the title compound.

92c. 5-(N-benzoylamino)methyl-3-(1-BOC-2-(S)-azetidinylmethoxy)-6-chloropyridine To 5-aminomethyl-3-(1-BOC-2-(S)-azetidinylmethoxy)-6-chloropyridine from step 92b (0.262 g, 0.80 mmol) were added $CH_2Cl_2$ (10 mL), triethylamine (0.1619 g, 1.60 mmol) and benzoyl chloride (0.1349 g, 1.0 mmol). The mixture was stirred at room temperature overnight, then concentrated under vacuum. The residue was chromatographed (silica gel; $CH_2Cl_2$/MeOH, 9/1) to afford a light brown foam (0.267 g, 77%). MS ($CI/NH_3$) m/z 432 (M+H$^+$), 449 (M+$NH_4^+$). $^1$H NMR ($CDCl_3$, 300 MHz): 1.57 (s, 9H), 2.25–2.37 (m, 2H), 3.87 (t, J=7.1 Hz, 2H), 4.11 (dd, J=2.7, 9.80 Hz, 1H), 4.31–4.39 (m, 1H), 4.49–4.55 (m, 1H), 4.68 (d, J=8.5 Hz, 2H), 6.75 (m, 1H), 7.42–7.56 (m, 4H), 7.79–7.82 (m, 2H), 8.03 (d, J=3.1 Hz, 1H).

92d. 3-(2-(S)-Azetidinylmethoxy)-5-(N-benzoylamino)methyl-6-chloropyridine hydrochloride 5-(N-benzoylamino)methyl-3-(1-BOC-2-(S)-azetidinylmethoxy)-6-chloropyridine from step 92c was dissolved in $CH_2Cl_2$ (10 mL). The mixture was cooled to 0° C., TFA (10 mL) was added and the reaction was stirred for 45 minutes as it warmed to room temperature. The mixture was concentrated in vacuo and taken up in a minimum amount of $H_2O$. The aqueous mixture was basified with 15% NaOH and extracted with $CH_2Cl_2$ (200 mL), which was dried ($MgSO_4$) and concentrated. The residue was chromatographed (silica gel; $CH_2Cl_2$/MeOH/$NH_4OH$, 90:10:1) to afford a colorless oil (0.101 g, 51%). The isolated free base was taken up in a minimum amount of $Et2O$, cooled to 0° C., and treated with HCl in EtOH to afford the hydrochloride salt. The material was dried overnight under vacuum to afford a white solid (0.124 g). MS ($CI/NH_3$) m/z: 332 (M+H$^+$). $^1$H NMR ($D_2O$, 300 MHz): 2.60–2.69 (m, 2H), 4.02–4.14 (m, 2H), 4.39 (d, J=6.0 Hz, 2H), 4.64 (s, 2H), 4.82–4.90 (m, 1H), 7.52–7.57 (m, 3H), 7.62–7.67 (m, 1H), 7.80–7.83 (m, 1H), 8.08 (d, J=3.0 Hz, 1H). Anal. Calcd. for $C_{17}H_{18}N_3O_2Cl \cdot 1.6HCl \cdot 0.40$ $H_2O \cdot 0.20Et_2O$: C, 51.87; H, 5.48; N, 10.19. Found: C, 51.82; H, 5.44; N, 10.08.

Example 93

5-((N-benzoylamino)methyl)-6-chloro-3-(1-methyl-2-(S)-azetidinylmethoxy)pyridine hydrochloride Following the procedure of Example 91b, substituting 5-((N-benzoylamino)methyl)-6-chloro-3-(2-(S)-azetidinylmethoxy)pyridine for the compound of 91a thereof, and carrying the reactions forward as described in Example 91b, the tide compound is prepared.

Examples 94–99

Following the procedure of Example 92, replacing the 5-bromo-6-chloro-3-(1-BOC-2-(S)-azetidinylmethoxy)pyridine starting material thereof with the starting materials shown in Table xxxxx below, and replacing the benzoyl chloride of step 92c with the acylating reagent shown in Table 2, the desired compounds 94–99 having $R^2$ and $R^6$ as described in Table 2 are prepared.

TABLE 2

| Example | n | * | $R^2$ | Acylating Reagent | $R^3$ |
|---|---|---|---|---|---|
| 94 | 1 | (R) | F | acetic anhydride | acetyl |
| 95 | 1 | (S) | F | 6-chlorohexanoyl chloride | 6-chlorohexanoyl |
| 96 | 2 | (R) | Cl | ethyl formate | H |
| 97 | 2 | (S) | Cl | dimethyl dicarbonate | methoxyl |

TABLE 2-continued

| Example | n | * | R² | Acylating Reagent | R³ |
|---|---|---|---|---|---|
| 98 | 3 | (R) | H | 2-(or 3-)furoyl chloride | 2-(or 3-)furanyl |
| 99 | 3 | (S) | H | 3-nicotinoyl chloride | 3-pyridyl |

Examples 100–105

Following the procedure of Example 92, replacing the 5-bromo-6-chloro-3-(1-methyl-2-(S)-pyridinylmethoxy) pyridine starting material thereof with the starting materials shown in Table xxxxx below, and replacing the benzoyl chloride of step 92c with the acylating reagent shown in Table 3, the desired compounds 100–105 R² and R⁶ as described in Table 3 are prepared.

TABLE 3

| Example | n | * | R² | Acylating Reagent | R³ |
|---|---|---|---|---|---|
| 100 | 1 | (R) | F | 3-phenylpropionoyl chloride | 2-phenylethyl |
| 101 | 1 | (S) | F | 4-chlorobenzoyl chloride | 4-chlorophenyl |
| 102 | 2 | (R) | Cl | 3-nitrobenzoyl chloride | 3-nitrophenyl |
| 103 | 2 | (S) | Cl | 2-pyrrole-carboxylic acid + EDC | 2-pyrrolyl |
| 104 | 3 | (R) | H | 5-nitro-2-furan-carboxylic acid + EDC | 5-nitrofuranyl |
| 105 | 3 | (S) | H | 2-pyrazine-carboxylic acid + EDC | 2-pyrazinyl |

Example 106

5-bromo-6-fluoro-3-(2-(S)-pyrrolidinylmethoxy)pyridine dihydrochloride 106a. 5-Hydroxy-3-bromo-2-(4-nitrophenylazo)pyridine 5-bromo-3-pyridinol (8.7 g, 0.05 mol) and potassium hydroxide (Fisher Scientific) were dissolved in water (200 ml). A suspension of p-nitrobenzenediazonium tetrafluoroborate (J. Org. Chem., Vol. 44, No 9. 1979 p 1572–1573) (11.845 g, 0.5 mol) was added, and the mixture was stirred for 1 hour, diluted with acetic acid (50 ml) and filtered. The crude product was allowed to dry in air, then was chromatographed (silica gel; CHCl₃/MeOH, 95:5 to 90:10) provided 5.45g (33.7 %) of the title compound. MS (CI/NH₃) m/e 323/325 (M+H)⁺. ¹H NMR (DMSO-d₆, 300 MHz) δ8.48–8.43 (m, 2H), 8.21–8.20 (d, J=2.37 Hz, 1H) 8.09–8.06 (m, 2H), 7.72–7.71 (d, J=2.37 Hz, 1H).

106b. 5-Hydroxy-3-bromo-2-aminopyridine

The compound from step 106a above (5.0 g 15.8 mmol) and tin chloride (Aldrich 25 g, 111 mmol) were suspended in conc. HCl (250 ml ) and, MeOH (150 ml) and heated to reflux for 1 hour. The mixture was cooled to 0° C. and then filtered. The solution was neutrilized with sodium bicarbonate(180 g) and extracted with EtOAc (4×200 ml). The extracts were washed with brine, dried (MgSO₄), and concentrated. The residue was chromatographed (silica gel; CHCl₃/MeOH/NH₄OH, 95:5:0.05 to 9:10: 1) to afford 3.3 g of the title compound along with substantial amount of tin chloride. MS (CI/NH₃) m/e 189/191 (M+H)⁺. ¹H NMR (DMSO-d₆, 300 MHz) δ7.57–7.56 (d, J=2.6 Hz, 1H), 7.43–7.42 (d, J=2.6 Hz, 1H)

106c. 3-bromo-2-fluoro-5-hydroxypyridine

The compound from step 106b above (3.0 g 15.9 mmol) was dissolved in 50 ml of HF pyridine (Aldrich) and cooled to 0° C. under nitrogen and sodium nitrite (1.09 g 15.8 mmol) was added in portions over 20 min. The reaction was heated to 50° C. for one hour, cooled to 0° C. and then basified with 20% sodium hydroxide. The aqueous phase was washed with CH₂Cl₂ (5×100 ml), neutralized with HCl (pH=7), and extracted with EtOAc (5×100 ml). These extracts were dried (MgSO₄), filtered, and concentrated in vacuo yielding the title compound as a tan solid. MS (CI/NH₃) m/e 192/194 (M+H)⁺. ¹H NMR (DMSO-d₆, 300 MHz) δ9.38 (d, J=2.6 Hz, 1H), 9.20–9.19 (d, J=2.6 Hz, 1H).

106d. 5-bromo-6-fluoro-3-(1-BOC-2-(S)-pyrrolidinylmethoxy)pyridine

A sample of 1-BOC-2-(S)-pyrrolidinemethanol, prepared as described above, and of 3-bromo-2-fluoro-5-hydroxypyridine, prepared as in step b above, are reacted with triphenylphosphine and DEAD in THF at room temperature for 16 hours, to give the title compound.

106e. 5-bromo-6-fluoro-3-(2-(S)-pyrrolidinylmethoxy) pyridine dihydrochloride

The BOC group is removed from the compound of step 106d by treatment with TFA in CH₂Cl₂ to give the free base of the title compound. The base is converted to the salt by treatment with hydrogen chloride saturated EtOH. The solvents are removed under vacuum to give the title compound.

Example 107

5-benzoyl-6-chloro-3-(2-(S)-azetidinylmethoxy)pyridine hydrochloride 107a. 5-benzoyl-6-chloro-3-(1-BOC-2-(S)-azetidinylmethoxy)pyridine.

The 5-cyano-6-chloro-3-(1-BOC-2-(S)-azetidinylmethoxy)pyridine of example 92a in anhydrous Et₂O at 0° C. is treated with 1.5 equivalents of phenylmagnesium bromide in Et₂O and stirring is maintained at 0 to 35° C. until the nitrile is largely consumed. The solvent is evaporated and the residue is treated with 2M aqueous potassium hydrogen sulfate to hydrolyze the intermediate imine. The solution is made basic with potassium carbonate and extracted with EtOAc. The combined extracts are dried (Na₂SO₄) and concentrated to a residue which is chromatographed (silica gel) to afford the title compound.

107b. 5-benzoyl-6-chloro-3-(2-(S)-azetidinylmethoxy) pyridine hydrochloride 5-benzoyl-6-chloro-3-(1-BOC-2-(S)-azetidinylmethoxy) pyridine from step 107a is dissolved in $CH_2Cl_2$ (10 mL). The mixture is cooled to 0° C, TFA (10 mL) is added and the reaction is stirred for 45 minutes as it warms to room temperature. The mixture is concentrated in vacuo and taken up in a minimum amount of $H_2O$. The aqueous mixture is basified with 15% NaOH and extracted with $CH_2Cl_2$ (200 mL), which is dried ($MgSO_4$) and concentrated. The residue is chromatographed (silica gel) to afford the free amine. The isolated free amine is taken up in a minimum amount of $Et_2O$, cooled to 0° C., and treated with HCl in EtOH to afford the hydrochloride salt.

Examples 108–111

Following the procedure of Example 107, replacing the 5-cyano-6-chloro-3-(1-BOC-2-(S)-azetidinylmethoxy) pyridine with the starting material compounds shown in Table 3 and replacing the phenylmagnesium bromide reagent thereof with a $R^3$—Mg—Br Grignard reagent or a $R^5$—Li reagent shown in Table 4 below, the desired compounds 108–111 having $R^2$ and $R^5$ as described in Table 4 are prepared.

TABLE 4

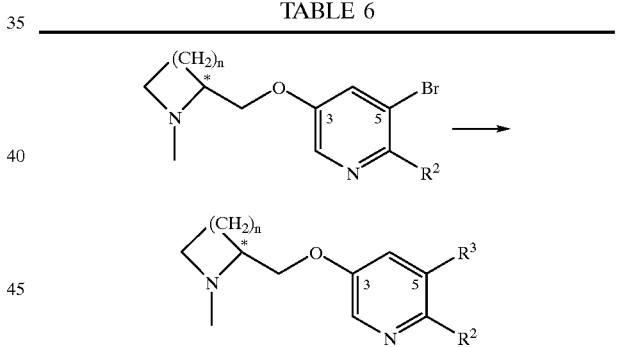

| Example | n | * | $R^2$ | $R^3$ of Grignard Reagent | $R^3$ |
|---|---|---|---|---|---|
| 108 | 1 | (R) | F | n-hexyl | n-hexyl |
| 109 | 1 | (S) | Cl | 3-quinolinyl | 3-quinolinyl |
| 110 | 2 | (R) | H | 2-naphthyl | 2-naphthyl |
| 111 | 2 | (S) | H | 4-methyl-1-naphthyl | 4-methyl-1-naphthyl |

Examples 112–117

Following the procedure of Example 107, replacing the 5-cyano-6-chloro-3-(1-BOC-2-(S)-azetidinylmethoxy) pyridine with the starting material compounds shown in Table 3 and replacing the phenylmagnesium bromide reagent thereof with a $R^3$—Mg—Br Grignard reagent shown in Table 5 below, the desired compounds 112–117 having $R^2$ and $R^5$ as described in Table 5 are prepared.

TABLE 5

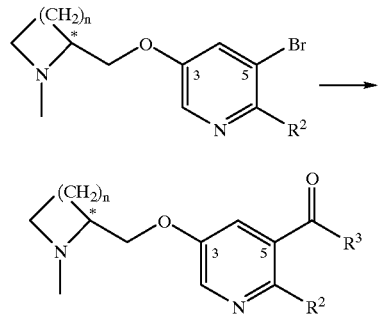

| Example | n | * | $R^2$ | $R^3$ of Grignard Reagent | $R^3$ |
|---|---|---|---|---|---|
| 112 | 1 | (R) | F | 3-pyridinyl | 3-pyridinyl |
| 113 | 1 | (S) | F | 5-pyrimidinyl | 5-pyrimidinyl |
| 114 | 2 | (R) | Cl | 3-pyridazinyl | 3-pyridazinyl |
| 115 | 2 | (S) | Cl | 2-thienyl | 2-thienyl |
| 116 | 3 | (R) | H | phenylmethyl | phenylmethyl |
| 117 | 3 | (S) | H | 2-(4-methoxyphenyl)ethyl | 2-(4-methoxy-phenyl)ethyl |

Examples 118–121

Following the procedure of Example 18, replacing the styrene starting material thereof with the starting material compounds shown in Table 7, then hydrogenating the product thereof with palladium on charcoal according to the procedure of Example 21 the desired compounds 118–121 having $R^2$ and $R^3$ as described in Table 6 are prepared.

TABLE 6

| Example | n | * | $R^2$ | Starting Material | $R^3$ |
|---|---|---|---|---|---|
| 118 | 2 | (S) | H | 5-carbomethoxy-3-ethenylpyridine | 2-(5-carbomethoxy-pyridinyl)ethyl |
| 119 | 2 | (S) | H | 5-bromo-3-ethenyl-pyridine | 2-(5-bromopyridinyl)-ethyl |
| 120 | 2 | (S) | H | 6-amino-5-bromo-3-ethenylpyridine | 2-(6-amino-5-bromo-pyridinyl)ethyl |
| 121 | 2 | (S) | H | 5-bromo-6-methyl-amino-3-ethenyl-pyridine | 2-(5-bromo-6-methyl-aminopyridinyl)ethyl |

Examples 122–130

Following the procedure of Example 7, replacing the 5-bromo-3-(1-methyl-2-(S)-pyrrolidinylmethoxy)-pyridine thereof with the starting material compound shown Table 7 and replacing the 3-pyridinyltributyltin reagent thereof with the regent shown in Table 7, the desired compounds 122–130 having $R^2$ and $R^3$ as described in Table 7 are prepared.

TABLE 7

| Example | n | * | R² | Reagent | R³ |
|---|---|---|---|---|---|
| 122 | 1 | (R) | H | 5-carbomethoxy-3-pyridinyltributyltin * | 5-carboxy-3-pyridinyl |
| 123 | 1 | (S) | H | 5-carbomethoxy-3-pyridinyltributyltin ** | 5-formyl-3-pyridinyl |
| 124 | 2 | (R) | H | 5-hydroxymethyl-3-pyridinyltributyltin | 5-hydroxymethyl-3-pyridinyl |
| 125 | 2 | (S) | H | 2,4-dimethoxy-5-pyrimidinyltributyltin | 2,4-dimethoxy-5-pyrimidinyl |
| 126 | 3 | (R) | H | 2-chloro-3-thienyl-tributyltin | 2-chloro-3-thienyl |
| 127 | 3 | (S) | H | 2-cyano-3-thienyl-tributyltin | 2-cyano-3-thienyl |
| 128 | 2 | (S) | H | 4-methyl-3-thienyl-tributyltin | 4-methyl-3-thienyl |
| 129 | 2 | (S) | H | 4-hydroxymethyl-5-carbomethoxy-3-thienyltributyltin | 4-hydroxymethyl-5-carbomethoxy-3-thienyl |
| 130 | 2 | (S) | H | 4-methoxymethoxy-5-carbomethoxy-3-thienyltributyltin | 4-methoxymethoxy-5-carbomethoxy-3-thienyl |

\* After following the procedures of Example 7, with substitutions as indicated, the carbomethoxy group is hydrolyzed with base as additional step in this preparation.

\*\* After following the procedures of Example 7, with substitutions as indicated, the additional steps are necessary: the carbomethoxy group is hydrolyzed with base; the resulting free acid is reduced to the alcohol with LAH, and the resulting alcohol is oxidized to the aldehyde with Jones' or Collins' reagents.

Examples 131–133

Following the procedure of Example 18, replacing the styrene starting material thereof with the starting material compounds shown in Table 8, then hydrogenating the product thereof with palladium on charcoal according to the procedure of Example 21 the desired compounds 131–133 having R² and R³ as described in Table 8 are prepared.

TABLE 8

| Example | n | * | R² | Starting Material | R³ |
|---|---|---|---|---|---|
| 131 | 2 | (S) | H | 4-methyl-3-ethenyl-benzene | 2-(4-methyl-3-phenyl)-ethyl |
| 132 | 2 | (S) | H | 4-methoxy-3-ethyl-benzene | 2-(4-methoxy-3-phenyl)ethyl |
| 133 | 2 | (S) | H | 4-trifluoromethyl-3-ethenylbenzene | 2-(4-trifluoromethyl-3-phenyl)ethyl |

Examples 134–137

Following the procedure of Example 3, replacing the 5-bromo-3-(1-methyl-2-(S)-pyrrolidinylmethoxy)-pyridine thereof with the starting material compound shown in Table 7 and replacing the 3-methoxyphenylboronic acid reagent thereof with the reagent shown in Table 9, the desired compounds 134–137 having R² and R³ as described in Table 9 are prepared.

TABLE 9

| Example | n | * | R² | Reagent | R³ |
|---|---|---|---|---|---|
| 134 | 1 | (R) | H | 2-hydroxy-1-naphthyl-boronic acid | 2-hydroxy-1-naphthyl |
| 135 | 1 | (S) | H | 4'-nitro-4-biphenyl-boronic acid | 4'-nitro-4-biphenyl |
| 136 | 2 | (R) | H | 4'-fluoro-4-biphenyl-boronic acid | 4'-fluoro-4-biphenyl |
| 137 | 2 | (R) | H | 4'-methyl-4-biphenyl-boronic acid | 4'-methyl-4-biphenyl |

Example 138

5-(5,5-Dimethyl-1,3-hexadienyl)-3-(2-(R)-pyrrolidinylmethoxy)pyridine dihydrochloride 138a. 3-(1-BOC-2-(R)-pyrrolidinylmethoxy)-5-(5,5-dimethyl-1,3-hexadienyl)pyridine A solution of 3-(1-BOC-2-(R)-pyrrolidinylmethoxy)-5-bromopyridine (500 mg, 1.4 mmol), 5-(5,5-dimethyl)-1,3-hexadiene (262 mg, 2.38 mmol), Pd(OAc)₄ (34 mg), tris(o- tolyl)phosphine (180 mg), and NEt₃ (4 mL) in acetonitrile (4.5 mL) was refluxed for 16 h. The solution was then diluted with EtOAc, and the mixture was washed with water and aqueous NaHCO₃ solution. The organic layer was dried and concentrated. The residue was chromatographed (silica gel; hexane/EtOAc, 4:1) to afford the title compound (135 mg, 28% yield): $^1$H NMR (CDCl₃, 300 MHz) δ1.08 (s, 9H), 1.48 (s, 9H), 1.84–2.10 (m, 3H), 3.30–3.48 (m, 2H), 3.92 (m, 1H), 4.10–4.31 (m, 2H), 5.95 (d, J=15.0, 1H), 6.16 (m, J=10.0, 15.0 Hz, 1H), 6.42 (d, J=15.0 Hz, 1H), 6.95 (m, 1H), 7.58 (m, 1H), 8.1–8.24 (m, 2H); MS (CI/NH₃) m/z 387 (M+H)⁺.

138b. 5-(5,5-Dimethyl-1,3-hexadienyl)-3-(2-(R)-pyrrolidinylmethoxy)pyridine dihydrochloride The product from step a above (149 mg, 0.39 mmol) was deprotected and converted to the salt by treatment with hydrogen chloride in Et₂O/THF to afford the title compound: mp 145–147° C.; $^1$H NMR (CD₃OD) δ1.10 (s, 9H), 1.97 (m, 1H), 2.08–2.16 (m, 2H), 2.13 (m, 1H), 3.20–3.43 (m, 2H), 4.14 (m, 1H), 4.23 (m, 1H), 4.41 (m, 1H), 6.17 (d, 1H, J=15.0 Hz), 6.29 (dd, 1H, J=8.5, 10.0 Hz), 6.62 (d, 1H, J=10.0 Hz), 7.26 (dd, 1H, J=8.5, 15.0 Hz), 8.22 (s, 1H), 8.43 (br s, 1H), 8.55 (br s, 1H); MS (CI/NH₃) m/z 287 (M+H)⁺. Anal. Calcd for C₁₈H₂₆N₂O·3.46 HCl: C, 52.40; H, 7.19; N, 6.78. Found: C, 52.79; H, 6.84; N, 6.38. $[\alpha]^{25}$D+3.65 (c 0.21, MeOH).

Example 139

5-(4-Chlorophenyl)-3-(2-(R)-pyrrolidinylmethoxy) pyridine dihydrochloride 139a. 3-(1-BOC-2-(R)-pyrrolidinylmethoxy)-5-(4-Chlorophenyl)pyridine To a solution of 3-(1-BOC-2-(S)-pyrrolidinylmethoxy)-5-bromopyridine (280 mg, 0.79 mmol) and 4-chlorophenylboronic acid (246 mg, 1.57 mmol, Lancaster Chemical Co.) in toluene (10 mL) was added Pd(0) (30 mg) and Na₂CO₃ (2.5 mL of a 2 M solution), and the mixture was heated at reflux for 6 h. The solvent was removed under vacuum, and the residue was chromatographed (silica gel; EtOAc/hexane, 1:5 to 1:2) to afford the title compound (370 mg, >100% yield): $^1$H NMR (CDCl₃, 300 MHz) δ1.47 (s, 9H), 1.80–2.10 (m, 3H), 3..30–3.49 (m, 2H), 3.90–4.30 (m, 3H), 7.40–7.60 (m, 5H), 8.31 (s, 1H), 8.42 (s, 1H); MS (CI/NH₃) m/z 389 (M+H)⁺.

139b. 5-(4-Chlorophenyl)-3-(2-(R)-pyrrolidinylmethoxy) pyridine hydrochloride

To a sample of the compound from step a above (170 mg, 0.44 mmol) in CH₂Cl₂ (3 mL) and TFA (2.5 mL) was stirred for 30 min at 0° C. The residue was neutralized with NaHCO₃ to pH 8, then extracted with CH₂Cl₂, which was dried (MgSO₄) and concentrated. The residue was chromatographed (silica gel; CH₂Cl₂/MeOH/NH₄OH, 10:1:0.1) to afford the free base of the title compound (83 mg, 65% yield). The free base was converted to the salt with HCl in THF to afford the title compound: mp 183–185° C.; $^1$H NMR (D₂O) δ1.95–2.36 (m, 4H), 3.44 (t, 2H, J=7.4 Hz), 4.16–4.23 (m, 1H), 4.21 (dd, 1H, J=3.5, 8.0 Hz), 4.62 (dd, 1H, J=3.5, 10.5 Hz), 7.59–7.62 (m, 2H), 7.68–7.73 (m, 1H), 8.18 (m, 1H), 8.45 (d, 1H, J=3.0 Hz), 8.65 (d, 1H, J=2.0 Hz); MS (CI/NH₃) m/z 289 (M+H)+. Anal. Calcd for C₁₆H₁₇ClN₂O·2HCl: C, 53.1; H, 5.30; N, 7.75. Found: C, 52.96; H, 5.08; N, 7.50. $[\alpha]^{25}$D −3.0 (c 0.31, MeOH).

Example 140

6-Chloro-5-(1-octynyl)-3-(2-(S)-pyrrolidinylmethoxy) pyridine dihydrochloride 140a. 3-(1-BOC-2-(R)-pyrrohdinylmethoxy)-6-chloro-5-(1-octnyl)pyridine A mixture of 3-(1-BOC-2-(S)-pyrrolidinylmethoxy)-chloro-6-chloropyridine from Example 69a (400 mg, 1.02 mmol), 1-octyne (0.23 mL, 1.54 mmol), Pd(PPh)₃Cl₂ (36 mg), CuI (catalytic amount) and NEt₃ (2.5 mL) in CH₂Cl₂ (8 mL) was heated at reflux for 16 h. Heating was continued until no starting material remained. The solvent was removed, and the residue was washed with 10% NaOH then extracted with CH₂Cl₂. The organic extract was dried (MgSO₄) and concentrated. The residue was chromatographed (silica gel; hexane:EtOAc, 3: 1) to afford the tide compound (335 mg, 72% yield): $^1$H NMR (CDCl₃, 300 MHz) δ0.91 (t, J=7.5 Hz, 3H), 1.23–1.40 (m, 4H), 1.48 (s, 9H), 1.56–1.69 (m, 2H), 1.81–2.06 (m, 5H), 2.46 (t, J=7.5 Hz, 2H), 3.27–3.47 (m, 2H), 3.98–4.21 (m, 4H), 7.29 (br s, 1H), 7.98 (d, J=3.0 Hz, 1H); MS (CI/NH₃) nmz 421 (M+H)⁺.

140b. 6-Chloro-5-(1-octynyl)-3-(2-(R)-pyrrolidinylmethoxy)pyridine dihydrochloride The compound from step a above (150 mg, 0.37 mmol) was dissolved in TFA (1 mL) and CH₂Cl₂ (2 mL), and the solution was stirred at room temperature for 16 h. The solution was made basic with saturated aqueous NaHCO₃. The basic mixture was extracted with CH₂Cl₂, which was dried (MgSO₄) and concentrated. The residue was chromatographed (silica gel; CH₂Cl₂/MeOH/NH₄OH, 10:1:0.1) to afford the free base of the title compound (75 mg, 64%). The base was converted to the salt by treatment with HCl in Et₂O to give the title compound: mp 133–135° C.; $^1$H NMR (D₂O) δ0.78 (t, 3H, J=7.5 Hz), 1.09–1.23 (m, 4H), 1.24–1.75 (m, 2H), 1.37–1.51 (m, 2H), 1.81 (m, 1H), 1.90–2.05 (m, 2H), 2.13 (m, 1H), 2.30 (m, 1H), 3.28 (t, 2H, J=7.5 Hz), 3.96 (m, IH), 4.46 (m, 1H), 4.10 (dd, 1H, J=7.5, 8.5 Hz), 4.32 (dd, 1H, J=3.5, 10.5 Hz), 7.73 (d, 1H, J=3.0 Hz), 7.96 (d, 1H, J=2.5 Hz); MS (CI/NH₃) m/z 321 (M+H)⁺. Anal. Calcd for C₁₈H₂₅ClN₂O·0.5 HCl·0.2 NH₄Cl·0.6 CHCl₃: C, 53.01; H, 6.43; N, 7.31. Found: C, 52.98; H, 6.09; N, 7.67. $[\alpha]^{25}$D+ 5.93 (c 0.15, MeOH).

Example 141

5-(4-Chlorophenyl)-3-(1-methyl-2-(R)-pyrrolidinylmethoxy)pyridine dihydrochloride Following the procedures of Example 37b, except substituting 4-chlorophenylboronic acid for the boronic acid reagent thereof and Pd(Ph₃P)₄ for the Pd(0), and carrying the product forward as in step 37c, the title compound was prepared (97 mg, 74%): mp 223–225° C.; $^1$H NMR (D₂O) δ2.04–2.30 (m, 3H), 2.41 (m, 1H), 3.06 (s, 1H), 3.27 (m, 1H), 3.77 (m, 1H), 3.96 (m, 1H), 4.44 (m, 1H), 4.61 (m, 1H), 7.57 (d, 2H, J=7.5 Hz), 7.63 (d, 2H, J=7.5 Hz), 7.87 (s, 1H), 8.36 (d, 1H, J=2.0 Hz), 8.54 (d, 1H, J=2.0 Hz); MS (CI/NH₃) m/z 303 (M+H)⁺. Anal. Calcd for C₁₇H₁₉N₂ClN₂O·2HCl: C, 54.35; H, 5.63; N, 7.46. Found: C, 54.40; H, 5.77; N, 7.67. $[\alpha]^{25}$D+8.89 (c 0.14, MeOH).

Example 142

3-(2-(S)-Azetidinylmethoxyl)-6-chloro-5-(4-chlorophenyl)pyridine citrate 142a. 3-(2-(S)-Azetidinylmethoxy)-6-chloro-5-(4-chlorophenyl)pyridine To a solution of 3-(1-BOC-2-(S)-azetidinylmethoxy)-5-bromo-6-chloropyridine (650 mg, 1.73 mmol) and 4-chlorophenylboronic acid (284 mg, 1.82 mmol, Lancaster Chemical Co.) in toluene (10 mL) was added Pd(0) (37 mg) and $Na_2CO_3$ (5 mL of a 2 M solution), and the mixture was heated at reflux for 14 h. The solvent was removed under vacuum, and the residue was chromatographed (silica gel; EtOAc/hexane, 1:5 to 1:2) to afford the title compound (665 mg, 94 % yield): $^1$H NMR ($CDCl_3$, 300 MHz) δ1.41 (s, 9H), 2.23–2.44 (m, 2H), 3.89 (t, J=7.5, Hz, 2H), 4.08–4.18 (m, 2H), 4.37 (m, 1H), 4.53 (m, 1H), 7.25 (d, J=3.0 Hz, 1H), 7.37–7.46 (m, 4H), 8.13 (d, J=3.0 Hz, 1H); MS (CI/$NH_3$) m/z 409 (M+H)$^+$.

142b. 3-(2-(S)-Azetidinylmethoxy)-6-chloro-5-(4-chlorophenyl)pyridine citrate

To a sample of the compound from step a above (665 mg, 1.63 mmol) in $CH_2Cl_2$ (8 mL) and TFA (4 mL) was stirred for 16 h at room temperature. The residue was neutralized with $NaHCO_3$ to pH 8, then extracted with $CH_2Cl_2$, which was dried ($MgSO_4$) and concentrated. The residue was chromatographed (silica gel; $CH_2Cl_2$/MeOH/$NH_4OH$, 10:1:0.1) to afford the free base of the title compound (83 mg, 65% yield). The free base was converted to the salt with citric acid in EtOH to afford the title compound: mp 78–79° C.; $^1$H NMR ($D_2O$) δ2.69 (q, 2H, J=9.0 Hz), 2.75 (d, 2H, J=15.5 Hz), 2.88 (d, 2H, J=15.5.Hz), 4.05–4.16 (m, 2H), 4.43 (d, 2H, J=4.0 Hz), 4.86 (m, 1H), 7.53 (d, 4H, J=5.0 Hz), 7.56 (d, 1H, J=3.0 Hz), 8.18 (d, 1H, J=3.0 Hz); MS (CI/$NH_3$) m/z 309 (M+H)+, 311 (M+3H)$^+$. Anal. Calcd for $C_{15}H_{14}Cl_2N_2O$·1.3 citric acid: C, 48.99; H, 4.40; N, 5.01. Found: C, 48.86; H, 4.57; N, 4.90. [a]$^{25}$D −3.1 (c 0.26, MeOH).

Example 143

6-Chloro-5-(4-chlorophenyl)-3-(1-2-(S)-azetidinylmethoxy)pyridine citrate

To the product obtained from Example 142a above (327 mg, 1 mmol) in ethanol (9 mL) was added formalin (37%, 1.5 mL) and HOAc (0.75 mL), and the pH was adjusted to 6. Then sodium cyanoborohydride (270 mg) was added, and the mixture was stirred at room temperature for 16 h. The mixture was diluted with water and saturated with $K_2CO_3$. The mixture was extracted with $CHCl_3$. The solvent was dried ($MgSO_4$), filtered and concentrated. The residue was chromatographed (silica gel; $CH_2Cl_2$/MeOH/$NH_4OH$, 10:0.8:0.1) to afford the free base (290 mg, 89%) of the title compound: $^1$H NMR ($CDCl_3$, 300 MHz) δ2.02–2.15 (m, 2H), 2.41 (s, 3H), 2.88 (m, 1H), 3.35–3.51 (m, 2H), 4.05 (d, J=6.0 Hz, 2H), 7.22 (d, J=3.0 Hz, 1H), 7.35–7.47 (m, 4H), 8.09 (d, J=3.0 Hz, 1H); MS (CI/$NH_3$) m/z 323 (M+H)$^+$. The salt was prepared by treatment with citric acid in EtOH, as described above, to give the title compound: mp 78–79° C.; $^1$H NMR ($D_2O$) δ2.53–2.71 (m, 2H), 2.74 (d, 2H, J=15.5 Hz), 2.86 (d, 2H, J=15.5 Hz), 4.04 (q, 1H, J=9.5 Hz), 4.28 (m, 1H), 4.36–4.53 (m, 2H), 4.60 (m, 1H), 7.43–7.59 (m, 5H), 8.16 (d, 1H, J=3.0 Hz); MS (CI/$NH_3$) m/z 323 (M+H)$^+$. Anal. Calcd for $C_{16}H_{16}Cl_2N_2O$·1.2 citric acid: C, 50.32; H, 4.66; N, 5.06. Found: C, 50.38; H, 4.86; N, 5.17. [α]$^{25}$D −10.6 (c 0.35, MeOH).

Example 144

5-(1-octynyl)-3-(2-(R)-pyrrolidinylmethoxy)pyridine dihydrochloride 144a. 3-(1-BOC-2-(R)-pyrrolidinylmethoxy)-5-(1-octynyl)pyridine A mixture of 3-(1-BOC-2-(R)-pyrrolidinylmethoxy)-5-bromopyridine (300 mg, 0.84 mmol), 1-octyne (0.2 mL, 1.4 mmol), Pd(PPh$_3$)$_3$Cl$_2$ (12 mg), CuI (catalytic amount) and NEt$_3$ (2.45 mL) in $CH_2Cl_2$ (7 mL) was heated at reflux for 16 h. The solvent was removed, and the residue was washed with 10% NaOH then extracted with $CH_2Cl_2$. The organic extract was dried ($MgSO_4$) and concentrated. The residue was chromatographed (silica gel; $CHCl_3$/MeOH, 10:1) to afford the title compound (302 mg) that contaminated with starting material.

144b. 5-(1-octynyl)-3-(2-(R)-pyrrolidinylmethoxy)pyridine dihydrochloride

The compound from step a above (300 mg, 0.78 mmol) was dissolved in TFA (2.5 mL) and $CH_2Cl_2$ (3 mL), and the solution was stirred at room temperature for 3 h. The solution was made basic with saturated aqueous $NaHCO_3$. The basic mixture was extracted with $CH_2Cl_2$, which was dried ($MgSO_4$) and concentrated. The residue was chromatographed (silica gel; $CH_2Cl_2$/MeOH/$NH_4OH$, 10:1:0.1) to give the free base of the title compound (105 mg). Since this material contaminated with bromide, it was then subjected to reaction with octyne as described in the step a above. The desired product was obtained as free base (105 mg): $^1$H NMR ($CDCl_3$, 300 MHz) δ0.92 (t, J=7.5 Hz, 3H), 1.26–1.39 (m, 4H), 1.39–1.50 (m, 2H), 1.54–1.71 (m, 4H), 1.80–2.20 (m, 4H), 2.43 (t, 2H, J=7.0 Hz), 3.02–3.16 (m, 2H), 3.66 (m, 1H), 3.94–4.08 (m, 2H), 7.20 (m, 1H), 8.21 (d, 1H, J=3.0 Hz), 8.23 (m, 1H); MS (CI/$NH_3$) m/z 287 (M+H)$^+$. The base was converted to the salt by treatment with HCl in $Et_2O$/THF to give the tide compound: $^1$H NMR ($D_2O$) δ0.88 (t, 3H, J=7.0 Hz), 1.20–1.40 (m, 4H), 1.40–1.48 (m, 2H), 1.55–1.69 (m, 2H), 1.95 (m, 1H), 2.03–2.23 (m, 2H), 2.29 (m, 1H), 2.49 (t, 2H, J=7.0 Hz), 3.41 (t, 2H, J=7.0 Hz), 4.14 (m, 1H), 4.32 (dd, 1H, J=7.5, 10.0 Hz), 4.53 (dd, 1H, J=4.0, 10.5 Hz), 7.89 (s, 1H), 8.36 (br s, 2H); MS (CI/$NH_3$) m/z 287 (M+H)+. Anal. Calcd for $C_{18}H_{26}N_2O$·2.3 HCl: C, 58.39; H, 7.70; N, 7.57. Found: C, 58.50; H, 7.47; N, 7.37. [α]$^{25}$D −0.74 (c 0.14, MeOH).

Example 145

3-(1-Methyl-2-(R)-pyrrolidinylmethoxy)-5-(1-octnyl)pridine dihydrochloride 3-(1-Methyl-2-(R)-pyrrolidinylmethoxy)-5-(1-octynyl)pyridine dihydrochloride To 3-(1 -BOC-2-(R)-pyrrolidinylmethoxy)-5-(1-octynyl)pyridine from Example 144a (73 mg, 0.26 mmol) was added formalin (37%, 2 mL) and formic acid (4 mL), and the mixture was heated at 80° C. for 16 h. The solvent was concentrated, and solid $NaHCO_3$ was added to the residue. At pH 8 the mixture was extracted with $CH_2Cl_2$, which was dried ($MgSO_4$) and concentrated. The residue was chromatographed (silica gel; $CH_2Cl_2$/MeOH/$NH_4OH$, 10:1:0.1) to give the free base of the title compound (70 mg). Since this material contaminated with bromide, it was then subjected to reaction with octyne as described in the step a above. The desired product was obtained as free base (70 mg). $^1$H NMR ($CDCl_3$, 300 MHz) δ0.92 (t, J=7.5 Hz, 3H), 1.24–1.37 (m, 4H), 1.39–1.51 (m, 2H), 1.52–1.68 (m, 4H), 1.67–1.97 (m, 3H), 2.06 (m, 1H), 2.43 (t, 2H, J=7.0 Hz), 2.53 (br s, 3H), 3.04–3.26 (m, 2H), 3.90–4.14 (m, 2H), 7.20 (m, 1H), 8.22 (d, 1H, J=3.0 Hz), 8.23 (m, 1H). MS (CI/$NH_3$) m/z 301 (M+H)$^+$. The base was converted to the salt by treatment with HCl in $Et_2O$ to give the title compound. mp 102–105° C. $^1$H NMR ($D_2O$) δ0.83–0.93 (m, 3H), 1.25–1.40 (m, 4H), 1.40–1.53 (m, 2H), 1.55–1.68 (m, 2H), 2.00–2.30 (m, 3H), 2.30–2.43 (m, 2H), 2.47 (t, 2H, J=7.0 Hz), 3.03 (s, 3H), 3.18–3.34 (m, 2H), 3.74 (m, 1H), 3.93 (m, 1H), 4.34 (m, 1H), 4.51 (m, 1H), 7.51 (s, 1H), 8.15–8.90 (m, 2H). MS (CI/$NH_3$) m/z 301 (M+H)$^+$. Anal. Calcd for $C_{19}H_{28}N_2O$·2.5 HCl: C, 58.28; H, 7.85; N, 7.15. Found: C, 57.91; H, 7.71; N, 6.83. [α]$^{25}$D+12.6 (c 0.14, MeOH).

Example 146

6-Chloro-3-(1-methyl-2-(S)-pyrrolidinylmethoxy)-5-(1-octynyl)pyridine dihydrochloride To 6-Chloro-5-(1-octynyl)-3-(2-(S)-pyrrolidinylmethoxy)pyridine from Example 140 above (330 mg, 0.78 mmol) was added formalin (37%, 4 mL) and formic acid (2 mL), and the mixture was heated at 80° C. for 10 h. The solvent was concentrated, and solid $NaHCO_3$ was added to the residue. At pH 8 the mixture was extracted with $CH_2Cl_2$, which was dried ($MgSO_4$) and concentrated. The residue was chromatographed (silica gel; $CH_2Cl_2$/MeOH/ $NH_4OH$, 10:1:0.1) to give the free base of the title compound (93 mg, 89% yield). The base was converted to the salt by treatment with HCl in $Et_2O$ to give the title compound: mp 223–225° C.; $^1H$ NMR ($D_2O$) δ0.83–0.93 (m, 3H), 1.20–1.30 (m, 4H), 1.34–1.46 (m, 2H), 1.48–1.68 (m, 2H), 1.96–2.20 (m, 3H), 2.28 (m, 1H), 2.34–2.45 (m, 2H), 2.94 (s, 3H), 3.18 (m, 1H), 3.64 (m, 1H), 3.83 (m, 1H), 4.24 (m, 1H), 4.36 (m, 1H), 7.43 (s, 1H), 8.68 (br s, 1H); MS ($CI/NH_3$) m/z 335 $(M+H)^+$. Anal. Calcd for $C_{19}H_{27}ClN_2O \cdot 1.5HCl \cdot 0.4 Et_2O$: C, 59.02; H, 7.81; N, 6.68. Found: C, 59.32; H, 7.54; N, 6.51. $[\alpha]^{25}D$ +8.99 (c 0.14, MeOH).

Example 147

6-Chloro-3-(1-methyl-2-(S)-pyrrolidinylmethoxy)-5-(3-pyridyl)pyridine dihydrochloride 147a. 6-Chloro-3-(1-methyl-2-(S)-pyrrolidinylmethoxy)-5-(3-pyridyl)pyridine To a solution of 3-(1-methyl-2-(S)-pyrrolidinylmethoxy)-5-bromo-6-chloropyridine (500 mg, 1.28 mmol) in toluene (10 mL) was added 3-pyridinyltributyltin (564 mg, 1.54 mmol) and tetrakis(triphenylphosphine)palladium(0) (45 mg, 0.04 mmol). After being heated under reflux for 16 h, the resulting mixture was cooled to room temperature. Solvent was removed, and the residue was chromatographed (silica gel; EtOAc/hexane, 2:19 to 1:1) to afford an oil (428 mg, 86%): $^1H$ NMR ($CDCl_3$, 300 MHz) δ1.45 (s, 9H), 1.94 (m, 1H), 1.98–2.10 (m, 2H), 3.31–3.45 (m, 2H), 3.88–4.30 (m, 4H), 7.22 (m, 1H), 7.40 (m, 1H), 7.83 (td, 1H, J=1.5, 9.0 Hz), 8.16 (d, 1H, J =3.0 Hz), 8.64–8.73 (m, 2H); MS ($CI/NH_3$) m/z 390 $(M+H)^+$.

147b. 6-Chloro-3-(1-methyl-2-(S)-pyrrolidinylmethoxy)-5-(3-pridyl)pyridine dihydrochloride To 6-Chloro-3-(1-methyl-2-(S)-pyrrolidinylmethoxy)-5-(3-pyridinyl)pyridine obtained from step a above (250 mg, 0.64 mmol) was added formalin (37%, 4 mL) and formic acid (2 mL), and the mixture was heated at 80° C. for 10 h. The solvent was concentrated, and solid $NaHCO_3$ was added to the residue. At pH 8 the mixture was extracted with $CH_2Cl_2$, which was dried ($MgSO_4$) and concentrated. The residue was chromatographed (silica gel; $CH_2Cl_2$/MeOH/ $NH_4OH$, 10:1:0.1) to afford the free base of the title compound (162 mg, 83% yield). The base was converted to the salt by treatment with HCl in $Et_2O$ to give the title compound (130 mg, 73%): mp 108–110° C.; $^1H$ NMR ($D_2O$) δ2.0–2.30 (m, 2H), 2.40 (m, 1H), 3.03 (s, 3H), 3.25 (m, 1H), 3.65–3.82 (m, 2H), 3.94 (m, 1H), 4.39 (dd, 1H, J=6.0, 11.0 Hz), 4.57 (dd, 1H, J=3.0, 11.0 Hz), 7.69 (d, 1H, J=3.0 Hz), 8.17 (m, 1H), 8.28 (d, 1H, J=3.0 Hz), 8.74 (d, 1H, J=8.0 Hz), 8.86 (d, 1H, J=5.5 Hz), 9.01 (s, 1H). MS ($CI/NH_3$) m/z 304 (M+H)+, 607 $(2M+H)^+$. Anal. Calcd for $C_{16}H_{18}ClN_3O \cdot 2.4$ $HCl \cdot 0.2 Et_2O$: C, 49.69; H, 5.56; N, 10.35. Found: C, 49.77; H, 5.38; N, 10.11. $[\alpha]^{25}D$ −1.5 (c 0.2, MeOH).

Example 148

6-Chloro-5-(5,5-dimethyl-1,3-hexadienyl -3-2-(S)-pyrrolidinylmethoxy)pyridine dihydrochloride 148a. 3-(1-BOC-2-(S)-pyrrolidinylmethoxy)-6-Chloro-5-(5,5-dimethyl-1,3-hexadienyl)pyridine A solution of 3-(1-BOC-2-(S)-pyrrolidinylmethoxy)-5-bromo-6-chloropyridine (1.0 g, 2.6 mmol), 5-(5,5-dimethyl)-1,3-hexadiene (560 mg, 5.2 mmol), $Pd(OAc)_4$ (120 mg), tris(o-tolyl)phosphine (400 mg), and NEt3 (4 mL) in acetonitrile (10 mL) was heated in a sealed tube at 85–90° C. for 32 h. The solution was then diluted with EtOAc, and the mixture was washed with water and aqueous $NaHCO_3$ solution. The organic layer was dried and concentrated. The residue was chromatographed (silica gel, hexane/EtOAc, 4:1) to afford the title compound (400 mg, 47% yield): $^1H$ NMR ($CDCl_3$, 300 MHz) δ1.08 (s, 9H), 1.48 (s, 9H), 1.84–2.06 (m, 3H), 3.28–3.46 (m, 2H), 3.92 (m, 1H), 4.06–4.28 (m, 2H), 5.98 (d, 1H, J=15.0 Hz), 6.13 (m, 1H, J=10.0, 15.0 Hz), 6.42 (d,1H, J=15.0 Hz), 7.72 (m, 1H), 7.92 (d, 1H, J=3.0 Hz); MS ($CI/NH_3$) m/z 421 $(M+H)^+$.

148b. 6-Chloro-5-(5,5-dimethyl-1,3-hexadienyl)-3-2-2-(R)-pyrrolidinylmethoxy)pyridine dihydrochloride The product from step a above (149 mg, 0.39 mmol) was deprotected and converted to the salt by treatment with hydrogen chloride in $Et_2O$/THF to afford the title compound: mp 206–208° C.; $^1H$ NMR ($CD_3OD$) δ1.10 (s, 9H), 1.95 (m, 1H), 2.08–2.18 (m, 2H), 2.29 (m, 1H), 3.37–3.42 (m, 2H), 4.06 (m, 1H), 4.25 (dd, 1H, J=5.5, 11.5 Hz), 4.46 (dd, 1H, J=3.5, 10.5 Hz), 6.06 (d, 1H, J=15.0 Hz), 6.28 (dd, 1H, J=9.5, 15.5 Hz), 6.71 (d, 1H, J=16.0 Hz), 7.00 (dd, 1H, J=10.0, 15.5 Hz), 7.73 (d, 1H, J=3.0 Hz), 7.98 (d, 1H, J=3.0 Hz); MS ($CI/NH_3$): m/z 321 $(M+H)^+$. Anal. Calcd for $C_{18}H_{25}ClN_2O \cdot 2$ $HCl \cdot 0.3$ $H_2O$: C, 54.16; H, 6.97; N, 7.02. Found: C, 54.17; H, 6.94; N, 6.93. $[\alpha]^{25}D$ +3.1 (c 0.35, MeOH).

Example 149

6-Chloro-5-(5,5-dimethyl- 1,3-hexadienyl)-3-(1-methyl-2-(S)-pyrrolidinylmethoxy)pyridine dihydrochloride To a solution of 6-chloro-5-(5,5-dimethyl-1,3-hexadienyl)-3-(2-(S)-pyrrolidinylmethoxy)pyridine from Example 148a (150 mg, 0.38 mmol) in EtOH (3.0 mL) was added formalin (37%, 5 mL), sodium cyanoborohydride (120 mg, 1.9 mmol) and acetic acid (0.1 mL), and the mixture was stirred at 25° C. for 16 h. The solvent was concentrated, and solid $NaHCO_3$ was added to the residue. At pH 8 the mixture was extracted with EtOAc, which was dried ($MSO_4$) and concentrated. The residue was converted to the salt by treatment with hydrogen chloride in $Et_2O$/THF to afford the title compound (143 mg, 100%): mp 220–220° C.; $^1H$ NMR ($CD_3OD$) δ1.10 (s, 9H), 2.08–2.18 (m, 2H), 2.23 (m, 1H), 2.41 (m, 1H), 3.08 (s, 3H), 3.23 (m, 1H), 3.75 (m, 1H), 3.92 (m, 1H), 4.35 (dd, 1H, J=5.5, 11.5 Hz), 4.53 (dd, 1H, J=3.5, 10.5 Hz), 6.05 (d, 1H, J=15.5 Hz), 6.28 (dd, 1H, J=9.5, 15.5 Hz), 6.73 (d, 1H, J=16.0 Hz), 7.00 (dd, 1H, J=10, 15.5 Hz), 7.75 (d, 1H, J=3.0 Hz), 8.00 (d, 1H, J=3.0 Hz); MS ($CI/NH_3$) m/z 335 (M+H+), 669 (2M+H)+. Anal. Calcd for $C_{19}H_{27}ClN_2O \cdot 1.1$ $HCl \cdot 0.5$ $H_2O$: C, 59.43; H, 7.64; N, 7.30. Found: C, 59.55; H, 7.69; N, 7.36. $[\alpha]^{25}D$ −4.5 (c 0.44, MeOH).

Example 150

6-Chloro-5-(4-chlorophenyl)-3-(2-(S)-pyrrolidinylmethoxy)pyridine dihydrochloride

150a. 3-(1-BOC-2-(S)-pyrrolidinylmethoxy)-6-Chloro-5-(4-chlorophenyl)pyridine

To a solution of 3-(1-BOC-2-(S)-pyrrolidinylmethoxy)-5-bromo-6-chloropyridine (1.64 g, 4.20 mmol) and 4-chlorophenylboronic acid (620 mg, 3.9 mmol.) in toluene (20 mL) was added Pd(0) (97 mg) and $Na_2CO_3$ (5 mL of a 2 M solution), and the mixture was heated at reflux for 16 h. The reaction mixture was quenched with saturated $NaHCO_3$ solution and extracted with $Et_2O$. The solvent was removed under vacuum, and the residue was chromatographed (silica gel; EtOAc/hexane, 1:4) to afford the title compound (430 mg, 24% yield): $^1H$ NMR ($CDCl_3$, 300 MHz) δ1.45 (s, 9H), 1.83–2.00 (m, 4H), 3.30–3.45 (m, 2H), 4.00 (m, 1H), 4.06–4.25 (m, 2H), 7.36–7.46 (m, 5H), 8.10 (s, 1H); MS ($CI/NH_3$) m/z 423 (M+H)+.

150b 6-Chloro-5-(4-chlorophenyl)-3-(2)-(S)-pyrrolidinylmethoxy)pyridine hydrochloride The product from step a above (430 mg, 1.02 mmol) was deprotected and converted to the salt by treatment with hydrogen chloride in $Et_2O$/THF to afford the title compound: mp 86–89° C.; $^1H$ NMR ($CD_3OD$) δ1.97 (m, 1H), 2.14 (m, 1H), 2.27 (m, 1H), 3.43 (t, 2H, J=7.5 Hz), 4.14 (m, 1H), 4.27 (dd, 1H, J=7.5, 10.5 Hz), 4.48 (dd, 1H, J=3.0, 10.5 Hz), 7.49–7.57 (m, 5H), 8.13 (d, 1H, J=3.0 Hz); MS ($CI/NH_3$) m/z 323 (M+H)+. Anal. Calcd for $C_{16}H_{16}Cl_2N_2O$·1.1HCl·0.1 $H_2O$: C, 53.42 H, 4.76; N, 7.79. Found: C, 52.37; H, 4.81; N, 7.63. $[α]^{25}D$ +6.6 (c 0.42, MeOH).

Example 151

6-Chloro-5-(4-chlorophenyl)-3-(1-methyl-2-(S)-pyrrolidinylmethoxy)pyridine dihydrochloride

To a solution of 6-Chloro-5-(4-chlorophenyl)-3-(2-(S)-pyrrolidinylmethoxy)pyridine from step 150b above (270 mg, 0.75 mmol) in EtOH (5.0 mL) was added formalin (37%, 5 mL), sodium cyanoborohydride (240 mg, 3.75 mmol) and acetic acid (0.15 mL), and the mixture was stirred at 25° C. for 16 h. The solvent was concentrated, and solid $NaHCO_3$ was added to the residue. At pH 8 the mixture was extracted with EtOAc, which was dried ($MgSO_4$) and concentrated. (320 mg). The residue was converted to the salt by treatment with hydrogen chloride in $Et_2O$/THF to afford the title compound (270 mg, 96%): mp 183–185° C.; $^1H$ NMR ($CD_3OD$) δ2.00–2.32 (m, 3H), 2.41 (m, 1H), 3.08 (s, 3H), 3.15 (m, 1H), 3.75 (m, 1H), 3.92 (m, 1H), 4.37 (dd, 1H, J=7.0, 11.0 Hz), 4.53 (dd, 1H, J=3, 11.0 Hz), 7.43–7.53 (m, 4H), 7.56 (d, 1H, J=4.5 Hz), 8.20 (d, 1H, J=3.0 Hz); MS ($CI/NH_3$) m/z 337 (M+H)+. Anal. Calcd for $C_{17}H_{18}Cl_2N_2O$·1.3 HCl·0.1 $H_2O$: C, 52.84; H, 5.09; N, 7.25. Found: C, 52.84; H, 4.84; N, 7.58. $[α]^{25}D$ −6.6 (c 0.42, MeOH).

Example 152

6-Chloro-3-(2-(S)-pyrrolidinylmethoxy)-5-(2-thienyl)pyridine dihydrochloride

152a. 3-(1-BOC-2-(S)-pyrrolidinylmethoxy)-6-chloro-5-(2-thienyl)pyridine

A mixture of 3-(1-BOC-2-(S)-pyrrolidinylmethoxy)-5-bromo-6-chloropyridine from Example 69a (1.5 g, 3.8 mmol), 2-thienylboronic acid (1.46 g, 11.5 mmol), 2 M $Na_2CO_3$ (5 mL) and Pd(0) (190 mg) were mixed together in toluene (20 mL), and the mixture was heated at reflux for 48 h. The mixture was cooled and extracted with EtOAc The EtOAc was removed under reduced pressure, and the residue was chromatographed (silica gel; hexane/EtOAc, 4: 1) to afford the title compound (340 mg, 32% yield): $^1H$ NMR ($CDCl_3$, 300 MHz) δ1.47 (s, 9H), 1.84–2.11 (m, 4H), 3.31–3.46 (m, 2H), 3.89 (m, 1H), 4.05–4.26 (m, 2H), 7.14 (dd, 1H, J=4.5, 6.0 Hz), 7.42–7.50 (m, 2H), 8.05 (d, 1H, J=3.0 Hz), 8.07 (m, 1H); MS ($CI/NH_3$) m/z 395 (M+H)+.

152b. 6-Chloro-3-(2-(S)-pyrrolidinylmethoxy)-5-(2-thienyl)pyridine dihydrochloride The compound from step a above (250 mg, 0.88 mmol) was deprotected by treatment with $HCl/Et_2O$ to give tthe title compound (118 mg, 81%): mp 208–210° C.; $^1H$ NMR ($D_2O$, 300 MHz) δ1.97 (m, 1H), 2.16 (m, 1H), 2.08–2.20 (m, 2H), 2.28 (m, 1H), 3.44 (t, 2H, J=7.5 Hz), 4.13 (m, 1H), 4.27 (dd, 1H, J=7.5, 11.5 Hz), 4.47 (dd, 1H, J=3.0, 7.5 Hz), 7.24 (dd, 1H, J=5.0, 5.5 Hz), 7.54 (dd, 1H, J=1.0, 4.0 Hz), 7.65–7.68 (m, 2H), 8.06 (d, J=3.0 Hz, 1H); MS ($CI/NH_3$) m/z 295 (M+H)+. Anal. Calcd for $C_{14}H_{15}ClN_2OS$·1.1 HCl·0.2 $H_2O$: C, 50.76; H, 4.87; N, 8.46. Found: C, 49.68; H, 4.91; N, 8.28. $[α]^{25}D$ +6.1 (c 0.31, MeOH).

Example 153

6-Chloro-3-(1-methyl-2-(S)-pyrrolidinylmethoxy)-5-(2-thienyl)pyridine dihydrochloride

To a solution of 6-chloro-3-(2-(S)-pyrrolidinylmethoxy)-5-(2-thienyl)pyridine from step 152b above (48 mg, 0.14 mmol) in EtOH (2 mL) was added formalin (37%, 2 mL), sodium cyanoborohydride (50 mg, 0.72 mmol) and acetic acid (0.05 mL), and the mixture was stirred at 25° C. for 24 h. The solvent was concentrated, and solid $NaHCO_3$ was added to the residue. At pH 8 the mixture was extracted with EtOAc, which was dried ($MgSO_4$) and concentrated. (44 mg, 100%). The residue was converted to the salt by treatment with hydrogen chloride in $Et_2O$/THF to afford the title compound: mp 160–163° C.; $^1H$ NMR ($D_2O$) δ1.86–1.96 (m, 2H), 2.06 (m, 1H), 2.24 (m, 1H), 2.88 (s, 3H), 3.09 (m, 1H), 3.61 (m, 1H), 3.72 (m, 1H), 4.12 (dd, 1H, J=3.5, 7.0 Hz), 4.27 (dd, 1H, J=1.5, 7.0 Hz), 7.05 (dd, 1H, J=2.0, 3.0 Hz), 7.34 (d, 1H, J=2.0 Hz), 7.41 (d, 1H, J=2.0 Hz), 7.47 (d, 1H, J=3.0 Hz), 7.83 (d, 1H, J=1.5 Hz); MS ($CI/NH_3$) m/z 309 (M+H)+. Anal. Calcd for $C_{15}H_{17}ClN_2OS$·HCl·0.3 $H_2O$: C, 51.37; H, 5.35; N, 7.99. Found: C, 51.38; H, 5.47; N, 7.85

Example 154

3-(2-(S)-Azetidinylmethoxy-5-(2-thienyl)pyridine dihydrochloride

154a. 3-(1-BOC-2-(S)-azetidinylmethoxy)-5-(2-thienyl)pyridine

To a mixture of 3-(1-BOC-2-(S)-azetidinylmethoxy)-5-bromopyridine (0.42 g, 1.2 mmol), tetrakis(triphenylphosphine)palladium(0) (40 mg, 0.034 mmol), sodium carbonate (2.0 M, 2 mL) in toluene (10 mL) was added 2-thienylboronic acid (0.38 g, 3.0 mmol). The reaction mixture was stirred and heated at 80° C. for 16 h. Solvent was evaporated. The residue was chromatographed (silica gel; hexane/EtOAC, 10:1 to 2:1) to afford an oil (0.24 g, 57%): $^1H$ NMR ($CDCl_3$, 300 MHz) δ1.42 (s, 9H), 2.26–2.90 (m, 2H), 3.86–3.94 (m, 2H), 4.20 (m, 1H), 4.39 (m, 1H), 4.55 (m, 1H), 7.12 (m, 1H), 7.36 (s, 1H), 7.44 (s, 1H), 8.26 (s, 1H), 8.50 (s, 1H); MS ($CI/NH_3$) m/z 347 (M+H)+.

154b. 3-(2-(S)-Azetidinylmethoxy)-5-(2-thienyl)pyridine

The product from step a above (0.11 g, 0.32 mmol) in $CH_2Cl_2$ (2 mL) was cooled to 0° C., and then TFA (0.8 mL) was added carefully. The reaction mixture was stirred at 0° C. for 40 min. The mixture was warmed to room temperature and kept stirring for 30 mnin. After neutralization with saturated sodium bicarbonate, the reaction mixture was extracted with $CH_2Cl_2$ (3X). The combined organic layers were dried ($MgSO_4$), concentrated and chromatographed (silica gel; $CH_2Cl_2$/MeOH/$NH_4OH$, 10:1:0 to 10:1:0.2) to afford a light yellow oil (63 mg, 80%): $^1H$ NMR ($CDCl_3$, 300 MHz) δ2.38–2.50 (m, 2H), 3.70 (m, 1H), 4.05–4.24 (m, 2H), 4.53 (m, 1H), 7.10 (dd, 1H, J=4.0, 5.0 Hz), 7.38 (d, 1H, J=5.0 Hz), 7.42 (t, 1H, J=3.0 Hz), 8.22 (s, 1H), 8.50 (s, 1H); MS (CI/$NH_3$) m/z 247 (M+H)$^+$.

154c. 3-(2-(S)-Azetidinylmethoxy)-5-(2-thienyy)pyridine dihydrochloride

The product from step b above in $Et_2O$ was added hydrogen chloride (1.0 M in $Et_2O$) carefully to afford the titde compound: $^1H$ NMR ($D_2O$) δ2.71 (d, 2H, J=8.5 Hz), 4.08–4.21 (m, 2H), 4.75 (m, 1H), 4.97 (m,1H), 7.22 (dd, 1H, J=4.0, 5.0 Hz), 7.58 (dd, 2H, J=4.0, 5.0 Hz), 7.72 (d, 1H, J=2.0 Hz), 8.25 (s, 1H), 8.52 (s, 1H); MS (CI/$NH_3$) m/z 247 (M+H)$^+$. Anal. Calcd for $C_{13}H_{14}N_2OS$·2.4 HCl: C, 46.77; H, 4.95; N, 8.39. Found: C, 46.76; H, 5.10; N, 8.39. $[\alpha]^{25}D$ −7.11 (c 1.1, MeOH).

Example 155

5-(2-(4-pyridinyl)ethenyl)-3-(2-(S)-pyrrolidinylmethoxy) pyridine trihydrochloride

155a. 3-(1-BOC-2-(S)-pyrrolidinyl-methoxy)-5-(4-pyridinyl-ethenyl)pyridine

To a solution of 3-(1-BOC-2-(S)-pyrrolidinylmethoxy)-5-bromopyridine (300 mg, 0.84 mmol) in acetonitrile (10 mL) and $NEt_3$ (1 mL) was added 4-vinylpyridine(0.15 mL, 1.34 mmol), palladium acetate (28 mg, 0.13 mmol) and tri-o-tolylphosphine (141 mg). The reaction mixture was heated in a sealed tube at 100° C. for 16 h. After cooling to room temperature, saturated $NaHCO_3$ solution was added. The mixture was extracted with EtOAc (2X). The combined organic solvent was dried ($MgSO_4$), concentrated and chromatographed (silica gel; hexane/EtOAc, 2:1 to 1:2) to afford an oil (255 mg, 80%): $^1H$ NMR ($CDCl_3$, 300 Hz) δ1.50 (s, 9H), 1.90 (m, 1H), 2.00–2.10 (m, 2H), 3.30–3.50 (m, 2H), 4.00 (m, 1H), 4.14–4.24 (m, 2H), 4.28 (m, 1H), 7.10 (m, 1H), 7.24 (m, 1H), 7.36–7.40 (m, 3H), 8.26 (s, 1H), 8.30 (s, 1H), 8.60 (d, 2H, J=6.5 Hz); MS (CI/$NH_3$) m/z 382 (M+H)$^+$.

155b. 5-(2-(4-Pyridinyl)ethenyl)-3-(2-(S) pyrrolidinylmethoxy)pyridine

The product from step a above (0.26 mg, 0.67 mmol) in $CH_2Cl_2$ (3 mL) was cooled to 0° C., and TFA (2 mL) was added carefully. The reaction mixture was stirred at 0° C. for 40 min. The mixture was warmed to room temperature and kept strinig for 30 min. After neutralization with saturated sodium bicarbonate solution, the reaction mixture was extracted with $CH_2Cl_2$ (X3). The combined organic layer was dried ($MgSO_4$), concentrated and chromatographed (silica gel; $CH_2Cl_2$/MeOH/$NH_4OH$, 10:1:0 to 10:1:0.4) to afford a light yellow oil (142 mg, 76%): $^1H$ NMR ($CDCl_3$, 300 Mz) δ1.70 (m, 1H), 1.84–2.00 (m, 2H), 2.05 (m, 1H), 3.05–3.15 (m, 2H), 3.70 (m, 1H), 4.04–4.14 (m, 2H), 7.06 (d, 1H, J=16.5 Hz), 7.24 (d, 1H, J=16.5 Hz), 7.38–7.50 (m, 3H), 8.24 (d, 1H, J=3.0 Hz), 8.34 (d, 1H, J=1.0 Hz), 8.60 (d, 1H, J=6.5 Hz); MS (CI/$NH_3$) m/z 282 (M+H)$^+$.

155c. 5-($^2$-($^4$-Pyridinyl)ethenyl)-3-(2-(S)-pyrrolidinylmethoxy)pyridine trihydrochloride The product from step b above in $Et_2O$ was added hydrogen chloride (1.0 M in $Et_2O$) carefully to afford the tittle compound: mp 240° C. (dec.); $^1H$ NMR ($D_2O$) 2.00 (m, 1H), 2.10–2.20 (m, 2H), 2.32 (m, 1H), 3.44 (t, 2H, J=7.5 Hz), 4.15 (m, 1H), 4.31 (dd, 1H, J=7.5, 11.0 Hz), 4.53 (dd, 1H, J=3.5, 11.0 Hz), 7.43 (d, 1H, J=16.0 Hz), 7.72 (d, 2H, J=16.0 Hz), 8.01 (d, 2H, J=7.0 Hz), 8.30 (d, 1H, J=3.0 Hz), 8.45 (d, 1H, J=1.0 Hz), 8.63 (d, 2H, J=6.5 Hz); MS (CI/$NH_3$): m/z 282 (M+H)$^+$. Anal. Calcd for $C_{17}H_{19}N3O$·3 HCl·$H_2O$·0.3 $Et_2O$: C, 50.72; H, 6.31; N, 9.75. Found: C, 50.76; H, 6.03; N, 9.38. $[\alpha]^{25}D$ +3.43 (c 0.70, MeOH).

Example 156

3-(2-(S)-Pyrrolidinylmethoxy)-5-(2-thienyl)pyridine dihydrochloride

156a. 3-(1-BOC-2-(S)-pyrrolidinylmethoxy)-5-(2-thienyl)pyridine

To a mixture of 3-(1-(S)-BOC-pyrrolidinylmethoxy)-5-bromopyridine (0.40 g, 1.1 mmol), tetrakis (triphenylphosphine)palladium(0) (40 mg, 0.034 mmol), sodium carbonate (2.0 M, 2 mL) in toluene was added 2-thienylboronic (0.32 g, 2.5 mmol). The reaction mixture was stirred and heated at 80° C. for 16 h. Solvent was evaporated and the residue was chromatographed (silica gel; hexane/EtOAC, 10:1 to 2:1) to afford an oil (0.12 mg, 30%): $^1H$ NMR ($CDCl_3$, 300 MHz) δ1.48 (s, 9H), 1.85–2.00 (m, 3H), 2.00–2.10 (m, 2H), 3.30–3.48 (m, 2H), 4.10–4.20 (m, 2H), 7.12 (m, 1H), 7.34–7.40 (m, 2H), 8.20–8.30 (m, 2H), 8.50 (s, 1H); MS (CI/$NH_3$) m/z 361 (M+H)$^+$.

156b. 3-(2-(S)-Pyrrolidinylmethoxy)-5-(2-thienyl-pyridine dihydrochloride

To the product obtained from step a above was added 4.0 M HCl in 1.4 dioxane (3 mL). It was stirred for 16 h to afford the title compound: $^1H$ NMR ($CD_3OD$) δ1.97 (m, 1H), 2.04–2.24 (m, 2H), 2.32 (m, 1H), 3.38–3.48 (m, 2H), 4.04—4.20 (m, 2H), 4.51 (m, 1H), 7.26 (dd, 1H, J=4.0, 5.0 Hz), 7.74 (dd, 1H, J=1.0 Hz), 7.86 (dd, 1H, J=1.0, 4.0 Hz), 8.43 (t, 1H, J=2.0 Hz), 8.58 (d, 1H, J=2.0 Hz), 8.65 (s, 1H); MS (CI/$NH_3$) m/z 261 (M+H)+. Anal. Calcd for $C_{14}H_{16}N_2OS$·3.1 HCl: C, 45.04; H, 5.16; N, 7.51. Found: C, 45.16; H, 4.76; N, 7.91. $[\alpha]^{25}D$ +18.3 (c 0.23, MeOH)

Example 157

5-Octynyl-3-(2-(S)-pyrrolidinylmethoxy)pyridine dihydrochloride

157a. 3-(1-BOC-$^2$-(S)-pyrrolidinylmethoxy)-5-octynylpyridine

To a solution of 3-(1-BOC-2-(S)-pyrrolidinylmethoxy)-5-bromopyridine (300 mg, 0.84 mmol) in $CH_2Cl_2$ (10 mL) and $NEt_3$ (0.4 mL) was added bis(triphenylphosphine) palladium (II) chloride (20 mg, 0.028 mmol), copper (1) iodide (2 mg) and 1-octyne (0.25 mL. 1.7 mmol). The reaction mixture was stirred and refluxed under $N_2$ atmosphere for two days and then cooled to room temperature. After washing with aqueous 10% NaOH (1X), the organic layer was dried ($MgSO_4$), concentrated and chromatographed (silica gel; hexane/EtOAc, 10: 1 to 10:2) to afford an oil (255 mg, 79%): $^1H$ NMR ($CDCl_3$, 300 MHz) δ0.88 (t, 3H, J=2.5 Hz), 1.20–1.38 (m, 4H), 1.42 (d, 4H, J=2.5 Hz), 1.44 (s, 9H), 1.90 (m, 1H), 2.00 (m, 1H), 2.40 (t, 2H, J=7.0 Hz), 3.12 (q, 4H, J=7.5 Hz), 3.32–3.44 (m, 2H), 3.90 (br, 1H), 4.08–4.20 (m, 2H), 7.10 (s, 1H), 8.08–8.30 (m, 2H); MS (CI/$NH_3$) m/z 387 (M+H)$^+$.

157b. 5-Octynyl-3-(2-(S)-pyrrolidinylmethoxy)pyridine

The product from step a above (0.25 g, 0.65 mmol) in $CH_2Cl_2$ (3 mL) was cooled to 0° C., TFA (2 mL) was then added carefiully. The reaction mixture was stirred at 0° C.

for 40 min. It was then warmed to room temperature and kept stirring for 30 min. The solution was basified with saturated sodium bicarbonate to pH 9, extracted with $CH_2Cl_2$ (3X). The combined organic layers were dried ($MgSO_4$), concentrated and chromatographed (silica gel; $CH_2Cl_2$/MeOH, 10:1 to 10:1) to afford a light yellow oil (180 mg, 97%): $^1$H NMR (CDCl$_3$, 300 MHz) δ0.90 (t, 3H, J=2.5 Hz), 1.30–1.38 (m, 4H), 1.40–1.50 (m, 2H), 1.52–1.65 (m, 2H), 1.80 (m, 1H), 2.05–2.15 (m, 2H), 2.24 (m, 1H), 2.40 (t, 2H, J=2.5 Hz), 3.18 (t, 2H, J=3.0 Hz), 3.80 (m, 1H), 4.05–4.25 (m, 2H), 7.15 (m, 1H), 8.18 (d, 1H, J=3.0 Hz), 8.23 (d, 1H, J=1.5 Hz); MS (C]7NH$_3$) m/z 287 (M+H)$^+$.

157c. 5-Octynyl-3-(2-(S)-pyrrolidinylmethoxy)pyridine dihydrochloride

To a solution of 5-octynyl-3-(2-(S)-pyrrolidinylmethoxy) pyridine from step b above in Et$_2$O was added hydrogen chloride (1.0 M in Et$_2$O) carefully to afford the tittle compound: $^1$H NMR (D$_2$O) δ0.87 (t, 3H, J=7.0 Hz), 1.32 (t, 4H, J=4.0 Hz), 1.45 (t, 2H, J=7.0 Hz), 1.96 (m, 1H), 2.02–2.20 (m, 2H), 2.29 (m, 1H), 2.49 (t, 2H, J=7.0 Hz), 3.41 (t, 2H, J=7.0 Hz), 4.14 (m, 1H), 4.33 (dd, 1H, J=7.5, 11.0 Hz), 4.54 (dd, 1H, J=3.5, 11.0 Hz), 7.90 (t, 1H, J=1.5 Hz), 8.37 (t, 2H, J=3.0 Hz); MS (CI/NH$_3$) m/z 287 (M+H)$^+$. Anal. Calcd for $C_{18}H_{26}N_2O\cdot1.7$ HCl: C, 62.06; H, 8.01; N, 8.04. Found: C, 62.03; H, 7.99; N, 7.74. $[\alpha]^{25}D$+7.0 (c 0.88, MeOH).

Example 158

5-(3-Aminophenyl)-3-(2-(S)-pyrrolidinylmethoxy) pyridine hydrochlorid 158a. 5-(3-Aminophenyl)-3-(1-BOC-2-(S)-pyrrolidinylmethoxy)pyridine To a mixture of 3-(1-(S)-BOC-pyrrolidinylmethoxy)-5-bromopyridine (0.42 g, 1.16 mmol), tetrakis(triphenylphosphine)palladium(0) (38 mg, 0.032 mmol), aqueous sodium carbonate (2.0 M, 1.5 mL) in toluene (10 mL) was added 3-amninophenylboronic acid (0.36 g, 2.32 mmol). The reaction mixture was stirred and heated at 80° C. for 16 h. Solvent was evaporated. The residue was chromatographed (silica gel; hexane/EtOAC, 10:1 to 1:5) to afford an oil (0.21g, 50%): $^1$H NMR (CDC$_3$, 300 MHz) δ1.46 (s, 9H), 1.90 (m, 1H), 2.02–2.10 (m, 2H), 3.34–3.48 (m, 2H), 3.78–3.82 (m, 2H), 4.08–4.30 (m, 2H), 6.72 (m, 1H), 6.90 (m, 1H), 6.98 (m, 1H), 7.22 (m, 1H), 7.50 (m, 1H), 8.38 (s, 1H), 8.42 (s, 1H); MS (CI/NH$_3$) m/z 370 (M+H)$^+$.

158b. 5-(3-Aminophenyl)-3-(2-(S)-pyrrolidinylmethoxy)pyridine

The product from step a above (0.21 g, 0.56 mmol) in $CH_2Cl_2$ (2 mL) was cooled to 0° C., TFA (1.7 mL) was then added carefully. The reaction mixture was stirred at 0° C. for 40 min. The mixture was then warmed to room temperature and kept stirring for 30 min. After neutralization with saturated sodium bicarbonate, the reaction mixture was extracted with $CH_2Cl_2$ (X3). The combined organic layers were dried (MgSO$_4$), concentrated and chromatographed (silica gel; $CH_2Cl_2$/MeOH/NH$_4$OH, 10:1 to 10:1:0.6) to afford a light yellow oil (110 mg, 73%): $^1$H NMR (CDCl$_3$, 300 MHz) δ1.60 (m, 1H), 1.70–1.90 (m, 2H), 1.98 (m, 1H), 2.95–3.10 (m, 2H), 3.58 (m, 1H), 3.94–4.05 (m, 2H), 6.72 (m, 1H), 6.88 (m, 1H), 6.96 (m, 1H), 7.25 (m, 1H), 7.36 (m, 1H), 8.28 (d, 1H, J=3.0 Hz), 8.42 (d, 1H, J=1.5 Hz); MS (CI/NH$_3$) m/z 270 (M+H)$^+$.

158c. 5-(3-Aminophenyl)-3-(2-(S)-pyrrolidinylmethoxy) pyridine hydrochloride

To a solution of compound obtained from step b above in Et$_2$O was added hydrogen chloride (1.0 M in Et$_2$O) carefully to afford the tittle compound: mp 68–70° C.; $^1$H NMR (CD$_3$OD) δ1.82 (m, 1H), 1.96–2.04 (m, 2H), 2.18 (m, 1H), 3.14–3.24 (m, 2H), 3.85 (m, 1H), 4.16 (dd, 1H, J=2.5, 8.0 Hz), 4.33 (dd, 1H, J=4.0, 10.0 Hz), 6.78 (m, 1H), 6.96 (m, 1H), 6.98 (t, 1H, J=2.0 Hz), 7.21 (t, 1H, J=8.0 Hz), 7.61 (dd, 1H, J=2.0, 3.0 Hz), 8.23 (d, 1H, J=3.0 Hz), 8.39 (d, 1H, J=2.0 Hz); MS (CI/NH$_3$) m/z 270 (M+H)$^+$. Anal. Calcd for $C_{16}H_{19}N_3O\cdot1.1$ HCl·0.3 MeOH: C, 61.36; H, 6.73; N, 13.17. Found: C, 61.62; H, 6.50; N, 12.84. $[\alpha]^{25}D$ +10.4 (c 0.90, MeOH).

Example 159

3-(2-(S)-Azetidinylmethoxy)-5-(N-methoxycarbonylamino)methylpyridine dihydrochloride 159a. 3-(1-BOC-2-(S)-azetidinylmethoxy)-5-(N-methoxycarbonylamino)methylpyridine Following the general procedure of Example 92c, substituting 5-aminomethyl-3-(1-BOC-2-(S)-azetidinylmethoxy) pyridine from Example 205b for 5-aminomethyl-3-(1-BOC-2-(S)-azetidinylmethoxy)-6-chloropyridine and methyl chloroformate for benzoyl chloride therein, the title compound (0.23 g, 94%) was prepared: $^1$H NMR (CDCl$_3$, 300 MHz) δ1.42 (s, 9H), 2.20–2.41 (m, 2H), 3.72 (s, 3H), 3.87 (t, J=7.5 Hz, 2H), 4.15 (dd, J=2.5, 10.0 Hz, 1H), 4.33–4.39 (m, 3H), 4.55 (m, 1H), 7.10 (s, 1H), 8.17 (s, 1H), 8.27 (d, J=1.5 Hz, 1H); MS (CI/NH$_3$) m/z 352 (M+H)$^+$.

159b. 3-(2-(S)-Azetidinylmethoxy)-5-(N-methoxycarbonylamino)methylpyridine dihydrochloride The product of step 159a (0.23 g, 0.70 mmol) was deprotected and isolated as the free base in 99% yield according to the procedure of Example 20b, followed by conversion to the dihydrochloride with excess HCl/Et$_2$O. $[\alpha]D^{23}$ +12.46 (c 0.1, MeOH); $^1$H NMR (D$_2$O, 300 MHz) δ2.65–2.75 (m, 2H), 3.66 (s, 3H), 4.08–4.19 (m, 2H), 4.43 (s, 2H), 4.53–4.69 (m, 2H), 4.90 (m, 1H), 8.22 (s, 1H), 8.44 (s, 1H), 8.63 (d, J=3.0 Hz, 1H); MS (CI/NH$_3$) m/z 252 (M+H)+. Anal. Calcd for $C_{12}H_{17}N_3O\cdot2.5$ HCl·1.5 $H_2O\cdot0.4$ Et$_2$O: C, 40.93; H, 6.69; N, 10.53. Found: C, 40.96; H, 6.63; N, 10.46.

Example 160

5-(5,5-Dimethyl-1,3-hexadienyl)3-(2-(S)-pyrrolidinylmethoxy)pyridine dihydrochloride 160a. 3-(1-BOC-2-(S)-pyrrolidinylmethoxy)-5-(5,5-Dimethyl-113-hexadienyl)pyridine To a solution of 3-(1-BOC-2-(S)-pyrrolidinylmethoxy)-5-bromopyridine (500 mg, 1.40 mmol) in acetonitrile (15 mL) and NEt$_3$ (3.2 mL) was added 5,5-dimethyl-hexadiene (0.5 g, 4.54 mmol), palladium acetate (35 mg, 0.16 mmol) and tri-o-tolylphosphine (175 mg). The reaction mixture was heated in a sealed tube at 100° C. for 16 h. After cooling to room temperature, saturated NaHCO$_3$ was added. The mixture was extracted with EtOAc (2X). The combined organic layers were dried (MgSO$_4$), concentrated and chromatographed (silica gel; hexane/EtOAc, 5:1 to 2:1) to afford an oil (403 mg, 75%): $^1$H NMR (CDCl$_3$, 300 Hz) δ 1.48 (s, 9H), 1.82–1.92 (m, 2H), 2.00–2.08 (m, 2H), 3.30–3.50 (m, 2H), 3.90 (br, 1H), 4.08–4.26 (m, 2H), 5.93 (d, 1H, J=15.5 Hz), 6.15 (dd, 1H, J=10.0, 15.0 Hz), 6.42 (d, 1H, J=16.0 Hz), 6.90 (m, 1H), 8.12 (s, 2H), 8.20 (s, 1H); MS (CI/NH$_3$) m/z 387 (M+H)$^+$.

160b. 5-(5,5-Dimethyl-1,3-hexadienyl)-3-(2-(S)-pyrrolidinylmethoxy)pyridine

The product from step a above (0.39 g, 1.02 mmol) in $CH_2Cl_2$ (3 mL) was cooled to 0° C. and TFA (3 mL) was then added carefully. The reaction mixture was stirred at 0° C. for 40 min. The solution was then warmed to room temperature and kept stirring for 30 min. After neutralization with saturated sodium bicarbonate, the reaction mixture was extracted with $CH_2Cl_2$ (3X). The combined organic layers were dried ($MgSO_4$), concentrated and chromatographed (silica gel; $CH_2Cl_2$/MeOH, 10:1 to 10:1) to afford a light yellow oil (290 mg, 100%): $^1$H NMR ($CDCl_3$, 300 MHz) δ 1.90 (m, 1H), 1.98–2.10 (m, 2H), 2.16 (m, 1H), 3.20–3.30 (m, 2H), 3.88 (m, 1H), 4.16–4.20 (m, 2H), 5.92 (d, 1H, J=16.0 Hz), 6.12 (dd, 1H, J=10.0, 15.0 Hz), 6.35 (d, 1H, J=16.0 Hz), 6.86 (dd, 1H, J=10, 16.0 Hz), 7.18 (m, 1H), 8.08 (m, 1H, J=2.5 Hz), 8.18 (d, 1H, J=1.0 Hz); MS ($CI/NH_3$) m/z 287 (M+H)$^+$.

160c. 3-(2-(S)-pyrrolidinylmethoxy)-5-(5,5-dimethyl-hexadienyl)pyridine dihydrochloride To a solution of 5-(5,5-dimethyl-hexadienyl)-3-(2-(S)-pyrrolidinyl-methoxy)pyridine from step b above in $Et_2O$ was added hydrogen chloride (1.0 M in $Et_2O$) carefully to afford the tittle compound: mp 92–94° C.; $^1$H NMR ($D_2O$) δ 1.95 (m, 1H), 2.04–2.20 (m, 2H), 2.30 (m, 1H), 3.43 (t, 2H, J=7.0 Hz), 4.17 (m, 1H), 4.38 (dd, 1H, J=7.5, 11.0 Hz), 4.59 (dd, 1H, J=3.5, 10.5 Hz), 6.23 (d, 1H, J=15.5 Hz), 6.35 (dd, 1H, J=10.0, 15.5 Hz), 6.58 (d, 1H, J=16.0 Hz), 7.14 (dd, 1H, J=16.0 Hz), 8.06 (t, 1H, J=2.5 Hz), 8.28 (d, 1H, J=2.5 Hz), 8.41 (s, 1H); MS ($CI/NH_3$) m/z 287 (M+H)$^+$. Anal. Calcd for $C_{18}H_{26}N_2O.2.7$ HCl: C, 56.18; H, 7.52; N, 7.28. Found: C, 56.12; H, 7.47; N, 7.14. $[\alpha]^{25}_D$ +6.98 (c 0.94, MeOH).

Example 161

5-Ethenyl-3-(1-methyl-2-(S)-pyrrolidinylmethoxy) pyridine dihydrochloride 161a. 3-(1-BOC-2-(S)-pyrrolidinylmethoxy)-5-ethenylpyridine To a mixture of 3-(1-(S)-BOC-azetidinylmethoxy)-5-bromopyridine (1.37 g, 3.99 mmol), tetrakis (triphenylphosphine)palladium(0) (140 mg, 0.2 mmol) in toluene tributyl(vinyl)tin (1.4 mL, 4.8 mmol) was added. The reaction mixture was stirred and heated at 90° C. for 3 h. Solvent was evaporated. The residue was chromatographed (silica gel; hexane/EtOAC, 10:1 to 1:1) to afford an oil (1.1 g, 92%): $^1$H NMR ($CDCl_3$, 300 MHz) δ 1.42 (s, 9H), 2.26–2.42 (m, 2H), 3.88–3.92 (m, 2H), 4.10–4.38 (m, 2H), 4.35 (m, 1H), 4.52 (m, 1H), 5.38 (d, 1H, J=11.0 Hz), 5.83 (d, 1H, J=18.0 Hz), 6.70 (dd, 1H, J=11.0, 18.0 Hz), 7.28 (m, 1H), 8.22 (d, 1H, J=1.0 Hz); MS ($CI/NH_3$) m/z 291 (M+H)$^+$.

161b. 5-Ethenyl-3-(1-methyl-2-(S)-pyrrolidinylmethoxy) pyridine

The product from step a above (294 mg, 1.0 mmol) was added formic acid (88%, 3 mL) and formaldehyde (37%, 6 mL). The reaction mixture was stirred and heated at 70° C. for 16 h. After neutralization with aqueous 10% NaOH, the reaction mixture was extracted with $CH_2Cl_2$ (3X). The combined organic layer was dried ($MgSO_4$), concentrated and chromatographed (silica gel; $CH_2Cl_2$/MeOH, 100:2 to 10:1) to afford an oil (62 mg, 30%): $^1$H NMR ($CDCl_3$, 300 MHz) δ 2.06–2.14 (m, 2H), 2.42 (s, 3H), 2.88 (m, 1H), 3.36–3.50 (m, 2H), 4.04 (d, 2H, J=5.0 Hz), 5.38 (d, 1H, J=11.0 Hz), 5.80 (d, 1H, J=18.0 Hz), 6.68 (dd, 1H, J=11.0, 18.0 Hz), 7.25 (m, 1H), 8.20–8.24 (m, 2H); MS (Cl/NH$_3$) m/z 205 (M+H)$^+$.

161c. 5-Ethenyl-3-(1-methyl-2-(S)-pyrrolidinylmethoxy) pyridine dihydrochloride

To a solution of 5-ethenyl-3-(1-methy-2-(S)-pyrrolidinyl-methoxy)pyridine from step b above in $Et_2O$ was added hydrogen chloride (1.0 M in $Et_2O$) carefully to afford the tittle compound: mp 118–120° C.; $^1$H NMR ($D_2O$) δ 2.56–2.76 (m, 3H), 3.00 (s, 3H), 4.03 (q, 1H, J=9.5 Hz), 4.29 (m, 1H), 4.52 (dd, 1H, J=5.5, 12.0 Hz), 4.60 (dd, 1H, J=3.0, 11.5 Hz), 5.65 (d, 1H, J=11.0 Hz), 6.09 (d, 1H, J=17.5 Hz), 6.84 (dd, 1H, J=11.0, 17.5 Hz), 8.02 (t, 1H, J=2.0 Hz), 8.36 (d, 1H, J=3.0 Hz), 8.43 (d, 1H, J=1.0 Hz); MS ($CI/NH_3$) m/z 205 (N+H)$^+$. Anal. Calcd for $C_{12}H_{16}N_2O.1.9$ HCl: C, 50.69; H, 6.77; N, 9.85. Found: C, 50.79; H, 7.05; N, 9.48. $[\alpha]^{25}_D$ −20.43 (c 0.7, MeOH).

Example 162

3-(2-(S)-Azetidinylmethoxy)-5-ethenylpyridine dihydrochloride 162a 3-(2-(S)-Azetidinylmethoxy)-5-ethenylpyridine The product from Example 161a above (191 mg, 0.66 mmol) in $CH_2Cl_2$ (2 mL) was cooled to 0° C. and then TFA (1.8 mL) was added carefully. The reaction mixture was stirred at 0° C. for 40 min. The solution was warmed to room temperature and kept stirring for 30 min. After neutralization with aqueous 10% NaOH, the reaction mixture was extracted with $CH_2Cl_2$ (3X). The combined organic layers were dried ($MgSO_4$), concentrated and chromatographed (silica gel; $CH_2Cl_2$/MeOH; 10:0.5 to 10:1) to afford a light yellow oil (101 mg, 81%): $^1$H NMR ($CDCl_3$, 300 MHz) δ 2.40–2.60 (m, 2H), 3.72 (m, 1H), 3.90 (m, 1H), 4.12–4.24 (m, 2H), 4.55 (m, 1H), 5.40 (d, 1H, J=11.0 Hz), 5.82 (d, 1H, J=17.5 Hz), 6.68 (dd, 1H, J=11.0, 17.5 Hz), 7.26 (m, 1H), 8.20 (d, 1H, J=3.0 Hz), 8.24 (d, 1H, J=1.0 Hz); MS ($CI/NH_3$) m/z 191 (M+H)$^+$.

162b. 3-(2-(S)-Azetidinylmethoxy)-5-ethenylpyridine dihydrochloride

To a solution of 5-ethenyl-3-(2-(S)-pyrrolidinylmethoxy) pyridine in $Et_2O$ was added hydrogen chloride (1.0 M in $Et_2O$) carefully to afford the tittle compound: mp 88–90° C. $^1$H NMR (D2O) δ 2.64–2.78 (m, 2H), 4.04–4.22 (m, 2H), 4.50 (d, 1H, J=4.0 Hz), 4.80 (m, 1H), 4.96 (m, 1H), 5.58 (dd, 1H, J=11.0 Hz), 6.04 (d, 1H, J=18.0 Hz), 6.83 (dd, 1H, J=11.0, 18.0 Hz), 7.85 (t, 1H, J=2.0 Hz), 8.31 (br s, 1H), 8.36 (br s, 1H); MS ($CI/NH_3$) m/z 191 (M+H)$^+$. Anal. Calcd for $C_{11}H_{14}N_2O.1.8$ HCl: C, 51.64; H, 6.22; N, 10.95. Found: C, 51.59; H, 5.92; N, 10.75. $[\alpha]^{25}_D$ +2.58 (c 0.62, MeOH).

Example 163

3-(2-(S)-Azetidinylmethoxy)-5-(5,5-dimethyl-1,3-hexadiene)pyridine dihydrochloride 163a. 3-(1-BOC-2-(S)-azetidinylmethoxy)-5-(5,5-dimethyl-1,3-hexadiene)pyridine To a solution of 3-(1-BOC-2-(S)-azetidinylmethoxy)-5-bromopyridine (600 mg, 1.75 mmol) in acetonitrile (20 mL) and $NEt_3$ (4 mL) was added 5,5-dimethyl-1,3-hexadiene (0.6 g, 5.45 mmol), palladium acetate (44 mg, 0.20 mmol) and tri-o-tolylphosphine (219 mg). The reaction mixture was heated in a sealed tube at 100° C. for 16 h. After cooling to room temperature, saturated $NaHCO_3$ was added. The mixture was extracted with EtOAc (2X). The combined organic layers were dried ($MgSO_4$), concentrated and chromatographed (silica gel: hexane/EtOAc, 5:1 to 2:1) to afford an oil (558 mg, 86%): $^1$H NMR ($CDCl_3$, 300 Hz) δ 1.08 (s, 9H), 1.42 (s, 9H), 2.24–2.40 (m, 2H), 3.86–3.92 (m, 2H), 4.14 (m, 1H), 4.34 (br s, 1H), 4.52 (m, 1H), 5.92 (d, 1H, J=15.5 Hz), 6.15 (dd, 1H, J=10.0, 15.5 Hz), 6.42 (d, 1H, J=16.0 Hz), 6.90 (dd, 1H, J=10.0, 15.5 Hz), 7.25 (s, 1H), 8.16 (d, 1H, J=3.0 Hz), 8.20 (s, 1H); MS ($CI/NH_3$) m/z 373 (M+H)$^+$.

163b. 3-(2-(S)-Azetidinyl-methoxy-5-(5,5-dimethyl-1,3-hexadiene)pyridine

The product from step a above (0.56 g, 1.5 mmol) in $CH_2Cl_2$ (6 mL) was cooled to 0° C., and TFA (5 mL) was then added carefully. The reaction mixture was stirred at 0° C. for 40 min. The mixture was then warmed to room temperature and kept stirring for 30 min. After neutralization with saturated aqueous sodium bicarbonate solution, the reaction mixture was extracted with $CH_2Cl_2$ (3X). The combined organic layers were dried ($MgSO_4$), concentrated and chromatographed (silica gel; $CH_2Cl_2$/MeOH, 10:0.5 to 10:1) to afford a light yellow oil (301 mg, 74%): $^1$H NMR ($CDCl_3$, 300 MHz) δ 1.08 (s, 9H), 2.20–2.34 (m, 2H), 3.48 (m, 1H), 3.72 (m, 1H), 4.00–4.10 (m, 2H), 4.30 (m, 1H), 5.92 (d, 1H, J=15.5 Hz), 6.12 (dd, 1H, J=10.0, 15.5 Hz), 6.42 (d, 1H, J=16.0 Hz), 6.88 (dd, 1H, J=10.0, 16.0 Hz), 7.20 (m, 1H), 8.12 (m, 1H, J=2.5 Hz), 8.20 (d, 1H, J=1.0 Hz); MS ($CI/NH_3$) m/z 273 (M+H)$^+$.

163c. 3-(2-(S)-Azetidinylmethoxy)-5-(5,5-dimethyl-1,3-hexadiene)pyridine dihydrochloride To a solution of 5-(5,5-dimethyl-1,3-hexadiene)-3-(2-(S)-pyrrolidinylmethoxy)pyridine from step b above in $Et_2O$ was added hydrogen chloride (1.0 M in $Et_2O$) carefully to afford the tittle compound: mp 142–144 ° C; $^1$H NMR ($D_2O$) δ 2.73 (q, 2H, J=8.5 Hz), 4.04–4.22 (m, 2H), 4.58 (d, 2H, J=4.0 Hz), 5.00 (m, 1H), 6.23 (d, 1H, J=15.5 Hz), 6.36 (dd, 1H, J=10.0, 15.5 Hz), 6.60 (d, 1H, J=16.0 Hz), 7.17 (dd, 1H, J=10.0, 15.5 Hz), 8.18 (t, 1H, J=2.0 Hz), 8.36 (d, 1H, J=2.5 Hz), 8.46 (d, 1H, J=1.5 Hz); MS ($CI/NH_3$) m/z 273 (M+H)$^+$. Anal. Calcd for $C_{17}H_{24}N_2O·3$ HCl: C, 53.48; H, 7.13; N, 7.34. Found: C, 53.57; H, 7.40; N, 7.31. $[\alpha]^{25}_D$+6.85(c 1.27, MeOH).

Example 164

5-Ethenyl-3-(2-(S)-pyrrolidinylmethoxy)pyridine dihydrochloride 164a. 3-(1-BOC-2-(S)-pyrrolidinylmethoxy)-5-ethenylpyridine To a mixture of 3-(1-(S)-BOC-azetidinylmethoxy)-5-bromopyridine (1.00 g, 2.80 mmol), tetrakis (triphenylphosphine)palladium(0) (98 mg, 0.14 mmol) in toluene, tributyl(vinyl)tin (0.98 mL, 3.36 mmol) was added. The reaction mixture was stirred and heated at 90° C. for 5 h. Solvent was evaporated. The residue was chromatographed (silica gel; hexane/EtOAC, 10:1 to 2:1) to afford an oil (605 mg, 71%): $^1$H NMR ($CDCl_3$, 300 MHz) δ 1.48 (s, 9H), 1.86–1.90 (m 2H), 2.00–2.10 (m, 2H), 3.40 (m, 1H), 3.94 (m, 1H), 4.10–4.24 (m, 2H), 5.38 (d, 1H, J=11.0 Hz), 5.83 (d, 1H, J=17.5 Hz), 6.70 (dd, 1H, J=11.0, 17.5 Hz), 7.38 (m, 1H), 8.20 (d, 1H, J=2.5 Hz); MS ($CI/NH_3$) m/z 305 (M+H)$^+$.

164b. 5-Ethenyl-3-(2-(S)-pyrrolidinylmethoxy)pyridine

The product from step a above (312 mg, 0.91 mmol) in $CH_2Cl_2$ (3 mL) was cooled to 0° C., TFA (3 mL) was then added carefully. The reaction mixture was stirred at 0° C. for 40 min. The mixture was then warmed to room temperature and kept stirring for 30 min. After neutralization with aqueous 10% NaOH, the reaction mixture was extracted with $CH_2Cl_2$ (3X). The combined organic layers were dried ($MgSO_4$), concentrated and chromatographed (silica gel; $CH_2Cl_2$/MeOH/$NH_4OH$, 10:0.3:0 to 10:1:0.04) to afford a light yellow oil (126 mg, 57%): $^1$H NMR (CDCl3, 300 MHz) δ 1.58 (m 1H), 1.72–1.90 (m, 2H), 1.95 (m, 1H), 3.00 (m, 2H), 3.54 (m, 1H), 3.88–4.02 (m, 2H), 5.38 (d, 1H, J=11.0 Hz), 5.82 (d, 1H, J=17.5 Hz), 6.68 (dd, 1H, J=11.0, 17.5 Hz), 7.22 (m, 1H), 8.20 (m, 1H); MS ($CI/NH_3$) m/z 205 (M+H)$^+$.

164c. 5-Ethenyl-3-(2-(S)-pyrrolidinylmethoxy)pyridine dihydrochloride

To a solution of 5-ethenyl-3-(2-(S)-pyrrolidinylmethoxy) pyridine from step b above in $Et_2O$ was added hydrogen chloride (1.0 M in $Et_2O$) carefully to afford the tittle compound: mp 97° C. (dec). $^1$H NMR ($D_2O$) δ 1.97 (m, 1H), 2.04–2.20 (m, 2H), 2.30 (m, 1H), 3.42 (t, 2H, J=7.0 Hz), 4.17 (m, 1H), 4.40 (dd, 1H, J=7.5, 10.5 Hz), 4.61 (dd, 1H, J=3.5, 10.5 Hz), 5.70 (d, 1H, J=11.0 Hz), 6.13 (d, 1H, J=17.5 Hz), 6.85 (dd, 1H, J=11.0, 17.5 Hz), 8.15 (t, 1H, J=3.0 Hz), 8.39 (d, 1H, J=2.5Hz), 8.48 (s, 1H). MS ($CI/NH_3$) m/z 205 (M+H)$^+$. Anal. Calcd for $C_{12}H_{16}N_2O·2$ HCl: C, 52.00; H, 6.55; N, 10.11. Found: C, 52.22; H, 6.42; N, 9.87. $[\alpha]^{25}_D$ +22.5 (c 0.68, MeOH).

Example 165

3-(2-(S)-Azetidinylmethoxy)-6-chloro-5-ethenylpyridine dihydrochloride 165a. 3-(1-BOC-2-(S)-azetidinylmethoxy)-6-chloro-5-ethenylpyridine To a mixture of 3-(1-(S)-BOC-azetidinylmethoxy)-5-bromo-6-chloropyridine (1.00 mg, 2.65 mmol), tetrakis (triphenylphosphine)palladium(0) (93 mg, 0.13 mmol) in toluene, was added tributyl(vinyl)tin (0.93 mL, 3.19 mmol). The reaction mixture was stirred and heated at 90° C. for 16 h. Solvent was evaporated. The residue was chromatographed (silica gel; $CH_2Cl_2$/MeOH, 10:1 to 2:1) to afford an oil (720 mg, 84%): $^1$H NMR ($CDCl_3$, 300 MHz) δ 1.42 (s, 9H), 2.22–2.40 (m, 2H), 3.88 (t, 2H, J=7.5 Hz), 4.15(dd, 1H, J=3.0, 10.0 Hz), 4.28–4.40 (m, 1H), 4.48–4.56 (m, 1H), 5.50 (d, 1H, J=10.5 Hz), 5.80 (d, 1H, J=17.0 Hz), 6.97 (dd, 1H, J=11.0, 17.5 Hz), 7.44 (d, 1H, J=3.0 Hz), 8.02 (d, 1H, J=3.0 Hz); MS ($CI/NH_3$) m/z 325 (M+H)$^+$.

165b. 3-(2-(S)-Azetidinylmethoxy)-6-chloro-5-ethenylpyridine

The product from step a above (317 mg, 0.99 mmol) in $CH_2Cl_2$ (3 mL) was cooled to 0° C., TFA (3 mL) was then added carefully. The reaction mixture was stirred at 0° C. for 40 min. The solution was warmed to room temperature and kept stirring for 30 min. After neutralization with aqueous 10% NaOH, the reaction mixture was extracted with $CH_2Cl_2$ (3X). The combined organic layers were dried ($MgSO_4$), concentrated and chromatographed (silica gel; $CH_2Cl_2$/MeOH/$NH_4OH$, 10:0.3:0 to 10:1:0.04) to afford a light yellow oil (125 mg, 75%): $^1$H NMR ($CDCl_3$, 300 MHz) δ 2.24–2.34 (m, 2H), 3.60 (m 1H), 3.82 (m 1H ), 4.08–4.20 (m, 2H), 4.42 (m, 1H), 5.48 (d, 1H, J=10.5 Hz), 5.78 (d, 1H, J=17.0 Hz), 6.97 (dd, 1H, J=11.0, 17.5 Hz), 7.42 (d, 1H, J=3.0 Hz), 8.00 (d, 1H, J=3.0 Hz); MS ($CI/NH_3$) m/z 225 (M+H)$^+$.

165c. 3-(2-(S)-Azetidinylmethoxy)-6-chloro-5-ethenylpyridine dihydrochloride

To a solution of 3-(2-(S)-azetidinylmethoxy)-6-chloro-5-ethenylpyridine from step b above in $Et_2O$ was added hydrogen chloride (1.0 M in $Et_2O$) carefully to afford the tittle compound: mp 121° C. (dec); $^1$H NMR ($D_2O$) δ 2.70 (q, 2H, J=8.5 Hz), 4.03–4.21 (m, 2H), 4.45 (d, 2H, J=4.0 Hz), 4.96 (m , 1H), 5.60 (d, 1H, J=11.0 Hz), 5.94 (d, 1H, J=17.0 Hz), 7.01 (dd, 1H, J=11.0, 17.5 Hz), 7.74 (d, 1H, J=3.0 Hz), 8.05 (d, 1H, J=3.0 Hz); MS ($CI/NH_3$) m/z 225 (M+H)$^+$, 242 (M+$NH_4$)$^+$. Anal. Calcd for $C_{11}H_{13}ClN_2O·1.1$ HCl: C, 49.90; H, 5.37; N, 10.58. Found: C, 49.84; H, 5.25; N, 10.27. $[\alpha]^{25}_D$ –9.9 (c 2.0, MeOH).

Example 166

5-(5,5-Dimethyl-1,3-hexadiene)-3-(1-methyl-2-(S)-azetidinylmethoxy)pvridine dihydrochloride 166a. 5-(5,5-Dimethyl-1,3-hexadiene)-3-(1 -methyl-2-(S)-azetidinyl-methoxy)pyridine 3-(1-BOC-2-(S)-azetidinylmethoxy)-5-(5,5-dimethyl-1,3-hexadiene)pyridine (0.44 g, 1.52 mmol) in formic acid (88%, 3.5 mL) was added formaldehyde (37%, 9 mL). The reaction mixture was stirred at 70° C. for 6 h. The mixture was cooled and basified with aqueous 10% NaOH to pH 11, the reaction mixture was extracted with $CH_2Cl_2$ (3X). The combined organic layers were dried ($MgSO_4$), concentrated and chromatographed (silica gel; $CH_2Cl_2$/MeOH, 10:0.5 to 10:1 to afford a light yellow oil (312 mg, 73%): $^1$H NMR ($CDCl_3$, 300 MHz) δ 1.08 (s, 9H), 2.04–2.16 (m, 2H), 3.40 (s, 3H), 3.84 (m, 1H), 3.36–3.50 (m, 2H), 4.03 (d, 1H, J=5.0 Hz), 5.92 (d, 1H, J=15.5 Hz), 6.16 (dd, 1H, J=10.0, 16.0 Hz), 6.42 (d, 1H, J=16.0 Hz), 6.81 (dd, 1H, J=10.0, 16.0 Hz), 7.20 (m, 1H), 8.13 (m, 1H, J=2.5 Hz), 8.19 (d, 1H, J=2.0 Hz); MS (CI/NH_3) m/z 287 (M+H)$^+$.

166b. 5-(5,5-Dimethyl-1,3-hexadiene)-3-(1-methyl-2-(S)-azetidinylmethoxy)pyridine dihydrochloride To a solution of compound from step b above in $Et_2O$ was added hydrogen chloride (1.0 M in $Et_2O$) carefully to afford the tittle compound: mp 143–145° C.; $^1$H NMR ($D_2O$) δ 2.60–2.80 (m, 2H), 3.02 (s, 3H), 4.06 (m, 1H), 4.31 (m, 1H), 4.48–4.60 (m, 2H), 4.86 (m, 1H), 6.18 (d, 1H, J=15.5 Hz), 6.34 (dd, 1H, J=10.0, 16.5 Hz), 6.57 (d, 1H, J=16.0 Hz), 7.09 (dd, 1H, J=10.0, 15.5 Hz), 7.86 (br, s, 1H), 8.27 (br, s, 1H), 8.35 (br, s, 1H); MS (CI/NH_3) m/z 287 (M+H)$^+$. Anal. Calcd for $C_{18}H_{26}N_2O.2.2$ HCl: C, 58.97; H, 7.75; N, 7.64. Found: C, 59.10; H, 7.63; N, 7.66. $[\alpha]^{25}_D$ –19.9 (c 0.98, MeOH).

Example 167

6-Chloro-5-ethenyl-3-(2-(R)-pyrrolidinylmethoxy)pyridine hydrochloride 167a. 3-(1-BOC-2-(R)-pyrrolidinylmethoxy)-6-chloro-5-ethenylpyridine To a mixture of 3-(1-(R)-BOC-pyrrolidinylmethoxy)-5-bromo-6-chloropyridine (1.00 g, 2.55 mmol), tetrakis(triphenylphosphine)palladium(0) (90 mg, 0.12 mmol) in toluene, tributyl(vinyl)tin (0.89 mL, 3.06 mmol) was added. The reaction mixture was stirred and heated at 90° C. for 16 h. Solvent was evaporated. The residue was chromatographed (silica gel; $CH_2Cl_2$/MeOH, 10:0.1 to 10:0.3) to afford an oil (610 mg, 71%): $^1$H NMR ($CDCl_3$, 300 MHz) δ 1.42 (s, 9H), 1.84–1.98 (m, 2H), 2.98–2.08 (m, 2H), 3.28–3.44 (m, 2H), 3.94 (m 1H), 4.04–4.24 (m, 2H), 5.50 (d, 1H, J=11.0 Hz), 5.80 (d, 1H, J=11.0 Hz), 6.97 (dd, 1H, J=11.0, 17.0 Hz), 7.38 (m, 1H), 8.0 (d, 1H, J=3.0 Hz); MS (CI/NH_3) m/z 339 (M+H)$^+$.

167b. 6-Chloro-5-ethenyl-3-(2-(R)-pyrrolidinylmethoxy)pyridine hydrochloride

The product from step a above was treated with 4.0 M HCl (in 1.4-dioxane) to afford the title compound: mp 182–184° C.; $^1$H NMR ($D_2O$) δ 1.99 (m, 1H), 2.04–2.44 (m, 2H), 2.31 (m, 1H), 3.44 (t, 2H, J=7.5 Hz), 4.14 (m, 1H), 4.28 (dd, 1H, J=7.5, 10.5 Hz), 4.50 (dd, 1H, J=3.5, 10.5 Hz), 5.61 (d, 1H, J=11.0 Hz), 5.94 (d, 1H, J=17.5 Hz), 7.00 (dd, 1H, J=11.0, 17.5 Hz), 7.70 (d, 1H, J=3.0 Hz), 8.01 (d, 1H, J=3.0 Hz): MS (CI/NH_3) m/z 239 (M+H)$^+$, 256 (M+NH_4)$^+$. Anal. Calcd for $C_{12}H_{15}ClN_2O.1.1$ HCl: C, 51.69; H, 5.82; N, 10.04. Found: C, 51.80; H, 5.52; N, 9.64. $[\alpha]^{25}_D$ –14.3 (c 0.52, MeOH).

Example 168

6-Chloro-5-ethenyl-3-(1-methyl-2-(R)-pyrrolidinylmethoxy)pyridine hydrochloride 168a. 6-Chloro-5-ethenyl-3-(1-methyl-2-(R)-pyrrolidinylmethoxy)pyridine To the product from 167a (328 mg, 0.97 mmol) was added formic acid (88%, 3 mL) and formaldehyde (37%, 6 mL). The mixture was stirred and heated at 70° C. for 6 h. After cooling to room temperature, the mixture was basified with aqueous 10% NaOH. The solution was then extracted with $CH_2Cl_2$ (3X), the combined organic layers were dried ($MgSO_4$), concentrated and chromatographed (silica gel; $CH_2Cl_2$, 10:0.3 to 10:1) to afford an oil (130 mg, 53%): $^1$H NMR ($CDCl_3$, 300 MHz) δ 1.70–1.90 (m, 3H), 2.02 (m, 1H), 2.32 (m, 1H), 2.48 (s, 3H), 2.66 (m, 1H), 3.12 (m, 1H), 3.98 (m, 2H), 5.48 (d, 1H, J=10.5 Hz), 5.76 (d, 1H, J=17.5 Hz), 6.98 (dd, 1H, J=11.0, 17.5 Hz), 7.40 (d, 1H, J=3.0 Hz), 8.00 (d, 1H, J=3.0 Hz); MS (CI/NH_3) m/z 253 (M+H)$^+$.

168b. 6-Chloro-5-ethenyl-3-(1-methyl-2-(R)-pyrrolidinylmethoxy)pyridine

To a solution of 6-chloro-5-ethenyl-3-(2-(R)-pyrrolidinylmethoxy)pyridine in $Et_2O$ was added hydrogen chloride (1.0 M in $Et_2O$) carefully to afford the tittle compound: mp 173–175° C.; $^1$H NMR ($D_2O$) δ 2.04–2.18 (m, 2H), 2.23 (m, 1H), 2.40 (m, 1H), 3.04 (s, 3H), 3.29 (m, 1H), 3.73 (m, 1H), 3.95 (m, 1H), 4.37 (dd, 1H, J=6.0, 11.0 Hz), 4.53 (dd, 1H, J=3.0, 11.0 Hz), 5.61 (d, 1H, J=11.0 Hz), 5.94 (d, 1H, J=17.5 Hz), 7.02 (dd, 1H, J=11.0, 17.5 Hz), 7.73 (d, 1H, J=3.0 Hz), 8.04 (d, 1H, J=3.0 Hz); MS (CI/NH_3) m/z 253 (M+H)$^+$. Anal. Calcd for $C_{13}H_{17}ClN_2O.1.1$ HCl: C, 53.32; H, 6.23; N, 9.57. Found: C, 53.51; H, 6.48; N, 9.20. $[\alpha]^{25}_D$ +7.4 (c 0.66, MeOH).

Example 169

6-Chloro-5-(5-pyrimidinyl)-3-(2-(S)-pyrrolidinylmethoxy)pyridine hydrochloride 169a. 5-Tributyl(pyrimidinyl)tin 5-pyrimidine (6.36 g, 40 mmol) in toluene (120 mL) was added tetrekis(triphenylphosphine) palladium (444 mg, 1%) and bis(tributyl)tin (26.2 mL, 52 mmol). the mixture was stirred and heated under reflux for 16 h. Solvent was evaporated and the residue was chromatographed (silica gel; hexane/EtOAc, 10:1 to 2:1) to afford a yellow oil (3.36 g, 23%): $^1$H NMR ($CDCl_3$, 300 MHz) δ 0.90 (t, 9H, J=7.5 Hz), 1.16 (t, 6H, J=7.5 Hz), 1.28–1.40 (m, 6H), 1.50–1.60 (m, 6H), 7.26 (s, 1H), 8.69 (s, 1H); MS (CI/NH_3) m/z 371 (M+H)$^+$.

169b. 3-(1-BOC-2-(S)-pyrrolidinylmethoxy)-6-chloro-5-(5-pyrimidinyl)pyridine 51560-212

To the solution of 3-(1-BOC-2-(S)-pyrrolidinylmethoxy)-5-bromo-6-chloropyridine (400 mg, 1.1 mmol) in toluene (10 mL) was added tetrekis(triphenylphosphine)palladium (40 mg, 1%) and tributyl(pyrimidinyl)tin (0.51 g, 1.38 mmol). The mixture was stirred and heated under reflux for 16 h. Solvent was evaporated and the residue was chromatographed (silica gel; hexane/EtOAc, 10:1 to 2:1) to afford an oil (500 mg, 100%): $^1$H NMR ($CDCl_3$, 300 MHz) δ 1.40 (s, 9H), 1.85–2.00 (m, 2H), 2.00–2.10 (m, 2H), 3.34–3.44 (m, 1H), 4.00 (m 1H), 4.14 (m, 1H), 4.24 (m, H), 7.40 (s, 1H), 8.20 (d, 1H, J=3.0 Hz), 8.88 (s, 2H), 9.28 (s, 1H); MS (CI/NH_3) m/z 391 (M+H)$^+$.

169c. 6-Chloro-5-(5-pyrimidinyl)-3-(2-(S)-pyrrolidinylmethoxy)pyridine hydrochloride The product from step b above was treated with 4.0 M HCl in 1,4- dioxane to afford the tiltle compound: mp 230° C. (dec); $^1$H NMR ($D_2O$) δ 1.96 (m, 1H), 2.04–2.40 (m, 2H), 2.29 (m, 1H), 3.42 (t, 2H, J=7.5 Hz), 4.14 (m, 1H), 4.30 (dd, 1H, J=7.5, 10.5 Hz), 4.51 (dd, 1H, J=3.5, 10.5 Hz), 7.66 (d, 1H, J=3.0 Hz), 8.23 (d, 1H, J=3.0 Hz), 9.00 (s, 2H), 9.23 (s, 1H); MS (CI/NH_3) m/z 291 (M+H)$^+$. Anal. Calcd for $C_{14}H_{15}ClN_4O.HCl$: C, 50.27; H, 4.88; N, 16.75. Found: C, 50.10; H, 4.69; N, 16.46. $[\alpha]^{25}_D$ –9.61 (0.77, MeOH).

Example 170

6-Chloro-3-(1-methyl-2-(S)-azetidinylmethoxy)-5-(5-pyrimidinyl)pyridine hydrochloride 170a. 6-Chloro-3-(1-methyl-2-(S)-azetidinylmethoxy)-5-(5-pyrimidinyl)pyridine The product from 169b (323 mg, 1.2 mmol) was dissolved in $H_2O$ (5 mL). Acetic acid (0.38 mL), formaldehyde (37%, 0.33 mL) and sodium cyanoborohydride (0.24 g, 4.1 mmol) were added to the solution. The reaction mixture was stirred at room temperature for 2 h. After neutralization with aqueous 10% NaOH, the organic layer was extracted with $CH_2Cl_2$ (3X). The combined organic layers were dried, concentrated and chromatographed (silica gel; $CH_2Cl_2$/MeOH, 10:0.3 to 10:1) to afford an oil (80.6 mg, 24%): $^1$H NMR (CDCl$_3$, 300 MHz) δ 2.04–2.16 (m, 2H), 2.40 (s, 3H), 2.90 (m, 1H), 3.38–3.50 (m, 2H), 4.07 (d, 2H, J=5.0 Hz), 7.28 (m, 1H), 8.18 (d, 1H, J=3.0 Hz), 8.87 (s, 2H), 9.28 (s, 1H); MS (CI/NH$_3$) m/z 291 (M+H)$^+$.

170a. 6-Chloro-3-(1-methyl-2-(S)-azetidinylmethoxy)-5-(5-pyrimidinyl)pyridine hydrochloride To a solution of 6-chloro-3-(1-methyl-2-(S)-azetidinylmethoxy)-5-(5-pyrimidinyl)pyridine in $Et_2O$ was added hydrogen chloride (1.0 M in $Et_2O$) carefully to afford the tittle compound: mp 143–144° C.; $^1$H NMR (D$_2$O) δ 2.56–2.76 (m, 2H), 3.80 (m, 1H), 4.26 (m, 1H), 4.44–4.58 (m, 2H), 4.79 (m, 1H), 7.70 (d, 1H, J=3.0 Hz), 8.28 (d, 1H, J=3.0 Hz), 9.00 (s, 2H), 9.22 (s, 1H); MS (CI/NH$_3$) m/z 291 (M+H)$^+$. Anal. Calcd for $C_{14}H_{15}ClN4O.HCl$: C, 51.39; H, 4.93; N, 17.12. Found: C, 51.51; H, 4.80; N, 16.82. $[α]^{25}_D$ −16.33 (c 0.74, MeOH).

Example 171

3-(2-(S)-Azetidinylmethoxy)-5-(5-pyrimldinyl)pyridine dihydrochloride 171a. 3-(1-BOC-2-(S)-azetidinylmethoxy)-5-(5-pyrimidinyl)pyridine To the solution of 3-(1-BOC-2-(S)-azetidinylmethoxy)-5-bromopyridine (580 mg, 1.69 mmol) in toluene (10 mL) was added tetrekis(triphenylphosphine)palladium (58 mg, 1%) and tributyl(pyrimidinyl)tin (0.75 g, 2.03 mmol). The mixture was stirred and heated under reflux for 16 h. Solvent was evaporated and the residue was chromatographed (silica gel; hexane/EtOAc, 10:1 to 2:3) to afford an oil (450 mg, 78%): $^1$H NMR (CDCl$_3$, 300 MHz) δ 1.40 (s, 9H), 2.30–2.44 (m, 2H), 3.88–3.96 (m, 2H), 4.22 (m, 1H), 4.44 (m, 1H), 4.58 (m, 1H), 7.44 (m, 1H), 8.44 (m, 2H), 8.98 (s, 2H); MS (CI/NH$_3$) m/z 343 (M+H)$^+$.

171b. 3-(2-(S)-Azetidinylmethoxy)-5-(5-pyrimldinyl)pyridine

The product from step a above (450 mg, 1.32 mmol) in $CH_2Cl_2$ (3 mL) was cooled to 0° C., TFA (2 mL) was then added carefully. The reaction mixture was stirred at 0° C. for 40 min. The mixture was then warmed to room temperature and kept stirring for 30 min. After neutralization with aqueous 10% NaOH, the reaction mixture was extracted with $CH_2Cl_2$ (3X). The combined organic layers were dried (MgSO$_4$), concentrated and chromatographed (silica gel; $CH_2Cl_2$/MeOH/NH$_4$OH, 10:0.3:0 to 10:1:0.04) to afford a light yellow oil (72 mg, 23%): $^1$H NMR (CDCl$_3$, 300 MHz) δ 2.32–2.56 (m, 2H), 3.58 (m, 1H), 3.82 (m, 1H), 4.12–4.24 (m, 2H), 4.42 (m, 1H), 7.42 (m, 1H), 8.42 (d, 1H, J=3.0 Hz), 8.46 (d, 1H, J=2.0 Hz), 8.96 (s, 2H), 9.27 (s, 1H); MS (CI/NH$_3$) m/z 243 (M+H)$^+$.

171c. 3-(2-(S)-Azetidinylmethoxy)-5-(5-pyrimidinyl)pyridine hydrochloride

To a solution of 3-(2-(S)-azetidinylmethoxy)-5-(5-pyrimidinyl)pyridine from step b above in $Et_2O$ was added hydrogen chloride (1.0 M in $Et_2O$) carefully to afford the tittle compound: mp 185° C. (dec); $^1$H NMR (D$_2$O) δ 2.64–2.78 (m, 2H), 3.59 (m, 1H), 4.08–4.22 (m, 2H), 4.52 (d, 1H, J=4.0 Hz), 4.97 (m, 1H), 7.84 (m, 1H), 8.36 (m, 1H), 8.93 (d, 1H, J=8.5 Hz), 9.11 (d, 1H, J=2.0 Hz), 9.17 (d, 1H, J=17.5 Hz); MS (CI/NH$_3$) m/z 243 (M+H)$^+$. Anal. Calcd for $C_{13}H_{14}N_4O.2$ HCl.H2O: C, 46.86; H, 5.44; N, 16.81. Found: C, 47.08; H, 5.50; N, 16.79. $[α]^{25}_D$ −6.32 (c 0.56, MeOH).

Example 172

3-(2-(S)-Azetidinylmethoxy)-6-chloro-5-(5-pyridinyl)pyridine dihydrochloride 172a. 3-(1-BOC-2-(S)-azetidinylmethoxy)-6-chloro-5-(5-pyrimidinyl)pyridine To the solution of 3-(1-BOC-2-(S)-azetidinylmethoxy)-5-bromo-6-chloropyridine (500 mg, 1.1 mmol) in toluene (10 mL) was added tetrekis(triphenylphosphine)palladium (50 mg, 1%) and tributyl(pyrimidinyl)tin (0.64 g, 1.72 mmol). The mixture was stirred and heated under reflux for 16 h. Solvent was evaporated and the residue was chromatographed (silica gel; hexane/EtOAc, 10:1 to 2:3) to afford an oil (500 mg, 100%): $^1$H NMR (CDCl$_3$, 300 MHz) δ 1.40 (s, 9H), 2.26–2.42 (m, 2H), 3.84–3.92 (m, 2H), 4.20 (m, 1H), 4.40 (m, 1H), 4.54 (m, 1H), 7.31 (d, 1H, J=3.0 Hz), 8.22 (d, 1H, J=3.0 Hz), 8.88 (s, 2H), 9.28 (s, 1H); MS (CI/NH$_3$) m/z 377 (M+H)$^+$.

172b. 3-(2-(S)-Azetidinylmethoxy)-6-chloro-5-(5-pyrimidinyl)pyridine

The product from step b above (530 mg, 1.14 mmol) in $CH_2Cl_2$ (3 mL) was cooled to 0° C., TFA (2 mL) was then added carefully. The reaction mixture was stirred at 0° C. for 40 min. The mixture was then warmed to room temperature and kept stirring for 30 min. After neutralization with aqueous 10% NaOH, the reaction mixture was extracted with $CH_2Cl_2$ (3X). The combined organic layers were dried (MgSO$_4$), concentrated and chromatographed (silica gel; $CH_2Cl_2$/MeOH/NH$_4$OH, 10:0.3:0 to 10:1:0.04) to afford a light yellow oil (410 mg, 100%): $^1$H NMR (CDCl$_3$, 300 MHz) δ 2.60–2.74 (m, 2H), 4.00–4.10 (m, 2H), 4.34–4.44 (m, 2H), 4.82 (m, 1H), 7.35 (d, 1H, J=3.0 Hz), 8.18 (d, 1H, J=3.0 Hz), 8.86 (s, 2H), 9.28 (s, 1H); MS (CI/NH$_3$) m/z 277 (M+H)$^+$.

172c. 3-(2-(S)-Azetidinylmethoxy)-6-chloro-5-(5-pyrimidinyl)pyridine dihydrochloride To a solution of 3-(2-(S)-azetidinylmethoxy)-6-chloro-5-(5-pyrimidinyl)pyridine from step c above in $Et_2O$ was added hydrogen chloride (1.0 M in $Et_2O$) carefully to afford the tittle compound: mp 144° C. (dec.); $^1$H NMR (D$_2$O) δ 2.70 (q, 2H, J=8.5 Hz), 4.04–4.18 (m, 2H), 4.48 (d, 2H, J=4.0 Hz), 4.97 (m, 1H), 7.70 (d, 1H, J=3.0 Hz), 8.28 (d, 1H, J=3.0 Hz), 9.00 (s, 2H), 9.22 (s, 1H); MS (CI/NH$_3$) m/z 278 (M+H)$^+$. Anal. Calcd for $C_{13}H_{13}ClN_4O.1.5$ HCl.0.1 H2O: C, 46.86; H, 4.45; N, 16.81. Found: C, 47.11; H, 4.63; N, 16.42. $[α]^{25}_D$ −9.20 (c 0.25, MeOH).

Example 173

6-Chloro-5-(5-pyrimidinyl)-3-(2-(R)-pyrrolidinylmethoxy)pyridine hydrochloride 173a. 3-(1-BOC-2-(R)-pyrimidinylmethoxy)-6-Chloro-5-(5-pyrimidinyl)pyridine To the solution of 3-(1-BOC-2-(R)-pyrrolidinylmethoxy)-5-bromo-6-chloro-pyridine (400 mg, 1.1 mmol) in toluene (10 mL) was added tetrekis(triphenylphosphine)palladium (40 mg, 1%) and tributyl(pyrimidinyl)tin (0.51 g, 1.38 mmol). The mixture was stirred and heated under reflux for 16 h. Solvent was evaporated and the residue was chromatographed (silica gel; hexane/EtOAc, 10:1 to 2:1) to afford an oil (335 mg, 80%): $^1$H NMR (CDCl$_3$, 300 MHz) δ 1.40 (s, 9H), 1.85–2.00 (m, 2H), 2.00–2.10 (m, 2H), 3.38 (m, 1H), 4.00 (m 1H), 4.14 (m, 1H), 4.24 (m, 1H), 7.40 (s, 1H), 8.20 (d, 1H, J=3.0 Hz), 8.88 (s, 2H), 9.28 (s, 1H); MS (CI/NH$_3$) m/z 277 (M+H)$^+$.

173b. 6-Chloro-5-(5-pyrimidinyl)-3-(2-(R)-pyrrolidinylmethoxy)pyridine hydrochloride The product from step a above was treated with 4.0 M HCl (in 1,4-dioxane) to afford the tiltle compound: mp 210° C. (dec); $^1$H NMR (D$_2$O) δ 1.98 (m, 1H), 2.04–2.22 (m, 2H), 2.30 (m, 1H), 3.43 (t, 2H, J=7.0 Hz), 4.15 (m, 1H), 4.30 (dd, 1H, J=8.0, 11.0 Hz), 4.52 (dd, 1H, J=3.5, 10.5 Hz), 7.66 (d, 1H, J=3.0 Hz), 8.23 (d, 1H, J=3.0 Hz), 9.00 (s, 2H), 9.22 (s, 1H); MS (CI/NH$_3$) m/z 291 (M+H)$^+$. Anal. Calcd for C$_{14}$H$_{15}$ClN$_4$O.1.2 HCl: C, 50.27; H, 4.88; N, 16.75. Found: C, 50.60; H, 4.83; N, 16.56. [α]$^{25}_D$ −8.24 (c 0.68, MeOH).

Example 174

5-(5-pyrimidinyl)-3-(2-(S)-pyrrolidinylmethoxy) pyridine trihydrochloride 174a. 3-(1-BOC-2-(S)-pyrrolidinylmethoxy)-5-(5-pyrimidiny)pyridine To the solution of 3-(1-BOC-2-(S)-pyrrolidinylmethoxy)-5-bromopyridine (670 mg, 1.88 mmol) in toluene (10 mL) was added tetrekis(triphenylphosphine)palladium (70 mg, 1%) and tributyl(pyrimidinyl)tin (0.84 g, 2.26 mmol). The mixture was stirred and heated under reflux for 16 h. Solvent was evaporated and the residue was chromatographed (silica gel; hexane/EtOAc, 10:1 to 2:1) to afford an oil (473 mg, 71%): $^1$H NMR (CDCl$_3$, 300 MHz) δ 1.44 (s, 9H), 1.88–2.00 (m, 2H), 2.05 (m, 1H), 3.30–3.48 (m, 2H), 4.04 (m, 1H), 4.10–4.22 (m, 2H), 4.30 (m, H), 7.64 (s, 1H), 8.42 (d, 1H, J=2.5 Hz), 8.45 (s, 1H), 8.98 (br s, 1H), 9.01 (s, 1H), 9.27 (s, 1H); MS (CI/NH$_3$) m/z 357 (M+H)$^+$.

174b. 5-(5-pyrimidinyl)-3-(2-(S)-pyrrolidinylmethoxy) pyridine trihydrochloride

The product from step a above was treated with 4.0 M HCl (in 1,4-dioxane) to afford the tiltle compound: mp 110–112° C.; $^1$H NMR (D$_2$O) δ 2.06 (m, 1H), 2.12–2.22 (m, 2H), 2.31(m, 1H), 3.42 (t, 2H, J=7.0 Hz), 4.20 (m, 1H), 4.46 (dd, 1H, J=8.0, 10.5 Hz), 4.67 (dd, 1H, J=3.5, 10.5 Hz), 8.37 (s, 1H), 8.63 (d, 1H, J=2.5 Hz), 9.17 (s, 2H), 9.28 (s, 1H); MS (CI/NH$_3$) m/z 357 (M+H)$^+$. Anal. Calcd for C$_{14}$H$_{16}$N$_4$O.3 HCl: C, 45.98; H, 5.24; N, 15.32. Found: C, 46.33; H, 5.61; N, 14.93. [α]$^{25}_D$ +4.86 (c 3.1, MeOH).

Example 175

3-(2-(S)-Azetidinylmethoxy)-6-chloro-5-ethynylpyridine hydrochloride 175a. 3-(1-BOC-2-(S)-azetidinylmethoxy)-6-chloro-5-(trimethylsilylethynyl)pyridine To a solution of 3-(1-BOC-2-(S)-azetidinylmethoxy)-5-bromo-6-chloropyridine (1.0 g, 2.6 mmol) in toluene (20 mL) was added NEt$_3$ (1 mL), copper (I) iodine (50 mg, 10%), tetrakis(triphenylphosphine)palladium (0) (305 mg, 10%) and (trimethylsilyl)acetylene (0.45 mL, 3.18 mmol). The reaction mixture was stirred and heated at 100° C. for 16 h. Solvent was evaporated and the residue was chromatographed (silica gel; hexane/EtoAc, 5:1 to 2:1) to afford an oil (770 mg, 74%): $^1$H NMR (CDCl$_3$, 300 MHz) δ 1.42 (s, 9H), 2.20–2.40 (m, 2H), 3.80–3.92 (m, 2H), 4.10 (m, 1H), 4.30 (m, 1H), 4.50 (m, 1H), 7.37 (d, 1H, J=3.0 Hz), 8.05 (d, 1H, J=3.0 Hz); MS (CI/NH$_3$) m/z 395 (M+H)$^+$.

175b. 3-(1-BOC-2-(S)-azetidinylmethoxy)-6-chloro-5-ethynylpyridine

The product from step a above (760 mg, 1.93 mmol) in MeOH (20 mL) was added potassium carbonate (293 mg, 2.12 mmol). It was allowed to stir at room temperature for 6 h. EtOAc was added. The reaction mixture was washed with H$_2$O (3X). The organic layers were dried (MgSO$_4$) and concentrated to afford the crude product (610 mg, 98%).

175c. 3-(2-(S)-Azetidinylmethoxy)-6-chloro-5-ethynylpyridine

The product from step b above (605 mg, 1.88 mmol) in CH$_2$Cl$_2$ (2 mL) was cooled to 0° C., TFA (2 mL) was then added carefully. The reaction mixture was stirred at 0° C. for 40 min. The mixture was then warmed to room temperature and kept stiring for 30 min. After neutralization with aqueous 10% NaOH, the reaction mixture was extracted with CH$_2$Cl$_2$ (3X). The combined organic layers were dried (MgSO$_4$), concentrated and chromatographed (silica gel; CH$_2$Cl$_2$/MeOH/NH$_4$OH, 10:0.3:0 to 10:1:0.03) to afford a light yellow oil (265 mg, 64%): $^1$H NMR (CDCl$_3$, 300 MHz) δ 2.26 (m, 1H), 2.38 (m, 1H), 3.44 (m, 1H), 3.74 (m, 1H), 3.98–4.04 (m, 2H), 4.30 (m, 1H), 7.38 (d, 1H, J=3.0 Hz), 8.08 (d, 1H, J=3.0 Hz); MS (CI/NH$_3$) m/z 223 (M+H)$^+$.

175d. 3-(2-(S)-Azetidinylmethoxy)-6-chloro-5-ethynylpyridine hydrochloride

To a solution of the compound obtained from step c above in Et$_2$O was added hydrogen chloride (1.0 M in Et$_2$O) carefully to afford the tittle compound: mp 90° C. (dec); $^1$H NMR (D$_2$O) δ 2.63 (q, 2H, J=8.5 Hz), 4.06–4.18 (m, 2H), 4.22 (d, 2H, J=9.0 Hz), 4.97 (m, 1H), 7.77 (d, 1H, J=3.5 Hz), 8.19 (d, 1H, J=3.0 Hz); MS (CI/NH$_3$) m/z 223 (M+H)$^+$, 240 (M+NH$_4$)$^+$. Anal. Calcd for C$_{11}$H$_{11}$ClN$_2$O.1.3 HCl.0.1 H2O: C, 48.60; H, 4.63; N, 10.30. Found: C, 48.70; H, 4.81; N, 10.01. [α]$^{25}_D$ −20.6 (c 0.50, MeOH).

Example 176

5-Allyl-3-(2-(S)-pyrrolidinylmethoxy)pyridine dihydrochloride 176a. 5-Allyl-3-(1-BOC-2-(S)-pyrrolidinylmethoxy) pyridine 5-Bromo-3-(1-BOC-2-(S)-pyrrolidinylmethoxy)pyridine (948 mg, 2.66 mmol) in toluene (10 mL) was added tetrakis (triphenylphosphine)palladium (15 mg) and allyltributyltin (0.18 mL, 0.56 mmol). The mixture was stirred and refluxed for two days. Solvent was evaporated and the residue was chromatographed (silica gel; hexane/EtOAc, 5:1 to 1:1) to afford an oil (617 mg, 73%): $^1$H NMR (CDCl$_3$, 300 MHz) δ 1.96 (m, 1H), 2.04–2.20 (m, 2H), 2.28 (m, 1H), 3.42 (t, 2H, J=7.0 Hz), 3.54 (d, 2H, J=7.0 Hz), 4.14 (m, 1H), 4.31 (dd, 1H, J=8.0, 10.5 Hz), 4.51 (dd, 1H, J=3.5, 10.5 Hz), 5.12–5.22 (m, 2H), 6.02 (m, 1H), 7.77 (s, 1H), 8.23 (s, 1H), 8.30 (d, 1H, J=2.5 Hz); MS (CI/NH$_3$) m/e 219 (M+H)$^+$.

176b. 5-Allyl-3-(2-(S)-pyrrolidinylmethoxy)pyridine dihydrochloride

The product from step a above was treated with 4.0 M HCl (in 1,4- dioxane) to afford the title compound: $^1$H NMR (D$_2$O) δ 1.95 (m, 1H), 2.04–2.40 (m, 2H), 2.30 (m, 1H), 3.42 (t, 2H, J=7.0 Hz), 3.55 (d, 2H, J=7.0 Hz), 4.14 (dd, 1H, J=3.5, 8.0 Hz), 4.31 (dd, 1H, J=8.0, 10.5 Hz), 4.53 (dd, 1H, J=3.5, 10.5 Hz), 5.22 (dd, 1H, J=1.5, 10.0 Hz), 5.98–6.05 (m, 2H), 7.77 (s, 1H), 8.23 (s, 1H), 8.29 (d, 1H, J=2.5 Hz); MS (CI/NH$_3$) m/z 219 (M+H)$^+$. Anal. Calcd for C$_{13}$H$_{18}$N$_2$O.2.4 HCl: C, 51.06; H, 6.72; N, 9.16. Found: C, 51.17; H, 6.67; N, 9.49. [α]$^{25}_D$ 11.29 (c 3.6, MeOH).

Example 177

5-Allyl-3-(1-methyl-2-(S)-pyrrolidinylmethoxy) pyridine dihydrochloride 177a. 5-Allyl-3-(1-methyl-2-(S)-pyrrolidinylmethoxy) pyridine The product from Example 176a (355 mg, 1.12 mmol) was added formic acid (88%, 3.3 mL) and formaldehyde (37%, 6.6 mL). The mixture was stirred and heated at 70° C. for 16 h. It was then cooled to room temperature and basified with aqueous 10% NaOH to pH 11. The solution was extracted with $CH_2Cl_2$ (3X), the combined organic layers were dried ($MgSO_4$), concentrated and chromatographed (silica gel; $CH_2Cl_2$/MeOH, 10:0.3 to 10:1) to afford an oil (250 mg, 96%): $^1H$ NMR ($CDCl_3$, 300 MHz) δ 1.60–1.90 (m, 2H), 2.02 (m, 1H), 2.30 (m, 1H), 2.48 (s, 3H), 2.64 (m, 1H), 3.12 (m, 1H), 3.36–3.42 (m, 2H), 3.94 (m, 1H), 4.00 (m, 1H), 4.20 (m, 1H), 4.88–4.96 (m, 2H), 5.92 (m, 1H), 7.03 (m, 1H), 8.06 (m, 1H), 8.16 (m, 1H); MS ($CI/NH_3$) m/z 233 (M+H)$^+$.

177b. 5-Allyl-3-(1-methyl-2-(S)-pyrrolidinylmethoxy) pyridine dihydrochloride

To a solution of 5-allyl-3-(1-methyl-2-(S)-pyrrolidinylmethoxy)pyridine in $Et_2O$ was added hydrogen chloride (1.0 M in $Et_2O$) carefully to afford the tittle compound: mp 65–67° C.; $^1H$ NMR ($D_2O$) δ 2.00–2.17 (m, 2H), 2.23 (m, 1H), 2.41 (m, 1H), 3.05 (s, 3H), 3.27 (m, 1H), 3.56 (dd, 2H, J=3.5, 7.0 Hz), 3.77 (m, 1H), 3.95 (m, 1H), 4.44 (dd, 1H, J=6.0, 11.0 Hz), 4.60 (dd, 1H, J=3.0, 11.0 Hz), 5.18–5.24 (m, 2H), 6.04 (m, 1H), 7.88 (s, 1H), 8.28 (s, 1H), 8.35 (s, 1H); MS ($CI/NH_3$) m/z 232 (M+H)$^+$. Anal. Calcd for $C_{14}H_{20}N_2O.2$ HCl.$H_2O$: C, 52.02; H, 7.48; N, 8.67. Found: C, 52.15; H, 7.42; N, 8.72. $[\alpha]^{25}_D$ −4.77 (c 2.41, MeOH).

Example 178

5-Allyl-3-(2-(S)-azetidinylmethoxy)-6-chloropyridine hydrochloride 178a. 5-Allyl-3-(1-BOC-2-(S)-azetidinylmethoxy)-6-chloropyridine 3-(1-BOC-2-(S)-Azetidinylmethoxy)-5-bromo-6-chloropyridine (1.0 g, 2.65 mmol) in toluene (10 mL) was added tetrakis(triphenylphosphine) palladium (100 mg) and allyltributyltin (0.99 mL, 3.18 mmol). The mixture was stirred and refluxed for two days. Solvent was evaporated and the residue was chromatographed (silica gel; hexane/EtOAc, 5:1 to 1:1) to afford an oil (750 mg, 83%): $^1H$ NMR ($CDCl_3$, 300 MHz) δ 1.42 (s, 9H), 2.20–2.40 (m, 2H), 3.43 (d, 2H, J=6.5 Hz), 3.88 (t, 2H, J=7.0 Hz), 4.12 (m, 1H), 4.30 (m, 1H), 4.50 (m, 1H), 5.10–5.20 (m, 2H), 5.92 (m, 1H), 7.18 (d, J=3.0 Hz), 7.98 (d, 1H, J=3.0 Hz); MS ($CI/NH_3$) m/z 339 (M+H)$^+$.

178b. 5-Allyl-3-(2-(S)-azetidinylmethoxy)-6-chloropyridine

The product from step a above (749 mg, 2.21 mmol) in $CH_2Cl_2$ (2.3 mL) was cooled to 0° C., TFA (3 mL) was then added carefully. The reaction mixture was stirred at 0° C. for 40 min. The mixture was then warmed to room temperature and kept stirring for 30 min. After neutralization with aqueous 10% NaOH, the reaction mixture was extracted with $CH_2Cl_2$ (3X). The combined organic layers were dried ($MgSO_4$), concentrated and chromatographed (silica gel; $CH_2Cl_2$/MeOH/$NH_4OH$, 10:0.3:0 to 10:1:0.03) to afford a light yellow oil (365 mg, 69%): $^1H$ NMR ($CDCl_3$, 300 MHz) δ 2.30 (m, 1H), 2.38 (m, 1H), 3.40–3.52 (m, 3H), 3.73 (q, 1H, J=8.0 Hz), 3.98–4.08 (m, 2H), 4.30 (m, 1H), 5.06–5.20 (m, 2H), 5.94 (m, 1H), 7.14 (d, 1H, J=3.0 Hz), 7.95 (d, 1H, J=3.0 Hz); MS ($CI/NH_3$) m/z 239 (M+H)$^+$.

178c. 5-Allyl-3-(2-(S)-azetidinylmethoxy)-6-chloropyridine hydrochloride

To a solution of 5-allyl-3-(2-(S)-azetidinylmethoxy)-6-chloropyridine in $Et_2O$ was added hydrogen chloride (1.0 M in $Et_2O$) carefully to afford the tittle compound: mp 90–92° C.; $^1H$ NMR ($D_2O$) δ 2.70 (q, 2H, J=8.5 Hz), 3.52 (d, 2H, J=6.5 Hz), 4.02–4.20 (m, 2H), 4.42 (d, 1H, J=4.0 Hz), 4.93 (m, 1H), 5.08–5.22 (m, 2H), 5.99 (m, 1H), 7.50 (d, 1H, J=3.0 Hz), 8.05 (d, 1H, J=3.0 Hz); MS ($CI/NH_3$) m/z 239 (M+H)$^+$. Anal. Calcd for $C_{12}H_{15}ClN_2O$.1.4 HCl: C, 49.74; H, 5.70; N, 9.67. Found: C, 49.99; H, 5.78; N, 9.41. $[\alpha]^{25}_D$ −6.9 (c 0.6, MeOH).

Example 179

5-Allyl-3-(1-methyl-2-(S)-azetidinylmethoxy)-6-chloropyridine hydrochloride 179a. 5-Allyl-6-chloro-3-(1-methyl-2-(S)-azetidinylmethoxy)pyridine The product from Example 178a (288 mg, 1.2 mmol) was dissolved in $H_2O$ (5 mL). Acetic acid (0.35 mL), formaldehyde (37%, 0.35 mL) and sodium cyanoborohydride (0.25 g, 4.1 mmol) were then added to the solution. The reaction mixture was stirred at room temperature for 2 h. After neutralization with aqueous 10% NaOH, the organic layer was extracted with $CH_2Cl_2$ (3X). The combined organic layers were dried, concentrated and chromatographed (silica gel; $CH_2Cl_2$/MeOH, 10:0.3 to 10:1) to afford an oil (250 mg, 82%): $^1H$ NMR ($CDCl_3$, 300 MHz) δ 2.04–2.16 (m, 2H), 2.40 (s, 3H), 2.90 (m, 1H), 3.40 (m, 1H), 3.42–3.50 (m, 3H), 4.00 (d, 1H, J=5.0 Hz), 5.08–5.20 (m, 2H), 5.96 (m, 1H), 7.13 (d, 1H, J=3.0 Hz), 7.95 (d, 1H, J=3.0 Hz); MS ($CI/NH_3$) m/z 253 (M+H)$^+$.

179b. 5-Allyl-6-chloro-3-(1-methyl-2-(S)-azetidinylmethoxy)pyridine hydrochloride To a solution of 5-allyl-6-chloro-3-(1-methyl-2-(S)-azetidinylmethoxy)pyridine in $Et_2O$ was added hydrogen chloride (1.0 M in $Et_2O$) carefully to afford the tittle compound: $^1H$ NMR ($D_2O$) δ 2.58–2.70 (m, 2H), 2.99 (s, 3H), 3.52 (d, 2H, J=6.5 Hz), 4.00 (m, 1H), 4.28 (m, 1H), 4.40–4.54 (m, 2H), 4.84 (m, 1H), 5.10–5.22 (m, 2H), 6.05 (m, 1H), 7.50 (d, 1H, J=3.0 Hz), 8.04 (d, 1H, J=3.0 Hz); MS ($CI/NH_3$) m/z 254 (M+H)$^+$. Anal. Calcd for $C_{13}H_{17}ClN_2O$.HCl: C, 53.99; H, 6.27; N, 9.69. Found: C, 53.73; H, 6.01; N, 9.57. $[\alpha]^{25}_D$ −22.55 (c 2.2, MeOH).

Example 180

6-Chloro-3-(1-methyl-2-(R)-pyrrolidinylmethoxy)-5-pyrimidinylpyridine hydrochloride 180a. 6-Chloro-3-(1-methyl-2-(R)-pyrrolidinylmethoxy)-5-pyrimidinylpyridine To the solution of 5-bromo-6-chloro-3-(1-methyl-2-(R)-pyrrolidinylmethoxy)-pyridine (450 mg, 1.47 mmol) in toluene (15 mL) was added tetrekis(triphenylphosphine) palladium (45 mg, 1%) and tributyl(pyrimidinyl)tin (0.65 g, 1.76 mmol). The mixture was stirred and heated under reflux for 24 h. Solvent was evaporated and the residue was chromatographed (silica gel; $CH_2Cl_2$/MeOH, 10:0.3 to 10:1) to afford an oil (163 mg, 36%): $^1H$ NMR ($CDCl_3$, 300 MHz) δ 1.62 (m, 1H), 1.68–1.90 (m, 2H), 2.02 (m, 1H), 2.32 (m, 1H), 2.50 (s, 3H), 2.70 (m, 1H), 3.12 (m, 1H), 3.98–4.06 (m, 2H), 7.25 (m, 1H), 8.18 (d, 1H, J=3.0 Hz), 8.87 (s, 2H), 9.29 (s, 1H); MS ($CI/NH_3$) m/z 305 (M+H)$^+$.

180b. 6-Chloro-3-(1-methyl-2-(R)-pyrrolidinylmethoxy)-5-(5-pyrimidinyl)pyridine hydrochloride To a solution of 6-chloro-3-(1-methyl-2-(R)-pyrrolidinylmethoxy)-5-(5-pyrimidinyl)pyridine in $Et_2O$ was added hydrogen chloride (1.0 M in Et$_2$O) carefully to afford the tittle compound: mp 195–197° C.; $^1$H NMR (D$_2$O) δ 2.02–2.18 (m, 2H), 2.24 (m, 1H), 2.40 (m, 1H), 3.05 (s, 3H), 3.26 (m, 1H), 3.36 (m, 1H), 3.95 (m, 1H), 4.40 (dd, 1H, J=6.0, 11.0 Hz), 4.57 (dd, 1H, J=3.0, 10.0 Hz), 7.66 (d, 1H, J=3.0 Hz), 8.24 (d, 1H, J=3.0 Hz), 8.99 (s, 2H), 9.21 (s, 1H); MS (CI/NH$_3$) m/z 306 (M+H)$^+$. Anal. Calcd for C$_{15}$H$_{17}$ClN$_4$O.1.6 HCl.0.1 H2O: C, 49.37; H, 5.19; N, 15.35. Found: C, 49.55; H, 5.13; N, 15.02. [α]$^{25}_D$ +8.1 (c 1.2, MeOH).

Example 181

5-Allyl-3-(2-(S)-azetidinylmethoxy)pyridine hydrochloride 181a. 5-Allyl-3-(1-BOC-2-(S)-azetidinylmethoxy)pyridine 3-(1-BOC-2-(S)-azetidinylmethoxy)-5-bromopyridine (0.95 g, 2.77 mmol) in toluene (10 mL) was added tetrakis (triphenylphosphine) palladium (100 mg) and allyltributyl-tin (1.72 mL, 5.54 mmol). The mixture was stirred and refluxed for two days. Solvent was evaporated and the residue was chromatographed (silica gel; hexane/EtOAc, 5:1 to 1:1) to afford an oil (250 mg, 30%): $^1$H NMR (CDCl$_3$, 300 MHz) δ 1.42 (s, 9H), 2.22–2.42 (m, 2H), 3.37 (d, 2H, J=7.0 Hz), 3.87–3.92 (m, 2H), 4.16 (m, 1H), 4.30 (m, 1H), 4.50 (m, 1H), 5.07–5.17 (m, 2H), 5.9 (m, 1H), 7.07 (m, 1H), 8.08 (m, 1H), 8.19 (d, 1H, J=3.0 Hz); MS (CI/NH$_3$) m/z 305 (M+H)$^+$.

181 b. 5-Allyl-3-(2-(S)-azetidinylmethoxy)pyridine

The product from step a above (250 mg, 0.82 mmol) in CH$_2$Cl$_2$ (2 mL) was cooled to 0° C., TFA (1.1 mL) was then added carefully. The reaction mixture was stirred at 0° C. for 40 min. The mixture was then warmed to room temperature and kept stirring for 30 min. After neutralization with aqueous 10% NaOH, the reaction mixture was extracted with CH$_2$Cl$_2$ (3X). The combined organic layers were dried (NgSO$_4$), concentrated and chromatographed (silica gel; CH$_2$Cl$_2$/MeOH/NH$_4$OH, 10:0.3:0 to 10:1:0.03) to afford a light yellow oil (365 mg, 69%): $^1$H NMR (CDCl$_3$, 300 MHz) δ 2.28 (m, 1H), 2.42 (m, 1H), 3.37 (d, 2H, J=6.5 Hz), 3.52 (m, 1H), 3.76 (m, 1H), 4.04 (m, 2H), 4.30 (m, 1H), 5.06–5.16 (m, 2H), 5.94 (m, 1H), 7.04 (m, 1H), 8.08 (d, 1H, J=2.0 Hz), 8.18 (d, 1H, J=3.0 Hz); MS (CI/NH$_3$) m/z 239 (M+H)$^+$.

181c. 5-Allyl-3-(2-(S)-azetidinylmethoxy)pyridine hydrochloride

To a solution of 5-allyl-3-(1-methyl-2-(R)-pyrrolidinylmethoxy)pyridine in Et$_2$O was added hydrogen chloride (1.0 M in Et$_2$O) carefully to afford the tittle compound: $^1$H NMR (D$_2$O) δ 2.70 (q, 2H, J=8.5 Hz), 3.49 (d, 2H, J=6.5 Hz), 4.02–4.20 (m, 2H), 4.44 (d, 2H, J=4.5 Hz), 4.95 (m, 1H), 5.12–5.20 (m, 2H), 6.05 (m, 1H), 7.53 (s, 1H), 8.15 (s, 1H), 8.24 (d, 1H, J=2.0 Hz); MS (CI/NH$_3$) m/z 205 (M+H)$^+$. Anal. Calcd for C$_{12}$H$_{16}$N$_2$O.2 HCl.0.2 H2O: C, 54.14; H, 6.82; N, 10.52. Found: C, 54.30; H, 6.82; N, 10.49. [α]$^{25}_D$ −3.5 (c 0.63, MeOH).

Example 182

6-Chloro-3-(1-methyl-2-(S)-pyrrolidinylmethoxy)-5-(5-pyrimidinyl)pyridine hydrochloride 182a. 6-Chloro-3-(1-methyl-2-(S)-pyrrolidinylmethoxy)-5-(5-pyrimidinyl)pyridine To the solution of 5-bromo-6-chloro-3-(1-methyl-2-(R)-pyrrolidinylmethoxy)-pyridine (390 mg, 1.27 mmol) in toluene (15 mL) was added tetrekis(triphenylphosphine) palladium (40 mg, 1%) and tributyl(pyrimidinyl)tin (0.57 g, 1.53 mmol). The mixture was stirred and heated under reflux for 6 h. Solvent was evaporated and the residue was chromatographed (silica gel; CH$_2$Cl$_2$/MeOH, 10:0.3 to 10:1) to afford an oil (193 mg, 50%): $^1$H NMR (CDCl$_3$, 300 MHz) δ 1.62 (m, 1H), 1.68–1.90 (m, 2H), 2.02 (m, 1H), 2.32 (m, 1H), 2.50 (s, 3H), 2.70 (m, 1H), 3.12 (m, 1H), 3.98–4.06 (m, 2H), 7.25 (m, 1H), 8.18 (d, 1H, J=3.0 Hz), 8.87 (s, 2H), 9.29 (s, 1H); MS (CI/NH$_3$) m/z 305 (M+H)$^+$.

182b. 6-Chloro-3-(1-methyl-2-(S)-pyrrolidinylmethoxy)-5-(5-pyrimidinyl)pyridine hydrochloride To a solution of 6-chloro-3-(1-methyl-2-(S)-pyrrolidinylmethoxy)-5-(5-pyrimidinyl)pyridine in Et$_2$O was added hydrogen chloride (1.0 M in Et$_2$O) carefully to afford the tittle compound: mp 200–202° C.; $^1$H NMR (D$_2$O) δ 2.03–2.17 (m, 2H), 2.24 (m, 1H), 2.39 (m, 1H), 3.05 (s, 3H), 3.13 (m, 1H), 3.75 (m, 1H), 3.96 (m, 1H), 4.41 (dd, 1H, J=6.0, 11.0 Hz), 4.58 (dd, 1H, J=3.0, 11.0 Hz), 7.67 (d, 1H, J=3.0 Hz), 8.25 (d, 1H, J=3.0 Hz), 9.00 (s, 2H), 9.22 (s, 1H); MS (CI/NH$_3$) m/z 306 (M+H)$^+$. Anal. Calcd for C$_{15}$H$_{17}$ClN$_4$O.1.4 HCl: C, 50.63; H, 5.21; N, 15.75. Found: C, 50.66; H, 4.94; N, 15.40. [α]$^{25}_D$ −8.16 (c 8.7, MeOH).

Example 183

5-Allyl-6-chloro-3-(2-(S)-pyrrolidinylmethoxy) pyridine hydrochloride 183a. 5-Allyl-3-(1-BOC-2-(S)-pyrrolidinylmethoxy)-6-chloropyridine 3-(1-BOC-2-(S)-pyrrolidinylmethoxy)-5-bromo-6-chloropyridine (2.0 g, 5.14 mmol) in toluene (15 mL) was added tetrakis(triphenylphosphine)palladium (15 mg) and allyltributyltin (3.2 mL, 10.2 mmol). The mixture was stirred and refluxed for 16 h. Solvent was evaporated and the residue was chromatographed (silica gel; hexane/EtOAc, 5:1 to 1:1) to afford an oil (2.0 g, 100%): $^1$H NMR (CDCl$_3$, 300 MHz) δ 1.24–1.40 (m, 2H), 1.46 (s, 9H), 1.62 (m, 1H), 1.88 (m, 1H), 2.02 (m, 1H), 3.38 (m, 1H), 3.45 (d, 2H, J=7.0 Hz), 3.90 (m, 1H), 4.16 (m, 2H), 5.10–5.20 (m, 2H), 5.94 (m, 1H), 7.14 (m, 1H), 7.96 (d, 1H, J=3.0 Hz); MS (CI/NH$_3$) m/e 352 (M+H)$^+$.

183b. 5-Allyl-6-chloro-3-(2-(S)-pyrrolidinylmethoxy) pyridine hydrochloride

To a solution of 5-allyl-6-chloro-3-(2-(S)-pyrrolidinylmethoxy)pyridine in Et$_2$O was added hydrogen chloride (1.0 M in Et$_2$O) carefully to afford the tittle compound: $^1$H NMR (D$_2$O) δ 1.94 (m, 1H), 2.04–2.22 (m, 2H), 2.30 (m, 1H), 3.42 (t, 2H, J=7 Hz), 3.51 (d, 2H, J=7.0 Hz), 4.10 (m, 1H), 4.23 (dd, 1H, J=7.5, 10.5 Hz), 4.45 (dd, 1H, J=3.5, 11.0 Hz), 5.06–5.20 (m, 2H), 6.04 (m, 1H), 7.45 (d, 1H, J=3.0 Hz), 7.99 (d, 1H, J=3.0 Hz); MS (CI/NH$_3$) m/z 353 (M+H)$^+$. Anal. Calcd for C$_{13}$H$_{17}$ClN$_2$O.1.4 HCl: C, 51.40; H, 6.10; N, 9.22. Found: C, 51.71; H, 5.92; N, 8.89. [α]$^{25}_D$ +16.70 (c 21.5, MeOH).

Example 184

5-Allyl-6-chloro-3-(2-(S)-pyrrolidinylmethoxy) pyridine hydrochloride 184a. 5-Allyl-6-chloro-3-(1-methyl-2-(S)-pyrrolidinylmethoxy)pyridine To the product from Example 183a (505 mg, 1.43 mmol) was added formic acid (88%, 4.6 mL) and formaldehyde (37%, 9.2 mL). The reaction mixture was stirred and heated at 70° C. for 6 h. After cooling to room temperature, the mixture was neutralized with aqueous 10% NaOH and extracted with CH$_2$Cl$_2$ (3X). The combined organic layers were dried (MgSO$_4$), concentrated and chromatograpged (silica gel; CH$_2$Cl$_2$/MeOH, 10:0.2 to 10:0.5) to afford an oil (275 mg, 72%): $^1$H NMR (CDCl$_3$, 300 MHz) δ 1.70–1.88

(m, 2H), 2.02 (m, 1H), 2.30 (m, 1H), 2.47 (s, 3H), 2.64 (m, 1H), 3.12 (m, 1H), 3.40–3.47 (m, 2H), 3.91 (dd, 1H, J=5.5, 9.0 Hz), 3.98 (dd, 1H, J=5.5, 9.0 Hz), 5.14 (m, 2H), 5.86–6.00 (m, 1H), 7.12 (d, 1H, J=3.0 Hz), 7.94 (d, 1H, J=3.0 Hz); MS (CI/NH$_3$) m/z 267 (M+H)$^+$.

184b. 5-Allyl-6-chloro-3-(1-methyl-2-(S)-pyrrolidinylmethoxy)pyridine hydrochloride To a solution of 5-allyl-6-chloro-3-(1-methyl-2-(S)-pyrrolidinylmethoxy)pyridine in Et$_2$O was added hydrogen chloride (1.0 M in Et$_2$O) carefully to afford the tittle compound: mp 150–152° C.; $^1$H NMR (D$_2$O) δ 2.02–2.18 (m, 2H), 2.24 (m, 1H), 2.40 (m, 1H), 3.04 (s, 3H), 3.23 (m, 1H), 3.52 (d, 2H, J=6.5 Hz), 3.74 (m, 1H), 3.95 (m, 1H), 4.34 (dd, 1H, J=6.0, 11.5 Hz), 4.51 (dd, 1H, J=3.0, 11.0 Hz), 5.12 (dd, 1H, J=2.0, 17.5 Hz), 5.20 (dd, 1H, J=1.5, 10.0 Hz), 6.04 (m, 1H), 7.47 (d, 1H, J=3.0 Hz), 8.03 (d, 1H, J=3.0 Hz); MS (CI/NH$_3$) m/z 267 (M+H)$^+$. Anal. Calcd for C$_{14}$H$_{19}$ClN$_2$O.1.1 HCl: C, 54.80; H, 6.60; N, 9.19. Found: C, 54.98; H, 6.37; N, 8.98. [α]$^{25}_D$ −6.62 (c 1.5, MeOH).

Example 185

5-Allyl-6-chloro-3-(2-(R)-pyrrolidinylmethoxy)pyridine hydrochloride 185a. 5-Allyl-3-(1-BOC-2-(R)-pyrrolidinylmethoxy)-6-chloropyridine 3-(1-BOC-2-(R)-pyrrolidinylmethoxy)-5-bromo-6-chloropyridine (1.0 g, 2.57 mmol) in toluene (10 mL) was added tetrakis(triphenylphosphine)palladium (15 mg) and allyltributyltin (1.6 mL, 5.1 mmol). The mixture was stirred and refluxed for 16 h. Solvent was evaporated and the residue was chromatographed (silica gel; hexane/EtOAc, 5:1 to 1:1) to afford an oil (660 mg, 73%): $^1$H NMR (CDCl$_3$, 300 MHz) δ 1.24–1.40 (m, 2H), 1.46 (s, 9H), 1.62 (m, 1H), 1.88 (m, 1H), 2.02 (m, 1H), 3.38 (m, 1H), 3.45 (d, 2H, J=7.0 Hz), 3.90 (m, 1H), 4.16 (m, 2H), 5.10–5.20 (m, 2H), 5.94 (m, 1H), 7.14 (m, 1H), 7.96 (d, 1H, J=3.0 Hz); MS (CI/NH$_3$) m/z 352 (M+H)$^+$.

185b. 5-Allyl-6-chloro-3-(2-(R)-pyrrolidinylmethoxy)pyridine dihydrochloride

To a solution of 5-allyl-3-(1-BOC-2-(R)-pyrrolidinylmethoxy)6-chloropyridine in Et$_2$O was added hydrogen chloride (4.0 M in 1,4-dioxane) carefully to afford the tittle compound: mp 90–92° C.; $^1$H NMR (D$_2$O) δ 1.92 (m, 1H), 2.02–2.20 (m, 2H), 2.27 (m, 1H), 3.40 (t, 2H, J=7.0 Hz), 3.49 (d, 2H, J=6.5 Hz), 4.11 (m, 1H), 4.21 (dd, 1H, J=7.5, 10.5 Hz), 4.43 (dd, 1H, J=3.5, 10.5 Hz), 5.10 (dd, 1H, J=1.5, 17.0 Hz), 5.18 (dd, 1H, J=2.0, 10.0 Hz), 6.03 (m, 1H), 7.44 (d, 1H, J=3.0 Hz), 7.98 (d, 1H, J=3.0 Hz); MS (CI/NH$_3$) m/z 253 (M+H)$^+$. Anal. Calcd for C$_{13}$H$_{17}$ClN$_2$O.2 HCl.0.8 H2O: C, 45.91; H, 6.11; N, 8.24. Found: C, 45.90; H, 6.36; N, 8.20. [α]$^{25}_D$ −11.2 (c 1.4, MeOH).

Example 186

3-(2-(R)-Azetidinylmethoxy)-6-chloro-5-phenylpyridine hydrochloride 186a. 3-(1-BOC-2-(R)-azetidinylmethoxy)-6-chloro-5-phenylpyridine To a mixture of 3-(1-BOC-2-(R)-azetidinylmethoxy)-5-bromo-6-chloropyridine (0.25 g, 0.68 mmol), tetrakis(triphenylphosphine)palladium(0) (25 mg, 1%), aqueous sodium carbonate (2.0 M, 1 mL) in toluene (10 mL), was added phenylboronic acid (0.108 g, 0.89 mmol). The reaction mixture was stirred and heated at 90° C. for 16 h. Solvent was evaporated. The residue was chromatographed (silica gel; hexane/EtOAC, 10:1 to 2:1) to afford an oil (0.20 g, 78%): $^1$H NMR (CDCl$_3$, 300 MHz) δ 1.40 (s, 4H), 1.58 (s, 5H), 2.24–2.40 (m, 2H), 3.89 (t, 2H, J=7.5 Hz), 4.15 (dd, 1H, J=3.0, 10.0 Hz), 4.36 (m, 1H), 4.52 (m, 1H), 7.27 (d, 1H, J=3.0 Hz), 7.45 (s, 5H), 8.12 (d, 1H, J=3.0 Hz); MS (CI/NH$_3$) m/z 347 (M+H)$^+$.

186b. 3-(2-(R)-Azetidinylmethoxy)-6-chloro-5-phenylpyridine

The product from step a above (192 mg, 0.82 mmol) in CH$_2$Cl$_2$ (2 mL) was cooled to 0° C., TFA (0.7 mL) was then added carefully. The reaction mixture was stirred at 0° C. for 40 min. It was then warmed to room temperature and kept stiring for 30 min. After neutralization with aqueous 10% NaOH, the reaction mixture was extracted with CH$_2$Cl$_2$ (3X). The combined organic layers were dried (MgSO$_4$), concentrated and chromatographed (silica gel; CH$_2$Cl$_2$/MeOH/NH$_4$OH, 10:0.3:0 to 10:1:0.03) to afford a light yellow oil (365 mg, 69%): $^1$H NMR (CDCl$_3$, 300 MHz) δ 2.30 (m, 1H), 2.40 (m, 1H), 3.50 (m, 1H), 3.78 (m, 1H), 4.08 (m, 2H), 4.37 (M, 1H), 7.22 (m, 1H), 7.42 (m, 5H), 8.08 (d, 1H, J=2.0 Hz); MS (CI/NH$_3$) m/z 239 (M+H)$^+$.

186c. 3-(2-(R)-Azetidinylmethoxy)-6-chloro-5-phenylpyridine hydrochloride

To a solution of 3-(2-(R)-azetidinylmethoxy)-6-chloro-5-phenyl-pyridine in Et$_2$O was added hydrogen chloride (1.0 M in Et$_2$O) carefully to afford the tittle compound: mp 143–145° C.; $^1$H NMR (D$_2$O) δ 2.70 (q, 2H, J=8.5 Hz), 4.02–4.22 (m, 2H), 4.46 (d, 2H, J=4.5 Hz), 4.97 (m, 1H), 7.57 (s, 5H), 7.60 (d, 1H, J=3.0 Hz), 8.19 (d, 1H, J=3.0 Hz); MS (CI/NH$_3$) m/z 275 (M+H)$^+$. Anal. Calcd for C$_{15}$H$_{15}$ClN$_2$O.1.4 HCl: C, 55.30; H, 5.07; N, 8.60. Found: C, 55.19; H, 5.25; N, 8.52. [α]$^{25}_D$ +9.4 (c 0.8, MeOH).

Example 187

6-Ethenyl-5-methyl-3-(2-(S)-pyrrolidinylmethoxy)pyridine hydrochloride 187a. 1-BOC-2-(S)-pyrrolidinylmethyltoluenesulfonate 1-BOC-2-(S)-pyrrolidinemethanol (10.0 g, 49.7 mmol) was dissolved in CH$_2$Cl$_2$ (200 mL) at 0° C. NEt$_3$ (27.6 mL, 0.20 mol) and p-toluenesulfonyl chloride (19.0 g, 99.4 mmol) were then added. The reaction mixture was warmed to room temperature and stirred for 16 h. CH$_2$Cl$_2$ (200 mL) was added. The mixture was washed with saturated aqueous K$_2$CO$_3$ (200 mL), water (150 mL), brine (25 mL) and dried (MgSO$_4$). The organic layer was concentrated and chromatographed (silica gel; hexane/EtOAc, 90:10) to afford a yellow oil (15.9 g, 90%): $^1$H NMR (CDCl$_3$, 300 MHz) δ 1.40 (s, 9H), 1.70–2.00 (m, 4H), 2.43 (s, 3H), 3.20–3.40 (m, 2H), 3.80–4.02 (m, 2H), 4.10 (m, 1H), 7.30–7.40 (m, 2H), 7.78 (s, 1H), 8.00 (s, 1H); MS (CI/NH$_3$) m/z 356 (M+H)$^+$ 187b. 3-(1-BOC-2-(S)-pyrrolidinylmethoxy)-6-chloro-5-methylpyridine To a solution of 5-acetoxy-2-chloro-3-methylpyridine (1.80 g, 8.9 mmol) in MeOH (5 mL) was added potassium carbonate (1.4 g, 10.1 mmol). The reaction mixture was allowed to stir at room tenperature for 2.5 h. Solvent was evaporated. The residue was then dissolved in DMF, and 1-BOC-2-(S)-methyltoluenesulfonate-pyrrolidine (2.0 g, 5.63 mmol) from a above was added. The reaction mixture was stirred at 60° C. for 16 h. Solvent was evaporated. The residue was chromatographed (silica gel; hexane/EtOAc, 10:1 to 3:1) to afford an oil (850 mg, 30%): $^1$H NMR δ 1.47 (s, 9H), 1.80–2.00 (m, 2H), 2.00–2.08 (m, 2H), 2.34 (s, 3H), 3.24–3.44 (m, 2H), 3.92 (m, 1H), 4.02–4.20 (m, 2H), 7.16 (m, 1H), 7.92 (d, 1H, J=2.5 Hz); MS (CI/NH$_3$) m/z 227 (M+H)$^+$.

187c. 3-(1-BOC-2-(S)-pyrrolidinylmethoxy)-6-ethenyl-5-methylpyridine 3-(1-BOC-2-(S)-pyrrolidinylmethoxy)-6-chloro-5-methylpyridine (830 mg, 2.57 mmol) in toluene (10 mL)

was added [1,1'-bis(diphenyl-phosphino)ferrocene] dichloropalladium(U) (83 mg) and allyltributyltin (1.3 mL, 5.1 mmol). The mixture was stirred and refluxed for 16 h. Solvent was evaporated and the residue was chromatographed (silica gel; hexane/EtOAc, 10:1 to 3:2) to afford an oil (450 mg, 57%): $^1$H NMR (CDCl$_3$, 300 MHz) δ 1.47 (s, 9H), 1.62 (m, 1H), 1.86 (m, 1H), 2.00–2.10 (m, 2H), 2.34 (s, 3H), 3.30–3.46 (m, 2H), 3.90 (m, 1H), 4.04–4.20 (m, 2H), 5.37 (d, 1H, J=11.0 Hz), 6.20 (d, 1H, J=17.0 Hz), 6.94 (dd, 1H, J=11.0, 17.0 Hz), 7.02 (br s, 1H), 8.14 (d, 1H, J=2.5 Hz); MS (CI/NH$_3$) m/z 319 (M+H)$^+$.

187d. 3-(1-BOC-2-(S)-pyrrolidinylmethoxy)-6-ethenyl-5-methylpyridine hydrochloride The product from step b above was treated with 4.0 M HCl (in 1,4-dioxane) to afford the title compound: mp 168–170° C.; $^1$H NMR (D$_2$O) δ 1.96 (m, 1H), 2.04–2.20 (m, 2H), 2.28 (m, 1H), 2.47 (s, 3H), 3.41 (q, 2H, J=7.0 Hz), 4.12 (m, 1H), 4.33 (dd, 1H, J=7.5, 10.5 Hz), 4.54 (dd, 1H, J=3.5, 10.5 Hz), 5.85 (d, 1H, J=11.5 Hz), 6.09 (d, 1H, J=17.5 Hz), 7.00 (dd, 1H, J=11.0, 17.5 Hz), 7.84 (d, 1H, J=3.0 Hz), 8.20 (d, 1H, J=3.0 Hz); MS (CI/NH$_3$) m/z 218 (M+H)$^+$. Anal. Calcd for C$_{13}$H$_{18}$N$_2$O.1.3 HCl: C, 51.68; H, 6.77; N, 9.27. Found: C, 51.63; H, 6.62; N, 9.35. [α]$^{25}_D$ +10.7 (c 0.54, MeOH).

Example 188

6-Ethenyl-5-methyl-3-(1-methyl-2-(S)-pyrrolidinylmethoxy)pyridine hydrochloride 188a. 6-Ethenyl-5-methyl-3-(1-methyl-2-(S)-pyrrolidinylmethoxy)pyridine To the product from Example 187c (570 mg, 1.79 mmol) was added formic acid (88%, 5.7 mL) and formaldehyde (37%, 11.5 mL). The reaction mixture was stirred and heated at 70° C. for 6 h. After cooling to room temperature, the mixture was neutralized with aqueous 10% NaOH and extracted with CH$_2$Cl$_2$ (3X). The combined organic layers were dried (MgSO$_4$), concentrated and chromatograpged (silica gel; CH$_2$Cl$_2$/MeOH, 10:0.2 to 10:0.5) to afford an oil (227 mg, 55%): $^1$H NMR (CDCl$_3$, 300 MHz) δ 1.70–1.98 (m, 4H), 2.04 (m, 1H), 2.37 (s, 3H), 2.50 (s, 3H), 2.68 (m, 1H), 3.16 (m, 1H), 3.96 (, 1H), 4.03 (m, 1H), 5.38 (dd, 1H, J=2.0, 11.0 Hz), 6.18 (dd, 1H, J=2.0, 18.0 Hz), 6.94 (dd, 1H, J=11.0, 18.0 Hz), 6.98 (m, 1H), 8.16 (d, 1H, J=3.0 Hz); MS (CI/NH$_3$) m/z 233 (M+H)$^+$.

188b. 6-Ethenyl-5-methyl-3-(1-methyl-2-(S)-pyrrolidinylmethoxy)pyridine dihydrochloride The product from step a above was treated with 4.0 M HCl (in 1,4-dioxane) to afford the title compound: mp 50° C. (dec); $^1$H NMR (D$_2$O) δ 2.04–2.38 (m, 3H), 2.41 (m, 1H), 2.45 (s, 3H), 3.05 (s, 3H), 3.26 (m, 1H), 3.77 (m, 1H), 3.94 (m, 1H), 4.41 (dd, 1H, J=6.0, 11.0 Hz), 4.57 (dd, 1H, J=3.0, 11.0 Hz), 5.75 (d, 1H, J=11.0 Hz), 6.06 (d, 1H, J=7.0 Hz), 7.02 (dd, 1H, J=11.0, 18.0 Hz), 7.70 (s, 1H), 8.19 (d, 1H, J=3.0 Hz); MS (CI/NH$_3$) m/z 233 (M+H)$^+$. Anal. Calcd for C$_{14}$H$_{20}$N$_2$O.2 HCl.0.8 H$_2$O: C, 52.60; H, 7.44; N, 8.76. Found: C, 52.68; H, 7.43; N, 8.96. [α]$_D^{23}$ −8.03 (c 1.34, MeOH).

Example 189

6-Chloro-3-(1-methyl-2-(R)-azetidinylmethoxy)-5-phenylpyridine hydrochloride 189a. 3-(2-(R)-azetidinylmethoxy)-6-chloro-5-phenylpyridine The product from Example 186b (160 mg, 0.55 mmol) was dissolved in H$_2$O (2 mL). Acetic acid (0.18 mL), formaldehyde (37%, 0.16 mL) and sodium cyanoborohydride was then added carefully. The reaction mixture was stirred at room temperature for 6 h. After neutralization with saturated aqueous 10% NaOH, the reaction mixture was extracted with CH$_2$Cl$_2$ (3X). The combined organic layers were dried (MgSO$_4$), concentrated and chromatographed (silica gel; CH$_2$Cl$_2$/MeOH/NH$_4$OH, 10:0.3:0 to 10:1:0.03) to afford a light yellow oil (82 mg, 52%): $^1$H NMR (CDCl$_3$, 300 MHz) δ 2.30 (m, 1H), 2.40 (m, 1H), 3.50 (m, 1H), 3.78 (m, 1H), 4.05 (d, 2H, J=5.0 Hz), 4.37 (m, 1H), 7.22 (m, 1H), 7.42 (m, 5H), 8.08 (d, 1H, J=2.0 Hz); MS (CI/NH$_3$) m/z 289 (M+H)$^+$.

189b. 6-Chloro-3-(1-methyl-2-(R)-azetidinylmethoxy)-5-phenylpyridine hydrochloride To a solution of 6-chloro-3-(1-methyl-2-(R)-azetidinylmethoxy)-5-phenylpyridine in Et$_2$O was added hydrogen chloride (1.0 M in Et$_2$O) carefully to afford the tittle compound: mp 173–175° C.; $^1$H NMR (D$_2$O) δ 2.60–2.78 (m, 3H), 3.00 (s, 3H), 4.02 (m, 1H), 4.25 (m, 1H), 4.60–4.78 (m, 2H), 7.56–7.60 (m, 6H), 8.18 (d, 1H, J=2.0 Hz); MS (CI/NH$_3$) m/z 289 (M+H)$^+$. Anal. Calcd for C$_{16}$H$_{17}$ClN$_2$O.1.1 HCl; C, 58.43; H, 5.55; N, 8.52. Found: C, 58.37; H, 5.56; N, 8.43. [α]$_D^{23}$ +40.37 (c 0.27, MeOH).

Example 190

3-(2-R)-Azetidinylmethoxy)-6-chloro-5-ethynylpyridine hydrochloride 190a. 3-(1-BOC-2-(R)-azetidinylmethoxy)-6-chloro-5-(trimethylsilylethynyl)pyridine To a solution of 3-(1-BOC-2-(R)-azetidinylmethoxy)-6-chloro-5-bromopyridine (660 mg, 1.75 mmol) in toluene (20 mL) was added NEt$_3$ (0.7 mL), copper (I) iodine (33 mg), tetrakis(triphenylphosphine)palladium (0) (201 mg) and (trimethylsilyl)acetylene (0.30 mL, 2.10 mmol). The reaction mixture was stirred and heated at 100° C. for 16 h. Solvent was evaporated and the residue was chromatographed (silica gel; hexane/EtoAc, 5:1 to 2:1) to afford an oil (430 mg, 62%): $^1$H NMR (CDCl$_3$, 300 MHz) δ 1.42 (s, 9H), 2.20–2.40 (m, 2H), 3.80–3.92 (m, 2H), 4.10 (m, 1H), 4.30 (m,1H), 4.50 (m, 1H), 7.37 (d, (H, J=3.0 Hz), 8.05 (d, 1H, J=3.0 Hz); MS (CI/NH$_3$) m/z 395 (M+H)$^+$.

190b. 3-(1-BOC-2-(R)-azetidinylmethoxy)-6-chloro-5-ethynylpyrdine

The product from step a above (430 mg, 1.09 mmol) in MeOH (10 mL) was added potassium carbonate (166 mg, 1.20 mmol). It was allowed to stir at room temperature for 6 h. EtOAc was added. The reaction mixture was washed with H$_2$O (3X). The organic layers were dried (MgSO$_4$), concentrated and chromatographed (silica gel; hexane/EtOAc, 5:1 to3:1) to afford an oil (165 mg, 47%): $^1$H NMR (CDCl$_3$, 300 MHz) δ 2.20–2.40 (m, 2H), 3.84–3.90 (m, 2H), 4.10 (m, 1H), 4.30 (m, 1H), 4.50 (m, 1H), 7.41 (d, 1H, J=5.0 Hz), 8.10 (d, 1H, J=3.0 Hz); MS (CI/NH$_3$) m/z 323 (N+H)$^+$.

190c. 3-(2-(R)-Azetidinylmethoxy)-6-chloro-5-ethynylpyridine

The product from step b above (160 mg, 0.50 mmol) in CH$_2$Cl$_2$ (1 mL) was cooled to 0° C., TFA (0.7 mL) was then added carefully. The reaction mixture was stirred at 0° C. for 40 min. The mixture was then warmed to room temperature and kept stirring for 30 min. After neutralization with saturated aqueous 10% NaOH, the reaction mixture was extracted with CH$_2$Cl$_2$ (3X). The combined organic layers were dried (MgSO$_4$), concentrated and chromatographed (silica gel; CH$_2$Cl$_2$/MeOH/NH$_4$OH, 10:0.3:0 to 10:1:0.03) to afford a light yellow oil (85 mg, 77%): $^1$H NMR (CDCl$_3$, 300 MHz) δ 2.26 (m, 1H), 2.38 (m, 1H), 3.44 (m, 1H), 3.74 (m, 1H), 3.98–4.04 (m, 2H), 4.30 (m, 1H), 7.38 (d, 1H, J=3.0 Hz), 8.08 (d, 1H, J=3.0 Hz); MS (CI/NH$_3$) m/z 223 (M+H)$^+$.

190d. 3-(2-(R)-Azetidinylmethoxy)-6-chloro-5-ethynylpyridine hydrochloride

To a solution of compound obtained above in $Et_2O$ was added hydrogen chloride (1.0 M in $Et_2O$) carefully to afford the tittle compound: mp 155–157° C.; $^1H$ NMR ($D_2O$) δ 2.68 (q, 2H, J=8.5 Hz), 4.10 (m, 2H), 4.41 (d, 2H, J=4.0 Hz), 4.94 (m, 1H), 7.75 (d, 1H, J=3.0 Hz), 8.16 (d, 1H, J=3.0 Hz); MS ($CI/NH_3$) m/z 223 (M+H)$^+$. Anal. Calcd for $C_{11}H_{11}ClN_2O$.1.4 HCl: C, 48.27; H, 4.57; N, 10.23. Found: C, 48.39; H, 4.52; N, 10.33. $[\alpha]_D^{23}$ +27.2 (c 0.36, MeOH).

Example 191

6-Chloro-5-ethenyl-3-(2-(S)-pyrrolidinylmethoxy)pyridine hydrochloride 191 a. 3-(1-BOC-2-(S)-pyrrolidinylmethoxy)-6-chloro-5-ethenyl-pyridine 3-(1-BOC-2-(S)-pyrrolidinylmethoxy)-5-bromo-6-chloro-pyridine from Example 69a (0.95 g, 2.4 mmol) and tetrakis(triphenylphophino) palladium (0.14 g, 0.12 mmol) were dissolved in toluene (50 mL) and degassed with nitrogen gas for 5 min. Vinyl tributyltin (0.78 mL, 2.67 mmol) was added and the mixture was heated to 90° C. for 1 day. The reaction solvent was evaporated and the crude residue was chromatographed (silica gel; hexanes/EtOAc, 4:1) to provide the title compound (0.69 g, 2.04 mmol, 85%). TLC $R_f$ 0.3 (4:1 hexanes/EtOAc). MS ($CI/NH_3$) m/z 339 (M+H)$^+$. Continued elution provided a minor amount of 5,6-diethenylpyridine (0.044 g, 0.13 mmol, 5.5%): TLC $R_f$ 0.25 (4:1 hexanes/EtOAc); MS ($CI/NH_3$) m/e 331 (M+H)$^+$.

191b. 6-Chloro-5-ethenyl-3-(2-(S)-pyrrolidinylmethoxy)pyridine hydrochloride

The compound from Example 191a (150 mg, 0.44 mmol) was treated with 4N HCl (10 mL) in dioxane at 0° C. and immediately allowed to warm to ambient temperature. After 30 min, the reaction was quenched withe $Et_2O$ and the resulting solid was collected, rinsed with fresh $Et_2O$ and dried in vacuo to provide the title compound (105 mg, 0.38 mmol, 86%): mp 195–7° C.; $^1H$ NMR ($CD_3OD$) δ 1.94 (m, 1H), 2.05–2.20 (m, 2H), 2.27 (m, 1H), 3.38 (t, 2H, J=7.0 Hz), 4.07 (m, 1H), 4.24 (dd, 1H, J=7.0, 11.0 Hz), 4.46 (dd, 1H, J=3.0, 11.0 Hz), 5.57 (d, 1H, J=12.0 Hz), 5.96 (d, 1H, J=17.0 Hz), 7.01 (dd, 1H, J=12.0, 17.0 Hz), 7.73 (d, 1H, J=3.0 Hz), 8.06 (d, 1H, J=3.0 Hz); MS ($CI/NH_3$) m/z 239 (M+H)$^+$, 258 (M+$NH_4$)$^+$. Anal. Calcd for $C_{12}H_{15}ClN_2O$.2 HCl: C, 46.25; H, 5.50; N, 8.99. Found: C, 46.08; H, 5.28; N, 8.82. $[\alpha]_D^{25}$ +10.3 (c 0.65, MeOH).

Example 192

6-Chloro-5-ethenyl-3-(1-methyl-2-(S)-pyrrolidinylmethoxy)pyridine hydrochloride

6-Chloro-5-ethenyl-3-(1-methyl-2-(S)-pyrrolidinylmethoxy)pyridine hydrochloride

The product of Example 191a (150 mg, 0.44 mmol) was treated with formalin (6 mL) and formic acid (3 mL) at 80° C. for 4 h. The reaction was cooled to ambient temperature and carefully poured into saturated bicarbonate solution and the product was then extracted into EtOAc. The EtOAc was washed with water and dried ($MgSO_4$). The crude neutral product was dissolved in $Et_2O$ and treated with 1M HCl in $Et_2O$ (1 mL) and the resulting solid was filtered and rinsed with fresh $Et_2O$ provide the title compound (72 mg, 0.25 mmol, 56%): mp 182–4° C.; $^1H$ NMR ($CD_3OD$) δ 2.02–2.25 (m, 3H), 2.34–2.45 (m, 1H), 3.08 (s, 3H), 3.74 (m, 1H), 3.90 (m, 1H), 3.37 (dd, 1H, J=7.0, 11.0 Hz), 4.52 (dd, 1H, J=4.0, 11.0 Hz), 5.58 (dd, 1H, J=1.0, 11.0 Hz), 5.99 (dd, 1H, J=1.0, 17.0 Hz), 7.01 (dd, 1H, J=11.0, 17.0 Hz), 7.76 (d, 1H, J=3.0 Hz), 8.09 (d, 1H, J=3.0 Hz); MS ($CI/NH_3$) m/z 253 (M+H)$^+$. Anal. Calcd for $C_{13}H_{17}ClN_2O$.1.2 HCl: C, 52.66; H, 6.19; N, 9.45. Found: C, 52.46; H, 6.11; N, 9.16. $[\alpha]_D^{25}$ –5.0 (c 0.5, MeOH).

Example 193

5,6-Diethenyl-3-(2-(S)-pyrrolidinylmethoxy)pyridine hydrochloride 5,6-Diethenyl-3-(2-(S)-pyrrolidinylmethoxy)pyridine hydrochloride The by product of example 191a (77 mg, 0.23 mmol) was treated with formalin (6 mL) and formic acid (3 mL) at 80° C. for 4 h. The reaction was cooled to ambient temperature and carefully poured into saturated bicarbonate solution and the product was then extracted into EtOAc. The EtOAc was washed with water and dried ($MgSO_4$). The crude neutral product was dissolved in $Et_2O$ and treated with 1M HCl in $Et_2O$ (1 mL) and the resulting solid was filtered and rinsed with fresh $Et_2O$ to provide the title compound (37 mg, 0.14 mmol, 61%): mp 186–8° C.; $^1H$ NMR ($CD_3OD$) δ 5.89–2.36 (m, 4H), 3.38–3.44 (m, 2H), 4.11 (m, 1H), 4.43 (dd, 1H, J=8.0, 11.0 Hz), 4.61 (dd, 1H, J=4.0, 11.0 Hz), 5.76 (d, 1H, J=11.0 Hz), 5.96 (d, 1H, J=11.0 Hz), 6.09 (d, 1H, J=17.0 Hz), 6.16 (d, 1H, J=17.0 Hz), 7.0–7.16 (m, 2H), 8.24 (d, 1H, J=3.0 Hz), 8.43 (d, 1H, J=3.0 Hz); MS ($CI/NH_3$) m/z 231 (M+H)$^+$. Anal. Calcd for $C_{14}H_{18}N_2O$.2.5 HCl: C, 52.31; H, 6.43; N, 8.71. Found: C, 52.33; H, 6.14; N, 8.47. $[\alpha]_D^{25}$ +6.7 (c 0.33, MeOH).

Example 194

6-Chloro-5-(ethynyl-3-(2-(S)-pyrrolidinylmethoxy)pyridine hydrochloride 194a. 6-Chloro-5-(2-trimethylsilylethynyl-3-(1-BOC-2-(S)-pyrrolidinylmethoxy)pyridine 3-(1-BOC-2-(S)-pyrrolidinylmethoxy)-5-bromo-6-chloropyridine from Example 69a (510 mg, 1.3 mmol) and tetrakis(triphenylphosphine)palladium (81 mg, 0.07 mmol) were dissolved in toluene (20 mL) and the solution was degassed by a nitrogen gas stream for 5 min. CuI (25 mg, 0.13 mmol) and trimethylsilylacetylene (0.22 mL, 1.56 mmol) were added and the reaction was heated at 90° C. for 2 days. The crude reaction mixture was chromatographed (silica gel; hexanes/EtOAc, 6:1) to provide the title compound (242 mg, 0.59 mmol, 46%): TLC $R_f$ 0.6 (2:1 hexanes/EtOAc); MS ($CI/NH_3$) m/z 409 (M+H)$^+$.

194b. 6-Chloro-5-ethynyl-3-(2-(S)-pyrrolidinylmethoxy)pyridine

The product of step a (154 mg, 0.38 mmol) was dissolved in MeOH (10 mL) and treated with potassium carbonate (57 mg, 0.42 mmol) for 2 H at ambient temperature. The reaction was poured into EtOAc and washed and dried ($MgSO_4$). TLC $R_f$ 0.5 (4:1 hexanes/EtOAc). MS ($CI/NH_3$) m/z 337. The residue was treated with 4N HCl in dioxane pre-cooled to 0° C. and allowed to warm to ambient temperature. After 30 min, the reaction was quenched by the addition of $Et_2O$ and the resulting solid was collected and rinsed with fresh ether to provide the title compound (87 mg, 0.32 mmol, 84%): TLC $R_f$ 0.6 (70:30:1 $CHCl_3$/MeOH/$NH_4OH$); mp 214–6° C.; $^1H$ NMR ($CD_3OD$) δ 1.91 (m, 1H), 2.04–2.18 (m, 2H), 2.28 (m, 1H), 3.38 (t, 2H, J=7 Hz), 4.03 (m, 1H), 4.12 (s, 1H), 4.20 (dd, 1H, J=8.0, 10.0 Hz), 4.42 (dd, 1H, J=3.0, 10.0 Hz), 7.66 (d, 1H, J=3.0 Hz), 8.14 (d, 1H, J=3.0 Hz); MS ($CI/NH_3$) m/z 237 (M+H)$^+$. Anal. Calcd for $C_{12}H_{13}ClN_2O$.1.2 HCl: C, 51.39; H, 5.10; N, 9.99. Found: C, 51.61; H, 4.91; N, 9.98. $[\alpha]_D^{25}$ +10 (c 0.67, MeOH).

Example 195

6-Chloro-5-ethynyl-3-(1-methyl-2-(S)-pyrrolidinylmethoxy)pyridine hydrochloride

The product from Example 194a (240 mg, 0.59 mmol) was treated with $K_2CO_3$ as in Example 194b followed, after extractive workup and evaporation, by treatment with formic acid and formic acid as in Example 193 with heating for 2 h at 80° C. to privide the neutral product (256 mg) which was dissolved in ether and treated with 1N HCl in ether to provide the title compound (92 mg, 0.32 mmol, 54%): TLC $R_f$ 0.25 (90:10:1 CHCl$_3$/MeOH/NH$_4$OH); mp 170 (dec); $^1$H NMR (CD$_3$OD, 300 MHz) δ 2.03–2.26 (m, 3H), 2.39 (m, 1H), 3.06 (s, 3H), 3.26 (m, 1H), 3.73 (br s, 1H), 3.90 (br s, 1H), 4.13(s, 1H), 4.32 (dd, 1H, J=7.0, 11.0 Hz), 4.50 (dd, H, J=3.0, 11.0 Hz), 7.70 (d, 1H, J=3.0 Hz), 8.18 (d, H, =3.0 Hz); Anal. Calcd for C$_{13}$H$_{15}$N$_2$OCl.1.2HCl: C, 53.02; H, 5.54; N, 9.51; Found: C, 52.82; H, 5.45; N, 9.2. [α]$^{25}_D$ –8.1 (c 0.54, MeOH)

Example 196

5-Ethenyl-6-methyl-3-(1-methyl-2-(S)-azetidinylmethoxy)pyridine 196a. 3-Bromo-2-methyl-5-nitropyridine 3-Bromo-2-chloro-5-nitropyridine (25 g, 105 mmol; prepared from 2-hydroxy-5-nitropyridine according to the procedure of V. Koch and S. Schnatterer, *Synthesis* 1990, 499–501) was treated with the sodium salt of diethylmalonate (17.6 mL, 116 mmol) according to the procedure of Odashima et al Bull Chem Soc Jpn 1993, 66, 797–803) to provide 17.1 g (78.8 mmol, 75%) of dark red oil: TLC $R_f$ 0.5 (4:1 hexanes/EtOAc); $^1$H NMR (CDCl$_3$, 300 MHz) δ 2.81 (s, 3H), 8.61 (d, 1H, J=2.0 Hz), 9.26 (d, 1H, J=2.0 Hz).

196b. 5-Amino-3-bromo-2-methylpyridine

The compound of 196a (17.1 g, 78.8 mmol) was dissolved in HOAc (50 mL) and water (150 mL) and treated with iron powder (13.3 g, 236 mmol) added in portions over 2 h. The reaction was filtered and the filtrate was extracted with EtOAc. The filter cake was also washed with EtOAc and all EtOAc washings were combined and extracted with 1M bicarbonate followed by water and dried (MgSO$_4$) to provide 12.65 g (67.6 mmol, 86%) of amine product: TLC $R_f$ 0.25 (2:1 hexanes/EtOAc); MS (CI/NH$_3$) m/z 187 (M+H)$^+$, 204 (M+NH$_4$)$^+$ 196c. 5-196c. Acetoxy-3-bromo-2-methylpyridine The compound of 196b (12.6 g, 67 mmol) was treated with tbutyl nitrite and boron trifluoride etherate followed by acetic anhydride as described by Doyle and Bryker (J Org Chem 1979, 44, 1572–3) and Koch and Schnatterer (Synthesis 1990, 499–501) to provide the title compound (12.0 g, 52 mmol, 58% yield) after chromatography on silica with hexanes-EtOAc (4:1) elution. TLC $R_f$ 0.5 (2:1 hexanes/EtOAc): MS (CI/NH$_3$) m/z 230 (M+H)$^+$.

196d. 3-bromo-5-hydroxy-2-methylpyridine

The compound of 196c was stirred with 75 mL of 15% NaOH at 0° C. and then allowed to warm to ambient temperature. After 1 h, the reaction was acidified with 6N HCl with cooling and the resulting suspension was extracted with EtOAc. The EtOAc was washed until neutral, dried (MgSO$_4$) and evaporated to provide the title compound (7.0 g, 37 mmol, 95%): TLC $R_f$ 0.25 (2:1 hexanes/EtOAc); MS (CI/NH$_3$) m/z 188 (M+H)$^+$, 207 (M+NH$_4$)$^+$; $^1$H NMR (CDCl$_3$, 300 MHz) δ 2.59 (s, 3H), 7.46 (d, 1H, J=2.0 Hz), 8.10 (d, 1H, J=2.0 Hz).

196e 3-(1-BOC-2-(S)-azetidinylmethoxy)-5-bromo-6-methyl-pyridine

Triphenylphosphine (6.3 g, 24 mmol) was dissolved in THF (100 mL), cooled to 0° C. and treated with diethylazodicarboxylate (3.8 mL, 24 mmol) for 15 min. Then the compound of 196d (3 g, 16 mmol) followed by 1-BOC-2-(S)-azetidinemethanol (3.4 g, 18 mmol) was added and the reaction was allowed to warm slowly to ambient temperature. After 3 days, the solvent was evaporated and the crude residue was chromatographed (silica gel; hexanes/EtOAc, 4:1) to provide an oil. The product was contaminated with a byproduct related to the DEAD reagent and was taken forward as is; the subsequent allowed isolation of the byproduct and revealed ~35 wt % contamination therefor the calculated yield was 70% (4.0 g, 11.2 mmol): TLC $R_f$ 0.6 (1:1 hexanes/EtOAc); MS (CI/NH$_3$) m/z 357 (M+H)$^+$.

196f 3-(1-BOC-2-(S)-azetidinylmethoxy)-5-ethenyl-6-methyl-pyridine

The product of 196e (1.0 g, 2.8 mmol) and tributylvinyl tin hydride (0.98 mL, 3.4 mmol) and tetrakis(triphenylphosphine)palladium (161 mg, 0.14 mmol) were as in Example 191a to provide the title compound (0.48 g, 1.58 mmol, 56%) after chromatography (silica gel; hexanes/EtOAc, 4:1): MS (CI/NH$_3$) 305 (M+H)$^+$.

196g 3-(1-Methyl-2-(S)-azetidinylmethoxy)-5-ethenyl-6-methyl-pyridine 3-(1-BOC-2-(S)-azetidinylmethoxy)-5-ethenyl-6-methyl-pyridinee (128 mL, 0.63 mmol) sodium cyanoborohydride (79 mg, 1.25 mmol), formalin (37%, 1 mL) and HOAc (0.5 mL) were mixed in water (5 mL) for 2 h. The reaction was poured into CH$_2$Cl$_2$, washed with 1N NaOH, then H$_2$O and dried (MgSO$_4$). Evaporation of the solvent provided the title compound (98 mg, 0.34 mmol, 53%): mp 140–3° C.; $^1$H NMR (CD$_3$OD, 300 MHz) δ 2.57–2.71 (m, 5H), 3.04 (s, 3H), 4.03 (dd, 1H, J=10.0, 19.0 Hz), 4.27 (m, 1H), 4.51–4.6 (m, 2H), 4.82 (m, 1H), 5.69 (d, 1H, J=11.0 Hz), 6.06 (d, 1H, J=17.0 Hz), 6.99( dd, 1H, J=11.0, 17.0 Hz), 8.11 (d, 1H, J=2.0 Hz), 8.37 (d, 1H, J=2.0 Hz); Anal. Calcd for C$_{13}$H$_{18}$N$_2$O.2.0 HCl.0.3 H2O: C, 52.64; H, 7.00; N, 9.44; Found: C, 52.66, H, 6.84; N, 9.82. [α]$^{25}_D$ –25.0 (0.5, MeOH).

Example 197

5-Methoxyethoxy-3-(2-(S)-pyrrolidinylmethoxy) pyridine dihydrochloride 197a. 3-Benzyloxy-5-bromopyridine NaH (60% in mineral oil) (40.9 g, 1.03 mol) in 800 mL of DMF was cooled to 0° C. and benzyl alcohol (105 mL, 1.02 mol) was added slowly. The reaction mixture was stirred for 1 h at 20° C., then 3,5-dibromopyridine (200.4 g, 846 mmol) was added and the mixture was stirred for 16 h. The mixture was quenched with saturated NH$_4$Cl (500 mL), diluted with 400 mL of water and extracted with Et$_2$O (5×300 mL). The combined Et$_2$O extracts were washed with 50% brine (6×300 mL) and dried (MgSO$_4$). The solvent was evaporated in vacuo and the crude product was recrystallized from Et$_2$O to afford 161 g (72%) of the title product: mp 63–68° C.; $^1$H NMR (CDCl$_3$, 300 MHz) δ 5.1 (s, 1H), 7.35–7.50 (m, 6H), 8.27–8.37 (m, 2H); MS (CI/NH$_3$) m/z 264, 266 (M+H)$^+$.

197b. 3-Amino-5-benzyloxypyridine

The product of Example 197a (41.3 g, 156 mmol), copper (I) bromide (22.43 g, 156 mmol), MeOH (275 mL), and liquid NH$_3$ (50 mL) were combined in a stainless steel reactor and heated to 130° C. for 24 h. The mixture was allowed to cool to ambient temperature, then concentrated. The residue was suspended in 300 mL of saturated aqueous Na$_2$CO$_3$ and extracted with CH$_2$Cl$_2$ (4×500 mL). The combined CH$_2$Cl$_2$ extracts were washed with brine, dried (MgSO$_4$), and concentrated. The crude product was chromatographed (silica gel; hexane/EtOAc, 9:1 to 7:3) to afford the title compound (15.6 g, 50 %): $^1$H NMR (CDCl$_3$, 300 MHz) δ 5.10 (s, 2H), 7.30–7.45 (m, 6H), 8.20–8.30 (m, 2H); MS (CI/NH$_3$) m/z 201 (M+H)$^+$.

197c. 3-Benzyloxy-5-methoxyethoxypyridine

To boron trifluoride etherate (9.3 mL, 75 mmol) that had been cooled to –15° C. under N$_2$ was added the product of Example 197b (10 g, 50 mmol) dissolved in DME (100 mL). Tert-butyl nitrite (7.8 mL, 65 mmol) was added at a rate which kept the temperature below −5° C. After 10 minutes at −10° C., the reaction was warmed to 5° C. and stirred for 30 min. Pentane (200 mL) was then added to the reaction mixture, and the solid was collected by suction filtration, washed with cold Et$_2$O, and then dissolved in DME (150 mL). The resulting solution was heated to 70° C. until N$_2$ evolution stopped. The solvent was removed in vacuo, and the residue was suspended in saturated aqueous Na$_2$CO$_3$ (150 mL) and extracted with Et$_2$O (2×150 mL). The Et$_2$O solution was dried (Na$_2$SO$_4$) and concentrated. The crude product was chromatographed (silica gel; hexane/EtOAc, 6:1) to yield the title compound (2.0 g): $^1$H NMR (CDCl$_3$, 300 MHz) δ 3.42 (s, 3H), 3.75 (t, 2H, J=6.0 Hz), 3.90 (t, 2H, J=6.0 Hz), 5.15 (s, 2H), 6.95 (br s, 1H), 7.38–7.45 (m, 5H), 7.62 (br s, 1H), 7.95 (d, 1H, J=3.0 Hz); MS (CI/NH$_3$) m/z 260 (M+H)$^+$, 277 (M+NH$_4$)$^+$.

197d. 3-Hydroxy-5-methoxyethoxypyridine

The product from Example 197c (1.0 g, 3.86 mmol) in MeOH (10 mL) was stirred under an atmosphere of H$_2$ in the presence of 10% Pd/C (50 mg) for 4 h. The mixture was filtered and concentrated to afford 650 mg (99%) of the title compound as white solid: $^1$H NMR (CDCl$_3$, 300 MHz) δ 3.50 (s, 3H), 3.85 (t, 2H, J=6.0 Hz), 4.02 (t, 2H, J=6.0 Hz), 7.12 (br s, 1H), 7.75 (br s, 1H), 7.82 (d, 1H, J=3.0 Hz); MS (CI/NH$_3$) m/z 170 (M+H)$^+$, 187 (M+NH$_4$)$^+$.

197e. 3-(1-BOC-2-(S)-pyrrolidinylmethoxy)-5-methoxyethoxypyridine

Triphenylphosphine (813 mg, 3.02 mmol) was dissolved in THF (15 mL), cooled to 0° C., and treated with DEAD (0.5 mL, 3.02 mmol) for 15 minutes. Then the compound from Example 197d (300 mg, 1.78 mmol) and 1-BOC-2-(S)-pyrrolidinemethanol (428 mg, 2.13 mmol) were added, and the mixture was allowed to warm slowly to ambient temperature. After 16 h, the solvent was evaporated and the residue was chromatographed (silica gel; hexane/EtOAc, 4:1) to provide the title compound (500 mg, 80%) as an oil: 1HNMR (CDCl$_3$, 300 MHz) δ 1.40 (s, 9H), 2.00–2.07 (m, 2H), 2.25–2.32 (m, 2H), 3.40 (s, 3H), 3.75 (t, 2H, J=6.0 Hz), 3.92 (t, 2H, J=6.0 Hz), 4.15–4.25 (m, 4H), 4.52 (m, 1H), 6.98 (br s, 1H), 7.45 (m, 1H), 7.85 (d, 1H, J=3.0 Hz); MS (CL/NH$_3$) m/z 353 (M+H)$^+$.

197f. 5-Methoxyethoxy-3-(2-(S)-pyrrolidinylmethoxy)pyridine dihydrochloride

To 3-(1-BOC-2-(S)-pyrrolidinylmethoxy)-5-methoxyethoxypyridine from step 197e (480 mg, 1.36 mmol) in CH$_2$Cl$_2$ at 0° C. was added a solution of HCl in Et$_2$O, and the solution was stirred for 2 h. The solvent was removed and the residue was recrystallized from EtOH/Et$_2$O to afford the title compound (215 mg): mp 182–184° C.; [α]$^{25}_D$ +22.8° (c 0.56, MeOH); $^1$H NMR (D$_2$O, 300 MHz) δ 1.98 (m, 1H), 2.00–2.06 (m, 2H), 2.25 (m, 1H), 3.00 (m, 1H), 3.05 (s, 3H), 3.65 (t, 2H, J=6.0 Hz), 3.85 (t, 2H, J=6.0 Hz), 4.15 (m, 1H), 4.30–4.35 (m, 2H), 4.52 (m, 1H), 7.15 (t, 1H, J=3.0 Hz), 8.02 (br s, 2H); MS (CI/NH$_3$) m/z 253 (M+H)$^+$, 279 (M+NH$_4$)$^+$; Anal. Calcd for C$_{13}$H$_{20}$N$_2$O$_3$.2.1 HCl: C, 47.48; H, 6.77; N, 8.52. Found: C, 47.56; H, 6.83; N, 8.51.

Example 198

5-Methoxyethoxy-3-(1-methyl-(2S)-pyrrolidinylmethoxy)pyridine dihydrochloride 198a. 5-Methoxyethoxy-3-(1-methyl-2-(S)-pyrrolidinylmethoxy)pyridine To 5-methoxyethoxy-3-(2-(S)-pyrrolidinylmethoxy) pyridine from Example 197f (450 mg, 1.78 mmol) was added formaldehyde (37%, 8 mL) and formic acid (88%, 4 mL), and the mixture was heated at 50° C. for 4 h and then allowed cool to room temperature. The mixture was basified with saturated NaHCO$_3$ and then extracted with Et$_2$O. The organic layer was dried over Na$_2$SO$_4$ and concentrated. The residue was chromatographed (silica gel; hexane/EtOAc, 2:1) to afford the title compound (402 mg, 85%): $^1$H NMR (CDCl$_3$, 300 MHz) δ 2.00–2.08 (m, 4H), 2.45 (m, 1H), 3.05 (s, 3H), 3.45 (s, 3H), 3.65 (t, 2H, J=6.0 Hz), 3.85 (t, 2H, J=6.0 Hz), 4.15 (m, 1H), 4.30–4.35 (m, 2H), 4.52 (m, 1H), 7.25 (t, 1H, J=3.0 Hz), 8.02 (br s, 2H); MS (CI/NH$_3$) m/z 267 (M+H)$^+$.

198b. 5-Methoxyethoxy-3-(1-methyl-2-(S)-pyrrolidinylmethoxy)pyridine dihydrochloride To 5-methoxyethoxy-3-(1-methyl-2-(S)-pyrrolidinylmethoxy)pyridine from step 198a (300 mg, 1.12 mmol) in CH$_2$Cl$_2$ at 0° C. was added a solution of HCl in Et$_2$O, and the solution was stirred for 2 h. Solvent was removed and the residue was recrystallized from EtOH/Et$_2$O to afford the title compound (225 mg, 95%): mp 196–197° C.; [α]$^{25}_D$+25.4° (c 0.61, MeOH); $^1$H NMR (D$_2$O, 300 MHz) δ 2.05–2.15 (m, 4H), 2.65 (m, 1H), 3.00 (s, 3H), 3.65 (s, 3H), 3.72 (t, 2H, J=6.0 Hz), 3.85 (t, 2H, J=6.0 Hz), 4.25 (m, 1H), 4.62–4.66 (m, 2H), 4.80 (m, 1H), 7.42 (t, 1H, J=3.0 Hz), 8.15 (br s, 2H); MS (CI/NH$_3$) m/z 267 (M+H)$^+$; Anal. Calcd for C$_{14}$H$_{22}$N$_2$O$_3$.2 HCl: C, 49.56; H, 7.13; N, 8.26. Found: C, 49.68; H, 7.05; N, 8.18.

Example 199

3-(2-(S)-Azetidinylmethoxy)-5-benzyloxypyridine dihydrochloride 199a. 3-Acetoxy-5-benzyloxypyridine To boron trifluoride etherate (9.3 mL, 75 mmol) that had been cooled to −15° C. under N$_2$ was added the product of Example 197b (10 g, 50 mmol) dissolved in DME (100 mL). Tert-butyl nitrite (7.8 mL, 65 mmol) was added at a rate which kept the temperature below −5° C. After 10 min at −10° C., the reaction was warmed to 5° C. and stirred for 30 min. Pentane (200 mL) was then added to the reaction mixture, and the solid was collected by suction filtration, washed with cold Et$_2$O, and then dissolved in acetic anhydride (150 mL). The resulting solution was heated to 70° C. until N$_2$ envolution stopped. The solvent was removed in vacuo, and the residue was suspended in saturated aqueous Na$_2$CO$_3$ (150 mL) and extracted with Et$_2$O (2×150 mL). The Et$_2$O extract was dried (Na$_2$SO$_4$) and concentrated. The crude product was chromatographed (silica gel; hexane/EtOAc, 6:1) to yield the title compound (2.0 g): $^1$H NMR (CDCl$_3$, 300 MHz) δ 2.35 (s, 3H), 5.15 (s, 2H), 7.15 (t, 1H, J=3.0 Hz), 7.35–7.42 (m, 5H), 8.15 (d, 1H, J=3.0 Hz), 8.30 (d, 1H, J=3.0 Hz); MS (CI/NH$_3$) m/z 244 (M+H)$^+$, 261 (M+NH$_4$)$^+$.

199b. 3-Benzyloxy-5-hydroxypyridine

The product of Example 199a (2 g, 8.4 mmol) was dissolved in MeOH (15 mL), and K$_2$CO$_3$ (600 mg, 4.34 mmol) was added. After complete consumption of the starting material, the solution was neutralized by addition of aqueous HCl (1N). The aqueous mixture was extracted with Et$_2$O (2×150 mL). The organic extracts were dried (Na$_2$SO$_4$) and concentrated. The crude product was triturated with hexane to provide the title compound (1.3 g, 82%) as white solid: $^1$H NMR (DMSO, 300 MHz) δ 5.15 (s, 2H), 6.80 (t, 1H, J=3.0 Hz), 7.35–7.42 (m, 5H), 7.75 (d, 1H, J=3.0 Hz), 7.85 (d, 1H, J=3.0 Hz), 9.95 (br s, 1H); MS (CI/NH$_3$) m/z 202 (M+H)$^+$, 219 (M+NH$_4$)$^+$.

199c. 5-Benzyloxy-3-(1-BOC-2-(S)-azetidinylmethoxy) pyridine

1-BOC-(S)-azetidinemethanol (36.5 g, 0.195 mol) was dissolved in $CH_2Cl_2$ (195 mL) followed by addition of $NEt_3$ (35.6 ml, 0.255 mol) and then toluenesulfonyl chloride (48.5 g, 0.254 mol). The resulting mixture was stirred at room temperature for 16 h. A 10% solution of NaOH was added rapidly and the mixture stirred for 1 h. After phase separation, the aqueous phase was extracted with additional $CH_2Cl_2$, combined with the organic phase, and then washed with $NaHCO_3$ solution and brine. The resulting solution was dried ($MgSO_4$), filtered, and concentrated in vacuo to give 1-BOC-2-(S)-azetidinemethyl-p-toluenesulfonate (63.1 g, 94.8%).

Next, a solution of 3-benzyloxy-5-hydroxypyridine (350 mg, 1.74 mmol), which from step 199b in DMF (20 mL) was treated with ground KOH (154 mg, 2.74 mmol) and stirred for 30 minutes at 80° C. To this mixture was rapdily added the 1-BOC-2-(S)-azetidinemethyl-p-toluenesulfonate (585 mg, 1.74 mmol) dissolved in DMF (5 mL) and subsequently stirred for 16 h at 80° C. The mixture was concentrated to remove the DMF and the resultant residue diluted with water and extracted with EtOAc (3×150 mL). The organic extracts were combined, dried ($Na_2SO_4$), filtered, and concentrated in vacuo to give 800 mg of unpurified product. This material was purified by flash silica gel chromatography using hexane/EtOAc, 10:1 as the mobile phase to give the title compound (575 mg, 90%): $^1$H NMR ($CDCl_3$, 300 MHz) δ 1.40 (s, 9H), 2.26–2.30 (m, 2H), 3.90–2.94 (m, 2H), 4.16 (m, 1H), 4.35 (m, 1H), 4.54 (m, 1H), 5.10 (s, 2H), 6.95 (s, 1H), 7.40–7.46 (m, 5H), 8.20 (br s, 2H); MS (CI/$NH_3$) m/z 371 (M+H)$^+$.

199d. 3-(2-(S)-Azetidinylmethoxy)-5-benzyloxypyridine dihydrochloride

The compound from step 199c was treated with TFA in $CH_2Cl_2$ at 0° C. for 30 minutes. The volatiles were then removed under vacuum. The residue was neutralized with $NaHCO_3$, extracted with $CH_2Cl_2$ and then dried ($MgSO_4$) and concentrated. The unpurified product was chromatographed (silica gel; $CHCl_3$/MeOH/$NH_4OH$, 800:120:9) to afford the free base of the title compound, which was converted to the salt by treatment with a saturated solution of HCl in $Et_2O$ to give the title compound: mp 172–174° C.; $[\alpha]^{25}_D$ -6.24° (c 0.55, MeOH); $^1$H NMR ($D_2O$, 300 MHz) δ 2.62–2.64 (m, 2H), 3.85–3.90 (m, 2H), 4.15 (m, 1H), 4.32 (m, 1H), 4.52 (m, 1H), 5.12 (s, 2H), 7.22 (t, 1H, J=3.0 Hz), 7.40–7.50 (m, 5H), 8.02 (br s, 2H); MS (CI/$NH_3$) m/z 271 (M+H)$^+$. Anal. Calcd for $C_{16}H_{18}N_2O_2$.2.3 HCl: C, 54.26; H, 5.78; N, 7.91. Found: C, 54.03; H, 5.99; N, 7.70.

Example 200

5-Benzyloxy-3-(1-methyl-2-(S)-azetidinylmethoxy) pyridine hydrochloride

5-Benzyloxy-3-(1-methyl-2-(S)-azetidinylmethoxy) pyridine hydrochloride

To 3-(2-(S)-azetidinylmethoxy)-5-benzyloxypyridine from Example 199d (440 mg, 1.63 mmol) in EtOH (3 mL) was added formalin (37%, 10 mL), and adjusted the pH to 6 with HOAc. Then sodium cyanoborohydride (125 mg, 1.96 mmol) was added, and the mixture was stirred at room temperature for 16 h. The mixture was diluted with water and saturated with $K_2CO_3$. The mixture was extracted with $CH_2Cl_2$. The solvent was dried ($MgSO_4$), filtered and concentrated. The residue was chromatographed (silica gel; MeOH/$CHCl_3$, 1:10) to afford the free base of the title compound, which was converted to the salt by treatment with a saturated solution of HCl in $Et_2O$ to give the title compound: mp 132–134° C.; $[\alpha]^{25}_D$ -9.90° (c 0.53, MeOH); $^1$H NMR ($D_2O$, 300 MHz) δ 2.60–2.68 (m, 2H), 3.00 (s, 3H), 3.95–4.00 (m, 2H), 4.15 (m, 1H), 4.32 (m, 1H), 4.52 (m, 1H), 5.30 (s, 2H), 7.45 (m, 1H), 7.40–7.50 (m, 5H), 8.18 (br s, 2H); MS (CI/$NH_3$) m/z 285 (M+H)$^+$. Anal. Calcd for $C_{17}H_{20}N_2O_2$. HCl.0.1 $H_2O$: C, 63.29; H, 6.62; N, 8.68. Found: C, 63.00; H, 6.62; N, 8.15.

Example 201

3-(2-(S)-Azetidinylmethoxy)-6-ethenylpyridine dihydrochloride 201a. 5-Acetoxy-2-chloropyridine To a solution of 5-amino-2-chloropyridine (110 g, 0.86 mol) in DME/$CH_2Cl_2$ (400 mL, 3:1) at -10° C. was slowly added boron trifluoride diethyl etherate (232 mL, 1.88 mol). Then a solution of tret-butyl nitrite (123 mL, 1.03 mol) in DME (100 mL) was slowly added over 15 min such that the reaction temperature remained below -5° C. The mixture was stirred for 10 min at -10° C., then warmed to 0° C. and stirred for an additional 30 min. Pentane was added and the solid was collected by suction filtration (cold pentane wash) to afford the tetrafluoroborate diazonium salt (250 g). The salt was dissolved in 500 mL of acetic anhydride, warmed to 75° C. ($N_2$ evolution) and stirred for 3 h. The volatiles were removed in vacuo and the dark residue was diluted with $Et_2O$ and washed with saturated aqueous $NaHCO_3$. The aqueous phase was extracted with $Et_2O$. The combined $Et_2O$ extracts were washed with brine, dried ($MgSO_4$), and concentrated. Purification by chromatography (silica gel; hexane/EtOAc, 9:1 to 7:3) afforded the title compound (58 g, 60%) as a white solid: mp 45–47° C.; $^1$H NMR ($CDCl_3$, 300 MHz) δ 2.35 (s, 3H), 7.35 (d, 1H, J=8.5 Hz), 7.48 (dd, 1H, J=3.0, 8.5 Hz), 8.21 (d, 1H, J=3.0 Hz); MS (CI/$NH_3$) m/z 172, 174 (M+H)$^+$; 189, 191 (M+$NH_4$)$^+$.

201b. 3-(1-BOC-2-(S)-azetidinylmethoxy)-6-chloropyridine

To a solution of 6-chloro-3-hydroxypyridine (1.2 g, 8.8 mmol) from atep a in DMF (25 mL) was treated with ground KOH (791 mg, 14.1 mmol) and stirred for 30 minutes at 80° C. To this mixture was rapdily added the 1-BOC-2-(S)-azetidinemethyl-p-toluenesulfonate (3.0 mg, 8.8 mmol) from Example 199c dissolved in DMF (5 mL) and subsequently stirred for 16 h at 80° C. The mixture was concentrated to remove the DMF and the resultant residue diluted with water and extracted with EtOAc (3×150 mL). The organic extracts were combined, dried ($Na_2SO_4$), filtered, and concentrated in vacua to give unpurified product (3.12 g). This material was purified by chromatography (silica gel; hexane/EtOAc, 10:1) to give the title compound (2.07 g, 80%): $^1$H NMR ($CDCl_3$, 300 MHz) δ 1.42 (s, 9H), 2.28–2.32 (m, 2H), 3.90–3.94 (m, 2H), 4.16 (m, 1H), 4.35 (m, 1H), 4.54 (m, 1H), 7.20–7.26 (m, 2H), 8.15 (m, 1H); MS (CI/$NH_3$) m/z 299 (M+H)$^+$, 316 (M+$NH_4$)$^+$.

201c. 3-(1-BOC-2-(S)-azetidinylmethoxy)-6-ethenylpyridine

To a solution of 3-(1-BOC-2-(S)-azetidinylmethoxy)-6-chloropyridine (1.8 g, 6.04 mmol) in toluene (25 mL) was added vinyltributyltin (2.7 mL, 9.06 mmol) and [1,1'-bis(diphenylphosphino)ferrocene]dichloropalladium(II) (180 mg). After heating at reflux for 16 h, the resulting mixture was cooled to room temperature and the solvent was removed. The residue was chromatographed (silica gel; hexane/EtOAc, 10:1) to afford the title compound (1.49 g, 85%): $^1$H NMR ($CDCl_3$, 300 MHz) δ 1.40 (s, 9H), 2.25–2.30 (m, 2H), 3.85–3.90 (m, 2H), 4.16 (m, 1H), 4.35 (m, 1H), 4.54 (m, 1H), 5.35 (dd, 1H, J=1.0, 12.0 Hz), 6.05 (dd, 1H, J=1.0, 18.0 Hz), 6.80 (dd, 1H, J=12.0, 18.0 Hz), 7.20–7.26 (m, 2H), 8.35 (d, 1H, J=3.0 Hz); MS (CI/NH$_3$) m/z 291 (M+H)$^+$, 319 (M+NH$_4$)$^+$.

201d. 3-(2-(S)-Azetidinylmethoxy)-6-ethenylpyridine dihydrochloride

The protecting group was removed from the compound from step 201b by treatment with TFA in CH$_2$Cl$_2$ at 0° C. for 30 min. The volatiles were then removed under vacuum. The residue was neutralized with NaHCO$_3$, then extracted with CH$_2$Cl$_2$, dried (MgSO$_4$) and concentrated. The free base was chromatographed (silica gel; MeOH/CHCl$_3$, 1:10) to afford the free base of the title compound, which was converted to the salt by treatment with a saturated solution of HCl in Et$_2$O to give the title compound (87 mg, 75%): mp 102–104° C.; [α]$^{25}_D$ −14.9 (c 0.51, MeOH); $^1$H NMR (D$_2$O, 300 MHz) δ 2.70 (q, 2H, J=9.0 Hz), 3.62 (m, 1H), 4.10–4.18 (m, 2H), 4.42 (m, 1H), 4.98 (m, 1H), 5.35 (d, 1H, J=12.0 Hz), 6.05 (d, 1H, J=18.0 Hz), 6.80 (dd, 1H, J=12.0, 18.0 Hz), 7.20–7.26 (m, 2H), 8.35 (d, 1H, J=3.0 Hz); MS (CI/NH$_3$) m/z 191 (M+H)$^+$. Anal. Calcd for C$_{11}$H$_{14}$N$_2$O.2.9 HCl.0.1 EtOH: C, 44.75; H, 5.87; N, 9.32. Found: C, 44.87; H, 5.98; N, 9.01.

Example 202

6-Ethenyl-3-(1-methyl-2-(S)-azetidinylmethoxy) pyridine dihydrochloride

6-Ethenyl-3-(1-methyl-2-(S)-azetidinylmethoxy)pyridine dihydrochloride

To 3-(2-(S)-azetidinylmethoxy)-6-ethenylpyridine from Example 201d (450 mg, 2.37 mmol) in EtOH (3 mL) was added formalin (37%, 10 mL), and adjusted the pH to 6 with HOAc. Then sodium cyanoborohydride (179 mg, 2.84 mmol) was added, and the mixture was stirred at room temperature for 16 h. The mixture was diluted with water and saturated with K$_2$CO$_3$. The mixture was extracted with CH$_2$Cl$_2$. The organic extract was dried (MgSO$_4$), filtered and concentrated. The residue was chromatographed (silica gel; MeOH/CHCl$_3$, 1:10) to afford the free base of the title compound (250 mg, 52%), which was converted to the salt by treatment with a saturated solution of HCl in Et$_2$O to give the title compound (215 mg, 95%): mp 105–107° C.; [α]$^{25}_D$ −29.6 (c 0.56, MeOH); $^1$H NMR (D$_2$O, 300 MHz) δ 2.65–2.70 (m, 2H), 3.00 (s, 3H), 4.00 (q, J=9.0 Hz, 1H), 4.30 (m, 1H), 4.50–4.54 (m, 2H), 4.75 (m, 1H), 5.50 (d, 1H, J=12.0 Hz), 6.10 (d, 1H, J=18.0 Hz), 6.90 (dd, 1H, J=12.0, 18.0 Hz), 7.60 (dd, 2H, J=3.0, 9.0 Hz), 8.30 (d, 1H, J=3.0 Hz); MS (CI/NH$_3$) m/z 205 (M+H)$^+$. Anal. Calcd for C$_{12}$H$_{16}$N$_2$O.2HCl.0.6 H$_2$O: C, 50.05; H, 6.72; N, 9.73. Found: C, 50.35; H, 6.55; N, 9.37.

Example 203

3-(2-(S)-Azetidinylmethoxy)-5-ethenyl-6-fluoropyridine tosylate 203a 5-Amino-3-ethenyl-2-fluoropyridine To a stirred solution of 5-amino-3-bromo-2-fluoropyridine (3.25 g, 17.0 mmol) in toluene (20 mL) was added tributyl(vinyl)tin (7.64 g, 20.4 mmol) followed by tetrakis(triphenylphosphine) palladium (Aldrich, 0.63 g, 1.7 mmol). The reaction mixture was heated at 100° C. for 24 h. The solvent was removed in vacuo and the residue was purified by column chromatography (silica gel; EtOAc/hexane, 4:6) to afford the title compound as a beige solid (2.30 g, 98%): $^1$H NMR (CDCl$_3$, 300 MHz) δ 3.61 (br s, 2H), 5.44 (d, J=11.5 Hz, 1H), 5.83 (d, J=17.5 Hz, 1H), 6.66 (m, 1H), 7.18 (dd, J=3.0, 5.0 Hz, 1H), 7.52 (m, 1H); MS (CI/NH$_3$) m/z 139 (M+H)$^+$, 156 (M+NH$_4$)$^+$.

203b. 5-Acetoxy-3-ethenyl-2-fluoropyridine

To a stirred solution of the 5-amino-2-fluoro-3-ethenylpyridine from a above (3.00 g, 21.7 mmol) in 3:1 DME:CH$_2$Cl$_2$ (50 mL) at −10° C. was slowly added borontrifluoride etherate (5.60 mL, 45.6 mmol). t-Butylnitrite (3.10 mL, 26.0 mmol) was added over the course of 15 min, keeping the reaction temperature below −5° C. The reaction mixture was warmed to 0° C. and stirred for 30 min. Pentane (500 mL) was added and the solid tetrafluoroborate diazonium salt was collected by filtration. The diazonium salt was dissolved in acetic anhydride (40 mL) and heated at 95° C. for 2 h—N$_2$ evolution was noted at 85° C. The solvent was evaporated, the residue was dissolved in Et$_2$O (250 mL), and washed with saturated, aqueous NaHCO$_3$ (2×150 mL). The combined aqueous phases were extracted with Et$_2$O (2×150 mL). The combined organic phases were washed with brine (50 mL), dried (MgSO$_4$), and concentrated. The crude product was purified by column chromatography (silica gel; EtOAc/hexane, 4:6) to afford the desired product as a yellow oil (1.51 g, 40%): $^1$H NMR (CDCl$_3$, 300 MHz) δ 2.35 (s, 3H), 5.54 (d, J=11.0 Hz, 1H), 5.90 (d, J=18.0 Hz, 2H), 6.75 (m, 1H), 7.66 (dd, J=2.0, 5.0 Hz, 1H); MS (CI/NH$_3$) m/z 182 (M+H)$^+$, 199 (M+NH$_4$)$^+$.

203c. 3-Ethenyl-2-fluoro-5-hydroxy-pyridine

To a stirred solution of the 5-acetoxy-2-fluoro-3-ethenylpyridine from b above (1.40 g, 7.70 mmol) in MeOH (50 mL) was added K$_2$CO$_3$ (0.53 g, 3.90 mmol). The reaction mixture was allowed to stir at room temperature 24 h. The solvent was evaporated and the residue was diluted with Et$_2$O (100 mL) and water (100 mL). The phases were separated and the aqueous phase was neutralized (pH=7) by the addition of 1 N aqueous HCl, and extracted with Et$_2$O (2×100 mL). The combined ethereal extracts were washed with brine (50 mL), dried (MgSO$_4$), and the solvent was evaporated. The crude product was purified by column chromatography (silica gel; EtOAc/hexane, 4:6) to afford the desired material as an off-white solid (0.81 g, 76%): $^1$H NMR (CDCl$_3$, 300 MHz) δ 5.50 (d, J=11.0 Hz, 1H), 5.87 (d, J=17.5 Hz, 1H), 6.75 (m, 1H), 7.72 (dd, J=3.0, 5.0 Hz, 1H), 7.69 (m, 1H); MS (CI/NH$_3$) m/z 140 (M+H)$^+$, 157 (M+NH$^4$)$^+$.

203d. 3-(1-BOC-2-(S)-azetidinylmethoxy)-5-ethenyl-6-fluoropyridine

To a solution of 2-fluoro-5-hydroxy-3-ethenylpyridine (0.60 g, 4.3 mmol) in DMF (10 mL) was added powdered potassium hydroxide (0.36 g, 6.5 mmol) and the reaction mixture was stirred at room temperature for 1.5 h until the KOH was dissolved. 1-BOC-2-(S)-azetidinemethyl-p-toluenesulfonate (1.96 g, 4.3 mmol) was then added and the reaction mixture was heated at 80° C. for 18 h. The reaction mixture was diluted with water (50 mL) and extracted with EtOAc (3×30 mL). The combined organic extracts were washed with brine (25 ml), dried (MgSO$_4$), and the solvent was removed in vacuo. The crude reaction product was purified by column chromatography (silica gel; CH$_2$Cl$_2$/MeOH, 98:2) to afford the desired material as a yellow oil (1.44 g, >100%): $^1$H NMR (CDCl$_3$, 300 MHz) δ 1.42 (s, 9H), 2.45 (m, 2H), 3.90 (m, 1H), 4.13 (dd, J=3.0, 7.5 Hz, 2H), 4.35 (m, 1H), 4.54 (m, 1H), 5.49 (d, J=11.0 Hz, 1H), 5.89 (d, J=17.5 Hz, 1H), 6.74 (m, 1H), 7.47 (m, 1H), 7.76 (m, 1H); MS (CI/NH$_3$) m/z 309 (M+H)$^+$, 326 (M+NH$_4$)$^+$.

203e. 3-(2-(S)-Azetidinylmethoxy)-5-ethenyl-6-fluoropyridine tosylate

A solution of the coupled product from d above (1.44 g, 4.7 mmol) was dissolved in dry CH$_2$Cl$_2$ (10 mL), and cooled to 0° C. Trifluoroacetic acid (10 mL) was added slowly, and the reaction was allowed to stir at 0° C. for 1 h. The reaction mixture was carefully poured into saturated aqueous NaHCO$_3$ (50 mL), and extracted with EtOAc (3×30 mL). The combined organic extracts were washed with brine (25 mL), dried (MgSO$_4$), and the solvent was evaporated. The crude product was purified by column chromatography (silica gel; MeOH/CH$_2$Cl$_2$, 1:9, then CHCl$_3$/MeOH/ NH$_4$OH, 80:20:1) to afford the desired material as a yellow oil (0.37 g, 41%). The oil was dissolved in EtOH, cooled to 0° C., and p-toluenesulfonic acid monohydrate (0.34 g, 1.8 mmol) was added. After stirring at 0° C. for 30 min, the solvent was evaporated and the residue was triturated from Et$_2$O to afford a light yellow solid (0.30 g, 48% from isolated free amine): mp 251–253° C.; [α]$_D^{25}$ +2.8 (c 0.4, MeOH); $^1$H NMR (DMSO-d$_6$, 300 MHz) δ 2.38 (m, 1H), 2.40 (s, 3H), 2.43 (m, 1H), 3.93 (br m, 2H), 4.37 (m, 1H), 4.44 (m, 1H), 4.74 (m, 1H), 5.60 (d, J=11.0 Hz, 1H), 6.09 (d, J=16.5 Hz, 1H), 6.74 (m, 1H), 7.11 (d, J=8.5 Hz, 2H), 7.48 (d, J=8.0 Hz, 2H), 7.87 (m, 2H), 8.86 (br s, 2H); MS (CI/NH$_3$) m/z 209 (M+H)$^+$, 226 (M+NH$^4$)$^+$; Anal. Calcd for C$_{11}$H$_{13}$FN$_2$O.1.3 TsOH: C, 56.61; H, 5.90; N, 6.67. Found: C,56.23; H, 5.68; N, 6.28.

Example 204

5-Ethenyl-6-fluoro-3-(1-methyl-2-(S)-azetidinylmethoxy) pyridine

5-Ethenyl-6-fluoro-3-(1-methyl-2-(S)-azetidinylmethoxy) pyridine

To a stirred solution of compund obtained from Example 203 above (0.17 g, 0.5 mmol) in 37% formaldehyde (10 mL) was added sodium cyanoborohydride (0.04 g, 0.6 mmol). The reaction mixture was allowed to stir at room temperature for 24 h, diluted with saturated aqueous NaHCO$_3$ (5.0 mL), stirred 15 min, and extracted with EtOAc (4×25 mL). The combined organic extracts were washed with brine (20 mL), dried (MgSO$_4$), and the solvent was evaporated. The crude material was purified by column chromatography (silica gel; MeOH/CH$_2$Cl$_2$, 1:9, then CHCl$_3$/MeOH/ NH$^4$OH, 80:20:1) to afford the desired material as a yellow oil (0.05 g, 45%). The oil was dissolved in EtOH, cooled to 0° C., and treated with p-toluenesulfonic acid monohydrate (0.04 g, 0.2 mmol). After stirring at 0° C. for 20 min, the solvent was evaporated and the residue was triturated from Et$_2$O as a yellow solid (0.04 g, 40%): mp 156–158° C.; [α]$_D^{23}$ +14.5 (c 0.5, MeOH); $^1$H NMR (DMSO-d$_6$, 300 MHz) δ 2.28 (s, 3H), 2.50 (m, 2H), 2.90 (m, 3H), 3.95 (m, 2H), 4.09 (m, 2H), 4.71 (m, 1H), 5.60 (d, J=11.0 Hz, 1H), 6.10 (d, J=7.5 Hz, 2H), 7.10 (d, J=8.5 Hz, 2H), 7.48 (d, J=8.0 Hz, 2H), 7.89 (m, 2H), 9.85 (br s, 1H); MS (CI/NH$_3$) m/z 223 (M+H)$^+$; Anal. Calcd for C$_{12}$H$_{15}$FN$_2$O.1.3 TsOH.0.5 H$_2$O: C, 55.68; H, 5.85; N, 6.15. Found: C, 55.45; H, 6.03; N, 6.29.

Example 205

5-Acetamidomethyl-3-(2-(S)-azetidinylmethoxy) pyridine dihydrochloride 205a. 3-(1-BOC-2-(S)-azetidinylmethoxy)-5-cyanopyridine 3-(1-BOC-2-(S)-azetidinylmethoxy)-5-bromopyridine (1.76 g, 5.10 mmol) from Example 54b was converted to the title compound in 86% yield according to the procedure of Example 92a. $^1$H NMR (CDCl$_3$, 300 MHz) δ 1.42 (s, 9H), 2.21–2.42 (m, 2H), 3.83–3.94 (m, 2H), 4.11 (dd, J=3.0, 10.5 Hz, 1H), 4.34 (m, 1H), 4.51 (m, 1H), 7.35 (s, 1H), 7.38 (d, J=3.0 Hz, 1H), 8.07 (d, J=3.0 Hz, 1H); MS (CI/NH$_3$) m/z 290 (M+H)$^+$.

205b. 5-Aminomethyl-3-(1-BOC-2-(S)-azetidinylmethoxy) pyridine

The product of step 205a (0.81 g, 2.80 mmol) was reduced to the title compound in 43% yield according to the procedure of Example 92b. $^1$H NMR (CDCl$_3$, 300 MHz) δ 1.42 (s, 9H), 2.28–2.42 (m, 2H), 3.88 (t, J=7.0 Hz, 4H), 4.16 (dd, J=3.0, 10.0 Hz, 1H), 4.36 (m, 1H), 4.55 (m, 1H), 7.21(t, J=1.5 Hz, 1H), 8.18 (s, 1H), 8.23 (d, J=2.5 Hz, 1H); MS (CI/NH$_3$) m/z 294 (M+H)$^+$.

205c. 5-Acetamidomethyl-3-(1-BOC-2-(S)-azetidinylmethoxy)pyridine

The product of step 205b (0.35 g, 1.20 mmol) in pyridine (3 mL) was treated with acetic anhydride (0.13 g, 1.30 mmol). After 1 h, the solvent was evaporated and the residue was chromatographed (silica gel; MeOH/CH$_2$Cl$_2$, 1:9) to afford the title compound (0.28 g, 71%): $^1$H NMR (CDCl$_3$, 300 MHz) δ 1.42 (s, 9H), 2.08 (s, 3H), 2.10–2.23 (m, 2H), 3.91 (t, J=7.5 Hz, 2H), 4.15 (dd, J=3.0, 10.0 Hz, 1H), 4.32 (m, 1H), 4.42 (d, J=7.0 Hz, 2H), 4.52 (m, 1H), 7.21 (d, J=2.0 Hz, 1H), 8.15 (d, J=2.0 Hz, 1H), 8.25 (d, J=3.0 Hz, 1H); MS (CI/NH$_3$) m/z 336 (M+H)$^+$.

205d. 5-Acetamidomethyl-3-(2-(S)-azetidinylmethoxy) pyridine dihydrochloride

The product of step 205c (0.28 g, 0.90 mmol) was deprotected and isolated as the free base in 97% yield according to the procedure of Example 20b. The free base was converted to the dihydrochloride salt using excess HCl in Et$_2$O to afford the title compound: [α]$_D^{23}$ +10.7 (c 0.3, MeOH); $^1$H NMR (D$_2$O, 300 MHz) δ 2.04 (s, 3H), 2.65 (dd, J=8.5, 17.0 Hz, 2H), 4.01–4.21 (m, 2H), 4.43–4.47 (m, 4H), 4.96 (m, 1H), 7.76 (br s, 1H), 8.24 (br s, 1H), 8.38 (d, J=3.0 Hz, 1H); MS (CI/NH$_3$) m/z 236 (M+H)$^+$. Anal. Calcd for C$_{12}$H$_{17}$N$_3$O$_2$.2.9 HCl: C, 42.26; H, 5.88; N, 12.32. Found: C, 42.58; H, 6.21; N, 11.98.

Example 206

5-Acetamidomethyl-3-(2-(S)-azetidinylmethoxy)-6-chloropyridine dihydrochloride 206a. 5-Acetamidomethyl-3-(1-BOC-2-(S)-azetidinylmethoxy)-6-chloropyridine 5-Aminomethyl-3-(1-BOC-2-(S)-azetidinylmethoxy)-6-chloropyridine (0.19 g, 0.60 mmol) from Example 92b was treated with acetic anhydride and further processed according to the procedure of Example 205c to afford the title compounds in 76% yield. $^1$H NMR (CDCl$_3$, 300 MHz) δ 1.40 (s, 9H), 2.04 (s, 3H), 2.10–2.19 (m, 2H), 3.85 (t, J=7.5 Hz, 2H), 4.10 (dd, J=3.0, 10.5 Hz, 1H), 4.31 (m, 1H), 4.42–4.57 (m, 3H), 7.38 (d, J=3.0 Hz, 1H), 8.04 (d, J=3.0 Hz, 1H); MS (CI/NH$_3$) m/z 370 (M+H)$^+$.

206b. 5-Acetamidomethyl-3-(2-(S)-azetidinylmethoxy)-6-chloropyridine dihydrochloride The product of step 206a (0.15 g, 0.40 mmol) was deprotected and isolated as the free base in 96% yield according to the procedure of Example 20b, followed by conversion to the dihydrochloride salt with excess HCl/ Et$_2$O. [α]$_D^{23}$ +10.0 (c 0.2, MeOH); $^1$H NMR (D$_2$O, 300 MHz) δ 2.10 (s, 3H), 2.65 (q, J=9.0, 17.0 Hz, 2H), 4.03–4.21 (m, 2H), 4.40–4.50 (m, 4H), 4.92 (m, 1H), 7.43 (d, J=3.0 Hz, 1H), 8.08 (d, J=3.0 Hz, 1H); MS (CI/NH$_3$) m/z 270 (M+H)$^+$. Anal. Calcd for C$_{12}$H$_{16}$ClN$_3$O$_2$.1.7 HCl.0.1 Et$_2$O: C, 43.92; H, 5.56; N, 12.39. Found: C, 43.96; H, 5.37; N, 12.06.

Example 207

3-(2-(S)-Azetidinylmethoxy)-6-chloro-5-(N-methoxycarbonylamino)methylpyridine hydrochloride 207a. 3-(1-BOC-2-(S)-azetidinylmethoxy)-6-chloro-5-(N-methoxycarbonylamino)methyl-pyridine 5-Aminomethyl-3-(1-BOC-2-(S)-azetidinylmethoxy)-6-chloropyridine (0.23 g, 0.70 mmol) from Example 92b in CH$_2$Cl$_2$ (5 mL) at 0° C. was treated with NEt$_3$ (0.2 mL, 1.40 mmol) and methyl chloroformate (0.061 mL, 0.80 mmol). The mixture was allowed to warm to room temperature and stir for 1 h. The volatile components were evaporated and the residue was chromatographed (silica gel; MeOH/CH$_2$Cl$_2$, 1:19) to afford the title compound as a yellow oil (0.22 g, 82%). $^1$H NMR (CDCl$_3$, 300 MHz) δ 1.42 (s, 9H), 2.28–2.35 (m, 2H), 3.71 (s, 3H), 3.89 (t, J=7.5 Hz, 2H), 4.10 (dd, J=3.0, 10.0 Hz, 1H), 4.36 (m, 1H), 4.40 (d, J=6.5 Hz, 2H), 4.54 (m, 1H), 7.35 (d, J=3.5 Hz, 1H), 8.01 (d, J=3.0 Hz, 1H); MS (CI/NH$_3$) m/z 386 (M+H)$^+$.

207b. 3-(2-(S)-Azetidinylmethoxy)-6-chloro-5-(N-methoxycarbonylamino)-methylpyridine hydrochloride The product of step 207a (0.20 g, 0.50 mmol) was deprotected and converted to the free base in 54% yield according to the procedure of Example 20b, followed by conversion to the monohydrochloride with HCl/Et$_2$O. [α]$_D^{23}$ +21.87 (c 0.5, MeOH); $^1$H NMR (D$_2$O, 300 MHz) δ 2.68 (q, J=8.5 Hz, 16.5 Hz, 2H), 3.70 (s, 3H), 4.04–4.21 (m, 2H), 4.40 (s, 2H), 4.43 (d, J=4.5 Hz, 2H), 4.86 (m, 1H), 7.53 (d, J=2.5 Hz, 1H), 8.08 (d, J=3.0 Hz, 1H); MS (CI/NH$_3$) m/z 286 (M+H)$^+$. Anal. Calcd for C$_{12}$H$_{16}$ClN$_3$O$_3$.1.1 HCl.0.4 H$_2$O: C, 43.28; H, 5.42; N, 12.62. Found: C, 43.53; H, 5.16; N, 12.14.

Example 208

5-Acetamidomethyl-6-chloro-3-(1-methyl-2-(S)-azetidinylmethoxy)pyridine hydrochloride To the free base of Example 206b (0.10 g, 0.40 mmol) in H$_2$O (3 mL) were added formalin (37%, 0.5 mL), and HOAc (0.5 mL), followed by sodium cyanoborohydride (0.07 g, 1.10 mmol). The mixture was stirred for 0.75 h, then treated with 15% NaOH and extracted with CH$_2$Cl$_2$. The extracts were dried (MgSO$_4$) and concentrated. The residue was chromatographed (silica gel, MeOH/CH$_2$Cl$_2$/NH$_4$OH, 1:9:0.1) to afford the free base (0.052 g, 49%), which was converted to the monohydrochloride with HCl/Et$_2$O. [α]$_D^{23}$ +21.8 (c 0.7, MeOH); $^1$H NMR (D$_2$O, 300 MHz) δ 2.05–2.11 (m, 5H), 2.42 (s, 3H), 2.93 (m, 1H), 3.38–3.59 (m, 2H), 3.98–4.14 (m, 2H), 4.46 (d, J=6.0 Hz, 2H), 7.36 (d, J=2.5 Hz, 1H), 8.00 (d, J=3.0 Hz, 1H); MS (CI/NH$_3$) m/z 284 (M+H)$^+$. Anal. Calcd for C$_{13}$H$_{18}$ClN$_3$O$_2$.1.4 HCl.0.9 H$_2$O: C, 44.48; H, 6.09; N, 11.97. Found: C, 44.74; H, 6.43; N, 11.63.

Example 209

5-Acetamidomethyl-3-(1-methyl-2-(S)-azetidinylmethoxy)pyridine dihydrochloride

The free base of Example 205d (0.21 g, 0.70 mmol) was converted to the title compound according to the procedure of Example 208 in about 70% yield. [α]$_D^{23}$ +10.0 (c 0.2, MeOH); $^1$H NMR (D$_2$O, 300 MHz) δ 2.02–2.10 (m, 5H), 2.42 (s, 3H), 2.92 (m, 1H), 3.44–3.54 (m, 2H), 3.98–4.10 (m, 2H), 4.39–4.50 (m, 2H), 7.20 (d, J=2.0 Hz, 1H), 8.13 (d, J=1.0 Hz, 1H), 8.24 (d, J=3.0 Hz, 1H); MS (CI/NH$_3$) m/z 250 (M+H)$^+$. Anal. Calcd for C$_{13}$H$_{19}$N$_3$O$_2$.2.3 HCl.0.1 H$_2$O: C, 46.61; H, 6.47; N, 12.54. Found: C, 46.87; H, 6.82; N, 12.20.

Example 210

6-Chloro-5-(N-methoxycarbonylamino)methyl)-3-(1-methyl-2-(S)-azetidinylmethoxy)pyridine hydrochloride The free base of Example 207b (0.04 g, 0.10 mmol) was converted to the title compound according to the procedure of Example 208 in about 43% yield. [α]$_D^{23}$ +22.1 (c 0.6, MeOH). $^1$H NMR (D$_2$O, 300 MHz) δ 2.65 (q, J=9.0, 18.0 Hz, 2H), 2.99 (s, 3H), 3.70 (s, 3H), 3.98–4.25 (m, 2H), 4.39 (s, 2H), 4.42–4.48 (m, 3H), 7.53 (d, J=3.0 Hz, 1H), 8.08 (d, J=3.0 Hz, 1H); MS (CI/NH$_3$) m/z 300 (M+H)$^+$. Anal. Calcd for C$_{13}$H$_{18}$ClN$_3$O$_3$.HCl.1.3 H$_2$O: C, 43.42; H, 6.05; N, 11.68. Found: C, 43.78; H, 5.85; N, 11.06.

Example 211

3-(2-(S)-Azetidinylmethoxy)-6-chloro-5-chloroacetamidomethylpyridine hydrochloride 211a. 3-(1-BOC-2-(S)-azetidinylmethoxy)-6-chloro-5-chloroacetamidomethylpyridine Following the procedure of Example 207a, substituting chloroacetyl chloride for methyl chloroformate therein, the title compound (0.34 g, 94%) was prepared: $^1$H NMR (CDCl$_3$, 300 MHz) δ 1.42 (s, 9H), 2.27–2.35 (m, 2H), 3.90 (t, J=7.5 Hz, 2H), 4.11–4.15 (m, 3H), 4.34 (m, 1H), 4.45–4.90 (m, 3H), 7.33 (d, J=3.0 Hz, 1H), 8.04 (d, J=2.7 Hz, 1H); MS (CI/NH$_3$) m/z 404 (M+H)$^+$.

211b. 3-(2-(S)-Azetidinylmethoxy)-6-chloro-5-chloroacetamidomethylpyridine hydrochloride The product of step 211a (0.34 g, 0.80 mmol) was deprotected and isolated as the free base in 37% yield according to the procedure of Example 20b, followed by conversion to the monohydrochloride with HCl/Et$_2$O: [α]$_D^{23}$ +16.82 (c 0.3, MeOH); $^1$H NMR (D$_2$O, 300 MHz) δ 2.72 (q, J=8.5, 16.5 Hz, 2H), 4.07–4.43 (m, 4H), 4.45 (s, 2H), 4.48 (d, J=4.5 Hz, 2H), 4.81 (m, 1H), 7.53 (d, J=3.0 Hz, 1H), 8.08 (d, J=3.0 Hz, 1H); MS (CI/NH$_3$) m/z 304 (M+H)$^+$. Anal. Calcd for C$_{12}$H$_{15}$Cl$_2$N$_3$O$_2$.HCl: C, 42.31; H, 4.73; N, 12.33. Found: C, 42.34; H, 5.00; N, 12.25.

Example 212

3-(2-(S)-Azetidinylmethoxy)-6-chloro-5-(N-3-nitrobenzolamino)methylpyridine dihydrochloride 212a. .3-(1-BOC-2-(S)-azetidinylmethoxy)-6-chloro-5-(N-3-nitrobenzoylamino)methylpyridine Following the procedure of Example 207a, substituting 3-nitrobenzoyl chloride for methyl chloroformate therein, the title compound (0.18 g, 76%) was prepared. $^1$H NMR (CDCl$_3$, 300 MHz) δ 1.42 (s, 9H), 2.26–2.33 (m, 2H), 3.85 (t, J=7.5 Hz, 2H), 4.00 (dd, J=3.0, 10.0 Hz, 1H), 4.35 (m, 1H), 4.40 (d, J=6.5 Hz, 2H), 4.51 (m, 1H), 7.35 (d, J=3.5 Hz, 1H), 7.57 (d, J=3.0 Hz, 1H), 8.01 (d, J=3.0 Hz, 1H), 8.19 (d, J=9.0 Hz, 1H), 8.43 (d, J=8.5 Hz, 1H), 8.61 (d, J=2.0 Hz, 1H); MS (CI/NH$_3$) m/z 477 (M+H)$^+$.

212b. 3-(2-(S)-Azetidinylmethoxy)-6-chloro-5-(N-3-nitrobenzoylamino)methylpyridine dihydrochloride The product of step 212a (0.18 g, 0.40 mmol) was deprotected and isolated as the free base in 37% yield according to the procedure of Example 20b, followed by conversion to the dihydrochloride with excess HCl/Et$_2$O. $^1$H NMR (D$_2$O, 300 MHz) δ 2.62–2.71 (q, J=8.5, 17.0 Hz, 2H), 4.01–4.18 (m, 2H), 4.41 (d, J=4.0 Hz, 2H), 4.65 (s, 2H), 4.88 (m, 1H), 7.57 (d, J=3.0 Hz, 1H), 7.78 (t, J=3.0 Hz, 1H), 8.09 (d, J=3.0 Hz, 1H), 8.19 (d, J=9.0 Hz, 1H), 8.43 (d, J=8.5 Hz, 1H), 8.61 (t, J=2.0 Hz, 1H); MS (CI/NH$_3$) m/z 377 (M+H)$^+$. Anal. Calcd for C$_{17}$H$_{17}$ClN$_4$O$_4$.2 HCl.H$_2$O: C, 43.65; H, 4.53; N, 11.98. Found: C, 43.97; H, 4.54; N, 11.53.

Example 213

3-(2-(S)-Azetidinylmethoxy)-6-chloro-5-(N-2-furoylamino)methylpyridine hydrochloride 213a. 3-(1-BOC-2-(S)-azetidinylmethoxy)-6-chloro-5-(N-2-furoylamino)methylpyridine Following the procedure of Example 207a, substituting 2-furoyl chloride for methyl chloroformate therein, the title compound (0.20 g, 74%) was prepared. $^1$H NMR (CDCl$_3$ 300 MHz) δ 1.40 (s, 9H), 2.28–2.38 (m, 2H), 3.88 (t, J=8.0 Hz, 2H), 4.12 (dd, J=3.0, 10.0 Hz, 1H), 4.30 (m, 1H), 4.50 (m, 1H), 4.63 (d, J=6.5 Hz, 2H), 6.53 (dd, J=1.5, 6.0 Hz, 1H), 7.16 (dd, J=1.0, 3.5 Hz, 1H), 7.40 (d, J=3.0 Hz, 1H), 7.44 (d, J=2.5 Hz, 1H), 8.02 (d, 3.0 Hz, 1H); MS (CI/NH$_3$) m/z 422 (M+H)$^+$.

213b. 3-(2-(S)-Azetidinylmethoxy)-6-chloro-5-(N-2-furoylamino)methylpyridine hydrochloride The product of step 213a (0.20 g, 0.50 mmol) was deprotected and isolated as the free base in 64% yield according to the procedure of Example 20b, followed by conversion to the hydrochloride with HCl/Et$_2$O. $[\alpha]_D^{23}$ +21.67 (c 0.7, MeOH); $^1$H NMR (D$_2$O, 300 MHz) δ 2.66 (dd, J=8.5, 16.5 Hz, 2H), 4.02–4.17 (m, 2H), 4.42 (d, J=4.0 Hz, 2H), 4.64 (s, 2H), 4.88 (m, 1H), 6.68 (dd, J=1.5, 5.5 Hz, 1H), 7.23 (dd, J=1.0, 3.5 Hz, 1H), 7.52 (d, J=3.0 Hz, 1H), 7.72 (d, J=1.5 Hz, 1H), 8.11 (d, J=2.5 Hz, 1H); MS (CI/NH$_3$) m/z 322 (M+H)$^+$. Anal. Calcd for C$_{15}$H$_{16}$ClN$_3$O$_3$.1.2 HCl.0.2 H$_2$O: C, 48.81; H, 4.81; N, 11.38. Found: C, 48.70; H, 4.76; N, 11.03.

We claim:

1. A compound having the structure

[structure: R$^1$—N-azetidine-(CH$_2$)$_n$ with CH$_2$O linked to pyridine bearing N, R$^2$, and L-R$^3$]

or a pharmaceutically acceptable salt or pro-drug thereof wherein n is selected from 1, 2 or 3;

R$^1$ is selected from the group consisting of
  hydrogen,
  allyl, and
  alkyl of one to six carbon atoms;

R$^2$ is selected from the group consisting of
  hydrogen,
  C$_1$–C$_3$ akyl
  fluorine,
  chlorine,
  ethenyl, and
  phenyl;

L is absent or is selected from the group consisting of
  alkylene of one to six carbon atoms,
  —C≡C—(C$_0$–C$_6$-alkyl)-, —(CH=CH)$_p$—(C$_0$–C$_6$-alkyl)— where p is one or two,

[structures: CH$_2$=C(C(=O)—)(C$_0$–C$_6$-alkyl)— ; —C(=O)(C$_0$–C$_6$-alkyl), and —CH$_2$—M—C(=O)(C$_0$–C$_6$-alkyl)—,]

where M is selected from —CH$_2$—, and —NH—; and
R$^3$ is selected from the group consisting of
  a) hydrogen,
  b) alkyl of one to eight carbon atoms,
  c) alkenyl of two to six carbon atoms
  d) haloalkyl of one to six carbon atoms,
  e) hydroxyalkyl of one to six carbon atoms,
  f) alkoxy of one to six carbon atoms,
  g) amino,
  h) alkylamino of one to six carbon atoms,
  h') azacycle attached to L through a nitrogen atom,
  i) dialkylamino in which the two alkyl groups are independently of one to six carbon atoms,
  j) phenyl
  k) naphthyl,
  l) biphenyl,
  m) furyl,
  n) thienyl,
  o) pyridinyl,
  p) pyrazinyl,
  q) pyridazinyl,
  r) pyrimidinyl,
  s) pyrrolyl,
  t) pyrazolyl,
  u) imidazolyl,
  v) indolyl,
  w) thiazolyl,
  x) oxazolyl,
  y) isoxazolyl,
  z) thiadiazolyl,
  aa) oxadiazolyl,
  bb) quinolinyl,
  cc) isoquinolinyl, and
  dd) any of b) or j) through cc) above substituted with one or two substituents independently selected from the group consisting of
    alkyl of one to six carbon atoms,
    haloalkyl of one to six carbon atoms,
    alkoxy of one to six carbon atoms,
    alkoxyalkyl in which the alkoxy and alkyl portions are independently of one to six carbon atoms,
    alkoxyalkoxy in which the alkoxy portions are independently of one to six carbon atoms,
    halogen,
    cyano,
    hydroxy,
    amino,
    alkylamino of one to six carbon atoms,
    carboxyl, and
    alkoxycarbonyl of two to six carbon atoms;
  with the provisos that
    i) when L is absent, R$^3$ may not be alkyl of one to eight carbon atoms, amino, alkylamino, dialkylamino, alkoxy of 1–6 carbons, CF$_3$ or CH$_2$OH;

ii) when L is absent and R³ is hydrogen, R² is selected from ethenyl, unsubstituted phenyl, and phenyl substituted as defined in dd) above; and iii) when L is alkylene, R³ may not be hydrogen or alkyl;

when L is

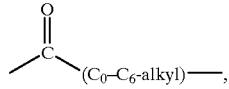

then R³ is selected from alkyl of one to eight carbon atoms, h'), i), j), k), l), m), n), o), p), q), bb), and cc) as defined above, or any of i), j), k), l), m), n),o), p), q), bb) and cc) optionally substituted as defined in dd) above;

when L is

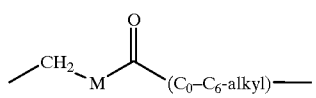

and M is —CH₂—, then R³ may not be hydrogen; and vi) f) through y) above may be substituted as defined in z) above by no more than one alkylamino, carboxyl, or alkoxycarbonyl substituent, or alternatively, L-R₃ is selected from —O—CH₂—R₄, wherein R₄ is selected from the group consisting of
(a) CH₃OCH₂—,
(b) i) through cc) as defined above for R³.

2. A compound having the structure

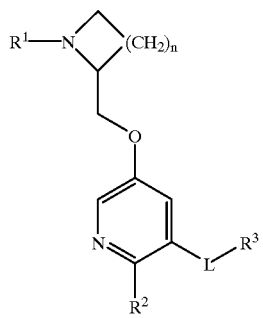

or a pharmaceutically acceptable salt thereof wherein
n is selected from 1, 2 or 3;
R¹ is selected from the group consisting of
hydrogen,
allyl, and
alkyl of one to six carbon atoms;
R² is selected from the group consisting of
hydrogen,
fluorine,
chlorine,
ethenyl, and
phenyl;
L is absent or is selected from the group consisting of
alkylene of one to six carbon atoms,
—C≡C—(C₀–C₆-alkyl)-,

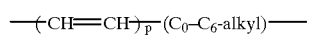

where p is one or two,

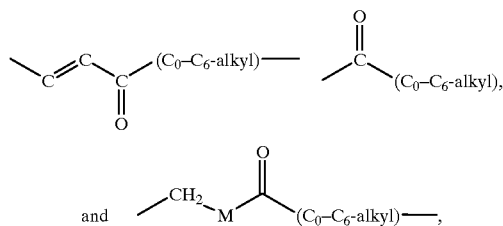

where M is selected from —CH₂—, and —NH—; and
R³ is selected from the group consisting of
a) hydrogen,
b) alkyl of one to eight carbon atoms,
c) haloalkyl of one to six carbon atoms,
d) hydroxyalkyl of one to six carbon atoms,
e) alkoxy of one to six carbon atoms,
f) amino,
g) alkylamino of one to six carbon atoms,
h) dialkylamino in which the two alkyl groups are independently of one to six carbon atoms,
h') azacycle attached to L through a nitrogen atom,
i) phenyl,
j) naphthyl,
k) biphenyl,
l) furyl,
m) thienyl,
n) pyridinyl,
o) pyrazinyl,
p) pyridazinyl,
q) pyrimidinyl,
r) pyrrolyl,
s) pyrazolyl,
t) imidazolyl,
u) indolyl,
v) thiazolyl,
w) oxazolyl,
x) isoxazolyl,
y) thiadiazolyl,
z) oxadiazolyl,
aa) quinolinyl,
bb) isoquinolinyl, and
cc) any of b) or i) through bb) above substituted with one or two substituents independently selected from the group consisting of
alkyl of one to six carbon atoms,
haloalkyl of one to six carbon atoms,
alkoxy of one to six carbon atoms,
alkoxyalkyl in which the alkoxy and alkyl portions are independently of one to six carbon atoms,
alkoxyalkoxyl in which the alkoxy portions are independently of one to six carbon atoms,
halogen,
cyano,
hydroxy,
amino,
alkylamino of one to six carbon atoms,
carboxyl, and
alkoxycarbonyl of two to six carbon atoms;
with the provisos that i) when L is absent, $R^3$ may not be alkyl of one to eight carbon atoms, amino, alkylamino, dialkylamino, $CF_3$, $CH_2OH$ or alkoxy of 1–6 carbons;

ii) when L is absent and $R^3$ is hydrogen, $R^2$ is selected from ethenyl, unsubstituted phenyl, and phenyl substituted as defined in dd) above; and iii) when L is alkylene, $R^3$ may not be hydrogen or alkyl;

iv) when L is

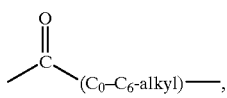

then $R^3$ is selected from alkyl of one to eight carbon atoms, h'), i), j), k), l), m), n), o), p), q), bb), and cc) as defined above, or any of i), j), k), l), m), n),o), p), q), bb) and cc) optionally substituted as defined in dd) above;

v) when L is

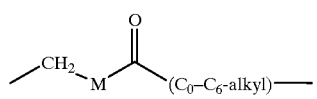

and M is —$CH_2$—, then $R^3$ may not be hydrogen; and vi) f) through y) above may be substituted as defined in z) above by no more than one alkylamino, carboxyl, or alkoxycarbonyl substituent.

3. A compound having the structure

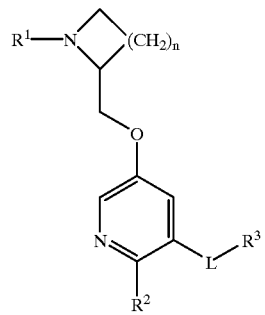

or a pharmaceutically acceptable salt thereof wherein
n is selected from 1, 2 or 3;
$R^1$ is selected from the group consisting of
  hydrogen,
  allyl, and
  alkyl of one to six carbon atoms;
$R^2$ is $C_1$–$C_3$ alkyl
L is absent or is selected from the group consisting of
  alkylene of one to six carbon atoms,
  —C≡C—($C_0$–$C_6$-alkyl)-,

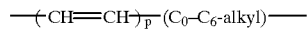

where p is one or two,

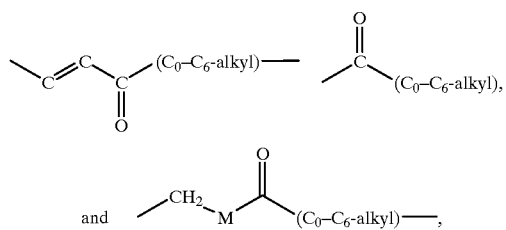

where M is selected from —$CH_2$—, and —NH—; and
$R^3$ is selected from the group consisting of
  a) hydrogen,
  b) alkyl of one to eight carbon atoms,
  c) alkenyl of two to six carbon atoms
  d) haloalkyl of one to six carbon atoms,
  e) hydroxyalkyl of one to six carbon atoms,
  f) alkoxy of one to six carbon atoms,
  g) amino,
  h) alkylamino of one to six carbon atoms,
  h') azacycle attached to L through a nitrogen atom,
  i) dialkylamino in which the two alkyl groups are independently of one to six carbon atoms,
  j) phenyl,
  k) naphthyl,
  l) biphenyl,
  m) furyl,
  n) thienyl,
  o) pyridinyl,
  p) pyrazinyl,
  q) pyridazinyl,
  r) pyrimidinyl,
  s) pyrrolyl,
  t) pyrazolyl,
  u) imidazolyl,
  v) indolyl,
  w) thiazolyl,
  x) oxazolyl,
  y) isoxazolyl,
  z) thiadiazolyl,
  aa) oxadiazolyl,
  bb) quinolinyl,
  cc) isoquinolinyl, and
  dd) any of b) or j) through cc) above substituted with one or two substituents independently selected from the group consisting of
    alkyl of one to six carbon atoms,
    haloalkyl of one to six carbon atoms,
    alkoxy of one to six carbon atoms,
    alkoxyalkyl in which the alkoxy and alkyl portions are independently of one to six carbon atoms,
    alkoxyalkoxy in which the alkoxy portions are independently of one to six carbon atoms,
    halogen,
    cyano,
    hydroxy,
    amino,
    alkylamino of one to six carbon atoms,
    carboxyl, and
    alkoxycarbonyl of two to six carbon atoms;
with the provisos that
  i) when L is absent, $R^3$ may not be alkyl of one to eight carbon atoms, amino, alkylamino, dialkylamino, alkoxy of 1–6 carbons, $CF_3$ or —$CH_2OH$;

ii) when L is absent and $R^3$ is hydrogen, $R^2$ is selected from ethenyl, unsubstituted phenyl, and phenyl substituted as defined in dd) above; and iii) when L is alkylene, $R^3$ may not be hydrogen or alkyl;

iv) when L is

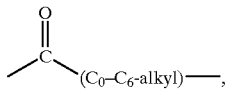

then $R^3$ is selected from alkyl of one to eight carbon atoms, h'), i), j), k), l), m), n), o), p), q), bb), and cc) as defined above, or any of i), j), k), l), m), n),o), p), q), bb) and cc) optionally substituted as defined in dd) above;

v) when L is

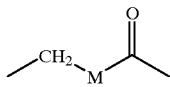

M is —$CH_2$—, then $R^3$ may not be hydrogen; and vi) f) through y) above may be substituted as defined in z) above by no more than one alkylamino, carboxyl, or alkoxycarbonyl substituent; or alternatively, $R^2$ is selected from the group consisting of
hydrogen,
$C_1$–$C_3$ alkyl
fluorine,
chlorine,
ethenyl;
phenyl; and n, $R^1$ and L are as defined above and $R^3$ is alkenyl of 2 to 6 carbon atoms; or, in a compound of formula I, L-$R^3$ is selected from
O—$CH_2$—$R^4$, wherein $R^4$ is selected from the group consisting of
(a) $CH_3OCH_2$—,
(b) j) through dd) as defined above.

4. A compound according to claims 1–3 wherein n is 1.
5. A compound according to claims 1–3 wherein n is 2.
6. A compound according to claims 1–3 wherein n is 3.
7. A compound according to claim 4 selected from the group consisting of:

5-phenyl-3-(2-(S)-azetidinylmethoxy)pyridine;
5-phenyl-3-(1-methyl-2-(S)-azetidinylmethoxy)pyridine;
5-(1-hexynyl)-3-(2-(S)-azetidinylmethoxy)pyridine;
5-(2-(4-pyridinyl)ethenyl)-3-(2-(S)-azetidinylmethoxy)pyridine;
5-(2-(4-pyridinyl)ethyl)-3-(2-(S)-azetidinylmethoxy)pyridine;
5-(2-(4-pyridinyl)ethenyl)-3-(1-methyl-2-(S)-azetidinylmethoxy)pyridine;
5-(2-(4-pyridinyl)ethyl)-3-(1-methyl-2-(S)-azetidinylmethoxy)pyridine;
5-(1-octynyl)-3-(2-(S)-azetidinylmethoxy)pyridine;
5-(1-octynyl)-3-(1-methyl-2-(S)-azetidinylmethoxy)pyridine;
5-(3-aminophenyl)-3-(2-(S)-azetidinylmethoxy)pyridine;
5-phenyl-6-chloro-3-(2-(S)-azetidinylmethoxy)pyridine;
5-phenyl-6-chloro-3-(1-methyl-2-(S)-azetidinylmethoxy)pyridine;

5-(2-(4-pyridinyl)ethenyl)-6-chloro-3-(2-(S)-azetidinylmethoxy)pyridine;
5-(3-thienyl)-3-(1-methyl-2-(R)-azetdinylmethoxy)pyridine;
5-((N-benzoylamino)methyl)-6-chloro-3-(2-(S)-azetidinylmethoxy)pyridine;
3-(2-(S)-Azetidinylmethoxy)-5-(N-benzoylamino)methyl-6-chloropyridine
5-(benzoylaminomethyl)-6-chloro-3-(1-methyl-2-(S)-azetidinylmethoxy)pyridine;
5-(acetamidomethyl)-6-chloro-3-(2-(R)-azetidinylmethoxy)pyridine;
5-(6-chlorohexanamidomethyl)-6-chloro-3-(2-(S)-azetidinylmethoxy)pyridine;
5-(3-phenylpropionamidomethyl)-6-chloro-3-(1-methyl-2-(R)-azetidinylmethoxy)pyridine;
5-(6-chlorobenzamidomethyl)-6-chloro-3-(1-methyl-2-(S)-azetidinylmethoxy)pyridine;
5-benzoyl-6-chloro-3-(2-(S)-azetidinylmethoxy)pyridine;
5-hexanoyl-6-chloro-3-(2-R)-azetidinylmethoxy)pyridine;
5-(3-quinolinoyl)-6-chloro-3-(2-(S)-azetidinylmethoxy)pyridine;
5-(3-nicotinoyl)-6-chloro-3-(1-methyl-2-(R)-azetidinylmethoxy)pyridine;
5-(5-pyrimidinecarbonyl)-6-chloro-3-(1-methyl-2-(S)-azetidinylmethoxy)pyridine;
5-(5-carboxy-3-pyridinyl)-3-(2-(R)-azetidinylmethoxy)pyridine;
5-(5-formyl-$^3$-pyridinyl)-3-(2-(S)-azetidinylmethoxy)pyridine;
5-(2-hydroxy-1-naphthyl)-3-(2-(R)-azetidinylmethoxy)pyridine; and
5-(4'-nitro-4-biphenyl)-3-(2-(S)-azetidinylmethoxy)pyridine;
3-(2-(S)-azetidinylmethoxy)-6-chloro-5-(4-chlorophenyl)pyridine;
6-Chloro-5-(4chloro-phenyl)-3-(1-methyl-2-(S)-azetidinylmethoxy)pyridine;
3-(2-(S)-Azetidinylmethoxy)-5-(2-thienyl)pyridine;
3- (2-(S)-Azetidinylmethoxy)-5-ethenylpyridine;
3-(2-(S)-Azetidinylmethoxy)-5-(5,5-dimethyl-1,3-hexadiene)pyridine;
3-(2-(S)-Azetidinylmethoxy)-6-chloro-5-ethenylpyridine;
5-(5,5-Dimethyl-1,3-hexadiene)-3-(1-methyl-2-(S)-azetidinylmethoxy)pyridine;
6-Chloro-3-(1-methyl-2-(S)-azetidinylmethoxyl)-5-(5-pyrimidinyl)pyridine;
3-(2-(S)-Azetidinylmethoxyl)-5-(5-pyrimidinyl)pyridine;
3-(2-(S)-Azetidinylmethoxyl)-6-chloro-5-(5-pyrimidinyl)pyridine;
3-(2-(S)-Azetidinylmethoxyl)-6-chloro-5-ethynylpyridine;
3-(2-(R)-Azetidinylmethoxyl)-6-chloro-5-phenylpyridine;
6-Chloro-3-(1-methyl-2-(R)-azetidinylmethoxyl)-5-phenylpyridine;
3-(2-(R)-Azetidinylmethoxyl)-6-chloro-5-ethynylpyridine;
5-Ethenyl-6-methyl-3-(1-methyl-2-(S)-azetidinylmethoxy)pyridine;

3-(2-(S)-Azetidinylmethoxy)-6-ethenylpyridine;
6-Ethenyl-3-(1-methyl-2-(S)-azetidinylmethoxy)pyridine;
3-(2-(S)-Azetidinylmethoxy)-5-ethenyl-6-fluoropyridine;
5-Ethenyl-6-fluoro-3-(1-methyl-2-(S)-azetidinylmethoxy)pyridine;
5-Acetamidomethyl-3-(2-(S)-azetidinylmethoxy)pyridine;
5-Acetamidomethyl-3-(2-(S)-azetidinylmethoxy)-6-chloropyridine;
3-(2-(S)-Azetidinylmethoxy)-6-chloro-5-(N-methoxycarbonylamino)methylpyridine;
5-Acetamidomethyl-6-chloro-3-(1-methyl-2-(S)-azetidinylmethoxy)pyridine;
5-Acetamidomethyl-3-(1-methyl-2-(S)-azetidinylmethoxy)pyridine;
6-Chloro-5-(N-methoxycarbonylamino)methyl-3-(1-methyl-2-(S)-azetidinylmethoxy)pyridine;
3-(2-(S)-Azetidinylmethoxy)-6-chloro-5-chloroacetamidomethylpyridine;
3-(2-(S)-Azetidinylmethoxy)-6-chloro-5-(N-3-nitrobenzoylamino)methylpyridine;
3-(2-(S)-Azetidinylmethoxy)-6-chloro-5-(N-2-furoylamino)methylpyridine;
3-(2-(S)-Azetidinylmethoxy)-5-benzyloxypyridine;
5-Benzyloxy-3-(1-methyl-2-(S)-azetidinylmethoxy)pyridine;
5-Allyl-3-(2-(S)-azetidinylmethoxyl)-6-chloropyridine;
5-Allyl-3-(1-methyl-2-(S)-azetidinylmethoxyl)-6-chloropyridine;
5-Allyl-3-(2-(S)-azetidinylmethoxyl)pyridine;
or a pharmaceutically acceptable salt thereof.

8. A compound according to claim 5 selected from the group consisting of:
5-(3-nitrophenyl)-3-(1-methyl-2-(S)-pyrrolidinylmethoxy)pyridine;
5-(1-naphthalenyl)-3-(1-methyl-2-(S)-pyrrolidinylmethoxy)pyridine;
5-(4-methoxyphenyl)-3-(1-methyl-2-(S)-pyrrolidinylmethoxy)pyridine;
5-hexynyl-3-(1-methyl-2-(S)-pyrrolidinylmethoxy)pyridine;
5-(2-furanyl)-3-(1-methyl-2-(S)-pyrrolidinylmethoxy)pyridine;
5-(2-thienyl)-3-(1-methyl-2-(S)-pyrrolidinylmethoxy)pyridine;
5-(3-pyridyl)-3-(1-methyl-2-(S)-pyrrolidinylmethoxy)pyridine;
5-ethenyl-3-(1-methyl-2-(S)-pyrrolidinylmethoxy)pyridine;
5-(1-decynyl)-3-(1-methyl-2-(S)-pyrrolidinylmethoxy)pyridine;
5-acetyl-3-(1-methyl-2-(S)-pyrrolidinylmethoxy)pyridine;
5-(4-fluorophenyl)-3-(1-methyl-2-(S)-pyrrolidinylmethoxy)pyridine,
5-hexyl-3-(1-methyl-2-(S)-pyrroli dinylmethoxy)pyridine;
5-(2-(4-pyridinyl)ethenyl)-3-(1-methyl-2-(S)-pyrrolidinylmethoxy)pyridine;
5-(5-cyano-1-pentynyl)-3-(1-methyl-2-(S)-pyrrolidinylmethoxy)pyridine;
5-(2-(methoxycarbonyl)ethyl)-3-(1-methyl-2-(S)-pyrrolidinylmethoxy)pyridine;
5-(2-(methoxycarbonyl)ethenyl)-3-(1-methyl-2-(S)-pyrrolidinylmethoxy)pyridine;
5-(5-phenyl-1-pentynyl)-3-(1-methyl-2-(S)-pyrrolidinylmethoxy)pyridine;
5-trans-(2-phenyethenyl)-3-(1-methyl-2-(S)-pyrrolidinylmethoxy)pyridine;
5-(1-pyrrolidinylcarbonyl)-3-(1-methyl-2-(S)-pyrrolidinylmethoxy)pyridine;
5-(4-chlorophenyl)-3-(2-(S)-pyrrolidinylmethoxy)pyridine;
5-(2-phenylethyl))-3-(1-methyl-2-(S)-pyrrolidinylmethoxy)pyridine;
5-(3-oxo-1-hexenyl)-3-(1-methyl-2-(S)-pyrrolidinylmethoxy)pyridinine;
5-(5-pyrimidinyl)-3-(1-methyl-2-(S)-pyrrolidinylmethoxy)pyridine;
5-phenyl-6-chloro-3-(1-methyl-2-(S)-pyrrolidinylmethoxy)pyridine;
5-methoxycarbonyl-3-(1-methyl-2-(S)-pyrrolidinylmethoxy)pyridine;
5-(6-hydroxy-1-hexynyl)-3-(1-methyl-2-(S)-pyrrolidinylmethoxy)pyridine;
5-(2-(4-pyridinyl)ethyl)-3-(1-methyl-2-(S)-pyrrolidinylmethoxy)pyridine;
5-(5,5-dimethyl-1,3-hexadienyl)-3-(1-methyl-2-(S)-pyrrolidinylmethoxy)pyridine;
5-(2-naphthalenyl)-3-(1-methyl-2-(S)-pyrrolidinylmethoxy)pyridine;
5-acetyl-6-chloro-3-(2-(S)-pyrrolidinylmethoxy)pyridine;
5-(2-(4-pyridinyl)ethenyl)-6-chloro-3-(2-(S)-pyrrolidinylmethoxy)pyridine;
5-(3-pyridinyl)-6-chloro-3-(2-(S)-pyrrolidinylmethoxy)pyridine;
5-(3-quinolinyl)-3-(1-methyl-2-(S)-pyrrolidinylmethoxy)pyridine;
5-(1-methyl-2-indolyl)-3-(1-methyl-2-(S)-pyrrolidinylmethoxy)pyridine;
5-(3,5-bis(trifluoromethyl)phenyl)-3-(1-methyl-2-(S)-pyrrolidinylmethoxy)pyridine;
5-(4-chlorophenyl)-3-(1-methyl-2-(S)-pyrrolidinylmethoxy)pyridine;
5-(2,4-dichlorophenyl)-3-(1-methyl-2-(S)-pyrrolidinylmethoxy)pyridine;
5-(2-phenylethynyl)-3-(1-methyl-2-(S)-pyrrolidinylmethoxy)pyridine;
5-(4-methylphenyl)-3-(1-methyl-2-(S)-pyrrolidinylmethoxy)pyridine;
5-(3-chloro-4-fluorophenyl)-3-(1-methyl-2-(S)-pyrrolidinylmethoxy)pyridine;
5-(3-aminophenyl)-3-(1-methyl-2-(S)-pyrrolidinylmethoxy)pyridine;
5-(2-formylphenyl)-3-(1-methyl-2-(S)-pyrrolidinylmethoxy)pyridine;
5-(2-methylphenyl)-3-(1-methyl-2-(S)-pyrrolidinylmethoxy)pyridine;
5-(4-(trifluoromethyl)phenyl)-3-(1-methyl-2-(S)-pyrrolidinylmethoxy)pyridine;
5-(3,3-dimethylbutynyl)-3-(1-methyl-2-(S)-pyrrolidinylmethoxy)pyridine;

5-(2-(4-methylphenyl)ethynyl)-3-(1-methyl-2-(S)-pyrrolidinylmethoxy)pyridine;
5-(1-octynyl)-3-(1-methyl-2-(S)-pyrrolidinylmethoxy)pyiidine;
5-(2-(4-pyridinyl)ethenyl)-6-chloro-3-(1-methyl-2-(S)-pyrrolidinylmethoxy)pyridine;
5-phenyl-3-(2-(S)-pyrrolidinylmethoxy)pyridine;
5-phenyl-3-(2-(R)-pyrrolidinylmethoxy)pyridine;
5-phenyl-3-(1-methyl-2-(R)-pyrrolidinylmethoxy)pyridine;
5-(5,5-dimethyl-1,3-hexadienyl)-6-chloro-3-(2-(R)-pyrrolidinylmethoxy)pyridine;
5-phenyl-6-chloro-3-(1-methyl-2-(R)-pyrrolidinylmethoxy)pyridine;
5-phenyl-6-chloro-3-(2-(R)-pyrrolidinylmethoxy)pyridine,
5,6-diphenyl-3-(2-(R)-pyrrolidinylmethoxy)pyridine;
5,6-diphenyl-3-(1-methyl-2-(R)-pyrrolidinylmethoxy)pyridine;
5-(3-aminophenyl)-6-chloro-3-(2-(R)-pyrrolidinylmethoxy)pyridine;
5-(4-chlorophenyl)-6-chloro-6-chloro-3-(1-methyl-2-(R)-pyrrolidinylmethoxy)pyridine;
5-(5,5-dimethyl-1,3-hexadienyl)-6-chloro-3-(2-(R)-pyrrolidinylmethoxy)pyridine;
5-(5,5-dimethyl-1,3-hexadienyl)-6-chloro-3-(1-methyl-2-(R)-pyrrolidinylmethoxy)pyridine;
5-(1-octynyl)-6-chloro-3-(2-(R)-pyrrolidinylmethoxy)pyridine;
5-(1-octynyl)-6-chloro-3-(1-methyl-2-(R)-pyrrolidinylmethoxy)pyridine;
5-(2-(4-pyridinyl)ethenyl)-6-chloro-3-(2-(R)-pyrrolidinylmethoxy)pyridine;
5-(2-(4-pyridinyl)ethenyl)-6-chloro-3-(1-methyl-2-(R)-pyrrolidinylmethoxy)pyridine;
5-(2-(4-pyridinyl)ethyl)-6-chloro-3-(1-methyl-2-(R)-pyrrolidinylmethoxy)pyridine;
5-phenyl-6-chloro-3-(2-(S)-pyrrolidinylmethoxy)pyridine;
5-(2-thienyl)-6-chloro-3-(2-(R)-pyrrolidinylmethoxy)pyridine;
5-(2-(4-pyridinyl)ethenyl)-3-(2-(R)-pyrrolidinylmethoxy)pyridine;
5-(2-(4-pyridinyl)ethyl)-3-(2-(R)-pyrrolidinylmethoxy)pyridine;
5-(3-aminophenyl)-3-(2-(R)-pyrrolidinylmethoxy)pyridine;
5-phenyl-3-(1-methyl-2-(S)-pyrrolidinylmethoxy)pyridine;
5-(formamidomethyl)-6-chloro-3-(2-(R)-pyrrolidinylmethoxy)pyridine;
5-((N-methoxycarbonylamino)methyl)-6-chloro-3-(2-(S)-pyrrolidinylmethoxy)pyridine;
5-(3-nitrobenzamidomethyl)-6-chloro-3-(1-methyl-2-(R)-pyrrolidinylmethoxy)pyridine;
5-((N-2-pyrrolycarbonylamino)methyl)-6-chloro-3-(1-methyl-2-(S)pyrrolidinylmethoxy)pyridine;
5-(2-naphthoyl)-6-chloro-3-(2-(R)-pyrrolidinylmethoxy)pyridine;
5-(4-methyl-1-naphthoyl)-6-chloro-3-(2-(S)-pyrrolidinylmethoxy)pyridine; methoxy)pyridine;

5-(3-pyridazinecarbonyl)-6-chloro-3-(1-methyl-2-(R)-pyrrolidinylmethoxy)pyridine;
5-(2-thiophenecarbonyl)-6-chloro-3-(1-methyl-2-(S)-pyrrolidinylmethoxy)pyridine;
5-(2-(5-carbomethoxypyridinyl)ethyl)-3-(2-(S)-pyrrolidinylmethoxy)pyridine;
5-(2-(5-bromopyridinyl)ethyl)-3-(2-(S)-pyrrolidinylmethoxy)pyridine;
5-(2-(6-amino-5-bromopyridinyl)ethyl)-3-(2-(S)-pyrrolidinylmethoxy)pyridine;
5-(2-(5-bromo-6-methylaminopyridinyl)ethyl)-3-(2-(S)-pyrrolidinylmethoxy)pyridine;
5-(5-hydroxymethyl-3-pyridinyl)-3-(2-(R)-pyrrolidinylmethoxy)pyridine;
5-(2,4-dimethoxy-5-pyrmdinyl)-3-(2-(S)-pyrrolidinylmethoxy)pyridine;
5-(4-methyl-3-thienyl)-3-(2-(R)-pyrrolidinylmethoxy)pyridine;
5-(4-hydroxymethyl-5-carbomethoxy-3-thienyl)-3-(2-(S)-pyrrolidinylmethoxy)pyridine;
5-(4-methoxymethyl-5-carbomethoxy-3-tbienyl)-3-(2-(S)-pyrrolidinylmethoxy)pyridine;
5-(2-(4-methyl-3-phenyl)ethyl)-3-(2-(S)-pyrrolidinylmethoxy)pyridine;
5-(2-(4-methoxy-3-phenyl)ethyl)-3-(2-(S)-pyrrolidinylmethoxy)pyridine;
5-(2-(4-trifloromethyl-3-phenyl)ethyl)-3-(2-(S)-pyrrolidinylmethoxy)pyridine;
5-(4'-fluoro-4-biphenyl)-3-(2-(R)-pyrrolidinylmethoxy)pyridine; and
5-(4'-methyl-4-biphenyl)-3-(2-(S)-pyrrolidinylmethoxy)pyridine;
5-(5,5-dimethyl-1,3-hexadienyl)-3-(2-(R)-pyrrolidinylmethoxy)pyridine;
5-(4-chlorophenyl)-3-(2-(R)-pyrrolidinylmethoxy)pyridine;
6-Chloro-5-(1-octynyl)-3-(2-(R)-pyrrolidinylmethoxy)pyridine;
5-(4-chlorophenyl)-3-(1-methyl-2-(R)-pyrrolidinylmethoxy)pyridine;
5-(1-Octynyl)-3-(2-(R)-pyrrolidinylmethoxy)pyiidine;
3-(1-Methyl-2-(R)-pyrrolidinylmethoxy)-5-(1-octynyl)pyridine;
6-Chloro-3-(1-methyl-2-(S)-pyrrolidinylrnethoxy)-5-(1-octynyl)pyridine;
6-Chloro-3-(1-methyl-2-(S)-pyrrolidinylmethoxy)-5-(3-pyridyl)pyridine;
6-Chloro-5-(5,5-dimethyl-1,3-hexadienyl)-3-(2-(S)-pyrrolidinylmethoxy)pyridine;
6-Chloro-5-(5,5-dimethyl-1,3-hexadienyl)-3-(1-methyl-2-(S)-pyrrolidinylmethoxy)pyridine;
6-Chloro-5-(4chlorophenyl)-3-(2-(S)-pyrrolidinylmethoxy)pyridine;
6-Chloro-5-(4-chlorophenyl)-3-(1-methyl-2-(S)-pyrrolidinylmethoxy)pyridine;
6-Chloro-3-(2-(S)-pyrrolidinylmethoxy)-5-(2-thienyl)pyridine;
6-Chloro-3-(1-methyl-2-(S)-pyrrolidinylmethoxy)-5-(2-thienyl)pyridine;
5-(2-(4-pyridinyl)ethenyl)-3-(2-(S)-pyrrolidinylmethoxyl)pyridine;

3-(2-(S)-Pyrrolidinylmethoxy)-5-(2-thienyl)pyridine;

5-Octynyl-3-(2-(S)-pyrrolidinylmethoxyl)pyridine;

5-(3-Aminophenyl)-3-(2-(S)-pyrrolidinylmethoxy)pyridine;

3-(2-(S)-Pyrrolidinylmethoxy)-5-(5,5-dimethyl-1,3-hexaldienyl)pyridine;

5-Ethenyl-3-(1-methyl-2-(S)-pyrrolidinylmethoxy)pyridine;

5-Ethenyl-3-(2-(S)-pyrrolidinylmethoxy)pyridine;

6-Chloro-5-ethenyl-3-(2-(R)-pyrrolidinylmethoxy)pyridine;

6-Chloro-5-ethenyl-3-(1-methyl-2-(R)-pyrrolidinylmethoxy)pyridine;

6-Chloro-5-(5-pyrimidinyl)-3-(2-(S)-pyrrolidinylmethoxyl)pyridine;

6-Chloro-5-(5-pyrimidinyl)-3-(2-(R)-pyrrolidinylmethoxyl)pyridine;

5-(5-Pyrimidinyl)-3-(2-(S)-pyrrolidinylmethoxyl)pyridine;

6-Chloro-3-(1-methyl-2-(R)-pyrrolidinylmethoxyl)-5-pyrimidinylpyridine;

6-Chloro-3-(1-methyl-2-(S)-pyrrolidinylmethoxyl)-5-(5-pyrimidinyl)pyridine;

6-Ethenyl-5-methyl-3-(2-(S)-pyrrolidinylmethoxyl)pyridine;

6-Ethenyl-5-methyl-3-(1-methyl-2-(S)-pyrrolidinylmethoxyl)pyridine;

6-Chloro-5-ethenyl-3-(2-(S)-pyrrolidinylmethoxy)pyridine;

6-Chloro-5-ethenyl-3-(1-methyl-2-(S)-pyrrolidinylmethoxy)pyridine;

5,6-Diethenyl-3-(2-(S)-pyrrolidinylmethoxy)pyridine;

6-Chloro-5-(ethynyl-3-(2-(S)-pyrrolidinylmethoxy)pyridine;

6-Chloro-5-ethynyl-3-(1-methyl-2-(S)-pyrrolidinylmethoxy)pyridine;

5-Methoxyethoxy-3-(2-(S)-pyrrolidinylmethoxy)pyridine;

5-Methoxyethoxy-3-(1-methyl-(2S)-pyrrolidinylmethoxy)pyridine;

5-Allyl-6-chloro-3-(2-(S )-pyrrolidinylmethoxyl)pyridine;

5-Allyl-6-chloro-3-(2-(S)-pyrrolidinylmethoxyl)pyridine;

5-Allyl-6-chloro-3-(2-(R)-pyrrolidinylmethoxyl)pyridine;

5-Allyl-3-(2-(S)-pyrrolidinylmethoxyl)pyridine;

5-Allyl-3-(1-methyl-2-(S)-pyrrolidinylmethoxyl)pyridine;

or a pharmaceutically acceptable salt thereof.

9. A compound according to claim 6 selected from the group consisting of:

5-(furamidomethyl)-6-chloro-3-(2-(R)-piperidinylmethoxy)pyridine;

5-(nicotinamidomethyl)-6-chloro-3-(2-(S)-piperidinylmethoxy)pyridine;

5-(5-nitro-2-furamidomethyl)-6-chloro-3-(1-methyl-2-(R)-piperidinylmethoxy)pyridine;

5-((N-2-pyrazincarbonylamino)methyl)-6-chloro-3-(1-methyl-2-(S)-piperidinylmethoxy)pyridine;

5-(2-phenylacetyl)-6-chloro-3-(1-methyl-2-(R)-piperidinylimethoxy)pyridine;

5-(3-(4-methoxyphenyl)propionyl)-6-chloro-3-(1-methyl-2-(S)-piperidinylmethoxy)pyridine;

5-(2-chloro-3-thienyl)-3-(2-(R)-piperidinylmethoxy)pyridine; and 5-(2-cyano-3-thiienyl)-3-(2-(S)-piperidinylmethoxy)pyridine; or a pharmaceutically acceptable salt thereof.

10. A process for producing a compound of formula (I) according to claim 1 comprising, (a) preparing a compound of formula (I) wherein $R^1$ is hydrogen, alkyl of one to six carbons, or a nitrogen protecting group, n is 1, 2, or 3, $R^2$ is hydrogen, fluoro, chloro, or $C_1$–$C_3$-alkyl, L is absent and $R_3$ is bromo or iodo (b) reacting the compound of formula (I) wherein $R^1$ is hydrogen, alkyl of one to six carbons, or a nitrogen protecting group, n is 1, 2, or 3, $R^2$ is hydrogen, fluoro, chloro, or $C_1$–$C_3$-alkyl, L is absent and $R_3$ is bromo or iodo with (i) an alkene, diene, alkyne, or carbon monoxide with C1–C3-alcohol;

(ii) an arylboronic acid;

(iii) an alkenyltin or alkyl Grignard reagent;

(iv) a metal cyanide;

to form in the case of step (i), a compound of formula (I) wherein $LR_3$ is an alkene, diene, alkyne, or alkoxycarbonyl; or in the case of step (ii), a compound of formula (I) wherein $LR_3$ is an aryl group; or in the case of step (iii), a compound of formula (I) wherein $LR_3$ is an alkenyl or alkyl group; or, in the case of step (iv), a compound of formula (I) wherein $LR_3$ is a cyano group, which is utilized as an intermediate to form a compound of formula (I) wherein L is carbonyl and $R_3$ is selected from alkyl of one to eight carbon atoms, h'), i), j), k), l), m), n), o), p), q), bb), and cc) as defined above, or any of i), j), k), l), m), n),o), p), q), bb) and cc) optionally substituted as defined in dd) above, or to form a compound of formula (I) wherein L is —CH$_2$NHC(=O)—($C_0$–$C_6$-alkyl)- and $R^3$ is selected from (a) through (dd) in claim 1 above.

11. A process according to claim 10 wherein the intermediate compound of formula (I) wherein $R^1$ is hydrogen, alkyl of one to six carbons, or a nitrogen protecting group, n is 1, 2, or 3, $R^2$ is hydrogen, fluoro, chloro, or $C_1$–$C_3$-alkyl, L is absent and $R_3$ is bromo or iodo is selected from:

3-(1-Boc-2-(S)-azetidinemethoxy)-5-bromo-6-chloropyridine;

3-(2-(S)-azetidinemethoxy)-5-bromo-6-chloropyridine;

5-bromo-6-chloro-3-(1-methyl-2-(S)-azetidinemethoxy)pyridine;

3-(1-Boc-2-(S)-azetidinemethoxy)-5-bromo-6-fluoropyridine;

3-(2-(S)-azetidinemethoxy)-5-bromo-6-fluoropyridine;

5-bromo-6-fluoro-3-(1-methyl-2-(S)-azetidinemethoxy)pyridine 3-(1-Boc-2-(S)-azetidinemethoxy)-5-bromo-6-methylpyridine;

3-(2-(S)-azetidinemethoxy)-5-bromo-6-methylpyridine;

5-bromo-6-methyl-3-(1-methyl-2-(S)-azetidinemethoxy)pyridine 5-bromo-6-chloro-3-(1-Boc-2-(S)-pyrrolidinemethoxy)pyridine;

5-bromo-6-chloro-3-(2-(S)-pyrrolidinemethoxy)pyridine;

5-bromo-6-chloro-3-(1-methyl-2-(S)-pyrrolidinemethoxy)pyridine;

3-(1-Boc-2-(S)-pyrrolidinemethoxy)-5-bromo-6-fluoropyridine;

5-bromo-6-fluoro-3-(2-(S)-pyrrolidinemethoxy)pyridine;

5-bromo-6-fluoro-3-(1-methyl-2-(S)-pyrrolidinemethoxy)pyridine 3-(1-Boc-2-(S)-pyrrolidinemethoxy)-5-bromo-6-methylpyridine;

5-bromo-6-methyl3-(2-(S)-pyrrolidinemethoxy)pyridine;

5-bromo-6-methyl-3-(1-methyl-2-(S)-pyrrolidinemethoxy)pyridine 3-(1-Boc-2-(R)-azetidinemethoxy)-5-bromo-6-chloropyridine;

3-(2-(R)-azetidinemethoxy)-5-bromo-6-chloropyridine;

5-bromo-6-chloro-3-(1-methyl-2-(R)-azetidinemethoxy)pyridine;

3-(1-Boc-2-(R)-azetidinemethoxy)-5-bromo-6-fluoropyridine;

3-(2-(R)-azetidinemethoxy)-5-bromo-6-fluoropyridine;

5-bromo-6-fluoro-3-(1-methyl-2-(R)-azetidinemethoxy)pyridine 3-(1-Boc-2-(R)-azetidinemethoxy)-5-bromo-6-methylpyridine;

3-(2-(R)-azetidinemethoxy)-5-bromo-6-methylpyridine;

5-bromo-6-methyl-3-(1-methyl-2-(R)-azetidinemethoxy)pyridine 5-bromo-6-chloro-3-(1-Boc-2-(R)-pyrrolidinemethoxy)pyridine;

5-bromo-6-chloro-3-(2-(R)-pyrrolidinemethoxy)pyridine;

5-bromo-6-chloro-3-(1-methyl-2-(R)-pyrrolidinemethoxy)pyridine;

3-(1-Boc-2-(R)-pyrrolidinemethoxy)-5-bromo-6-fluoropyridine;

5-bromo-6-fluoro-3-(2-(R)-pyrrolidinemethoxy)pyridine;

5-bromo-6-fluoro-3-(1-methyl-2-(R)-pyrrolidinemethoxy)pyridine 3-(1-Boc-2-(R)-pyrrolidinemethoxy)-5-bromo-6-methylpyridine;

5-bromo-6-methyl3-(2-(R)-pyrrolidinemethoxy)pyridine;

5-bromo-6-methyl-3-(1-methyl-2-(R)-pyrrolidinemethoxy)pyridine.

12. A pharmaceutical composition for selectively controlling synaptic transmission, comprising a pharmaceutically-acceptable carrier and a therapeutically-effective amount of a compound according to claim 1.

13. A method for selectively controlling synaptic transmission comprising administering to a host mammal in need of such treatment a therapeutically-effective amount of a compound according to claim 1.

* * * * *

UNITED STATES PATENT AND TRADEMARK OFFICE
CERTIFICATE OF CORRECTION

PATENT NO. : 6,127,386
DATED : October 3, 2000
INVENTOR(S) : Nan-Horng Lin et al.

It is certified that error appears in the above-identified patent and that said Letters Patent is hereby corrected as shown below:

Column 133,
Line 31, replace "alkoxycarbonyl substituent, or" with -- alkoxycarbonyl substituent; or --.

Column 142,
Line 23, replace "5-(4-methoxy methoxy- 5-carbomethoxy-3- tbienyl)-3" with -- 5-(4-methoxymethoxy-5-carbomethoxy-3-thienyl)-3 --.

Column 144,
Line 5, replace "5-(2-cyano-3-thiinyl)-3" with -- 5-(2-cyano-3-thienyl)-3 --.

Signed and Sealed this

First Day of January, 2002

Attest:

Attesting Officer

JAMES E. ROGAN
Director of the United States Patent and Trademark Office